US009056875B2

(12) United States Patent
Lindsley et al.

(10) Patent No.: US 9,056,875 B2
(45) Date of Patent: Jun. 16, 2015

(54) SUBSTITUTED PYRAZOLO[3',4':4,5]THIENO[2,3-C]PYRIDAZIN-3-AMINE ANALOGS AS POSITIVE ALLOSTERIC MODULATORS OF THE MUSCARINIC ACETYLCHOLINE RECEPTOR M4

(71) Applicant: Vanderbilt University, Nashville, TN (US)

(72) Inventors: Craig W. Lindsley, Brentwood, TN (US); P. Jeffrey Conn, Brentwood, TN (US); Michael R. Wood, Brentwood, TN (US); James M Salovich, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/974,858

(22) Filed: Aug. 23, 2013

(65) Prior Publication Data

US 2014/0364409 A1    Dec. 11, 2014

Related U.S. Application Data

(60) Provisional application No. 61/696,014, filed on Aug. 31, 2012.

(51) Int. Cl.
| | | |
|---|---|---|
| A01N 43/58 | (2006.01) | |
| A61K 31/50 | (2006.01) | |
| C07D 237/36 | (2006.01) | |
| C07D 495/14 | (2006.01) | |

(52) U.S. Cl.
CPC .................................... *C07D 495/14* (2013.01)

(58) Field of Classification Search
USPC .......................................... 514/248; 544/234
See application file for complete search history.

(56) References Cited

U.S. PATENT DOCUMENTS 4,220,776 A    9/1980 Whitney et al.

FOREIGN PATENT DOCUMENTS

| WO | WO-96/09304 A1 | 3/1996 |
| WO | WO-2011/041143 A1 | 4/2011 |
| WO | WO-2013/040534 A1 | 3/2013 |

OTHER PUBLICATIONS

Burger et al (1997).*
Wolff et al (1997).*
Grant MH84659.
Grant MH74427.
Jeon J, et al. (2010) A Subpopulation of Neuronal M4 Muscarinic Acetylcholine Receptors Plays a Critical Role in Modulating Dopamine-Dependent Behaviors. J. Neurosci., 30(6): 2396-2405.
Shannon, et al. (1999) Muscarinic Receptor Agonists, Like Dopamine Receptor Antagonist Antipsychotics, Inhibit Conditioned Avoidance ; Response in Rats. J. Pharmacol. Exp. Ther., 290: 901-907.
Shannon, et al. (2000) Xanomeline, an M1/M4 preferring muscarinic cholinergic receptor agonist, produces antipsychotic-like activity in rats ; and mice. Schizophrenia Res., 42: 249-259.
Bodick, et al. (1997) Effects of Xanomeline, a Selective Muscarinic Receptor Agonist, on Cognitive Function and Behavioral Symptoms in ; Alzheimer Disease. Arch. Neurol., 54: 465-473.
Bymaster, et al. (1998) Unexpected antipsychotic-like activity with the muscarinic receptor ligand ; (5R, 6R)6-(3-propylthio-1,2,5-thiadiazol-4-yl)-1-azabicyclo[3.2.1]octane. Eur. J. Pharmacol. 356: 109-119.
Bymaster, et al. (1999) Potential Role of Muscarinic Receprors in Schizophrenia. Life Sci., 64: 527-534.
U.S. Appl. No. 14/345,244, Conn et al.
U.S. Appl. No. 61/535,828, Conn et al.
U.S. Appl. No. 61/696,014, Lindsley et al.
Levy AI, et al., "Identification and localization of muscarinic acetylcholine receptor proteins in brain with subtype-specific antibodies," J. Neurosci., 11(10): 3218-3226.
Abstract of Grant MH087965, Award Notice Date Feb. 18, 2010.
Abstract of Grant MH086601, Award Notice Date Aug. 27, 2009.
Abstract of Grant MH082867, Award Notice Date May 20, 2008.
Abstract of Grant MH073676, Award Notice Date Dec. 26, 2005.
Abstract of Grant MH089870, Award Notice Date Sep. 28, 2009.
Abstract of Grant NS065867, Award Notice Date Mar. 19, 2010.
Abstract of Grant MH084659, Award Notice Date Aug. 29, 2008.
Abstract of Grant MH074427, Award Notice Date Jun. 15, 2005.
U.S. Appl. No. 14/345,244, filed Sep. 2, 1980, Whitney et al.
U.S. Appl. No. 61/535828, Conn et al.
U.S. Appl. No. 61/696014, Lindsley et al.
Almarasson O, et al., "Crystal Engineering of the Composition of Pharmaceutical Phases. Do Pharmaceutical Co-crystals Represent a New path to Improved Medicines?", The Royal Society of Chemistry, 1889-1896 (2004).
Banker, et al., "Modern Pharmaceutics," Third Edition, Drugs and the Pharmaceutical Sciences Series (1995).
Levy AI, et al., "Identification and localization of muscarinic acetylcholine receptor proteins in brain with subtype-specific antibodies," J. Neurosci., 11(10): 3218-3226, (1991).
Wolff Me, et al., "Burger's Medicinal Chemistry and Drug Discovery," Fifth Edition, vol. 1; Principles and Practice, A Wiley-Interscience Publication, 975-977 (1997).

(Continued)

*Primary Examiner* — Paul V. Ward
(74) *Attorney, Agent, or Firm* — Michael Best & Friedrich LLP

(57) ABSTRACT

In one aspect, the invention relates to substituted pyrazolo[3',4':4,5]thieno[2,3-c]pyridazine-3-amine analogs, derivatives thereof, and related compounds, which are useful as positive allosteric modulators of the muscarinic acetylcholine receptor $M_4$ (mAChR $M_4$); synthesis methods for making the compounds; pharmaceutical compositions comprising the compounds; and methods of treating neurological and psychiatric disorders associated with muscarinic acetylcholine receptor dysfunction using the compounds and compositions. This abstract is intended as a scanning tool for purposes of searching in the particular art and is not intended to be limiting of the present invention.

14 Claims, 1 Drawing Sheet

(56) References Cited

OTHER PUBLICATIONS

International Preliminary Report on Patentability issued Mar. 18, 2014 for PCT/US2012/055686 filed Sep. 16, 2012 and published as WO 2013/040534 on Mar. 21, 2013 (Applicants—Vanderbilt University; Inventors—Conn et al.) (5 pages).

International Search Report mailed Nov. 23, 2012 for PCT/US2012/055686 filed Sep. 16, 2012 and published as WO 2013/040534 on Mar. 21, 2013 (Applicants—Vanderbilt University; Inventors—Conn et al.) (2 pages).

Written Opinion mailed Nov. 23, 2012 for PCT/US2012/055686 filed Sep. 16, 2012 and published as WO 2013/040534 on Mar. 21, 2013 (Applicants—Vanderbilt University; Inventors—Conn et al.) (4 pages).

Grant MH73676, Submission Date Nov. 4, 2009. Award Notice Date Dec. 26, 2005.

Grant MH74427, Submission Date Sep. 17, 2004. Award Notice Date Jun. 15, 2005.

Grant MH82867, Submission Date Jul. 2, 2012. Award Notice Date May 20, 2008.

Grant MH84659, Submission Date Jan. 10, 2008. Award Notice Date Aug. 29, 2008.

Grant MH86601, Submission Date Oct. 6, 2008. Award Notice Date Aug. 27, 2009.

Grant MH87965, Submission Date Feb. 24, 2009. Award Notice Date Feb. 18, 2010.

Grant MH89870, Submission Date May 29, 2009. Award Notice Date Sep. 28, 2009.

Grant NH77607, Submission Date Sep. 14, 2005.

Grant NS65867, Submission Date Jul. 6, 2009. Award Notice Date Mar. 19, 2010.

\* cited by examiner

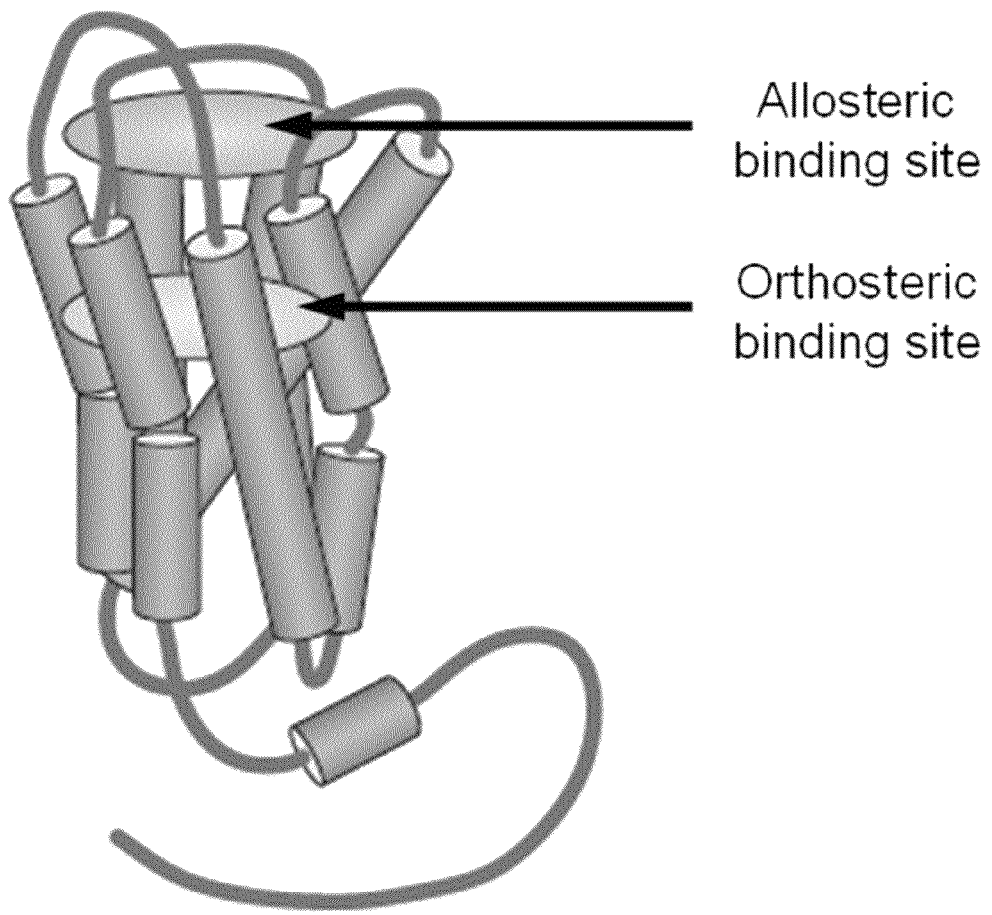

SUBSTITUTED PYRAZOLO[3',4':4,5]THIENO[2,3-C]PYRIDAZIN-3-AMINE ANALOGS AS POSITIVE ALLOSTERIC MODULATORS OF THE MUSCARINIC ACETYLCHOLINE RECEPTOR M4

CROSS-REFERENCE TO RELATED APPLICATIONS

This Application claims the benefit of U.S. Provisional Application No. 61/696,014, filed on Aug. 31, 2012, which is incorporated herein by reference in its entirety.

STATEMENT REGARDING FEDERALLY SPONSORED RESEARCH

This invention was made with government support under grant numbers MH87965, MH86601, MH82867, MH73676, MH89870, NS65867, MH77607, MH84659 and MH74427 awarded by the National Institutes of Health (NIH). The United States government has certain rights in the invention.

BACKGROUND

Cholinergic neurotransmission involves the activation of nicotinic acetylcholine receptors (nAChRs) or the muscarinic acetylcholine receptors (mAChRs) by the binding of the endogenous orthosteric agonist acetylcholine (ACh). Conditions associated with cognitive impairment, such as Alzheimer's disease, are accompanied by a reduction of acetylcholine content in the brain. This is believed to be the result of degeneration of cholinergic neurons of the basal forebrain, which widely innervate multiple areas of the brain, including the association cortices and hippocampus, which are critically involved in higher processes. Clinical data supports that cholinergic hypofunction contributes to the cognitive deficits of patients suffering from schizophrenia. Efforts to increase acetylcholine levels have focused on increasing levels of choline, the precursor for acetylcholine synthesis, and on blocking acetylcholinesterase (AChE), the enzyme that metabolizes acetylcholine. As a result, acetylcholinesterase (AChE) inhibitors, which inhibit the hydrolysis of ACh, have been approved in the United States for use in the palliative, but not disease-modifying, treatment of the cognitive deficits in AD patients.

Attempts to augment central cholinergic function through the administration of choline or phosphatidylcholine have not been successful. AChE inhibitors have shown therapeutic efficacy, but have been found to have frequent cholinergic side effects due to peripheral acetylcholine stimulation, including abdominal cramps, nausea, vomiting, and diarrhea. These gastrointestinal side effects have been observed in about a third of the patients treated. In addition, some AChE inhibitors, such as tacrine, have also been found to cause significant hepatotoxicity with elevated liver transaminases observed in about 30% of patients. The adverse effects of AChE inhibitors have severely limited their clinical utility. An alternative approach to pharmacologically target cholinergic hypofunction is the activation of mAChRs, which are widely expressed throughout the body.

The mAChRs are members of the family A GPCRs and include five subtypes, designated $M_1$-$M_5$. The $M_1$, $M_3$ and $M_5$ subtypes mainly couple to $G_q$ and activate phospholipase C, whereas the $M_2$ and $M_4$ subtypes mainly couple to $G_{i/o}$ and associated effector systems. These five distinct mAChR subtypes have been identified in the mammalian central nervous system where they are prevalent and differentially expressed.

The mAChR $M_1$-$M_5$ subtypes have varying roles in cognitive, sensory, motor and autonomic functions. Thus, without wishing to be bound by a particular theory, it is believed that selective agonists of mAChR subtypes that regulate processes involved in cognitive function could prove superior to be superior therapeutics for treatment of psychosis, schizophrenia and related disorders. The muscarinic $M_4$ receptor has been shown to have a major role in cognitive processing and is believed to have a major role in the pathophysiology of psychotic disorders, including schizophrenia.

Evidence suggests that the most prominent adverse effects of AChE inhibitors and other cholinergic agents are mediated by activation of peripheral $M_2$ and $M_3$ mAChRs and include bradycardia, GI distress, excessive salivation, and sweating. In contrast, $M_4$ has been viewed as the most likely subtype for mediating the effects of muscarinic acetylcholine receptor dysfunction in psychotic disorders, including schizophrenia, cognition disorders, and neuropathic pain. Because of this, considerable effort has been focused on developing selective $M_4$ agonists for treatment of these disorders. Unfortunately, these efforts have been largely unsuccessful because of an inability to develop compounds that are highly selective for the mAChR $M_4$. Because of this, mAChR agonists that have been tested in clinical studies induce a range of adverse effects by activation of peripheral mAChRs. To fully understand the physiological roles of individual mAChR subtypes and to further explore the therapeutic utility of mAChR ligands in psychosis, including schizophrenia, cognition disorders and other disorders, it can be important to develop compounds that are highly selective activators of mAChR $M_4$ and other individual mAChR subtypes.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly-conserved. This approach is proving to be highly successful in developing selective ligands for multiple GPCR subtypes. In the case of mAChRs, a major goal has been to develop allosteric ligands that selectively increase activity of mAChR $M_4$ or other mAChR subtypes. Allosteric activators can include allosteric agonists, that act at a site removed from the orthosteric site to directly activate the receptor in the absence of ACh as well as positive allosteric modulators (PAMs), which do not activate the receptor directly but potentiate activation of the receptor by the endogenous orthosteric agonist ACh. Also, it is possible for a single molecule to have both allosteric potentiator and allosteric agonist activity.

Recently, muscarinic agonists including xanomeline have been shown to be active in animal models with similar profiles to known antipsychotic drugs, but without causing catalepsy (Bymaster et al., Eur. J. Pharmacol. 1998, 356, 109, Bymaster et al., Life Sci. 1999, 64, 527; Shannon et al., J. Pharmacol. Exp. Ther. 1999, 290, 901; Shannon et al., Schizophrenia Res. 2000, 42, 249.). Further, xanomeline was shown to reduce psychotic behavioral symptoms such as delusions, suspiciousness, vocal outbursts, and hallucinations in Alzheimer's disease patients (Bodick et al., Arch. Neurol. 1997, 54, 465.), however treatment induced side effects, e.g., gastrointestinal effects, have severely limited the clinical utility of this compound.

Despite advances in muscarinic acetylcholine receptor research, there is still a scarcity of compounds that are potent, efficacious and selective activators of the $M_4$ mAChR and also effective in the treatment of neurological and psychiatric disorders associated with cholinergic activity and diseases in which the muscarinic $M_4$ receptor is involved. These needs and other needs are satisfied by the present invention.

SUMMARY

In accordance with the purpose(s) of the invention, as embodied and broadly described herein, the invention, in one aspect, relates to compounds useful as positive allosteric modulators (i.e., potentiators) of the muscarinic acetylcholine receptor $M_4$ (mAChR $M_4$), methods of making same, pharmaceutical compositions comprising same, and methods of treating neurological and psychiatric disorders associated with muscarinic acetylcholine receptor dysfunction using same.

Disclosed are compounds having a structure represented by a formula:

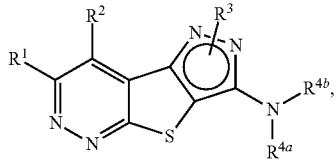

wherein $R^1$ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino; wherein $R^2$ is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino; or wherein $R^1$ and $R^2$ are optionally covalently bonded and, together with the intermediate atoms, comprise a 3- to 7-membered cycle and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino; wherein $R^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-; wherein each of $R^{4a}$ and $R^{4b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{40}$R$^{41}$, —(C1-C6 alkyl)-NR$^{40}$(C=O)R$^{41}$, —(C1-C6 alkyl)-NR$^{40}$(C=O)OR$^{41}$, —(C1-C6 alkyl)-NR$^{40}$(C=O)R$^{41}$, —(C1-C6 monohaloalkyl)-NR$^{40}$(C=O)OR$^{41}$, —(C1-C6 polyhaloalkyl)-NR$^{40}$(C=O)OR$^{41}$, —(C1-C8 alkyl)-Cy$^1$, Cy$^1$, —(C1-C8 alkyl)-Ar$^1$, —(C2-C8 alkynyl)-Ar$^1$, and Ar$^1$; wherein each R$^{40}$, when present, is independently selected from hydrogen and C1-C8 alkyl; wherein each R$^{41}$, when present, is independently selected from hydrogen, C1-C8 alkyl, C1-C8 monohaloalkyl, C1-C8 polyhaloalkyl, —(C1-C8 alkyl)-Cy$^1$, Cy$^1$, —(C1-C8 alkyl)-Ar$^1$, and Ar$^1$; wherein each Ar$^1$, when present, is independently selected from phenyl, naphthyl, and heteroaryl, and wherein each Ar$^1$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C8 alkyl)-Ar$^{20}$, Ar$^{20}$, —(C1-C8 alkyl)-Cy$^{20}$, Cy$^{20}$, and R$^{57}$; wherein each m is an integer independently selected from 0, 1 and 2; wherein each Ar$^{20}$, when present, is independently selected from phenyl, naphthyl, and heteroaryl, and wherein each Ar$^{20}$ is independently substituted with 0, 1, 2, or 3 groups independently selected from halogen, —NH$_2$, —OH, —CN, —S(O)$_m$R$^{50}$, C1-C8 alkyl, C1-C8 monohaloalkyl, C1-C8 polyhaloalkyl, C1-C8 alkoxy, C1-C8 alkylamino, and C1-C8 dialkylamino; wherein each Cy$^{20}$, when present, is independently selected from C3-C9 cycloalkyl and C2-C7 heterocycloalkyl, and wherein each Cy$^{20}$ is independently substituted with 0, 1, 2, or 3 groups independently selected from halogen, —NH$_2$, —OH, —CN, —S(O)$_m$R$^{50}$, C1-C8 alkyl, C1-C8 monohaloalkyl, C1-C8 polyhaloalkyl, C1-C8 alkoxy, C1-C8 alkylamino, and C1-C8 dialkylamino; wherein each R$^{50}$, when present, is independently selected from hydrogen and C1-C8 alkyl; wherein each R$^{51}$, when present, is independently selected from hydrogen and C1-C8 alkyl; wherein each R$^{52}$, when present, is independently selected from hydrogen and C1-C8 alkyl; wherein each R$^{53}$, when present, is independently selected from hydrogen and C1-C8 alkyl; wherein each R$^{54}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{21}$, and Ar$^{21}$; wherein each Ar$^{21}$, when present, is independently selected from phenyl, naphthyl, and heteroaryl, and wherein each Ar$^{21}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{55}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{22}$, and Ar$^{22}$; wherein each Ar$^{22}$, when present, is independently selected from phenyl, naphthyl, and heteroaryl, and wherein each Ar$^{22}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{50}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{23}$, and Ar$^{23}$; wherein each Ar$^{23}$, when present, is independently selected from phenyl, naphthyl, and heteroaryl, and wherein each Ar$^{23}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{57}$, when present, is independently selected from C1-C4 alkyl, C1-C4 alkoxy, C1-C4 monoalkylamino, or C1-C4 dialkylamino substituted with 1 or 2 groups selected from —F, —CH$_3$, —CF$_3$, —OH, —NH$_2$, and —CN; wherein each Cy$^1$, when present, is independently selected from C3-C9 cycloalkyl and C2-C7 heterocycloalkyl, and wherein each Cy$^1$ is independently substituted with 0, 1, 2, or 3 groups independently selected from halogen, —NH₂, —OH, —CN, —N₃, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C8 alkyl)-Ar$^{20}$, Ar$^{20}$, —(C1-C8 alkyl)-Cy$^{20}$, Cy$^{20}$, and R$^{57}$; or wherein R$^{4a}$ and R$^{4b}$ are optionally covalently bonded and, together with the intermediate nitrogen, comprise a 3- to 10-membered heterocycloalkyl substituted with 0, 1, 2, or 3 groups independently selected from halogen, —NH₂, —OH, —CN, —N₃, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C8 alkyl)-Ar$^{30}$, Ar$^{30}$, —(C1-C8 alkyl)-Cy$^{30}$, Cy$^{30}$, and R$^{57}$; wherein each Ar$^{30}$, when present, is independently selected from phenyl, naphthyl, and heteroaryl, and wherein each Ar$^{30}$ is independently substituted with 0, 1, 2, or 3 groups independently selected from halogen, —NH₂, —OH, —CN, —S(O)$_m$R$^{65}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$; wherein each R$^{65}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Ar$^{40}$, when present, is independently selected from phenyl, naphthyl, and heteroaryl, and wherein each Ar$^{40}$ is independently substituted with 0, 1, 2, or 3 groups independently selected from halogen, —NH₂, —OH, —CN, —S(O)$_m$R$^{66}$, C1-C8 alkyl, C1-C8 monohaloalkyl, C1-C8 polyhaloalkyl, C1-C8 alkoxy, C1-C8 alkylamino, and C1-C8 dialkylamino; wherein each R$^{66}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Cy$^{40}$, when present, is independently selected from C3-C9 cycloalkyl and C2-C7 heterocycloalkyl, and wherein each Cy$^{40}$ is independently substituted with 0, 1, 2, or 3 groups independently selected from halogen, —NH₂, —OH, —CN, —S(O)$_m$R$^{66}$, C1-C8 alkyl, C1-C8 monohaloalkyl, C1-C8 polyhaloalkyl, C1-C8 alkoxy, C1-C8 alkylamino, and C1-C8 dialkylamino; wherein each Cy$^{30}$, when present, is independently selected from C3-C9 cycloalkyl and C2-C7 heterocycloalkyl, and wherein each Cy$^{30}$ is independently substituted with 0, 1, 2, or 3 groups independently selected from halogen, —NH₂, —OH, —CN, —S(O)$_m$R$^{65}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$; or a pharmaceutically acceptable salt, solvate, or polymorph thereof.

Also disclosed are compounds having a structure represented by a formula:

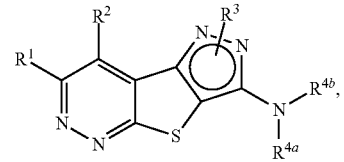

wherein R$^1$ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino; wherein R$^2$ is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino; or wherein R$^1$ and R$^2$ are optionally covalently bonded and, together with the intermediate atoms, comprise a 3- to 7-membered cycle and substituted with 0, 1 or 2 groups independently selected from halogen, —NH₂, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino; wherein R$^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-; wherein each of R$^{4a}$ and R$^{4b}$ is independently selected from hydrogen, C1-C8 alkyl, C1-C8 monohaloalkyl, C1-C8 polyhaloalkyl, Cy$^1$, Cy$^1$-(C1-C6 alkyl)-, Ar$^1$, and Ar$^1$—(C1-C6 alkyl)-; wherein each Ar$^1$, when present, is independently selected from phenyl and heteroaryl, and wherein each Ar$^1$ is independently substituted with 0, 1, 2, or 3 groups independently selected from halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein two of the groups are optionally covalently bonded, and together with the intermediate atoms, comprise an optionally substituted 3- to 6-membered fused ring group; and wherein m is an integer selected from 0, 1 and 2; and wherein each Ar$^2$, when present, is independently selected from phenyl and heteroaryl, and wherein each Ar$^2$ is independently substituted with 0, 1, 2, or 3 groups independently selected from halogen, —NH₂, —OH, —CN, C1-C8 alkyl, C1-C8 monohaloalkyl, C1-C8 polyhaloalkyl, C1-C8 alkoxy, C1-C8 alkylamino, C1-C8 dialkylamino, and —S(O)$_m$R$^5$; wherein each R$^5$, when present, is independently selected from hydrogen, C1-C8 alkyl, C3-C8 cycloalkyl, C1-C8 monohaloalkyl, C1-C8 polyhaloalkyl, —(C1-C3)-Ar$^2$, and Ar$^2$; wherein each R$^6$, when present, is selected from C1-C4 alkyl, C1-C4 alkoxy, C1-C4 monoalkylamino, or C1-C4 dialkylamino substituted with 1 or 2 groups selected from fluoro, trifluoromethyl, methyl, —OH, —NH₂, and —CN; wherein each Cy$^1$, when present, is independently selected from C3-C8 cycloalkyl and C2-C7 heterocycloalkyl, and wherein each Cy$^1$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, —S(O)$_m$R$^5$, R$^6$, and Ar$^2$; and wherein two of the groups are optionally covalently bonded, and together with the intermediate atoms, comprise an optionally substituted 3- to 6-membered fused ring group; or wherein R$^{4a}$ and R$^{4b}$ are optionally covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, C3-C8 cycloalkyl, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, —S(O)$_m$R$^5$, and Ar$^2$; and wherein two of the groups are optionally covalently bonded, and together with the intermediate atoms, comprise an optionally substituted 3- to 6-membered fused ring group; or a pharmaceutically acceptable salt, solvate, or polymorph thereof.

Also disclosed are pharmaceutical compositions comprising a therapeutically effective amount of one or more disclosed compounds, or pharmaceutically acceptable salt, hydrate, solvate, or polymorph thereof, and a pharmaceutically acceptable carrier.

Also disclosed are methods for the treatment of a neurological and/or psychiatric disorder associated with muscarinic acetylcholine receptor dysfunction in a mammal comprising the step of administering to the mammal a therapeutically effective amount of at least one disclosed compound or pharmaceutically acceptable salt, hydrate, solvate, or polymorph thereof.

Also disclosed are methods for potentiation of muscarinic acetylcholine receptor activity in a mammal comprising the step of administering to the mammal a therapeutically effective amount of at least one disclosed compound or pharmaceutically acceptable salt, hydrate, solvate, or polymorph thereof.

Also disclosed are methods for enhancing cognition in a mammal comprising the step of administering to the mammal an effective amount of at least one disclosed compound or pharmaceutically acceptable salt, hydrate, solvate, or polymorph thereof.

Also disclosed are methods for potentiation of muscarinic acetylcholine receptor activity in at least one cell, comprising the step of contacting the cell with an effective amount of at least one disclosed compound or pharmaceutically acceptable salt, hydrate, solvate, or polymorph thereof.

Also disclosed are uses of a disclosed compound, a disclosed product of making, or a pharmaceutically acceptable salt, hydrate, solvate, or polymorph thereof.

Also disclosed are uses of a disclosed compound, a disclosed product of making, or a pharmaceutically acceptable salt, hydrate, solvate, or polymorph thereof, in the manufacture of a medicament for the treatment of a disorder associated with a muscarinic acetylcholine receptor dysfunction in a mammal.

Also disclosed are methods for the manufacture of a medicament to activate the mAChR M$_4$ in a mammal comprising combining at least one disclosed compound or at least one disclosed product of making with a pharmaceutically acceptable carrier or diluent.

Also disclosed are kits comprising at least one disclosed compound, or a pharmaceutically acceptable salt, hydrate, solvate, or polymorph thereof, and one or more of: (a) at least one agent known to increase mAChR M$_4$ activity; (b) at least one agent known to decrease mAChR M$_4$ activity; (c) at least one agent known to treat a disorder associated with cholinergic activity; (d) instructions for treating a disorder associated with cholinergic activity; (e) instructions for treating a disorder associated with mAChR M$_4$ receptor activity; or (f) instructions for administering the compound in connection with cognitive or behavioral therapy.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 1 is a schematic illustration of ligand binding to the orthosteric site and an allosteric site in the muscarinic acetylcholine receptor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor. For example, the orthosteric site in the mAChR $M_4$ receptor is the site that acetylcholine binds.

As used herein, the term "mAChR $M_4$ receptor positive allosteric modulator" refers to any exogenously administered compound or agent that directly or indirectly augments the activity of the mAChR $M_4$ receptor in the presence or in the absence of acetylcholine, or another agonist, in an animal, in particular a mammal, for example a human. For example, a mAChR $M_4$ receptor positive allosteric modulator can increase the activity of the mAChR $M_4$ receptor in a cell in the presence of extracellular acetylcholine. The cell can be Chinese hamster ovary (CHO-K1) cells transfected with human mAChR $M_4$. The cell can be Chinese hamster ovary (CHO-K1) cells transfected with rat mAChR $M_4$ receptor. The cell can be Chinese hamster ovary (CHO-K1) cells transfected with a mammalian mAChR $M_4$. The term "mAChR $M_4$ receptor positive allosteric modulator" includes a compound that is a "mAChR $M_4$ receptor allosteric potentiator" or a "mAChR $M_4$ receptor allosteric agonist," as well as a compound that has mixed activity comprising pharmacology of both a "mAChR $M_4$ receptor allosteric potentiator" and a "mAChR $M_4$ receptor allosteric agonist." The term "mAChR $M_4$ receptor positive allosteric modulator also includes a compound that is a "mAChR $M_4$ receptor allosteric enhancer."

As used herein, the term "mAChR $M_4$ receptor allosteric potentiator" refers to any exogenously administered compound or agent that directly or indirectly augments the response produced by the endogenous ligand (such as acetylcholine) when the endogenous ligand binds to the orthosteric site of the mAChR $M_4$ receptor in an animal, in particular a mammal, for example a human. The mAChR $M_4$ receptor allosteric potentiator binds to a site other than the orthosteric site, that is, an allosteric site, and positively augments the response of the receptor to an agonist or the endogenous ligand. In one aspect, an allosteric potentiator does not induce desensitization of the receptor, activity of a compound as a mAChR $M_4$ receptor allosteric potentiator provides advantages over the use of a pure mAChR $M_4$ receptor orthosteric agonist. Such advantages can include, for example, increased safety margin, higher tolerability, diminished potential for abuse, and reduced toxicity.

As used herein, the term "mAChR $M_4$ receptor allosteric enhancer" refers to any exogenously administered compound or agent that directly or indirectly augments the response produced by the endogenous ligand (such as acetylcholine) in an animal, in particular a mammal, for example a human. In one aspect, the allosteric enhancer increases the affinity of the natural ligand or agonist for the orthosteric site. In another aspect, an allosteric enhancer increases the agonist efficacy.

The mAChR $M_4$ receptor allosteric enhancer binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

As used herein, the term "mAChR $M_4$ receptor allosteric agonist" refers to any exogenously administered compound or agent that directly activates the activity of the mAChR $M_4$ receptor in the absence of the endogenous ligand (such as acetylcholine) in an animal, in particular a mammal, for example a human. The mAChR $M_4$ receptor allosteric agonist binds to a site that is distinct from the orthosteric acetylcholine site of the mAChR $M_4$ receptor. Because it does not require the presence of the endogenous ligand, activity of a compound as a mAChR $M_4$ receptor allosteric agonist provides advantages over the use of a pure mAChR $M_4$ receptor allosteric potentiator, such as more rapid onset of action.

As used herein, the term "mAChR $M_4$ receptor neutral allosteric ligand" refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with muscarinic acetylcholine receptor dysfunction prior to the administering step. In some aspects of the disclosed method, the subject has been diagnosed with a need for positive allosteric modulation of muscarinic acetylcholine receptor activity prior to the administering step. In some aspects of the disclosed method, the subject has been diagnosed with a need for partial agonism of muscarinic acetylcholine receptor activity prior to the administering step. In some aspects of the disclosed method, the subject has been diagnosed with a neurological and/or psychiatric disorder, e.g. schizophrenia, Alzheimer's disease, a cognitive disorder, or neuropathic pain prior to the administering step. In some aspects of the disclosed method, the subject has been identified with a disorder treatable by activation of the mAChR $M_4$ receptor and/or or a need for activation/agonism of mAChR $M_4$ activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mAChR $M_4$" means having been subjected to a physical examination by a person of skill, for example, a physician, and found to have a condition that can be diagnosed or treated by a compound or composition that can modulate mAChR $M_4$. As a further example, "diagnosed with a need for modulation of mAChR $M_4$" refers to having been subjected to a physical examination by a person of skill, for example, a physician, and found to have a condition characterized by mAChR $M_4$ activity. Such a diagnosis can be in reference to a disorder, such as a neurodegenerative disease, and the like, as discussed herein. For example, the term "diagnosed with a need for positive allosteric modulation of muscarinic acetylcholine receptor activity" refers to having been subjected to a physical examination by a person of skill, for example, a physician, and found to have a condition that can be diagnosed or treated by positive allosteric modulation of muscarinic acetylcholine receptor activity. For example, "diagnosed with a need for partial agonism of muscarinic acetylcholine receptor activity" means having been subjected to a physical examination by a person of skill, for example, a physician, and found to have a condition that can be diagnosed or treated by partial agonism of muscarinic acetylcholine receptor activity. For example, "diagnosed with a need for treatment of one or more neurological and/or psychiatric disorder associated with acetylcholine dysfunction" means having been subjected to a physical examination by a person of skill, for example, a physician, and found to have one or more neurological and/or psychiatric disorder associated with acetylcholine dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mAChR $M_4$ activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor (e.g. a muscarinic acetylcholine receptor), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an appropriate assay of the target activity. For example, an $EC_{50}$ for the mAChR $M_4$ receptor can be determined in an in vitro or cell-based assay system. Such in vitro assay systems frequently utilize a cell line that either expresses endogenously a target of interest, or has been transfected with a suitable expression vector that directs expression of a recombinant form of the target such as the mAChR $M_4$ receptor. For example, the $EC_{50}$ for mAChR $M_4$ can be determined using Chinese hamster ovary (CHO-K1) cells transfected with human mAChR $M_4$. Alternatively, the $EC_{50}$ for mAChR $M_4$ can be determined using Chinese hamster ovary (CHO-K1) cells transfected with rat mAChR $M_4$. In another example, the $EC_{50}$ for mAChR $M_4$ can be determined using Chinese hamster ovary (CHO-K1) cells transfected with a mammalian mAChR $M_4$.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay. For example, an $IC_{50}$ for mAChR $M_4$ receptor can be determined in an in vitro or cell-based assay system. Frequently, receptor assays, including suitable assays for mAChR $M_4$, make use of a suitable cell-line, e.g. a cell line that either expresses endogenously a target of interest, or has been transfected with a suitable expression vector that directs expression of a recombinant form of the target such as mAChR $M_4$. For example, the $IC_{50}$ for mAChR $M_4$ can be determined using Chinese hamster ovary (CHO-K1) cells transfected with human mAChR $M_4$. Alternatively, the $IC_{50}$ for mAChR $M_4$ can be determined using Chinese hamster ovary (CHO-K1) cells transfected with rat mAChR $M_4$. In another example, the $IC_{50}$ for mAChR $M_4$ can be determined using Chinese hamster ovary (CHO-K1) cells transfected with a mammalian mAChR $M_4$.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized $\pi 0$ electrons above and below the plane of the molecule, where the $\pi$ clouds contain (4n+2) $\pi$ electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —$N(-alkyl)_2$ where alkyl is a described herein, and it is understood that each alkyl group can be independently selected from each other. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1O(O)C-A^2-C(O)O)_a$— or -($A^1O(O)C-A^2-OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1O-A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide", as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s)

that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)_mR^\circ_2$; $-N(R^\circ)C(S)_mR^\circ_2$; $-(CH_2)_{0-4}N(R^\circ)C(O)OR^\circ$; $-N(R^\circ)_m(R^\circ)C(O)R^\circ_2$; $-N(R^\circ)_m(R^\circ)C(O)_mR^\circ_2$; $-N(R^\circ)_m(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)_mR^\circ_2$; $-C(S)_mR^\circ_2$; $-C(S)SR^\circ$; $-(CH_2)_{0-4}OC(O)_mR^\circ_2$; $-C(O)_m(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)_mRO_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched)alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)_mR^\dagger_2$, $-C(NH)_mR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

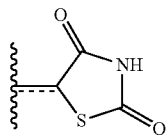

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium mixture of tautomers. For example, ketones with an α-hydrogen can exist in an equilibrium mixture of the keto form and the enol form.

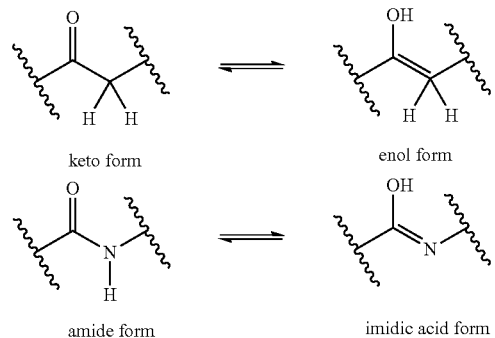

keto form    enol form amide form    imidic acid form

Likewise, amides with an N-hydrogen can exist in an equilibrium mixture of the amide form and the imidic acid form. As another example, pyrazoles can exist in two tautomeric forms, $N^1$-unsubstituted, 3-$A^3$ and $N^1$-unsubstituted, 5-$A^3$ as shown below.

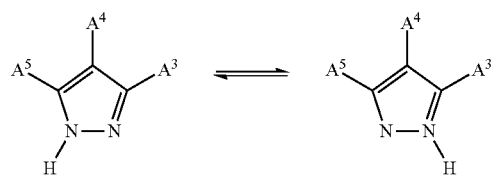

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

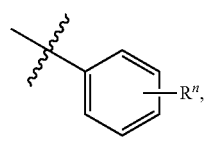

which is understood to be equivalent to a formula:

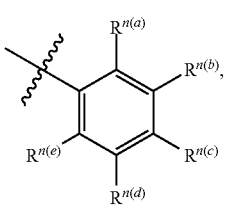

wherein n is typically an integer. That is, R" is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as positive allosteric modulators of the muscarinic acetylcholine receptor $M_4$ (mAChR $M_4$). More specifically, in one aspect, the present invention relates to compounds that allosterically modulate mAChR $M_4$ receptor activity, affecting the sensitivity of mAChR $M_4$ receptors to agonists without acting as orthosteric agonists themselves. The compounds can, in one aspect, exhibit subtype selectivity.

In one aspect, the disclosed compounds exhibit positive allosteric modulation of mAChR $M_4$ response to acetylcholine as an increase in response to non-maximal concentrations of acetylcholine in Chinese hamster ovary (CHO-K1) cells transfected with rat mAChR $M_4$ in the presence of the compound, compared to the response to acetylcholine in the absence of the compound. In further aspect, the Chinese hamster ovary (CHO-K1) cells are transfected with human mAChR $M_4$. In yet a further aspect, Chinese hamster ovary (CHO-K1) cells are transfected with mAChR $M_4$ of a mammal.

In one aspect, the compounds of the invention are useful in the treatment neurological and psychiatric disorders associated with muscarinic acetylcholine receptor dysfunction and other diseases in which muscarinic acetylcholine receptors are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

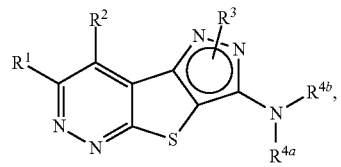

wherein $R^1$ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino; wherein $R^2$ is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino; or wherein $R^1$ and $R^2$ are optionally covalently bonded and, together with the intermediate atoms, comprise a 3- to 7-membered cycle and substituted with 0, 1 or 2 groups independently selected from halogen, —$NH_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino; wherein $R^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-; wherein each of $R^{4a}$ and $R^{4b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-$NR^{40}R^{41}$, —(C1-C6 alkyl)-$NR^{40}$(C=O)$R^{41}$, —(C1-C6 alkyl)-$NR^{40}$(C=O)O$R^{41}$, —(C1-C6 alkyl)-$NR^{40}$(C=O)$R^{41}$, —(C1-C6 monohaloalkyl)-$NR^{40}$(C=O)O$R^{41}$, —(C1-C6 polyhaloalkyl)-$NR^{40}$(C=O)O$R^{41}$, —(C1-C8 alkyl)-$Cy^1$, $Cy^1$, —(C1-C8 alkyl)-$Ar^1$, —(C2-C8 alkynyl)-$Ar^1$, and $Ar^1$; wherein each $R^{40}$, when present, is independently selected from hydrogen and C1-C8 alkyl; wherein each $R^{41}$, when present, is independently selected from hydrogen, C1-C8 alkyl, C1-C8 monohaloalkyl, C1-C8 polyhaloalkyl, —(C1-C8 alkyl)-$Cy^1$, $Cy^1$, —(C1-C8 alkyl)-$Ar^1$, and $Ar^1$; wherein each $Ar^1$, when present, is independently selected from phenyl, naphthyl, and heteroaryl, and wherein each $Ar^1$ is independently substituted with 0, 1, 2, or 3 groups independently selected from halogen, —$NH_2$, —OH, —CN, —$N_3$, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-$NR^{51}R^{52}$, —(C1-C6 alkyl)-$NR^{50}$(C=O)$R^{55}$, —(C1-C6 alkyl)-$NR^{50}$(C=O)O$R^{55}$, —(C1-C6 alkyl)-$NR^{50}$(C=O)$R^{55}$, —(C1-C6 alkyl)-$NR^{50}$S(O)$_m R^{55}$, —$NR^{50}$(C1-C6 alkyl)-(C=O)$R^{55}$, —$NR^{50}$(C1-C6 alkyl)-(C=O)O$R^{55}$, —$NR^{50}$(C1-C6 alkyl)-(C=O)$R^{55}$, —$NR^{50}$(C1-C6 alkyl)-S(O)$_m R^{55}$, —$NR^{50}$(C1-C6 alkyl)-S(O)$_m NR^{53}R^{54}$, —$NR^{50}$(C=O)$R^{55}$, —$NR^{50}$(C=O)O$R^{55}$, —$NR^{50}$(C=O)$R^{55}$, —$NR^{50}$S(O)$_m R^{55}$, —(C1-C6 alkyl)-(C=O)$R^{55}$, —(C1-C6 alkyl)-(C=O)O$R^{55}$, —(C1-C6 alkyl)-(C=O)$R^{55}$, —(C1-C6 alkyl)-S(O)$_m R^{55}$, —(C1-C6 alkyl)-S(O)$_m NR^{53}R^{54}$, —(C=O)$R^{55}$, —(C=O)O$R^{55}$, —S(O)$_m R^{55}$, —S(O)$_m NR^{53}R^{54}$, —(C1-C8 alkyl)-$Ar^{20}$, $Ar^{20}$, —(C1-C8 alkyl)-$Cy^{20}$, $Cy^{20}$, and $R^{57}$; wherein each m is an integer independently selected from 0, 1 and 2; wherein each $Ar^{20}$, when present, is independently selected from phenyl, naphthyl, and heteroaryl, and wherein each $Ar^{20}$ is independently substituted with 0, 1, 2, or 3 groups independently selected from halogen, —$NH_2$, —OH, —CN, —S(O)$_m R^{50}$, C1-C8 alkyl, C1-C8 monohaloalkyl, C1-C8 polyhaloalkyl, C1-C8 alkoxy, C1-C8 alkylamino, and C1-C8 dialkylamino; wherein each $Cy^{20}$, when present, is independently selected from C3-C9 cycloalkyl and C2-C7 heterocycloalkyl, and wherein each $Cy^{20}$ is independently substituted with 0, 1, 2, or 3 groups independently selected from halogen, —$NH_2$, —OH, —CN, —S(O)$_m R^{50}$, C1-C8 alkyl, C1-C8 monohaloalkyl, C1-C8 polyhaloalkyl, C1-C8 alkoxy, C1-C8 alkylamino, and C1-C8 dialkylamino; wherein each $R^{50}$, when present, is independently selected from hydrogen and C1-C8 alkyl; wherein each $R^{51}$, when present, is independently selected from hydrogen and C1-C8 alkyl; wherein each $R^{52}$, when present, is independently selected from hydrogen and C1-C8 alkyl; wherein each $R^{53}$, when present, is independently selected from hydrogen and C1-C8 alkyl; wherein each $R^{54}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-$Ar^{21}$, and $Ar^{21}$; wherein each $Ar^{21}$, when present, is independently selected from phenyl, naphthyl, and heteroaryl, and wherein each $Ar^{21}$ is independently substituted with 0, 1, 2, or 3 groups independently selected from halogen, —$NH_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each $R^{55}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-$Ar^{22}$, and $Ar^{22}$; wherein each $Ar^{22}$, when present, is independently selected from phenyl, naphthyl, and heteroaryl, and wherein each $Ar^{22}$ is independently substituted with 0, 1, 2, or 3 groups independently selected from halogen, —$NH_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each $R^{56}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-$Ar^{23}$, and $Ar^{23}$; wherein each $Ar^{23}$, when present, is independently selected from phenyl, naphthyl, and heteroaryl, and wherein each $Ar^{23}$ is independently substituted with 0, 1, 2, or 3 groups independently selected from halogen, —$NH_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each $R^{57}$, when present, is independently selected from C1-C4 alkyl, C1-C4 alkoxy, C1-C4 monoalkylamino, or C1-C4 dialkylamino substituted with 1 or 2 groups selected from —F, —$CH_3$, —$CF_3$, —OH, —$NH_2$, and —CN; wherein each $Cy^1$, when present, is independently selected from C3-C9 cycloalkyl and C2-C7 heterocycloalkyl, and wherein each $Cy^1$ is independently substituted with 0, 1, 2, or 3 groups independently selected from halogen, —$NH_2$, —OH, —CN, —$N_3$, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-$NR^{51}R^{52}$, —(C1-C6 alkyl)-$NR^{50}$(C=O)$R^{55}$, —(C1-C6 alkyl)-$NR^{50}$(C=O)O$R^{55}$, —(C1-C6 alkyl)-$NR^{50}$(C=O)$R^{55}$, —(C1-C6 alkyl)-$NR^{50}$S(O)$_m R^{55}$, —$NR^{50}$(C1-C6 alkyl)-(C=O)$R^{55}$, —$NR^{50}$(C1-C6 alkyl)-(C=O)O$R^{55}$, —$NR^{50}$(C1-C6 alkyl)-(C=O)$R^{55}$, —$NR^{50}$(C1-C6 alkyl)-S(O)$_m R^{55}$, —$NR^{50}$(C1-C6 alkyl)-S(O)$_m NR^{53}R^{54}$, —$NR^{50}$(C=O)$R^{55}$, —$NR^{50}$(C=O)O$R^{55}$, —$NR^{50}$(C=O)$R^{55}$, —$NR^{50}$S(O)$_m R^{55}$, —(C1-C6 alkyl)-(C=O)$R^{55}$, —(C1-C6 alkyl)-(C=O)O$R^{55}$, —(C1-C6 alkyl)-(C=O)$R^{55}$, —(C1-C6 alkyl)-S(O)$_m R^{55}$, —(C1-C6 alkyl)-S(O)$_m NR^{53}R^{54}$, —(C=O)$R^{55}$, —(C=O)O$R^{55}$, —S(O)$_m R^{55}$, —S(O)$_m NR^{53}R^{54}$, —(C1-C8 alkyl)-$Ar^{30}$, $Ar^{30}$, —(C1-C8 alkyl)-$Cy^{30}$, $Cy^{30}$, and $R^{57}$; wherein each $Ar^{30}$, when present, is independently selected from phenyl, naphthyl, and heteroaryl, and wherein each Ar$^{30}$ is independently substituted with 0, 1, 2, or 3 groups independently selected from halogen, —NH$_2$, —OH, —CN, —S(O)$_m$R$^{65}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$; wherein each R$^{65}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Ar$^{40}$, when present, is independently selected from phenyl, naphthyl, and heteroaryl, and wherein each Ar$^{40}$ is independently substituted with 0, 1, 2, or 3 groups independently selected from halogen, —NH$_2$, —OH, —CN, —S(O)$_m$R$^{66}$, C1-C8 alkyl, C1-C8 monohaloalkyl, C1-C8 polyhaloalkyl, C1-C8 alkoxy, C1-C8 alkylamino, and C1-C8 dialkylamino; wherein each R$^{66}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl; wherein each Cy$^{40}$, when present, is independently selected from C3-C9 cycloalkyl and C2-C7 heterocycloalkyl, and wherein each Cy$^{40}$ is independently substituted with 0, 1, 2, or 3 groups independently selected from halogen, —NH$_2$, —OH, —CN, —S(O)$_m$R$^{66}$, C1-C8 alkyl, C1-C8 monohaloalkyl, C1-C8 polyhaloalkyl, C1-C8 alkoxy, C1-C8 alkylamino, and C1-C8 dialkylamino; wherein each Cy$^{30}$, when present, is independently selected from C3-C9 cycloalkyl and C2-C7 heterocycloalkyl, and wherein each Cy$^{30}$ is independently substituted with 0, 1, 2, or 3 groups independently selected from halogen, —NH$_2$, —OH, —CN, —S(O)$_m$R$^{65}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$; or a pharmaceutically acceptable salt, solvate, or polymorph thereof.

In a further aspect, the invention relates to a compound having a structure represented by a formula:

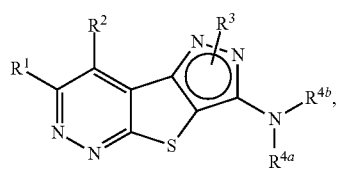

wherein R$^1$ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino; wherein R$^2$ is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino; or wherein R$^1$ and R$^2$ are optionally covalently bonded and, together with the intermediate atoms, comprise a 3- to 7-membered cycle and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino; wherein R$^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-; wherein each of R$^{4a}$ and R$^{4b}$ is independently selected from hydrogen, C1-C8 alkyl, C1-C8 monohaloalkyl, C1-C8 polyhaloalkyl, Cy$^1$, Cy$^1$-(C1-C6 alkyl)-, Ar$^1$, and Ar$^1$—(C1-C6 alkyl)-; wherein each Ar$^1$, when present, is independently selected from phenyl and heteroaryl, and wherein each Ar$^1$ is independently substituted with 0, 1, 2, or 3 groups independently selected from halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^{55}$, —(C1-C6 alkyl)-(C=O)OR$^{55}$, —(C1-C6 alkyl)-S(O)$_m$R$^{55}$, —(C=O)R$^{55}$, —(C=O)OR$^{55}$, —S(O)$_m$R$^{55}$, R$^{57}$, and Ar$^{20}$; and wherein two of the groups are optionally covalently bonded, and together with the intermediate atoms, comprise an optionally substituted 3- to 6-membered fused ring group; and wherein m is an integer selected from 0, 1 and 2; and wherein each Ar$^{20}$, when present, is independently selected from phenyl, naphthyl, and heteroaryl, and wherein each Ar$^{20}$ is independently substituted with 0, 1, 2, or 3 groups independently selected from halogen, —NH$_2$, —OH, —CN, —S(O)$_m$R$^{50}$, C1-C8 alkyl, C1-C8 monohaloalkyl, C1-C8 polyhaloalkyl, C1-C8 alkoxy, C1-C8 alkylamino, and C1-C8 dialkylamino; wherein each R$^{55}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{22}$, and Ar$^{22}$; wherein each Ar$^{22}$, when present, is independently selected from phenyl, naphthyl, and heteroaryl, and wherein each Ar$^{22}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{50}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{23}$, and Ar$^{23}$; wherein each Ar$^{23}$, when present, is independently selected from phenyl, naphthyl, and heteroaryl, and wherein each Ar$^{23}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino; wherein each R$^{57}$, when present, is independently selected from C1-C4 alkyl, C1-C4 alkoxy, C1-C4 monoalkylamino, or C1-C4 dialkylamino substituted with 1 or 2 groups selected from —F, —CH$_3$, —CF$_3$, —OH, —NH$_2$, and —CN; wherein each Cy$^1$, when present, is independently selected from C3-C8 cycloalkyl and C2-C7 heterocycloalkyl, and wherein each Cy$^1$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^{55}$, —(C1-C6 alkyl)-(C=O)OR$^{55}$, —(C1-C6 alkyl)-S(O)$_m$R$^{55}$, —(C=O)R$^{55}$, —(C=O)OR$^{55}$, —S(O)$_m$R$^{55}$, R$^{57}$, and Ar$^{20}$; and wherein two of the groups are optionally covalently bonded, and together with the intermediate atoms, comprise an optionally substituted 3- to 6-membered fused ring group; or wherein R$^{4a}$ and R$^{4b}$ are optionally covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, —(C1-C6 alkyl)-(C=O)R$^{55}$, —(C1-C6 alkyl)-(C=O)OR$^{55}$, —(C1-C6 alkyl)-S(O)$_m$R$^{55}$, —(C=O)R$^{55}$, —(C=O)OR$^{55}$, —S(O)$_m$R$^{55}$, and Ar$^{20}$; and wherein two of the groups are optionally covalently bonded, and together with the intermediate atoms, comprise an optionally substituted 3- to 6-membered fused ring group; or a pharmaceutically acceptable salt, solvate, or polymorph thereof.

In various aspects, the invention relates to a compound having a structure represented by a formula:

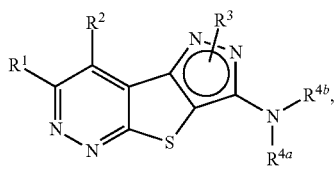

wherein $R^1$ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino; wherein $R^2$ is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino; or wherein $R^1$ and $R^2$ are optionally covalently bonded and, together with the intermediate atoms, comprise a 3- to 7-membered cycle and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino; wherein $R^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-; wherein each of $R^{4a}$ and $R^{4b}$ is independently selected from hydrogen, C1-C8 alkyl, C1-C8 monohaloalkyl, C1-C8 polyhaloalkyl, $Cy^1$, $Cy^1$-(C1-C6 alkyl)-, $Ar^1$, and $Ar^1$—(C1-C6 alkyl)-; wherein each $Ar^1$, when present, is independently selected from phenyl and heteroaryl, and wherein each $Ar^1$ is independently substituted with 0, 1, 2, or 3 groups independently selected from halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)$R^{55}$, —(C1-C6 alkyl)-(C=O)O$R^{55}$, —(C1-C6 alkyl)-S(O)$_m$$R^{55}$, —(C=O)$R^{55}$, —(C=O)O$R^{55}$, —S(O)$_m$$R^{55}$, $R^{57}$, and $Ar^2$; and wherein two of the groups are optionally covalently bonded, and together with the intermediate atoms, comprise an optionally substituted 3- to 6-membered fused ring group; and wherein m is an integer selected from 0, 1 and 2; and wherein each $Ar^2$, when present, is independently selected from phenyl and heteroaryl, and wherein each $Ar^2$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, and —S(O)$_m$$R^{55}$; wherein each $R^{55}$, when present, is independently selected from hydrogen, C1-C8 alkyl, C3-C8 cycloalkyl, C1-C8 monohaloalkyl, C1-C8 polyhaloalkyl, —(C1-C3)-$Ar^2$, and $Ar^2$; wherein each $R^{57}$, when present, is selected from C1-C4 alkyl, C1-C4 alkoxy, C1-C4 monoalkylamino, or C1-C4 dialkylamino substituted with 1 or 2 groups selected from fluoro, trifluoromethyl, methyl, —OH, —NH$_2$, and —CN; wherein each $Cy^1$, when present, is independently selected from C3-C8 cycloalkyl and C2-C7 heterocycloalkyl, and wherein each $Cy^1$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)$R^{55}$, —(C1-C6 alkyl)-(C=O)O$R^{55}$, —(C1-C6 alkyl)-S(O)$_m$$R^{55}$, —(C=O)$R^{55}$, —(C=O)O$R^{55}$, —S(O)$_m$$R^{55}$, $R^{57}$, and $Ar^2$; and wherein two of the groups are optionally covalently bonded, and together with the intermediate atoms, comprise an optionally substituted 3- to 6-membered fused ring group; or wherein $R^{4a}$ and $R^{4b}$ are optionally covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, —(C1-C6 alkyl)-(C=O)$R^{55}$, —(C1-C6 alkyl)-(C=O)O$R^{55}$, —(C1-C6 alkyl)-S(O)$_m$$R^{55}$, —(C=O)$R^{55}$, —(C=O)O$R^{55}$, —S(O)$_m$$R^{55}$, and $Ar^2$; and wherein two of the groups are optionally covalently bonded, and together with the intermediate atoms, comprise an optionally substituted 3- to 6-membered fused ring group; or a pharmaceutically acceptable salt, solvate, or polymorph thereof.

In various aspects, the invention relates to a compound having a structure represented by a formula:

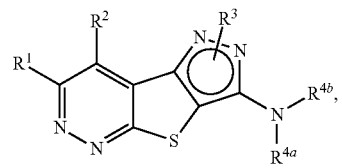

wherein $R^1$ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino; wherein $R^2$ is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino; or wherein $R^1$ and $R^2$ are optionally covalently bonded and, together with the intermediate atoms, comprise a 3- to 7-membered cycle and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino; wherein $R^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-; wherein each of $R^{4a}$ and $R^{4b}$ is independently selected from hydrogen, C1-C8 alkyl, C1-C8 monohaloalkyl, C1-C8 polyhaloalkyl, $Cy^1$, $Cy^1$-(C1-C6 alkyl)-, $Ar^1$, and $Ar^1$—(C1-C6 alkyl)-; wherein each $Ar^1$, when present, is independently selected from phenyl and heteroaryl, and wherein each $Ar^1$ is independently substituted with 0, 1, 2, or 3 groups independently selected from halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)$R^5$, —(C1-C6 alkyl)-(C=O)O$R^5$, —(C1-C6 alkyl)-S(O)$_m$$R^5$, —(C=O)$R^5$, —(C=O)O$R^5$, —S(O)$_m$$R^5$, $R^6$, and $Ar^2$; and wherein two of the groups are optionally covalently bonded, and together with the intermediate atoms, comprise an optionally substituted 3- to 6-membered fused ring group; and wherein m is an integer selected from 0, 1 and 2; and wherein each $Ar^2$, when present, is independently selected from phenyl and heteroaryl, and wherein each $Ar^2$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, and —S(O)$_m$R$^5$; wherein each R$^5$, when present, is independently selected from hydrogen, C1-C8 alkyl, C3-C8 cycloalkyl, C1-C8 monohaloalkyl, C1-C8 polyhaloalkyl, —(C1-C3)-Ar$^2$, and Ar$^2$; wherein each R$^6$, when present, is selected from C1-C4 alkyl, C1-C4 alkoxy, C1-C4 monoalkylamino, or C1-C4 dialkylamino substituted with 1 or 2 groups selected from fluoro, trifluoromethyl, methyl, —OH, —NH$_2$, and —CN; wherein each Cy$^1$, when present, is independently selected from C3-C8 cycloalkyl and C2-C7 heterocycloalkyl, and wherein each Cy$^1$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C═O) R$^5$, —(C1-C6 alkyl)-(C═O)OR$^5$, —(C1-C6 alkyl)-S(O)$_m$ R$^5$, —(C═O)R$^5$, —(C═O)OR$^5$, —S(O)$_m$R$^5$, R$^6$, and Ar$^2$; and wherein two of the groups are optionally covalently bonded, and together with the intermediate atoms, comprise an optionally substituted 3- to 6-membered fused ring group; or wherein R$^{4a}$ and R$^{4b}$ are optionally covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, —S(O)$_m$R$^5$, and Ar$^2$; and wherein two of the groups are optionally covalently bonded, and together with the intermediate atoms, comprise an optionally substituted 3- to 6-membered fused ring group; or a pharmaceutically acceptable salt, solvate, or polymorph thereof.

In a further aspect, each m is an integer independently selected from 0 and 1. In a still further aspect, each m is an integer independently selected from 1 and 2. In a yet further aspect, each m is an integer independently selected from 0 and 2. In an even further aspect, each m is an integer with a value of 0. In a still further aspect, each m is an integer with a value of 1. In a yet further aspect, each m is an integer with a value of 2.

In a further aspect, the compound has a structure represented by a formula listed below:

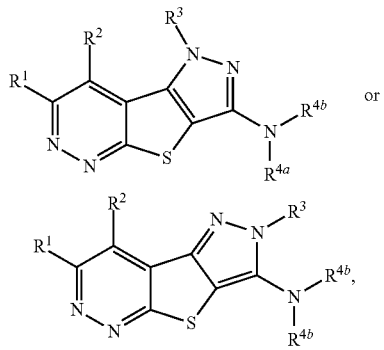

and wherein all variables are as defined herein. In a still further aspect, the compound has a structure represented by a formula listed below:

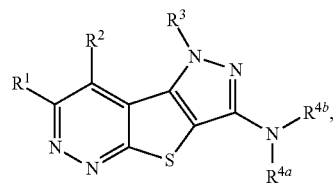

and wherein all variables are as defined herein. In a yet further aspect, the compound has a structure represented by a formula listed below:

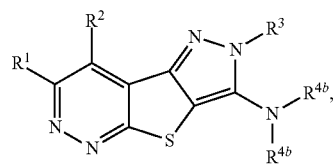

and wherein all variables are as defined herein.

In a further aspect, the compound has a structure represented by a formula listed below:

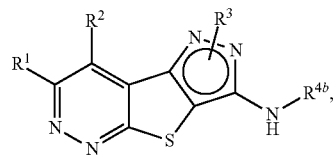

and wherein all variables are as defined herein. In a still further aspect, the compound has a structure represented by a formula listed:

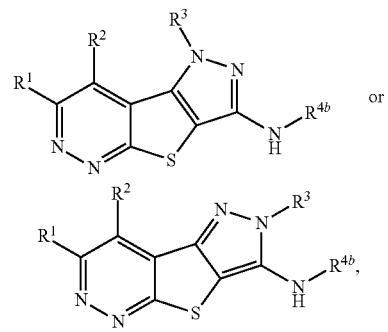

and wherein all variables are as defined herein. In a yet further aspect, the compound has a structure represented by a formula listed:

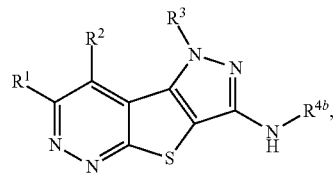

and wherein all variables are as defined herein. In an even further aspect, the compound has a structure represented by a formula listed:

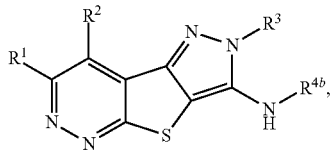

and wherein all variables are as defined herein.

In a further aspect, the compound has a structure represented by a formula listed below:

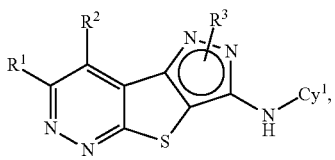

and wherein all variables are as defined herein. In a still further aspect, the compound has a structure represented by a formula listed:

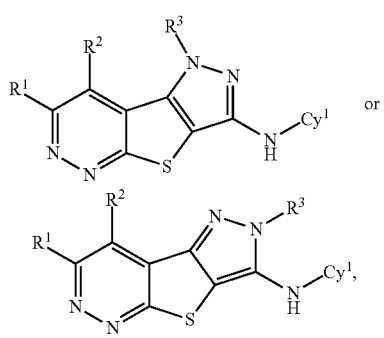

or and wherein all variables are as defined herein. In a yet further aspect, the compound has a structure represented by a formula listed:

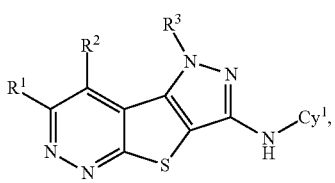

and wherein all variables are as defined herein. In an even further aspect, the compound has a structure represented by a formula listed:

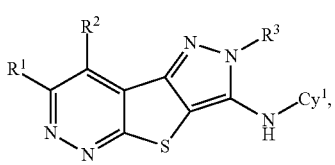

and wherein all variables are as defined herein. In a further aspect, the compound has a structure represented by a formula listed below:

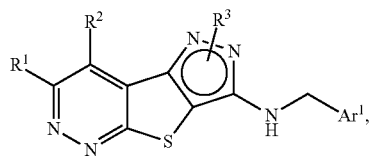

and wherein all variables are as defined herein. In a still further aspect, the compound has a structure represented by a formula listed:

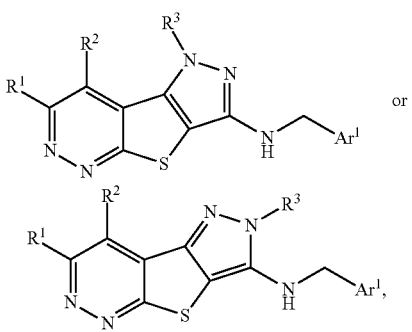

or and wherein all variables are as defined herein. In a yet further aspect, the compound has a structure represented by a formula listed:

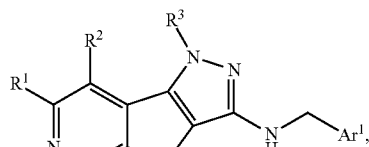

and wherein all variables are as defined herein. In an even further aspect, the compound has a structure represented by a formula listed:

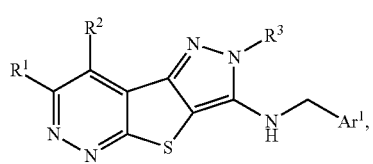

and wherein all variables are as defined herein.

In a further aspect, the compound has a structure represented by a formula listed below:

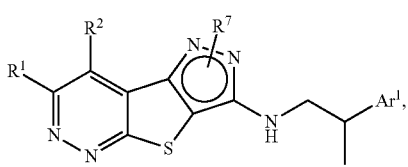

and wherein all variables are as defined herein. In a still further aspect, the compound has a structure represented by a formula listed:

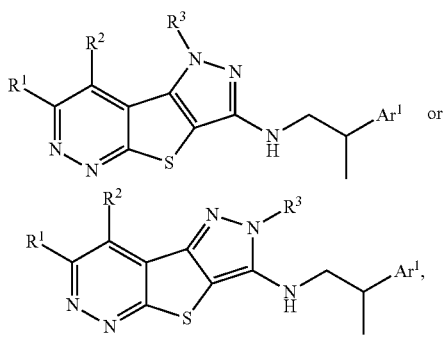

and wherein all variables are as defined herein. In a yet further aspect, the compound has a structure represented by a formula listed:

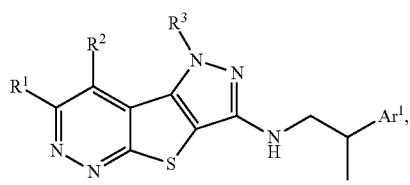

and wherein all variables are as defined herein. In an even further aspect, the compound has a structure represented by a formula listed:

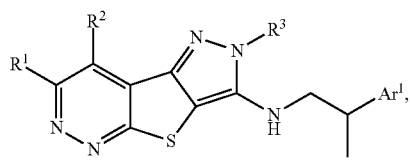

and wherein all variables are as defined herein.

In a further aspect, the compound has a structure represented by a formula listed below:

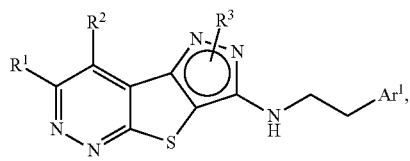

and wherein all variables are as defined herein. In a still further aspect, the compound has a structure represented by a formula listed:

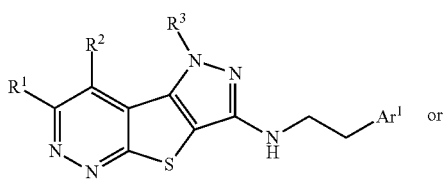

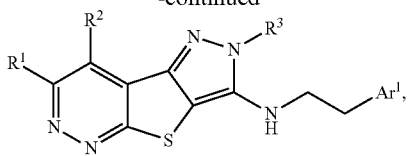

and wherein all variables are as defined herein. In a yet further aspect, the compound has a structure represented by a formula listed:

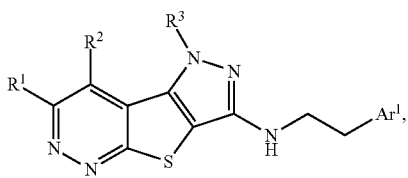

and wherein all variables are as defined herein. In an even further aspect, the compound has a structure represented by a formula listed:

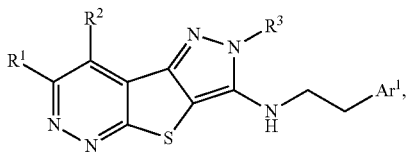

and wherein all variables are as defined herein.

In a further aspect, the compound has a structure represented by a formula listed below:

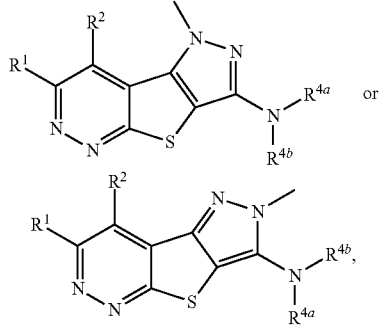

and wherein all variables are as defined herein. In a still further aspect, the compound has a structure represented by a formula listed:

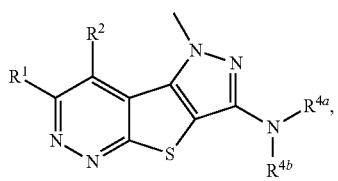

and wherein all variables are as defined herein. In a yet further aspect, the compound has a structure represented by a formula listed:

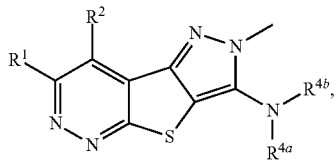

and wherein all variables are as defined herein.

In a further aspect, the compound has a structure represented by a formula listed below:

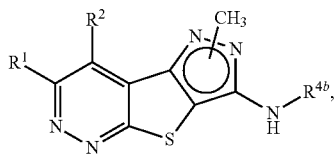

and wherein all variables are as defined herein. In a still further aspect, the compound has a structure represented by a formula listed:

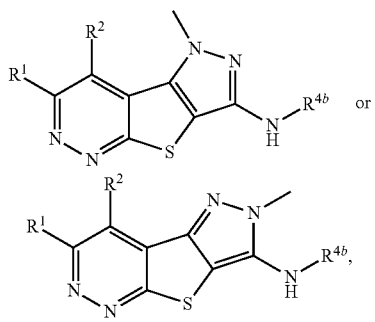

and wherein all variables are as defined herein. In a yet further aspect, the compound has a structure represented by a formula listed:

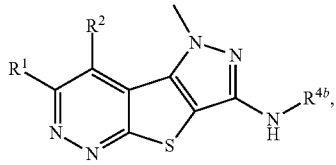

and wherein all variables are as defined herein. In an even further aspect, the compound has a structure represented by a formula listed:

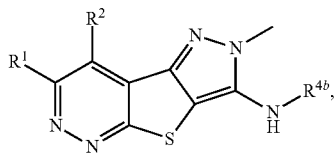

and wherein all variables are as defined herein.

In a further aspect, the compound has a structure represented by a formula listed below:

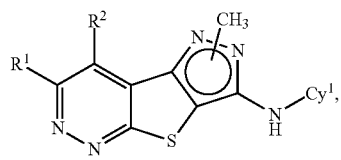

and wherein all variables are as defined herein. In a still further aspect, the compound has a structure represented by a formula listed:

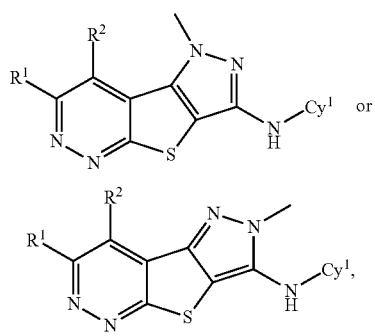

and wherein all variables are as defined herein. In a yet further aspect, the compound has a structure represented by a formula listed:

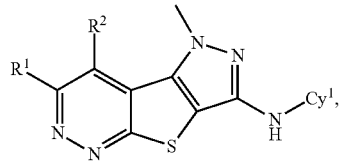

and wherein all variables are as defined herein. In an even further aspect, the compound has a structure represented by a formula listed:

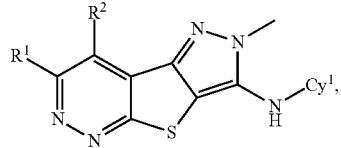

and wherein all variables are as defined herein.

In a further aspect, the compound has a structure represented by a formula listed below:

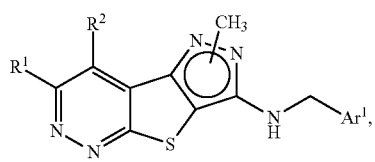

and wherein all variables are as defined herein. In a still further aspect, the compound has a structure represented by a formula listed:

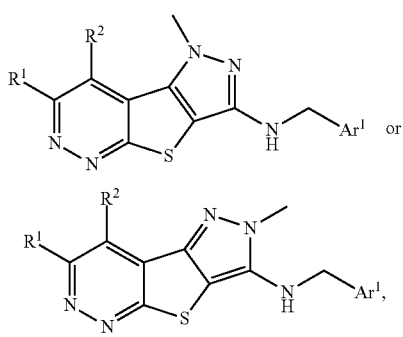 or

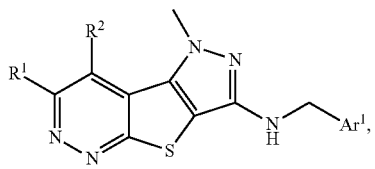

and wherein all variables are as defined herein. In a yet further aspect, the compound has a structure represented by a formula listed:

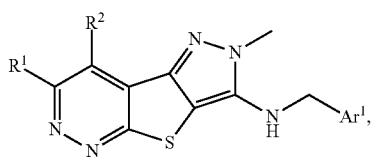

and wherein all variables are as defined herein. In an even further aspect, the compound has a structure represented by a formula listed

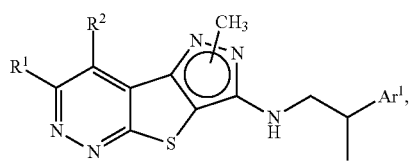

and wherein all variables are as defined herein.

In a further aspect, the compound has a structure represented by a formula listed below:

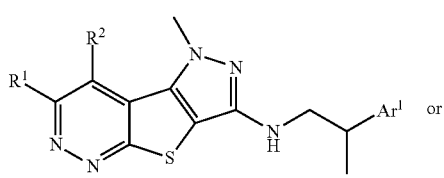

and wherein all variables are as defined herein. In a still further aspect, the compound has a structure represented by a formula listed:

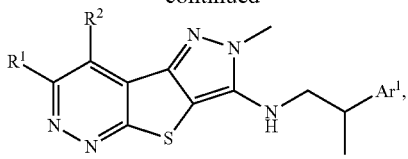

and wherein all variables are as defined herein. In a yet further aspect, the compound has a structure represented by a formula listed:

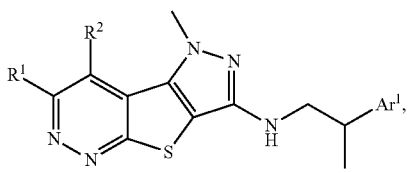

and wherein all variables are as defined herein. In an even further aspect, the compound has a structure represented by a formula listed:

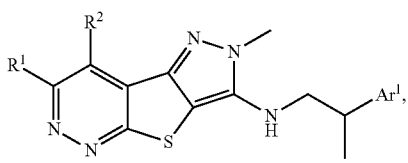

and wherein all variables are as defined herein.

In a further aspect, the compound has a structure represented by a formula listed below:

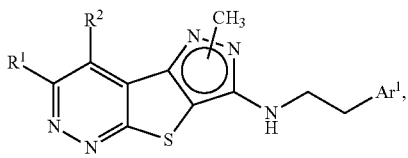

and wherein all variables are as defined herein. In a still further aspect, the compound has a structure represented by a formula listed:

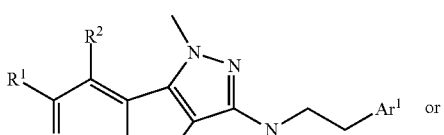

and wherein all variables are as defined herein. In a yet further aspect, the compound has a structure represented by a formula listed:

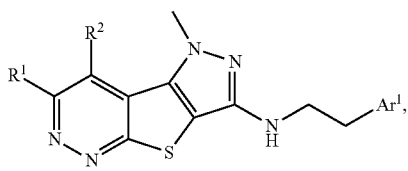

and wherein all variables are as defined herein. In an even further aspect, the compound has a structure represented by a formula listed:

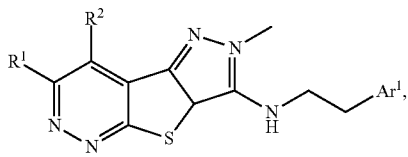

and wherein all variables are as defined herein.

In a further aspect, the compound has a structure represented by a formula listed below:

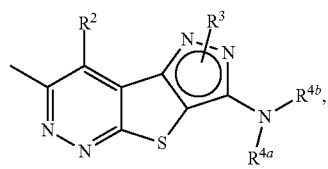

and wherein all variables are as defined herein. In a still further aspect, the compound has a structure represented by a formula listed:

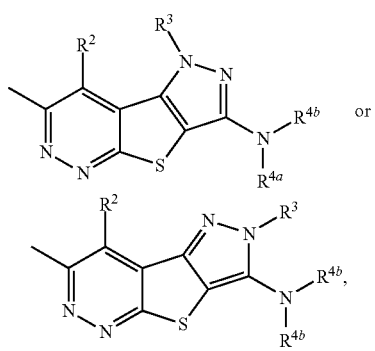

and wherein all variables are as defined herein. In a yet further aspect, the compound has a structure represented by a formula listed:

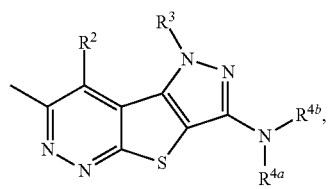

and wherein all variables are as defined herein. In an even further aspect, the compound has a structure represented by a formula listed:

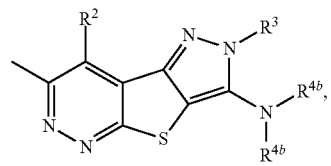

and wherein all variables are as defined herein.

In a further aspect, the compound has a structure represented by a formula listed below:

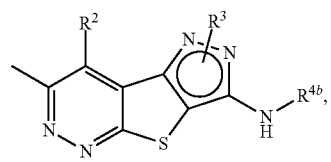

and wherein all variables are as defined herein. In a still further aspect, the compound has a structure represented by a formula listed:

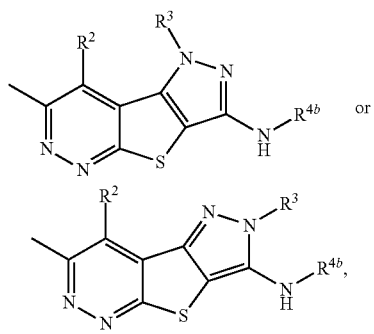

and wherein all variables are as defined herein. In a yet further aspect, the compound has a structure represented by a formula listed:

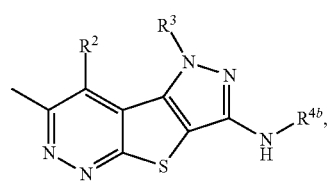

and wherein all variables are as defined herein. In an even further aspect, the compound has a structure represented by a formula listed:

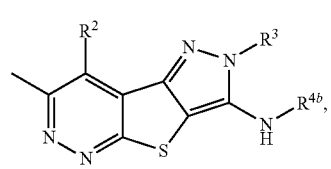

and wherein all variables are as defined herein.

In a further aspect, the compound has a structure represented by a formula listed below:

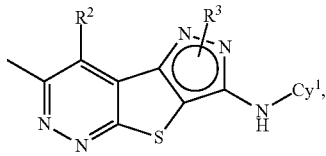

and wherein all variables are as defined herein. In a still further aspect, the compound has a structure represented by a formula listed:

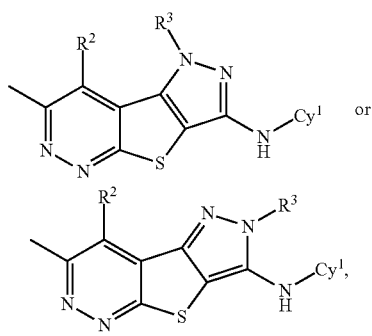

and wherein all variables are as defined herein. In a yet further aspect, the compound has a structure represented by a formula listed:

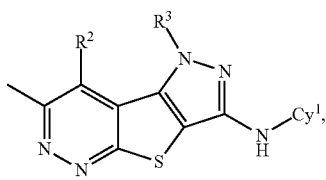

and wherein all variables are as defined herein. In an even further aspect, the compound has a structure represented by a formula listed:

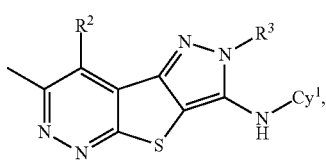

and wherein all variables are as defined herein.

In a further aspect, the compound has a structure represented by a formula listed below:

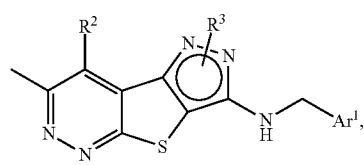

and wherein all variables are as defined herein. In a still further aspect, the compound has a structure represented by a formula listed:

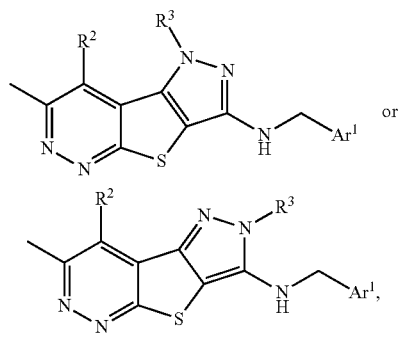

and wherein all variables are as defined herein. In a yet further aspect, the compound has a structure represented by a formula listed:

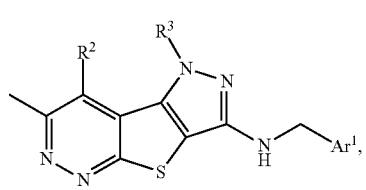

and wherein all variables are as defined herein. In an even further aspect, the compound has a structure represented by a formula listed:

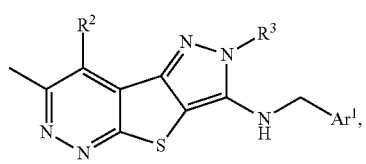

and wherein all variables are as defined herein.

In a further aspect, the compound has a structure represented by a formula listed below:

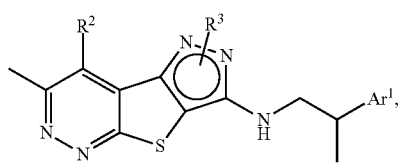

and wherein all variables are as defined herein. In a still further aspect, the compound has a structure represented by a formula listed:

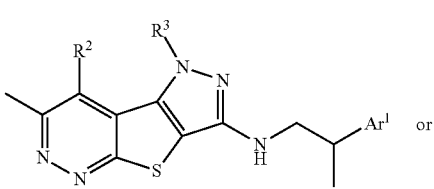

-continued

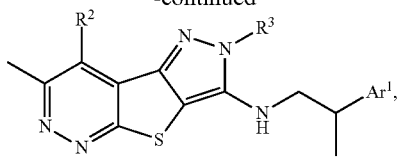

and wherein all variables are as defined herein. In a yet further aspect, the compound has a structure represented by a formula listed:

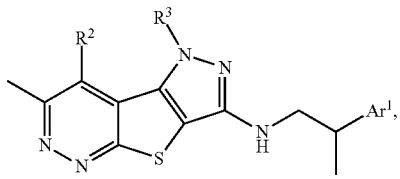

and wherein all variables are as defined herein. In an even further aspect, the compound has a structure represented by a formula listed:

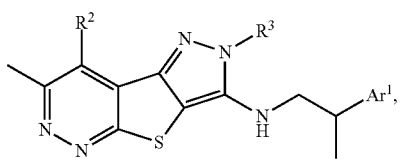

and wherein all variables are as defined herein.

In a further aspect, the compound has a structure represented by a formula listed below:

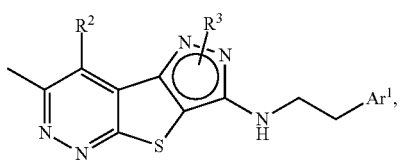

and wherein all variables are as defined herein. In a still further aspect, the compound has a structure represented by a formula listed:

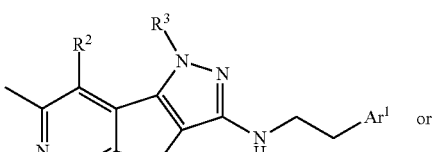

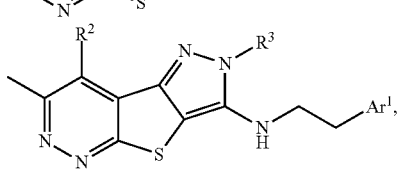

and wherein all variables are as defined herein. In a yet further aspect, the compound has a structure represented by a formula listed:

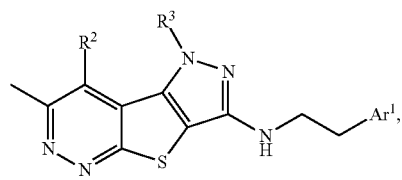

and wherein all variables are as defined herein. In an even further aspect, the compound has a structure represented by a formula listed:

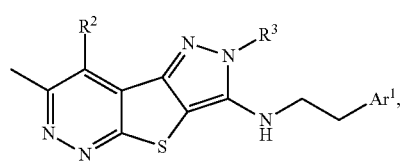

and wherein all variables are as defined herein.

In a further aspect, the compound has a structure represented by a formula listed below:

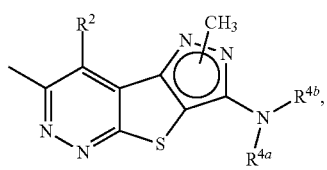

and wherein all variables are as defined herein. In a still further aspect, the compound has a structure represented by a formula listed:

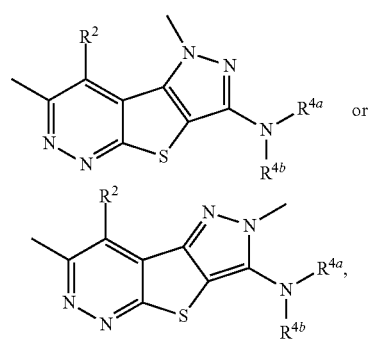

and wherein all variables are as defined herein. In a yet further aspect, the compound has a structure represented by a formula listed:

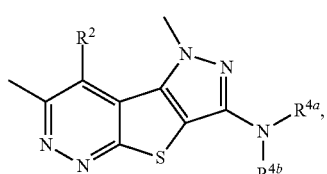

and wherein all variables are as defined herein. In an even further aspect, the compound has a structure represented by a formula listed:

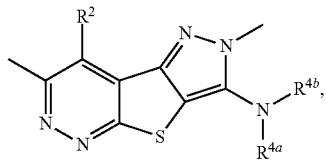

and wherein all variables are as defined herein.

In a further aspect, the compound has a structure represented by a formula listed below:

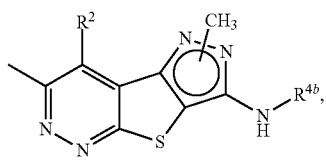

and wherein all variables are as defined herein. In a still further aspect, the compound has a structure represented by a formula listed:

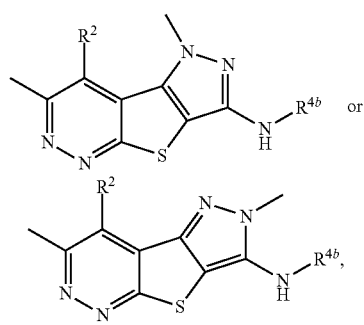

and wherein all variables are as defined herein. In a yet further aspect, the compound has a structure represented by a formula listed:

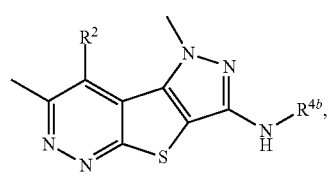

and wherein all variables are as defined herein. In an even further aspect, the compound has a structure represented by a formula listed:

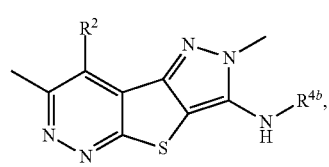

and wherein all variables are as defined herein.

In a further aspect, the compound has a structure represented by a formula listed below:

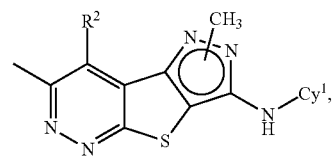

and wherein all variables are as defined herein. In a still further aspect, the compound has a structure represented by a formula listed:

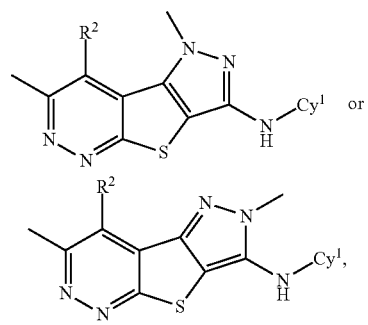

and wherein all variables are as defined herein. In a yet further aspect, the compound has a structure represented by a formula listed:

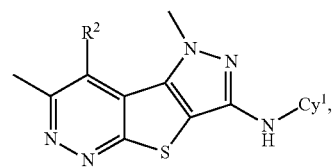

and wherein all variables are as defined herein. In an even further aspect, the compound has a structure represented by a formula listed:

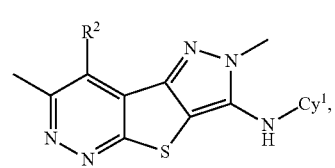

and wherein all variables are as defined herein.

In a further aspect, the compound has a structure represented by a formula listed below:

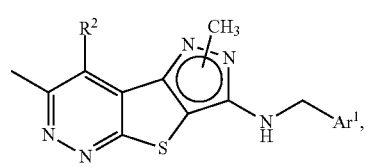

and wherein all variables are as defined herein. In a still further aspect, the compound has a structure represented by a formula listed:

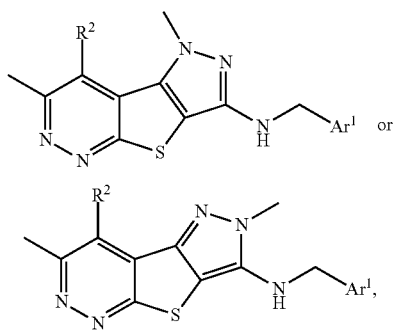

and wherein all variables are as defined herein. In a yet further aspect, the compound has a structure represented by a formula listed:

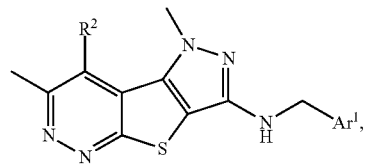

and wherein all variables are as defined herein. In an even further aspect, the compound has a structure represented by a formula listed:

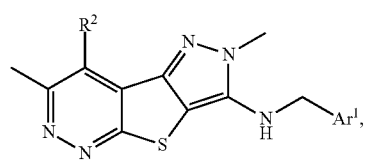

and wherein all variables are as defined herein.

In a further aspect, the compound has a structure represented by a formula listed below:

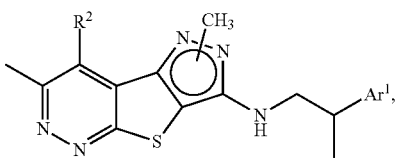

and wherein all variables are as defined herein. In a still further aspect, the compound has a structure represented by a formula listed:

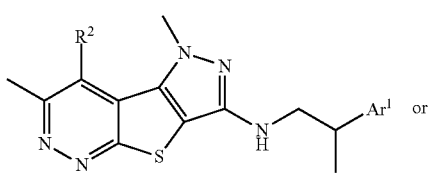

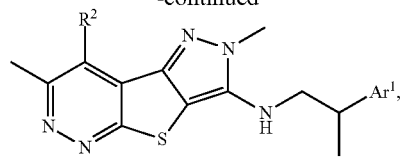

and wherein all variables are as defined herein. In a yet further aspect, the compound has a structure represented by a formula listed:

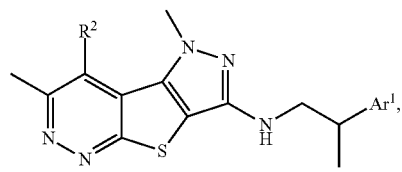

and wherein all variables are as defined herein. In an even further aspect, the compound has a structure represented by a formula listed:

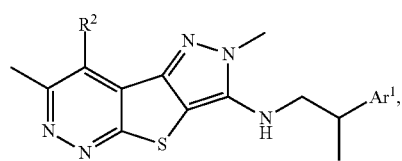

and wherein all variables are as defined herein.

In a further aspect, the compound has a structure represented by a formula listed below:

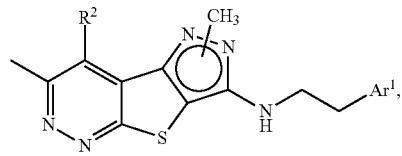

and wherein all variables are as defined herein. In a still further aspect, the compound has a structure represented by a formula listed:

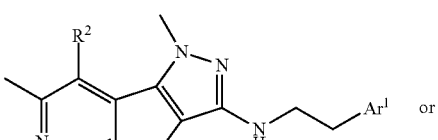

and wherein all variables are as defined herein. In a yet further aspect, the compound has a structure represented by a formula listed:

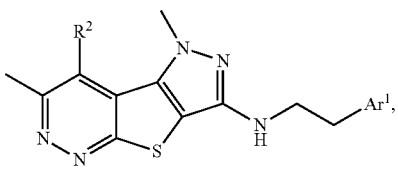

and wherein all variables are as defined herein. In an even further aspect, the compound has a structure represented by a formula listed:

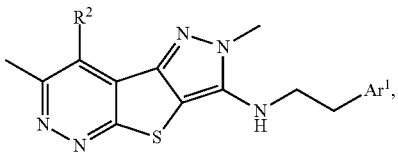

and wherein all variables are as defined herein.

In a further aspect, the compound has a structure represented by a formula listed below:

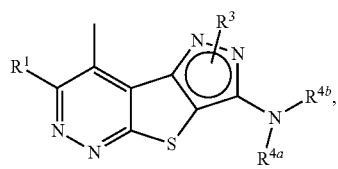

and wherein all variables are as defined herein. In a still further aspect, the compound has a structure represented by a formula listed:

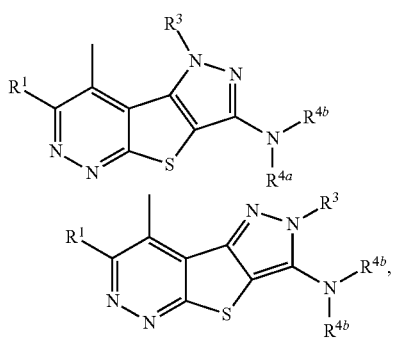

and wherein all variables are as defined herein. In a yet further aspect, the compound has a structure represented by a formula listed:

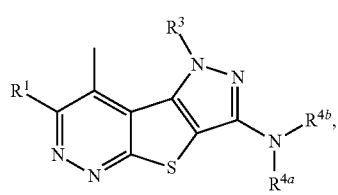

and wherein all variables are as defined herein. In an even further aspect, the compound has a structure represented by a formula listed:

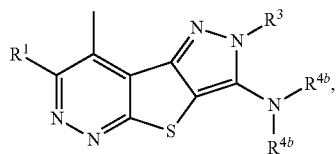

and wherein all variables are as defined herein.

In a further aspect, the compound has a structure represented by a formula listed below:

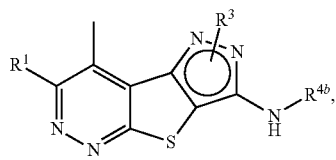

and wherein all variables are as defined herein. In a still further aspect, the compound has a structure represented by a formula listed:

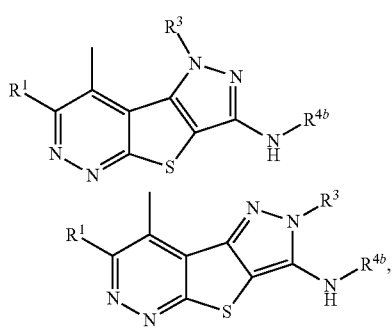

and wherein all variables are as defined herein. In a yet further aspect, the compound has a structure represented by a formula listed:

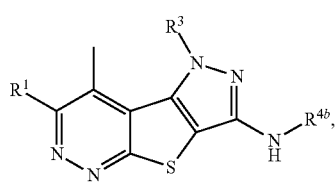

and wherein all variables are as defined herein. In an even further aspect, the compound has a structure represented by a formula listed:

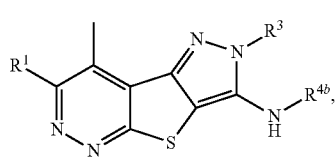

and wherein all variables are as defined herein.

In a further aspect, the compound has a structure represented by a formula listed below:

and wherein all variables are as defined herein. In a still further aspect, the compound has a structure represented by a formula listed:

and wherein all variables are as defined herein. In a yet further aspect, the compound has a structure represented by a formula listed:

and wherein all variables are as defined herein. In an even further aspect, the compound has a structure represented by a formula listed:

and wherein all variables are as defined herein.

In a further aspect, the compound has a structure represented by a formula listed below:

and wherein all variables are as defined herein. In a still further aspect, the compound has a structure represented by a formula listed:

or and wherein all variables are as defined herein. In a yet further aspect, the compound has a structure represented by a formula listed:

and wherein all variables are as defined herein. In an even further aspect, the compound has a structure represented by a formula listed:

and wherein all variables are as defined herein.

In a further aspect, the compound has a structure represented by a formula listed below:

and wherein all variables are as defined herein. In a still further aspect, the compound has a structure represented by a formula listed:

or

-continued

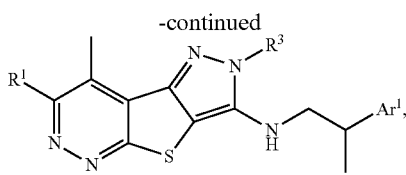

and wherein all variables are as defined herein. In a yet further aspect, the compound has a structure represented by a formula listed:

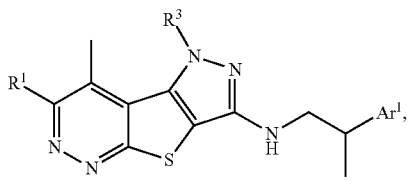

and wherein all variables are as defined herein. In an even further aspect, the compound has a structure represented by a formula listed:

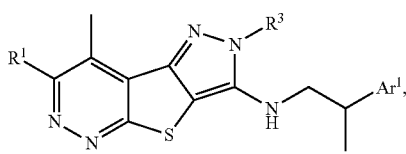

and wherein all variables are as defined herein.
In a further aspect, the compound has a structure represented by a formula listed below:

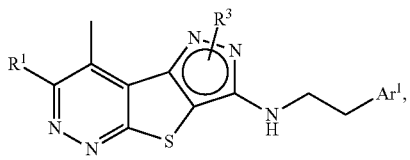

and wherein all variables are as defined herein. In a still further aspect, the compound has a structure represented by a formula listed:

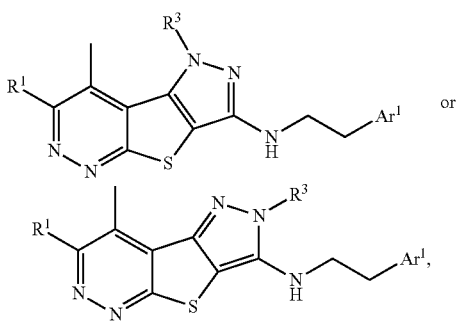

and wherein all variables are as defined herein. In a yet further aspect, the compound has a structure represented by a for- mula listed:

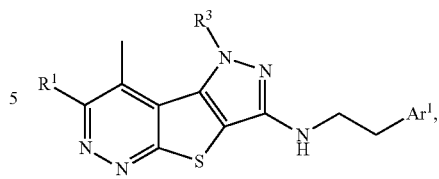

and wherein all variables are as defined herein. In an even further aspect, the compound has a structure represented by a formula listed:

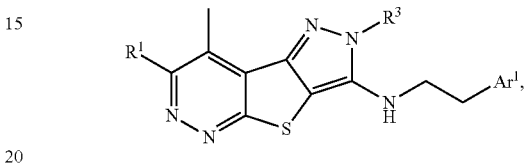

and wherein all variables are as defined herein.
In a further aspect, the compound has a structure represented by a formula listed below:

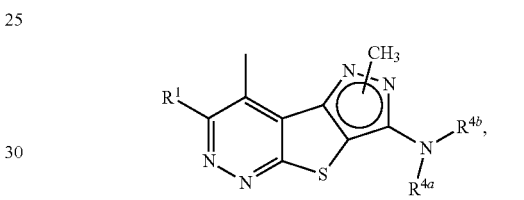

and wherein all variables are as defined herein. In a still further aspect, the compound has a structure represented by a formula listed:

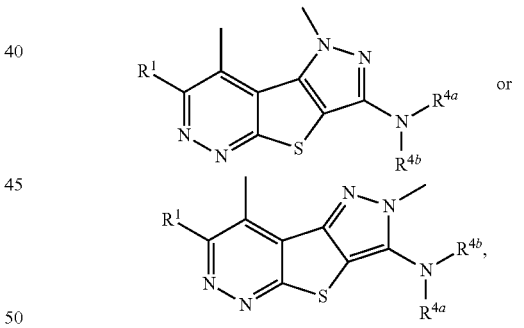

and wherein all variables are as defined herein. In a yet further aspect, the compound has a structure represented by a for- mula listed:

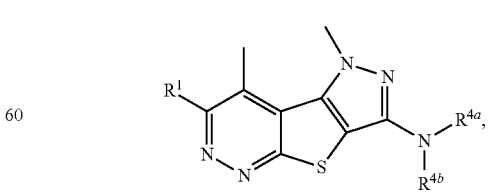

and wherein all variables are as defined herein. In an even further aspect, the compound has a structure represented by a formula listed:

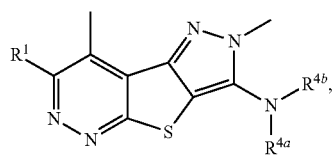

and wherein all variables are as defined herein.

In a further aspect, the compound has a structure represented by a formula listed below:

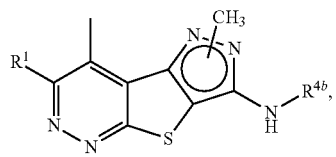

and wherein all variables are as defined herein. In a still further aspect, the compound has a structure represented by a formula listed:

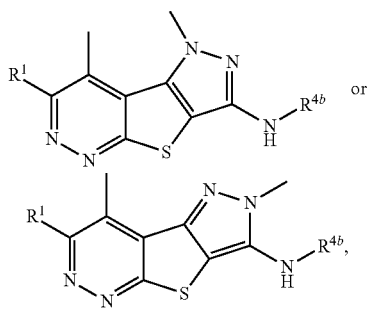

and wherein all variables are as defined herein. In a yet further aspect, the compound has a structure represented by a formula listed:

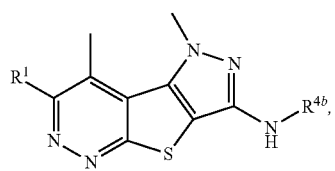

and wherein all variables are as defined herein. In an even further aspect, the compound has a structure represented by a formula listed:

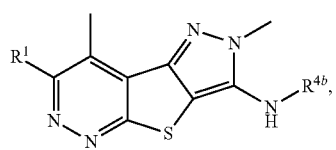

and wherein all variables are as defined herein.

In a further aspect, the compound has a structure represented by a formula listed below:

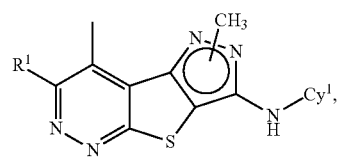

and wherein all variables are as defined herein. In a still further aspect, the compound has a structure represented by a formula listed:

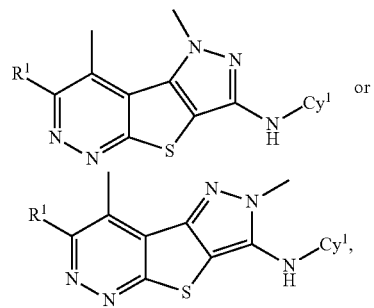

and wherein all variables are as defined herein. In a yet further aspect, the compound has a structure represented by a formula listed:

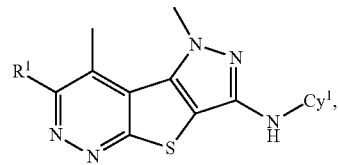

and wherein all variables are as defined herein. In an even further aspect, the compound has a structure represented by a formula listed:

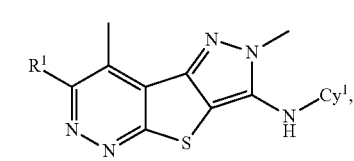

and wherein all variables are as defined herein.

In a further aspect, the compound has a structure represented by a formula listed below:

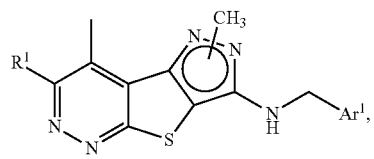

and wherein all variables are as defined herein. In a still further aspect, the compound has a structure represented by a formula listed:

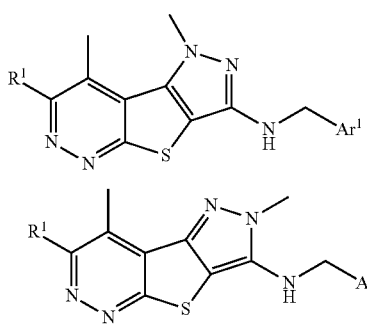 or

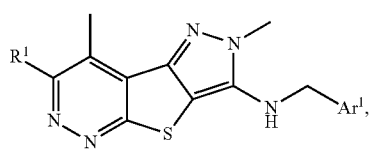

and wherein all variables are as defined herein. In a yet further aspect, the compound has a structure represented by a formula listed:

and wherein all variables are as defined herein. In an even further aspect, the compound has a structure represented by a formula listed:

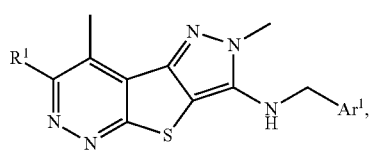

and wherein all variables are as defined herein.

In a further aspect, the compound has a structure represented by a formula listed below:

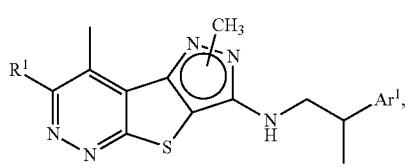

and wherein all variables are as defined herein. In a still further aspect, the compound has a structure represented by a formula listed:

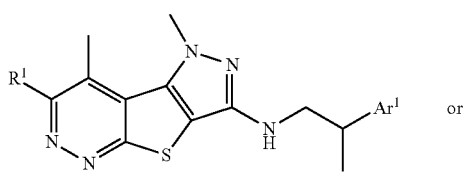 or

-continued

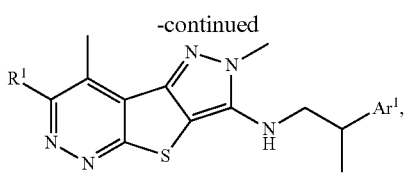

and wherein all variables are as defined herein. In a yet further aspect, the compound has a structure represented by a formula listed:

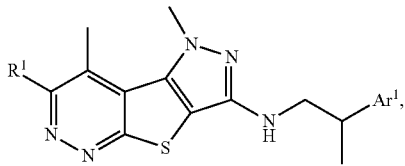

and wherein all variables are as defined herein. In an even further aspect, the compound has a structure represented by a formula listed:

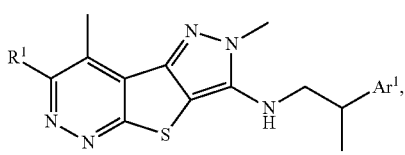

and wherein all variables are as defined herein.

In a further aspect, the compound has a structure represented by a formula listed below:

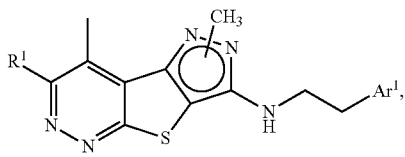

and wherein all variables are as defined herein. In a still further aspect, the compound has a structure represented by a formula listed:

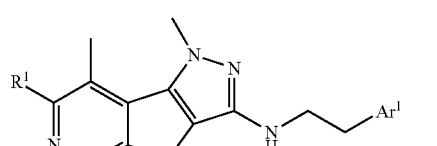 or

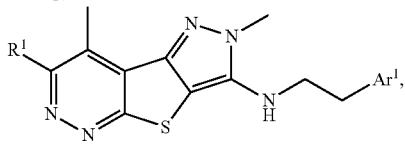

and wherein all variables are as defined herein. In a yet further aspect, the compound has a structure represented by a formula listed:

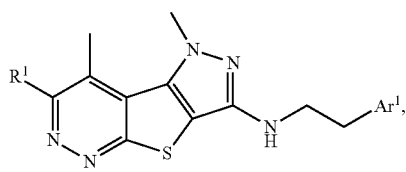

and wherein all variables are as defined herein. In an even further aspect, the compound has a structure represented by a formula listed:

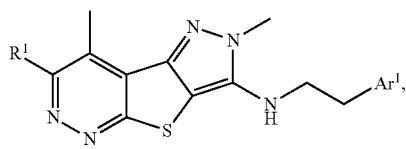

and wherein all variables are as defined herein.

In a further aspect, the compound has a structure represented by a formula listed below:

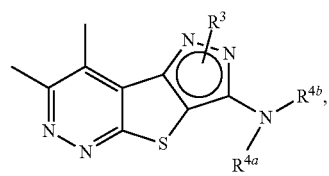

and wherein all variables are as defined herein. In a still further aspect, the compound has a structure represented by a formula listed:

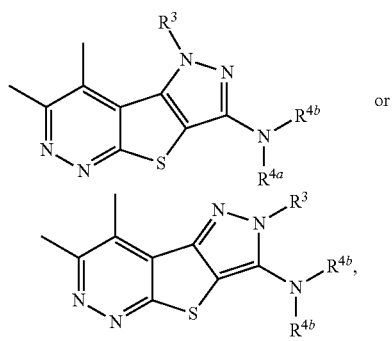

and wherein all variables are as defined herein. In a yet further aspect, the compound has a structure represented by a formula listed:

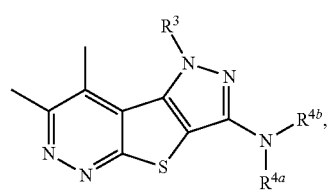

and wherein all variables are as defined herein. In an even further aspect, the compound has a structure represented by a formula listed:

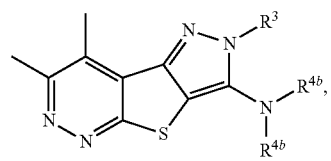

and wherein all variables are as defined herein.

In a further aspect, the compound has a structure represented by a formula listed below:

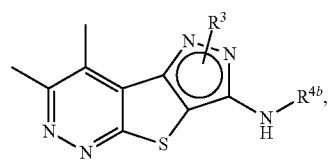

and wherein all variables are as defined herein. In a still further aspect, the compound has a structure represented by a formula listed:

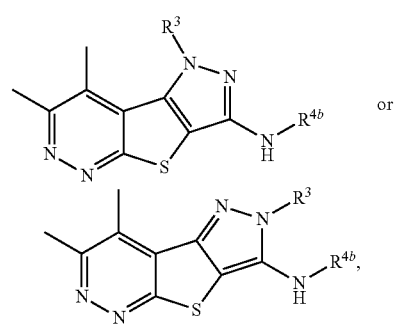

and wherein all variables are as defined herein. In a yet further aspect, the compound has a structure represented by a formula listed:

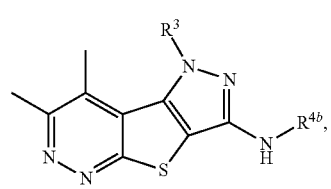

and wherein all variables are as defined herein. In an even further aspect, the compound has a structure represented by a formula listed:

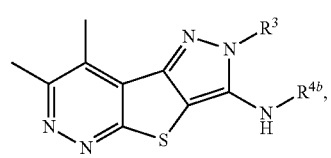

and wherein all variables are as defined herein.

In a further aspect, the compound has a structure represented by a formula listed below:

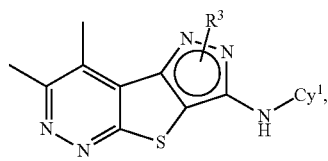

and wherein all variables are as defined herein. In a still further aspect, the compound has a structure represented by a formula listed:

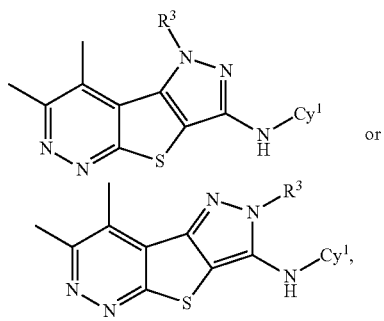

and wherein all variables are as defined herein. In a yet further aspect, the compound has a structure represented by a formula listed:

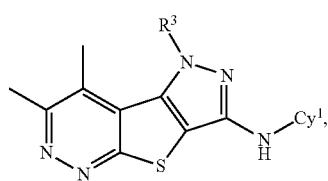

and wherein all variables are as defined herein. In an even further aspect, the compound has a structure represented by a formula listed:

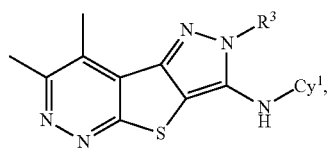

and wherein all variables are as defined herein.

In a further aspect, the compound has a structure represented by a formula listed below:

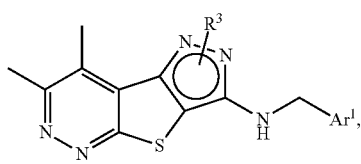

and wherein all variables are as defined herein. In a still further aspect, the compound has a structure represented by a formula listed:

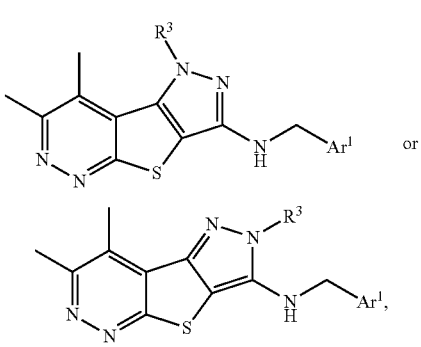

and wherein all variables are as defined herein. In a yet further aspect, the compound has a structure represented by a formula listed:

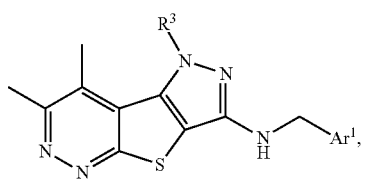

and wherein all variables are as defined herein. In an even further aspect, the compound has a structure represented by a formula listed:

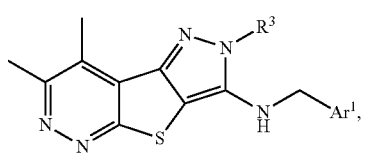

and wherein all variables are as defined herein.

In a further aspect, the compound has a structure represented by a formula listed below:

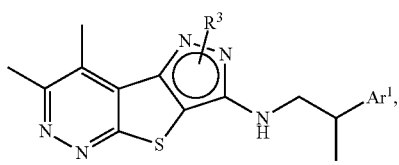

and wherein all variables are as defined herein. In a still further aspect, the compound has a structure represented by a formula listed:

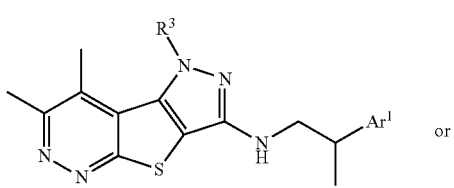

-continued

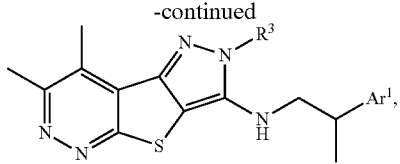

and wherein all variables are as defined herein. In a yet further aspect, the compound has a structure represented by a formula listed:

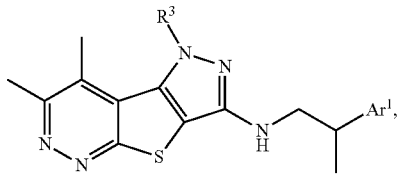

and wherein all variables are as defined herein. In an even further aspect, the compound has a structure represented by a formula listed:

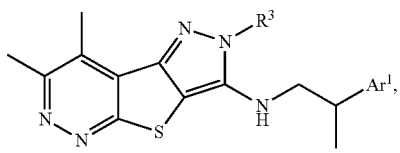

and wherein all variables are as defined herein.

In a further aspect, the compound has a structure represented by a formula listed below:

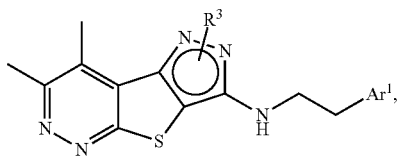

and wherein all variables are as defined herein. In a still further aspect, the compound has a structure represented by a formula listed:

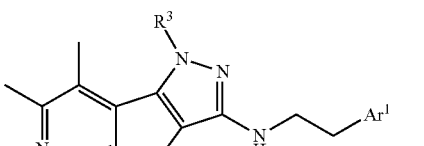

or

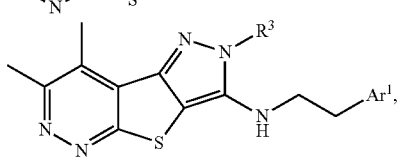

and wherein all variables are as defined herein. In a yet further aspect, the compound has a structure represented by a formula listed:

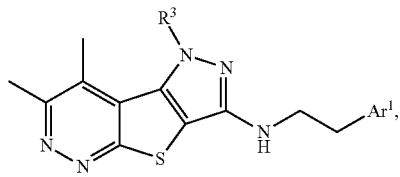

and wherein all variables are as defined herein. In an even further aspect, the compound has a structure represented by a formula listed:

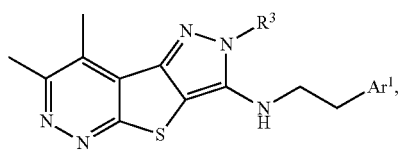

and wherein all variables are as defined herein.

In a further aspect, the compound has a structure represented by a formula listed below:

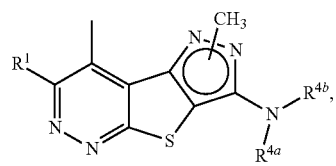

and wherein all variables are as defined herein. In a still further aspect, the compound has a structure represented by a formula listed:

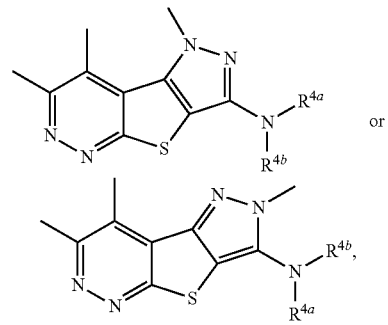

or and wherein all variables are as defined herein. In a yet further aspect, the compound has a structure represented by a formula listed:

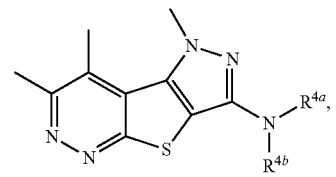

and wherein all variables are as defined herein. In an even further aspect, the compound has a structure represented by a formula listed:

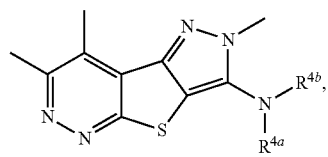

and wherein all variables are as defined herein.

In a further aspect, the compound has a structure represented by a formula listed below:

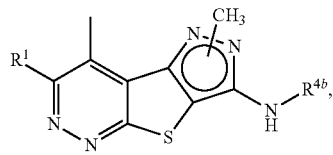

and wherein all variables are as defined herein. In a still further aspect, the compound has a structure represented by a formula listed:

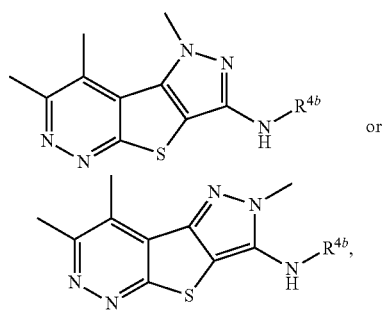

and wherein all variables are as defined herein. In a yet further aspect, the compound has a structure represented by a formula listed:

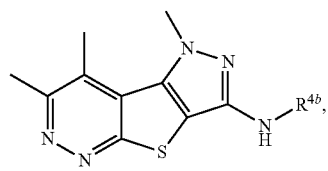

and wherein all variables are as defined herein. In an even further aspect, the compound has a structure represented by a formula listed:

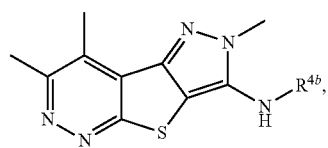

and wherein all variables are as defined herein.

In a further aspect, the compound has a structure represented by a formula listed below:

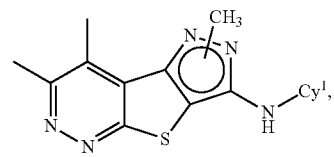

and wherein all variables are as defined herein. In a still further aspect, the compound has a structure represented by a formula listed:

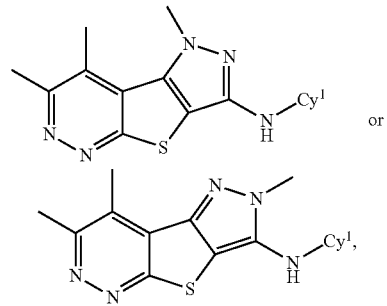

and wherein all variables are as defined herein. In a yet further aspect, the compound has a structure represented by a formula listed:

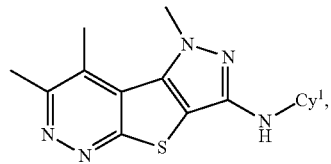

and wherein all variables are as defined herein. In an even further aspect, the compound has a structure represented by a formula listed:

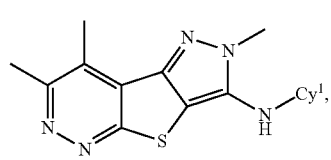

and wherein all variables are as defined herein.

In a further aspect, the compound has a structure represented by a formula listed below:

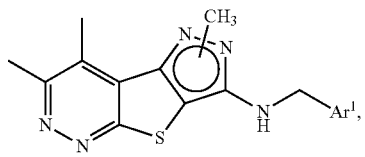

and wherein all variables are as defined herein. In a still further aspect, the compound has a structure represented by a formula listed:

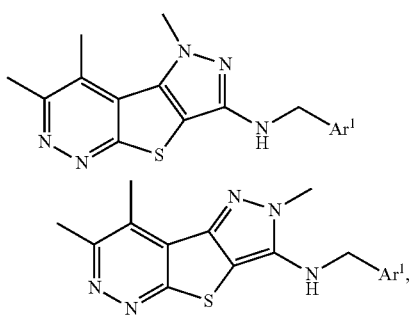

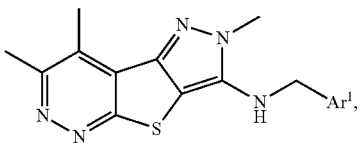

and wherein all variables are as defined herein. In a yet further aspect, the compound has a structure represented by a formula listed:

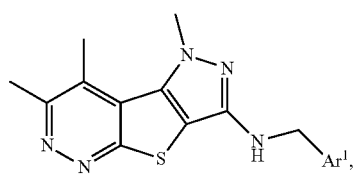

and wherein all variables are as defined herein. In an even further aspect, the compound has a structure represented by a formula listed:

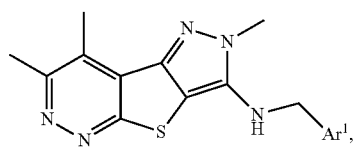

and wherein all variables are as defined herein.

In a further aspect, the compound has a structure represented by a formula listed below:

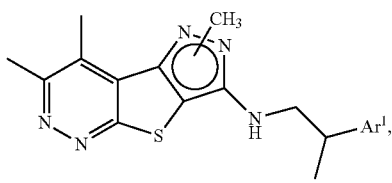

and wherein all variables are as defined herein. In a still further aspect, the compound has a structure represented by a formula listed:

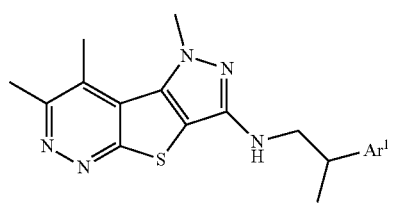

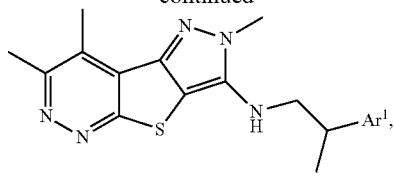

and wherein all variables are as defined herein. In a yet further aspect, the compound has a structure represented by a formula listed:

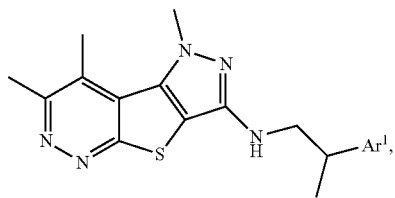

and wherein all variables are as defined herein. In an even further aspect, the compound has a structure represented by a formula listed:

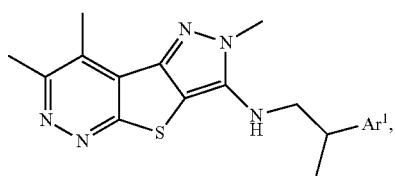

and wherein all variables are as defined herein.

In a further aspect, the compound has a structure represented by a formula listed below:

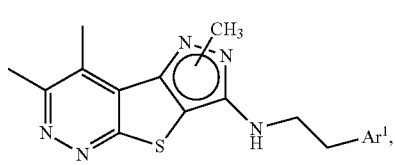

and wherein all variables are as defined herein. In a still further aspect, the compound has a structure represented by a formula listed:

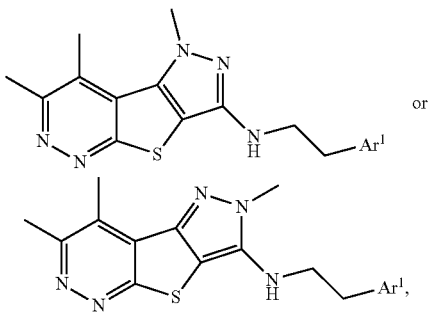

and wherein all variables are as defined herein. In a yet further aspect, the compound has a structure represented by a formula listed:

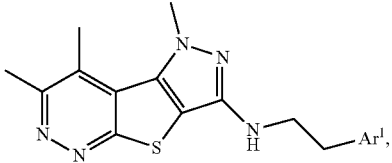

and wherein all variables are as defined herein. In an even further aspect, the compound has a structure represented by a formula listed:

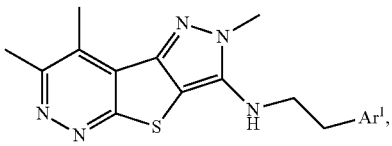

and wherein all variables are as defined herein.

In a further aspect, the compound has a structure represented by a formula listed below:

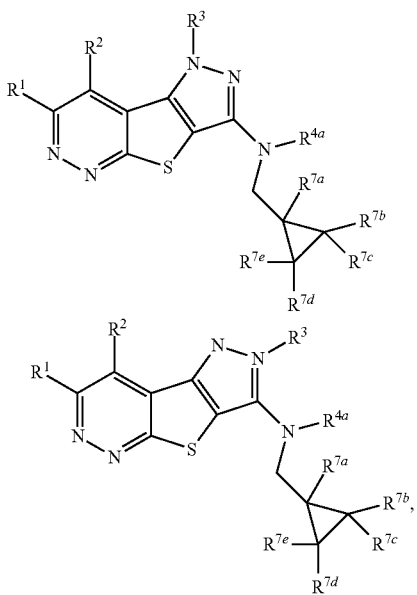

wherein each of $R^{7a}$, $R^{7b}$, $R^{7c}$, $R^{7d}$, and $R^{7e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$, provided that at least two of $R^{7a}$, $R^{7b}$, $R^{7c}$, $R^{7d}$, and $R^{7e}$ are hydrogen; and wherein all variables are as defined herein. In a still further aspect, the compound has a structure represented by a formula listed below:

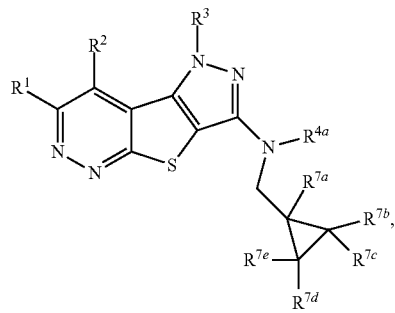

and wherein all variables are as defined herein.

In a further aspect, the compound has a structure represented by a formula listed below:

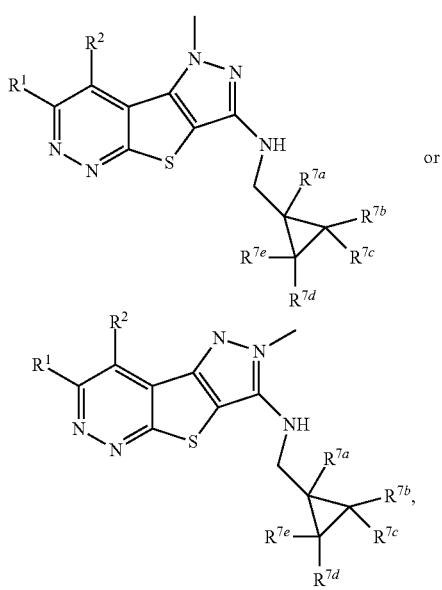

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{7a}$, $R^{7b}$, $R^{7c}$, $R^{7d}$, and $R^{7e}$ is independently selected from hydrogen, —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CHF, —CHF$_2$, —CF$_3$, —OCH$_3$, —NHCH$_3$, —N(CH$_3$)$_2$, —SCH₃, —SCH₂F, —SCHF₂, —SCF, —(S=O)CH₃, —(S=O)CH₂F, —(S=O)CHF₂, —(S=O)CF₃, —SO₂CH₃, —SO₂CH₂F, —SO₂CHF₂, —SO₂CF₃, —SO₂-cyclopropyl, and —SO₂-phenyl; wherein at least two of $R^{7a}$, $R^{7b}$, $R^{7c}$, $R^{7d}$, and $R^{7e}$ are hydrogen; and wherein all variables are as defined herein. In a still further aspect, the compound has a structure represented by a formula listed below:

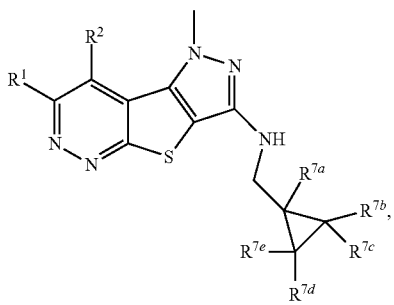

and wherein all variables are as defined herein.

In a further aspect, the compound has a structure represented by a formula listed below:

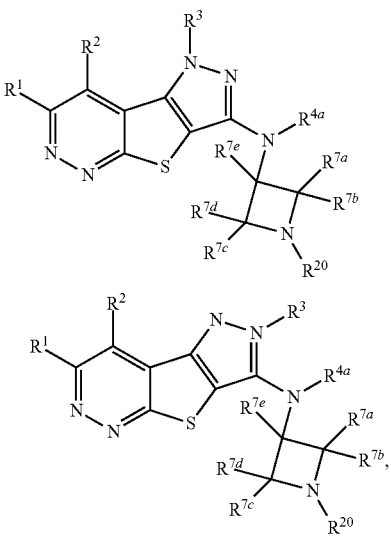

wherein each of $R^{7a}$, $R^{7b}$, $R^{7c}$, $R^{7d}$, and $R^{7e}$ is independently selected from hydrogen, halogen, —NH₂, —OH, —CN, C1-C8 alkyl, C1-C8 haloalkyl, C1-C8 polyhaloalkyl, C1-C8 alkoxy, C1-C8 alkylamino, C1-C8 dialkylamino, —(C1-C6 alkyl)-(C=O)$R^5$, —(C1-C6 alkyl)-(C=O)O$R^5$, —(C1-C6 alkyl)-S(O)$_m R^5$, —(C=O)$R^5$, —(C=O)O$R^5$, —S(O)$_m R^5$, $R^6$, and $Ar^2$; wherein $R^{20}$ is selected from hydrogen, C1-C8 alkyl, C1-C8 haloalkyl, C1-C8 polyhaloalkyl, —(C1-C6 alkyl)-(C=O)$R^5$, —(C1-C6 alkyl)-(C=O)O$R^5$, —(C1-C6 alkyl)-S(O)$_m R^5$, —(C=O)$R^5$, —(C=O)O$R^5$, —S(O)$_m R^5$, $R^6$, and $Ar^2$; wherein that at least three of $R^{7a}$, $R^{7b}$, $R^{7c}$, $R^{7d}$, $R^{7e}$, and $R^{20}$ are hydrogen; and wherein all variables are as defined herein. In a still further aspect, the compound has a structure represented by a formula listed below:

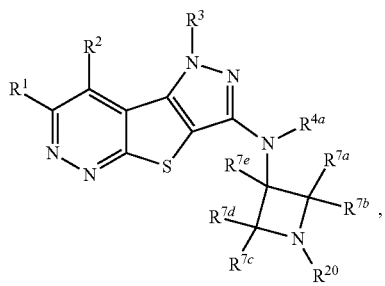

and wherein all variables are as defined herein.

In a further aspect, the compound has a structure represented by a formula listed below:

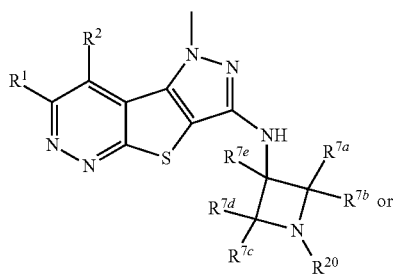

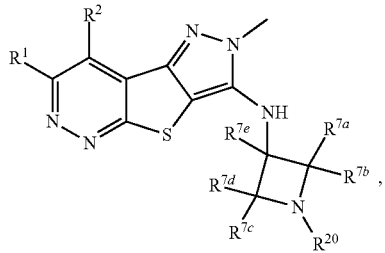

wherein $R^1$ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein $R^2$ is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of $R^{7a}$, $R^{7b}$, $R^{7c}$, $R^{7d}$, and $R^{7e}$ is independently selected from hydrogen, —F, —Cl, —Br, —NH₂, —OH, —CN, methyl, CH₂F, —CH₂Cl, —CHF₂, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O)OCH₃, —(C=O)OCH₃, —CF(CF₃)CH₃, —C(OH)(CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH₂)CH₃, and $Ar^2$; wherein $R^{20}$ is selected from hydrogen, methyl, CH₂F, —CH₂Cl, —CHF₂, —CF₃, —CHCl₂, —CCl₃, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O)OCH₃, —(C=O)OCH₃, —CF(CF₃)CH₃, —C(OH)(CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; wherein that at least three of R$^{7a}$, R$^{7b}$, R$^{7c}$, R$^{7d}$, R$^{7e}$, and R$^{20}$ are hydrogen; and wherein all variables are as defined herein. In a still further aspect, the compound has a structure represented by a formula listed below:

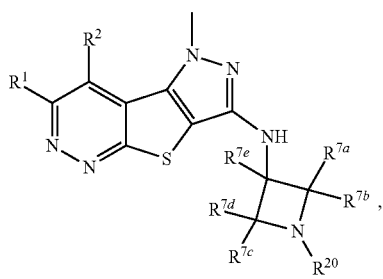

and wherein all variables are as defined herein.

In a further aspect, the compound has a structure represented by a formula listed below:

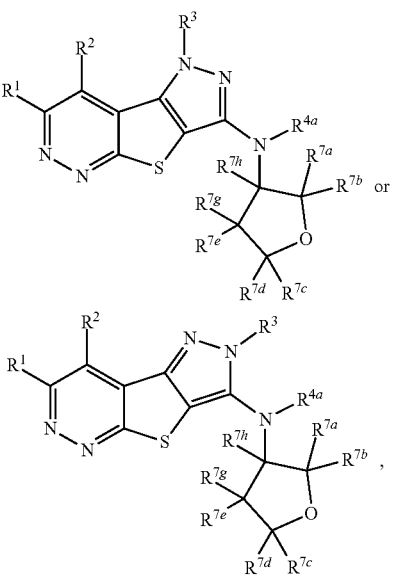

wherein each of R$^{7a}$, R$^{7b}$, R$^{7c}$, R$^{7d}$, R$^{7e}$, R$^{7g}$, and R$^{7h}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$, provided that at least four of R$^{7a}$, R$^{7b}$, R$^{7c}$, R$^{7d}$, R$^{7e}$, R$^{7g}$, and R$^{7h}$ are hydrogen; and wherein all variables are as defined herein. In a still further aspect, the compound has a structure represented by a formula listed below:

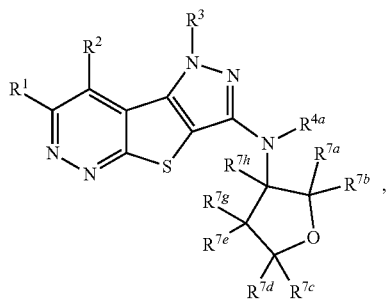

and wherein all variables are as defined herein.

In a further aspect, the compound has a structure represented by a formula listed below:

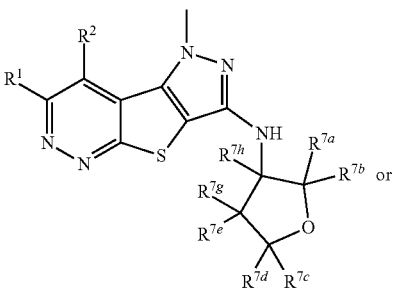

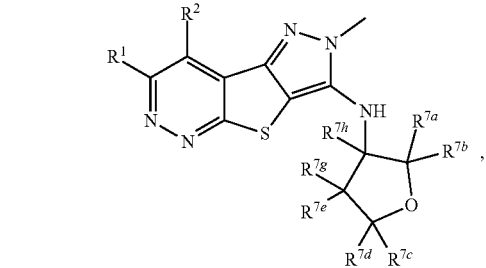

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of R$^{7a}$, R$^{7b}$, R$^{7c}$, R$^{7d}$, R$^{7e}$, R$^{7g}$, and R$^{7h}$ is independently selected from hydrogen, —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF₃, —(S=O)CH₃, —(S=O)CH₂F, —(S=O)CHF₂, —(S=O)CF₃, —SO₂CH₃, —SO₂CH₂F, —SO₂CHF₂, —SO₂CF₃, —SO₂-cyclopropyl, and —SO₂-phenyl; wherein at least four of $R^{7a}$, $R^{7b}$, $R^{7c}$, $R^{7d}$, $R^{7e}$, $R^{7g}$, and $R^{7h}$ are hydrogen; and wherein all variables are as defined herein. In a still further aspect, the compound has a structure represented by a formula listed below:

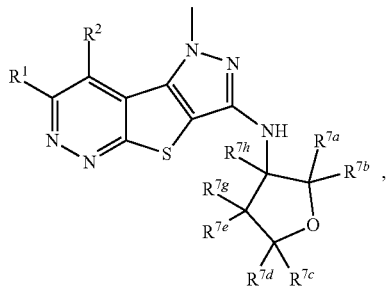

and wherein all variables are as defined herein.

In a further aspect, the compound has a structure represented by a formula listed below:

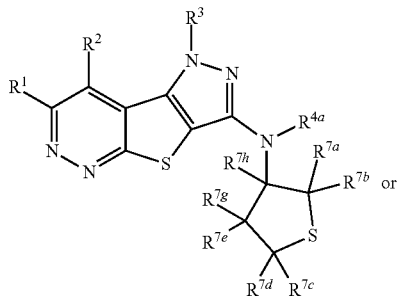

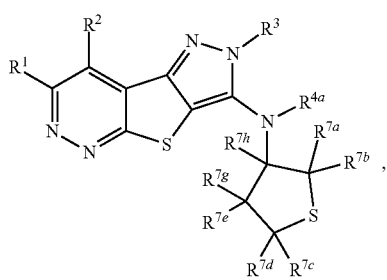

wherein each of $R^{7a}$, $R^{7b}$, $R^{7c}$, $R^{7d}$, $R^{7e}$, $R^{7g}$, and $R^{7h}$ is independently selected from hydrogen, halogen, —NH₂, —OH, —CN, C1-C8 alkyl, C1-C8 haloalkyl, C1-C8 polyhaloalkyl, C1-C8 alkoxy, C1-C8 alkylamino, C1-C8 dialkylamino, —(C1-C6 alkyl)-(C=O)R⁵, —(C1-C6 alkyl)-(C=O)OR⁵, —(C1-C6 alkyl)-S(O)ₘR⁵, —(C=O)R⁵, —(C=O)OR⁵, —S(O)ₘR⁵, R⁶, and Ar², provided that at least four of $R^{7a}$, $R^{7b}$, $R^{7c}$, $R^{7d}$, $R^{7e}$, $R^{7g}$, and $R^{7h}$ are hydrogen; and wherein all variables are as defined herein. In a still further aspect, the compound has a structure represented by a formula listed below:

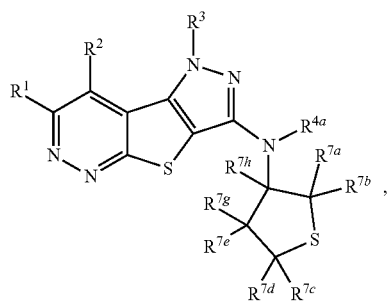

and wherein all variables are as defined herein.

In a further aspect, the compound has a structure represented by a formula listed below:

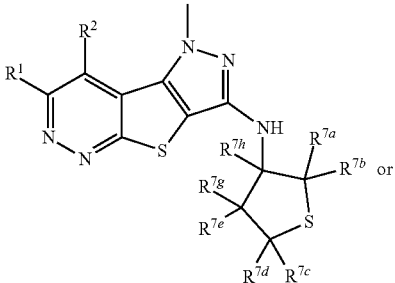

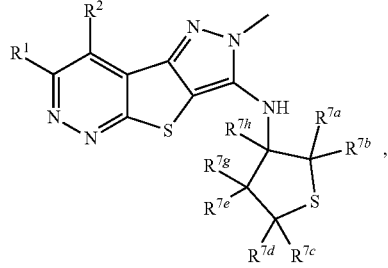

wherein R¹ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein R² is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of $R^{7a}$, $R^{7b}$, $R^{7c}$, $R^{7d}$, $R^{7e}$, $R^{7g}$, and $R^{7h}$ is independently selected from hydrogen, —F, —Cl, —Br, —NH₂, —OH, —CN, methyl, CH₂F, —CH₂Cl, —CHF₂, —CF₃, —CHCl₂, —CCl₃, —OCH₃, —OCH₂CH₃, —NHCH₃, N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O)OCH₃, —(C=O)OCH₃, —CF(CF₃)CH₃, —C(OH)(CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH₂)CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S=O)CH₃, —(S=O)CH₂F, —(S=O)CHF₂, —(S=O)CF₃, —SO₂CH₃, —SO₂CH₂F, —SO₂CHF₂, —SO₂CF₃, —SO₂-cyclopropyl, and —SO₂-phenyl; wherein at least four of $R^{7a}$, $R^{7b}$, $R^{7c}$, $R^{7d}$, $R^{7e}$, $R^{7g}$, and $R^{7h}$ are hydrogen; and wherein all variables are as defined herein. In a still further aspect, the compound has a structure represented by a formula listed below:

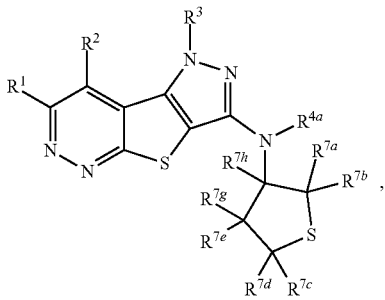

and wherein all variables are as defined herein.

In a further aspect, the compound has a structure represented by a formula listed below:

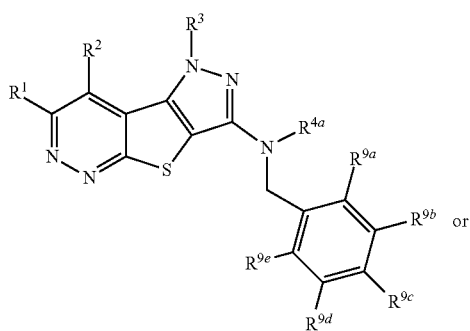

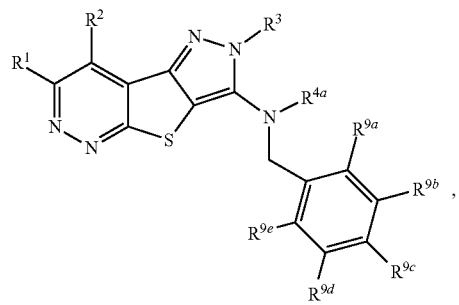

wherein each of $R^{9a}$, $R^{9b}$, $R^{9c}$, $R^{9d}$, and $R^{9e}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$, provided that at least two of $R^{9a}$, $R^{9b}$, $R^{9c}$, $R^{9d}$, and $R^{9e}$ are hydrogen; and wherein all variables are as defined herein. In a still further aspect, the compound has a structure represented by a formula listed below:

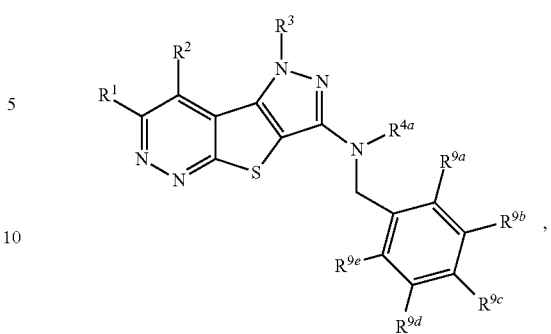

and wherein all variables are as defined herein.

In a further aspect, the compound has a structure represented by a formula listed below:

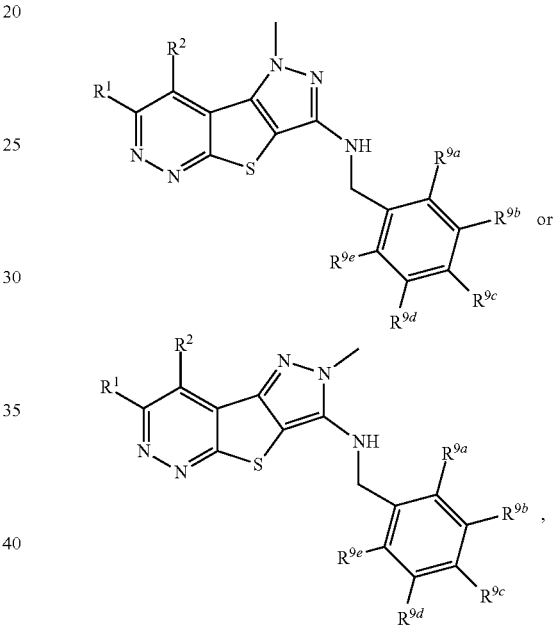

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$, $R^{9b}$, $R^{9c}$, $R^{9d}$, and $R^{9e}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH₃, —N(CH₃)₂, —SCH₃, —SCH₂F, —SCHF₂, —SCF₃, —(S═O)CH₃, —(S═O)CH₂F, —(S═O)CHF₂, —(S═O)CF₃, —SO₂CH₃, —SO₂CH₂F, —SO₂CHF₂, —SO₂CF₃, —SO₂-cyclopropyl, and —SO₂-phenyl; wherein at least two of R$^{9a}$, R$^{9b}$, R$^{9c}$, R$^{9d}$, and R$^{9e}$ are hydrogen; and wherein all variables are as defined herein. In a still further aspect, the compound has a structure represented by a formula listed below:

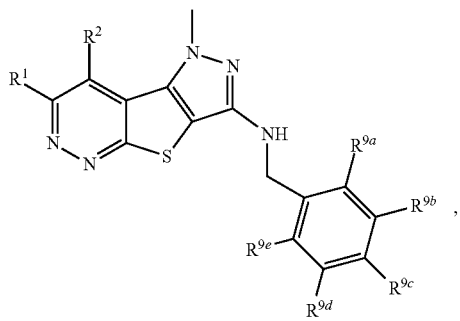

and wherein all variables are as defined herein.

In a further aspect, the compound has a structure represented by a formula listed below:

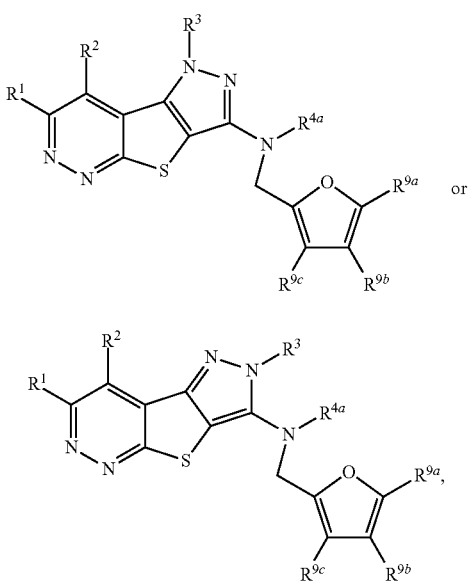

wherein each of R$^{9a}$, R$^{9b}$, and R$^{9c}$ is independently selected from hydrogen, halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C═O)R⁵, —(C1-C6 alkyl)-(C═O)OR⁵, —(C1-C6 alkyl)-S(O)$_m$R⁵, —(C═O)R⁵, —(C═O)OR⁵, —S(O)$_m$R⁵, R⁶, and Ar²; and wherein all variables are as defined herein. In a still further aspect, the compound has a structure represented by a formula listed below:

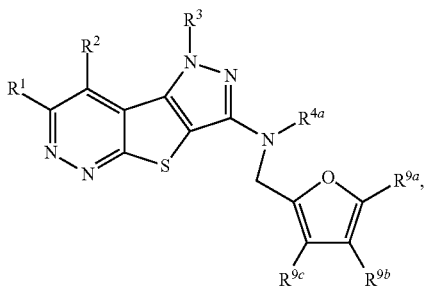

and wherein all variables are as defined herein.

In a further aspect, the compound has a structure represented by a formula listed below:

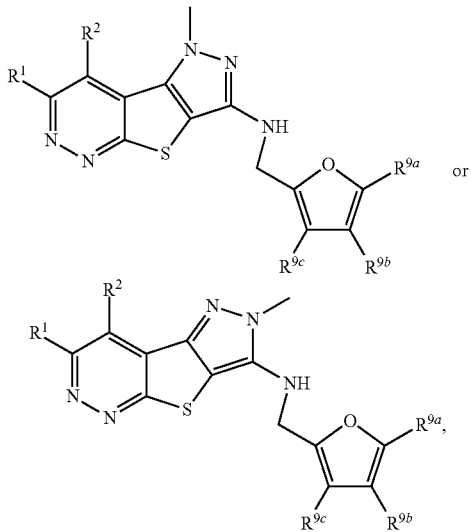

wherein R¹ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein R² is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of R$^{9a}$, R$^{9b}$, and R$^{9c}$ is independently selected from hydrogen, —F, —Cl, —Br, —NH₂, —OH, —CN, —SF₅, methyl, CH₂F, —CH₂Cl, —CHF₂, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C═O)CH₃, —(C═O)CH₃, —(CH₂)—(C═O) OCH₃, —(C═O)OCH₃, —CF(CF₃)CH₃, —C(OH)(CF₃) CH₃, —C(CF₃)(NH₂)CH₃, —C(CF₃)(CN)CH₃, —C(CF₃)₂ CH₃, —CF(OH)CH₃, —CF(NH₂)CH₃, —CF(CN)CH₃, —C(OH)(NH₂)CH₃, —C(OH)(CN)CH₃, —C(CN)(NH₂) CH₃, and Ar²; and wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S═O)CH₃, —(S═O)CH₂F, —(S═O)CHF₂, —(S═O)CF₃, —SO₂CH₃, —SO₂CH₂F, —SO₂CHF₂, —SO₂CF₃, —SO₂-cyclopropyl, and —SO₂-phenyl; and wherein all variables are as defined herein. In a still further aspect, the compound has a structure represented by a formula listed below:

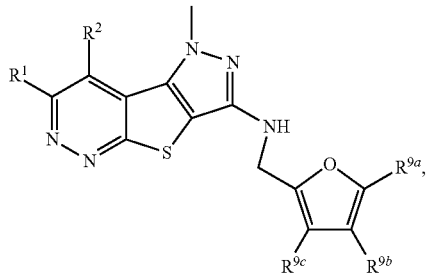

and wherein all variables are as defined herein.

In a further aspect, the compound has a structure represented by a formula listed below:

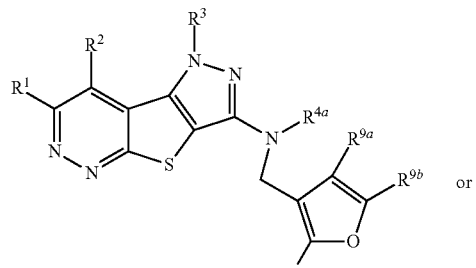

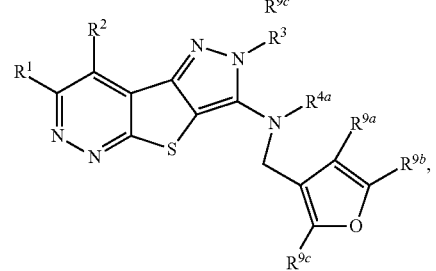

wherein each of $R^{9a}$, $R^{9b}$, and $R^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein all variables are as defined herein. In a still further aspect, the compound has a structure represented by a formula listed below:

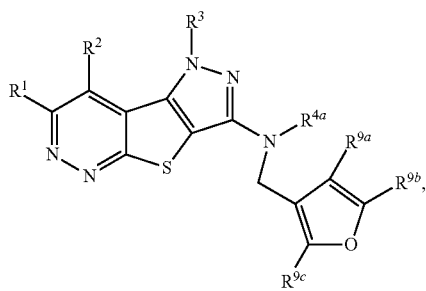

and wherein all variables are as defined herein.

In a further aspect, the compound has a structure represented by a formula listed below:

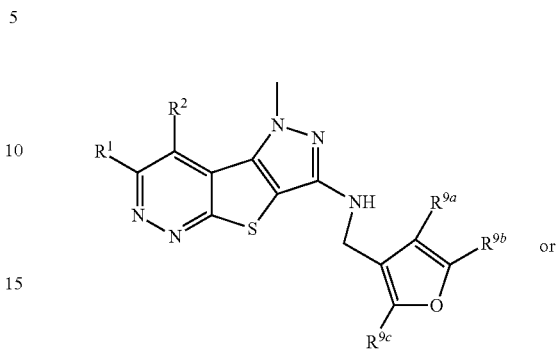

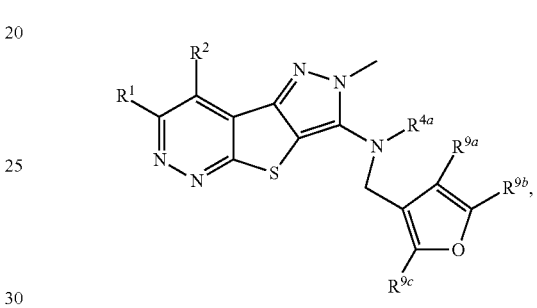

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$, $R^{9b}$, and $R^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; and wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein all variables are as defined herein. In a still further aspect, the compound has a structure represented by a formula listed below:

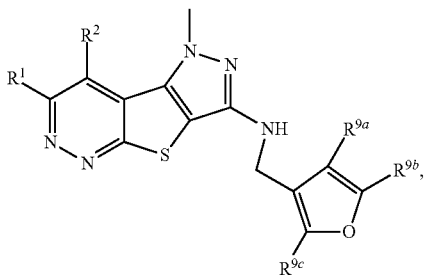

and wherein all variables are as defined herein.

In a further aspect, the compound has a structure represented by a formula listed below:

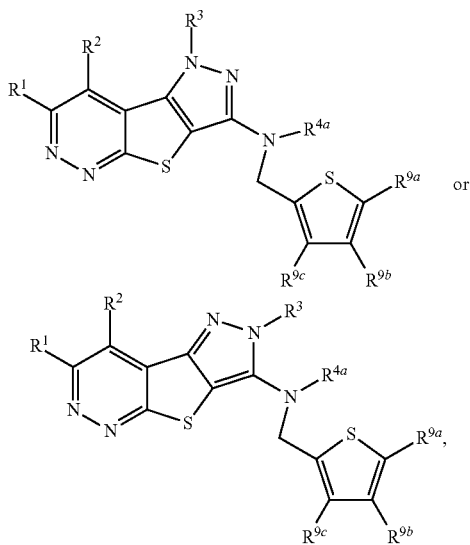

wherein each of $R^{9a}$, $R^{9b}$, and $R^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein all variables are as defined herein. In a still further aspect, the compound has a structure represented by a formula listed below:

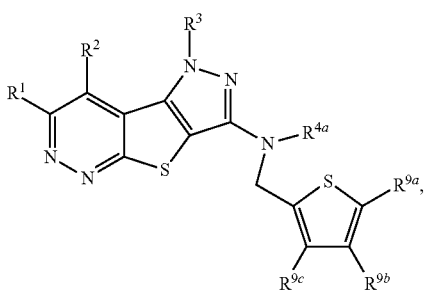

and wherein all variables are as defined herein.

In a further aspect, the compound has a structure represented by a formula listed below:

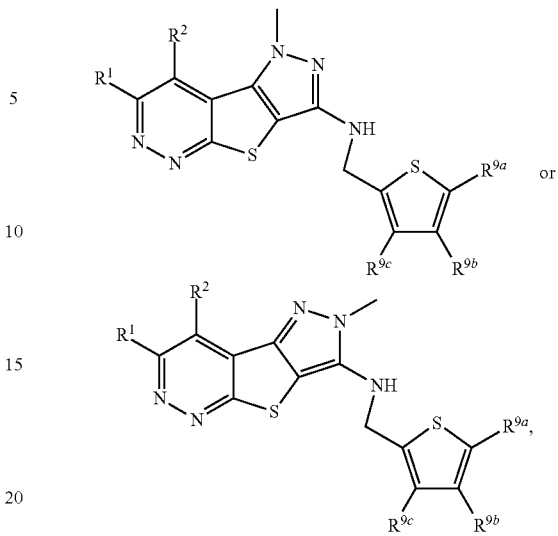

wherein $R^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein $R^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$, $R^{9b}$, and $R^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; and wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein all variables are as defined herein. In a still further aspect, the compound has a structure represented by a formula listed below:

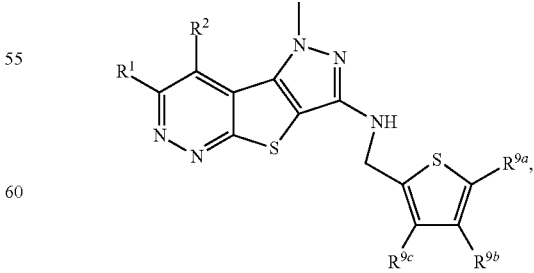

and wherein all variables are as defined herein.

In a further aspect, the compound has a structure represented by a formula listed below:

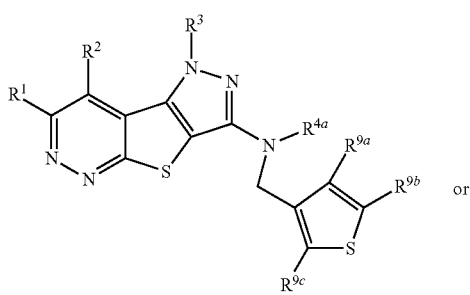

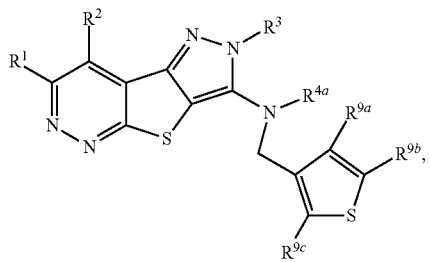

wherein each of $R^{9a}$, $R^{9b}$, and $R^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein all variables are as defined herein. In a still further aspect, the compound has a structure represented by a formula listed below:

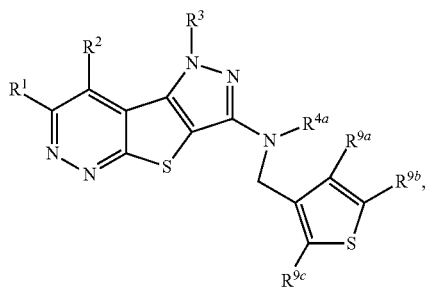

and wherein all variables are as defined herein.

In a further aspect, the compound has a structure represented by a formula listed below:

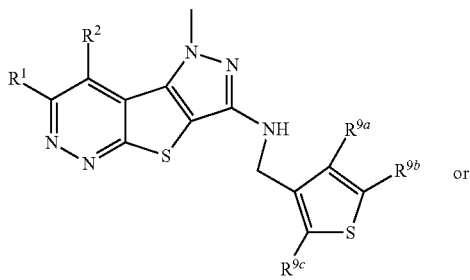

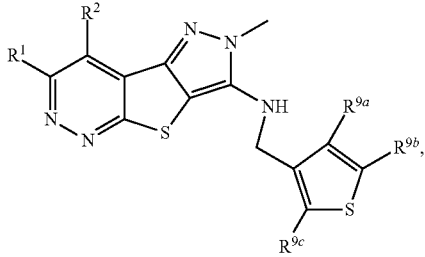

wherein $R^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein $R^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$, $R^{9b}$, and $R^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; and wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein all variables are as defined herein. In a still further aspect, the compound has a structure represented by a formula listed below:

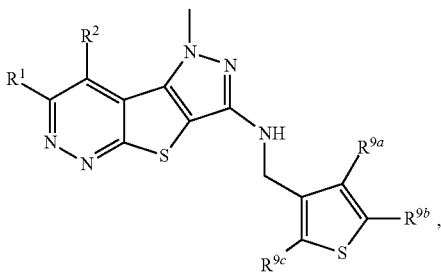

and wherein all variables are as defined herein.

In a further aspect, the compound has a structure represented by a formula listed below:

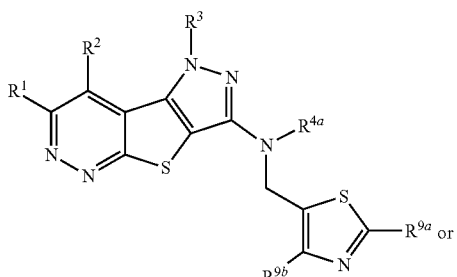

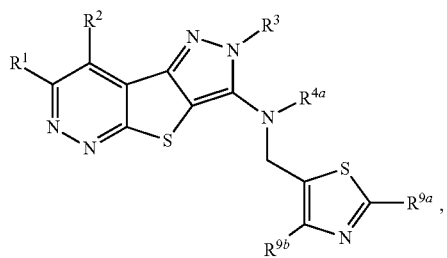

wherein each of $R^{9a}$ and $R^{9b}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein all variables are as defined herein. In a still further aspect, the compound has a structure represented by a formula listed below:

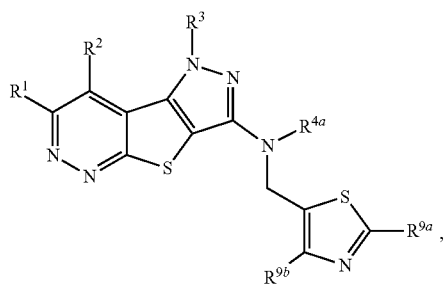

and wherein all variables are as defined herein.

In a further aspect, the compound has a structure represented by a formula listed below:

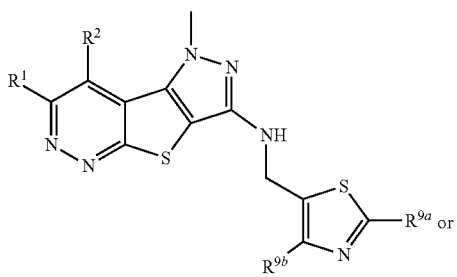

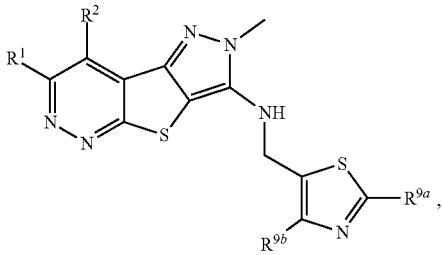

wherein $R^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein $R^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$ and $R^{9b}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; and wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein all variables are as defined herein. In a still further aspect, the compound has a structure represented by a formula listed below:

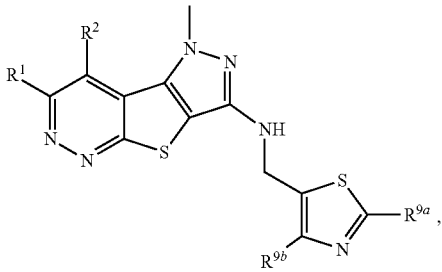

and wherein all variables are as defined herein.

In a further aspect, the compound has a structure represented by a formula listed below:

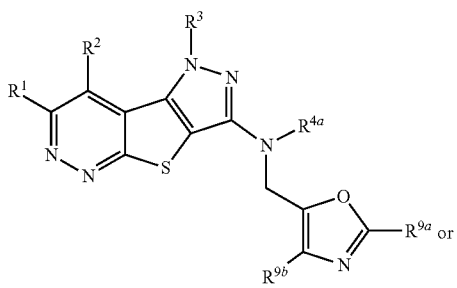

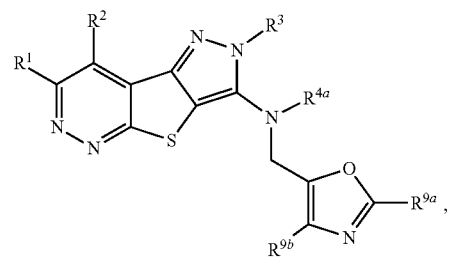

wherein each of $R^{9a}$ and $R^{9b}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein all variables are as defined herein. In a still further aspect, the compound has a structure represented by a formula listed below:

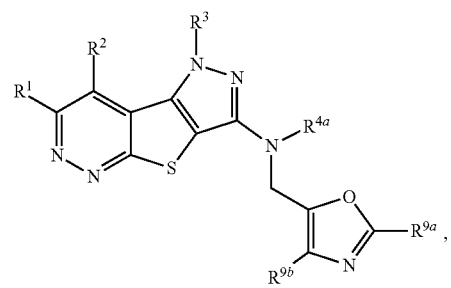

and wherein all variables are as defined herein.

In a further aspect, the compound has a structure represented by a formula listed below:

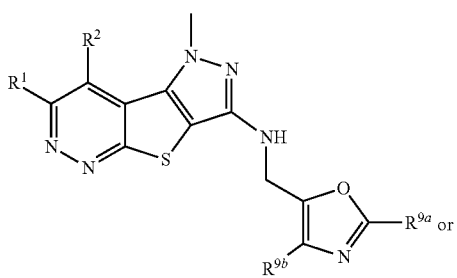

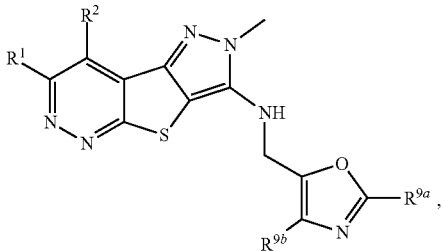

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$ and $R^{9b}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; and wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein all variables are as defined herein. In a still further aspect, the compound has a structure represented by a formula listed below:

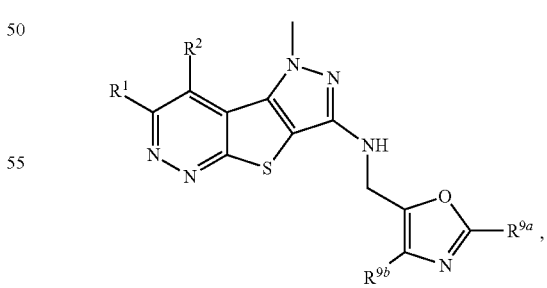

and wherein all variables are as defined herein.

In a further aspect, the compound has a structure represented by a formula listed below:

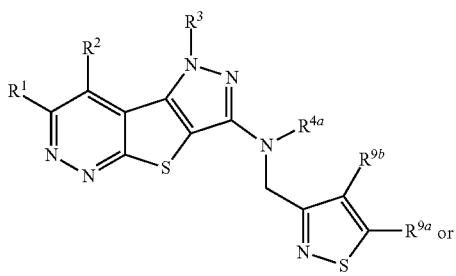

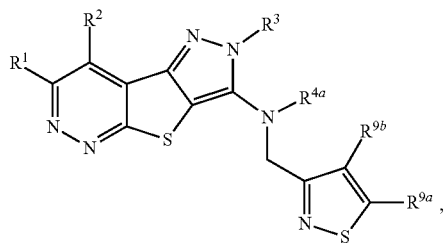

wherein each of $R^{9a}$ and $R^{9b}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein all variables are as defined herein. In a still further aspect, the compound has a structure represented by a formula listed below:

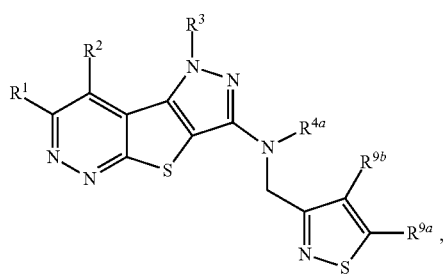

and wherein all variables are as defined herein.

In a further aspect, the compound has a structure represented by a formula listed below:

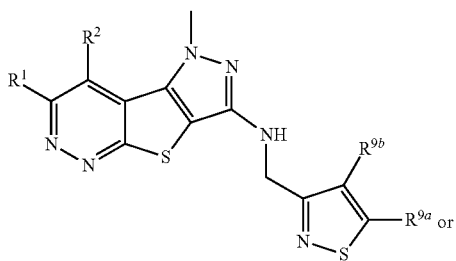

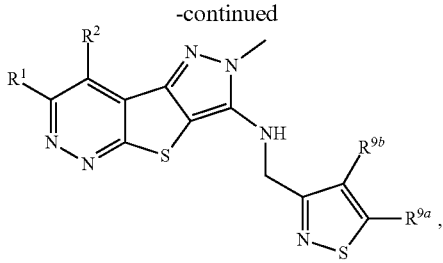

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$ and $R^{9b}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; and wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein all variables are as defined herein. In a still further aspect, the compound has a structure represented by a formula listed below:

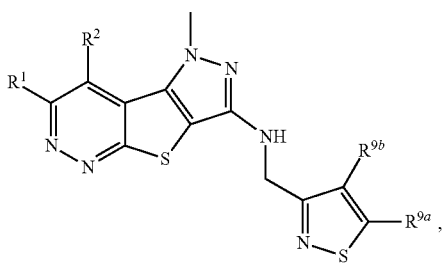

and wherein all variables are as defined herein.

In a further aspect, the compound has a structure represented by a formula listed below:

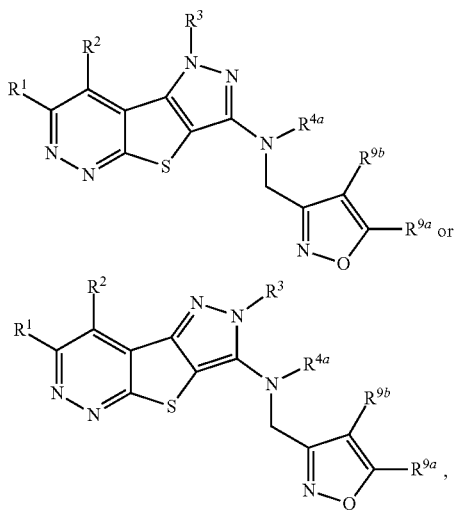

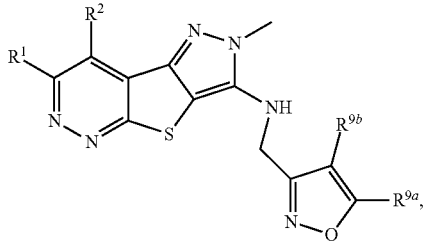

wherein each of $R^{9a}$ and $R^{9b}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, —S(O)$_m$R$^5$, R$^6$, and Ar$^2$; and wherein all variables are as defined herein. In a still further aspect, the compound has a structure represented by a formula listed below:

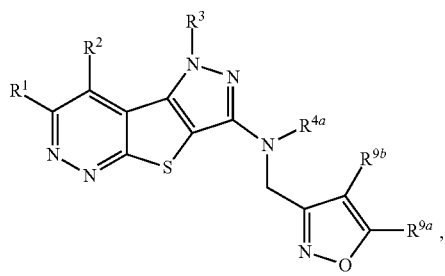

and wherein all variables are as defined herein.

In a further aspect, the compound has a structure represented by a formula listed below:

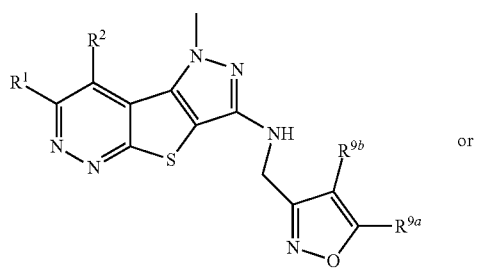

or wherein $R^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein $R^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of $R^{9a}$ and $R^{9b}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C═O)CH$_3$, —(C═O)CH$_3$, —(CH$_2$)—(C═O)OCH$_3$, —(C═O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; and wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S═O)CH$_3$, —(S═O)CH$_2$F, —(S═O)CHF$_2$, —(S═O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein all variables are as defined herein. In a still further aspect, the compound has a structure represented by a formula listed below:

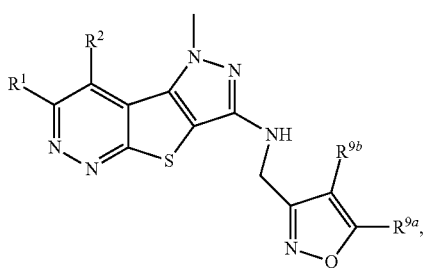

and wherein all variables are as defined herein.

In a further aspect, the compound has a structure represented by a formula listed below:

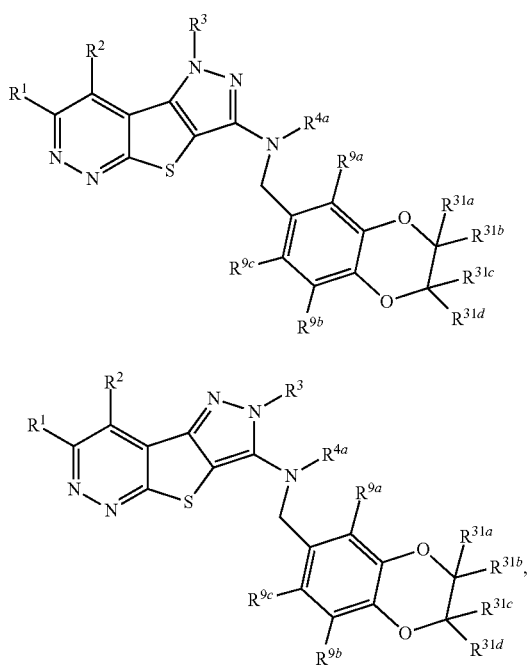

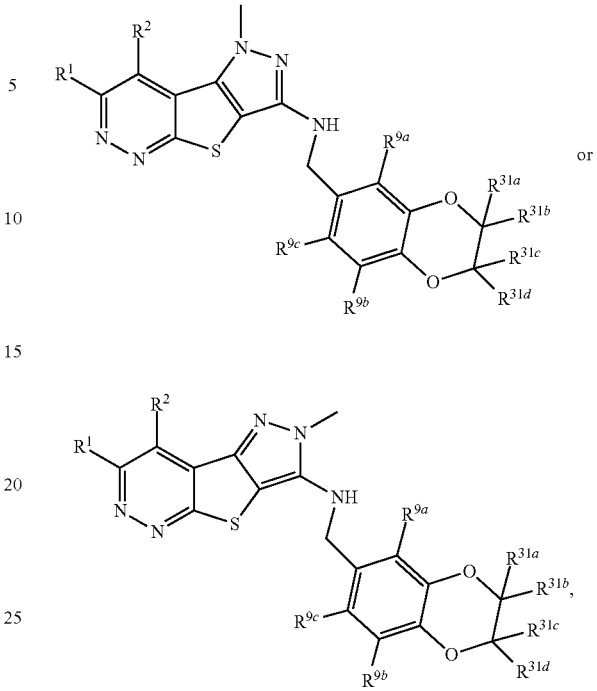

wherein each of $R^{9a}$, $R^{9b}$, and $R^{9c}$ is independently selected from hydrogen, halogen, —$NH_2$, —OH, —CN, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)$R^5$, —(C1-C6 alkyl)-(C=O)O$R^5$, —(C1-C6 alkyl)-S(O)$_m$$R^5$, —(C=O)$R^5$, —(C=O)O$R^5$, —S(O)$_m$$R^5$, $R^6$, and $Ar^2$; wherein at least two of $R^{9a}$, $R^{9b}$, and $R^{9c}$ are hydrogen; wherein each of $R^{31a}$, $R^{31b}$, $R^{31c}$, and $R^{31d}$ is independently selected from hydrogen and C1-C3 alkyl; and wherein all variables are as defined herein. In a still further aspect, the compound has a structure represented by a formula listed below:

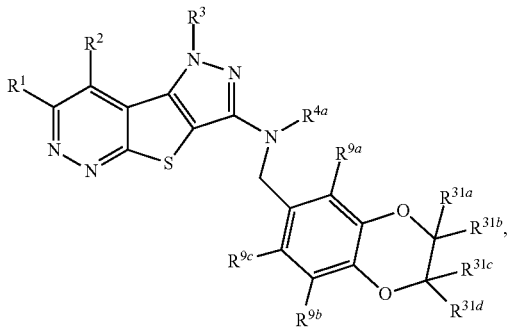

and wherein all variables are as defined herein.

In a further aspect, the compound has a structure represented by a formula listed below:

wherein $R^1$ is selected from hydrogen, —F, —Cl, methyl, —$CH_2F$, —$CH_2Cl$, —$CHF_2$, —$CF_3$, —$CHCl_2$, —$CCl_3$, —$OCH_3$, —$OCH_2CH_3$, —$NHCH_3$, and —$N(CH_3)_2$; wherein $R^2$ is selected from —F, —Cl, —Br, methyl, —$CH_2F$, —$CH_2Cl$, —$CHF_2$, —$CF_3$, —$CHCl_2$, —$CCl_3$, —$OCH_3$, —$OCH_2CH_3$, —$NHCH_3$, and —$N(CH_3)_2$; wherein each of $R^{9a}$, $R^{9b}$, and $R^{9c}$ is independently selected from hydrogen, —F, —Cl, —Br, —$NH_2$, —OH, —CN, —$SF_5$, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$(CH_2)$— $SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—(C=O)$CH_3$, —(C=O)$CH_3$, —$(CH_2)$—(C=O) $OCH_3$, —(C=O)$OCH_3$, —$CF(CF_3)CH_3$, —$C(OH)(CF_3)$ $CH_3$, —$C(CF_3)(NH_2)CH_3$, —$C(CF_3)(CN)CH_3$, —$C(CF_3)_2$ $CH_3$, —$CF(OH)CH_3$, —$CF(NH_2)CH_3$, —$CF(CN)CH_3$, —$C(OH)(NH_2)CH_3$, —$C(OH)(CN)CH_3$, —$C(CN)(NH_2)$ $CH_3$, and $Ar^2$; wherein each $Ar^2$, when present, is phenyl independently substituted with 0, 1, or 2 groups independently selected from —F, —$NH_2$, —OH, —CN, methyl, —$CH_2F$, —$CHF_2$, —$CF_3$, —$OCH_3$, —$NHCH_3$, —$N(CH_3)_2$, —$SCH_3$, —$SCH_2F$, —$SCHF_2$, —$SCF_3$, —(S=O)$CH_3$, —(S=O)$CH_2F$, —(S=O)$CHF_2$, —(S=O)$CF_3$, —$SO_2CH_3$, —$SO_2CH_2F$, —$SO_2CHF_2$, —$SO_2CF_3$, —$SO_2$-cyclopropyl, and —$SO_2$-phenyl; wherein at least two of $R^{9a}$, $R^{9b}$, and $R^{9c}$ are hydrogen; wherein each of $R^{31a}$, $R^{31b}$, $R^{31c}$, and $R^{31d}$ is independently selected from hydrogen and C1-C3 alkyl; and wherein all variables are as defined herein. In a still further aspect, the compound has a structure represented by a formula listed below:

105

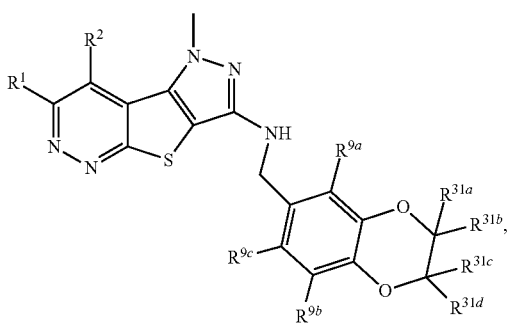

and wherein all variables are as defined herein.

In a further aspect, the compound has a structure represented by a formula listed below:

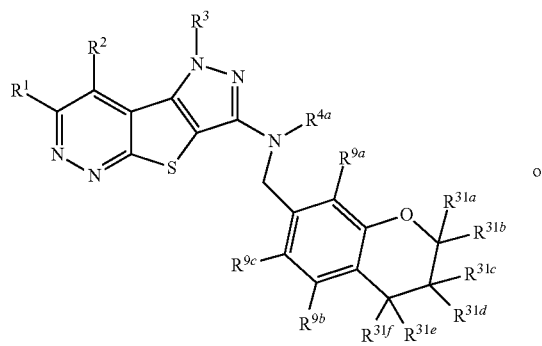

wherein each of $R^{9a}$, $R^{9b}$, and $R^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; wherein at least two of R$^{9a}$, R$^{9b}$, and R$^{9c}$ are hydrogen; wherein each of R$^{31a}$, R$^{31b}$, R$^{31c}$, R$^{31d}$, R$^{31e}$, and R$^{31f}$ is independently selected from hydrogen and C1-C3 alkyl, provided that at least two of R$^{31a}$, R$^{31b}$, R$^{31c}$, R$^{31d}$, R$^{31e}$, and R$^{31f}$ are hydrogen; and wherein all variables are as defined herein. In a still further aspect, the compound has a structure represented by a formula listed below:

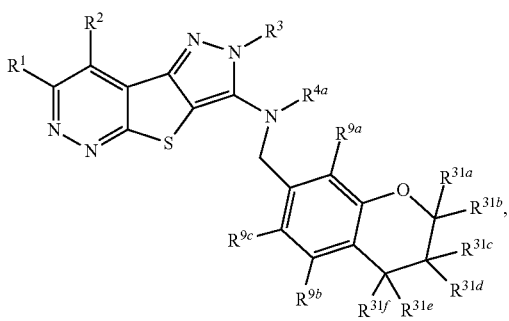

106

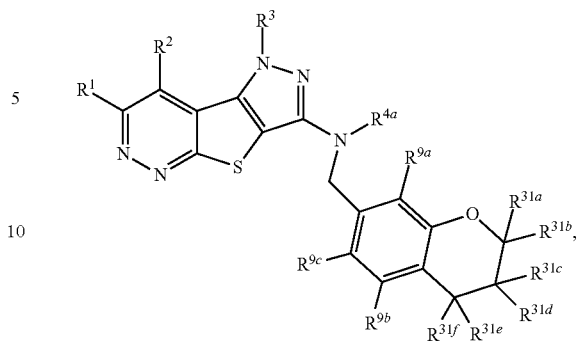

and wherein all variables are as defined herein.

In a further aspect, the compound has a structure represented by a formula listed below:

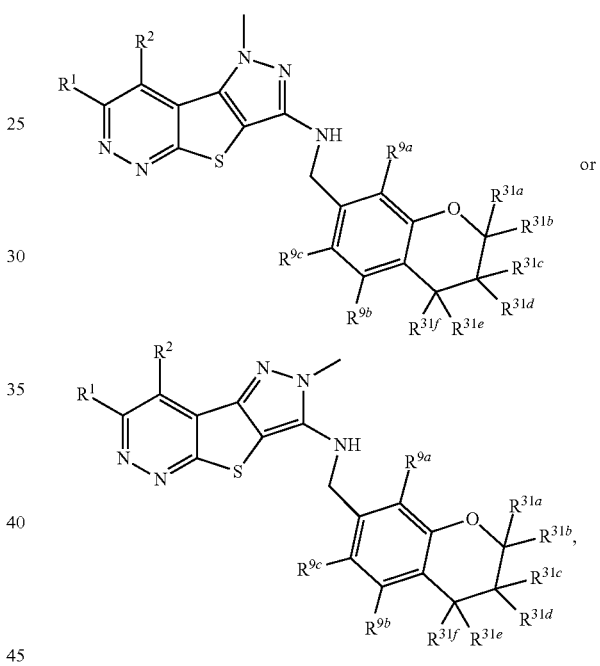

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of R$^{9a}$, R$^{9b}$, and R$^{9c}$ is independently selected from hydrogen, —F, —Cl, —Br, —NH$_2$, —OH, —CN, —SF$_5$, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; wherein at least two of R$^{9a}$, R$^{9b}$, and R$^{9c}$ are hydrogen; wherein each of R$^{31a}$, R$^{31b}$, R$^{31c}$, R$^{31d}$, R$^{31e}$, and R$^{31f}$ is independently selected from hydrogen and C1-C3 alkyl, provided that at least two of R$^{31a}$, R$^{31b}$, R$^{31c}$, R$^{31d}$, R$^{31e}$, and R$^{31f}$ are hydrogen; and wherein all variables are as defined herein. In a still further aspect, the compound has a structure represented by a formula listed below:

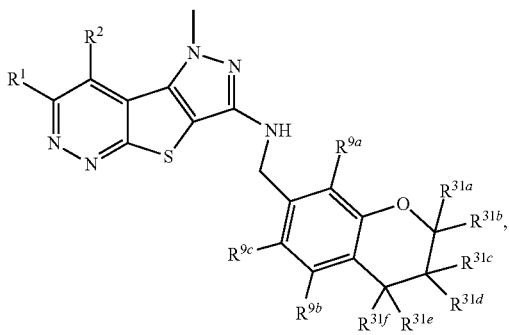

and wherein all variables are as defined herein.

In a further aspect, the compound has a structure represented by a formula listed below:

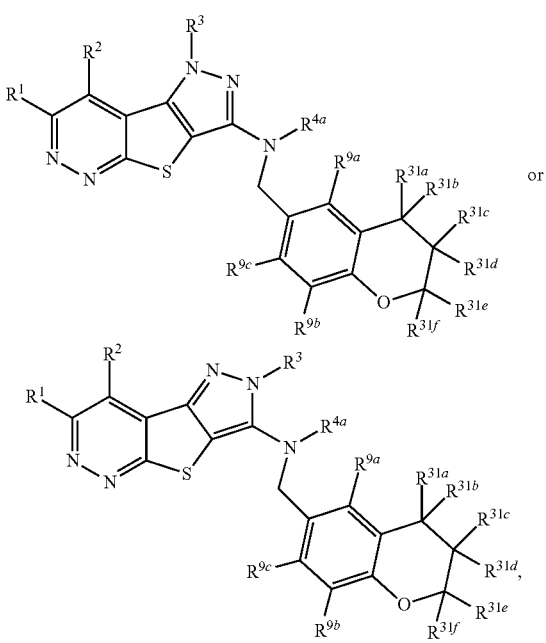

wherein each of R$^{9a}$, R$^{9b}$, and R$^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; wherein at least two of R$^{9a}$, R$^{9b}$, and R$^{9c}$ are hydrogen; wherein each of R$^{31a}$, R$^{31b}$, R$^{31c}$, R$^{31d}$, R$^{31e}$, and R$^{31f}$ is independently selected from hydrogen and C1-C3 alkyl, provided that at least two of R$^{31a}$, R$^{31b}$, R$^{31c}$, R$^{31d}$, R$^{31e}$, and R$^{31f}$ are hydrogen; and wherein all variables are as defined herein. In a still further aspect, the compound has a structure represented by a formula listed below:

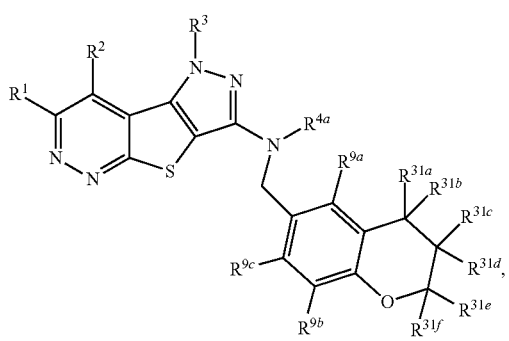

and wherein all variables are as defined herein.

In a further aspect, the compound has a structure represented by a formula listed below:

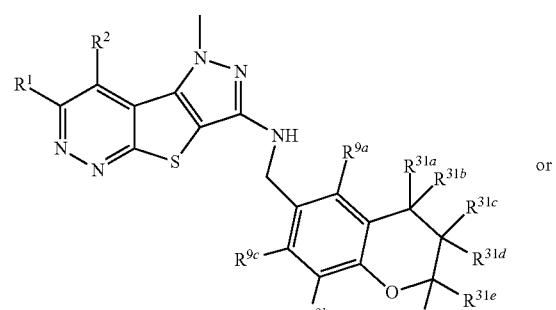

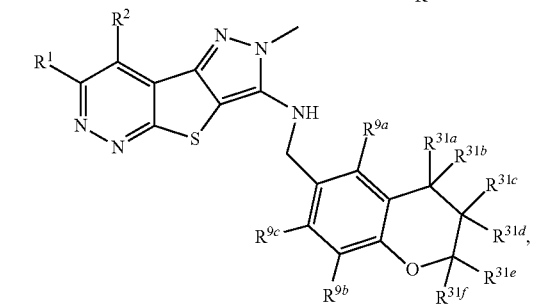

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of R$^{9a}$, R$^{9b}$, and R$^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O) OCH$_3$, —(C=O)OCH$_3$, —CF(CF$_3$)CH$_3$, —C(OH)(CF$_3$) CH$_3$, —C(CF$_3$)(NH$_2$)CH$_3$, —C(CF$_3$)(CN)CH$_3$, —C(CF$_3$)$_2$ CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)

CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S═O)CH₃, —(S═O)CH₂F, —(S═O)CHF₂, —(S═O)CF₃, —SO₂CH₃, —SO₂CH₂F, —SO₂CHF₂, —SO₂CF₃, —SO₂-cyclopropyl, and —SO₂-phenyl; wherein at least two of $R^{9a}$, $R^{9b}$, and $R^{9c}$ are hydrogen; wherein each of $R^{31a}$, $R^{31b}$, $R^{31c}$, $R^{31d}$, $R^{31e}$, and $R^{31f}$ is independently selected from hydrogen and C1-C3 alkyl, provided that at least two of $R^{31a}$, $R^{31b}$, $R^{31c}$, $R^{31d}$, $R^{31e}$, and $R^{31f}$ are hydrogen; and wherein all variables are as defined herein. In a still further aspect, the compound has a structure represented by a formula listed below:

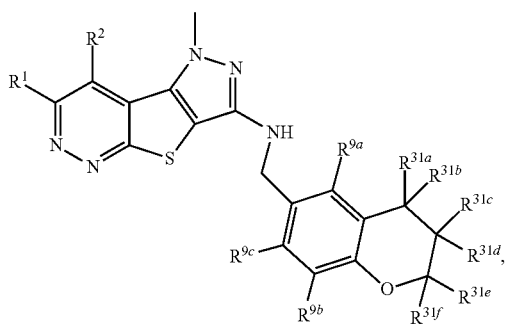

and wherein all variables are as defined herein.

In a further aspect, the compound has a structure represented by a formula listed below:

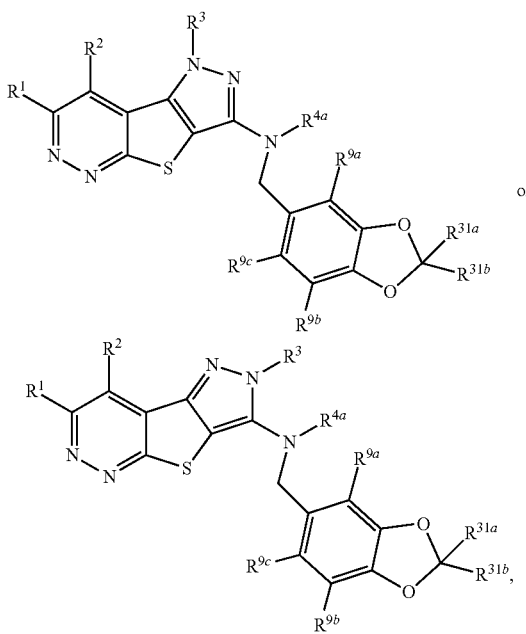

wherein each of $R^{9a}$, $R^{9b}$, and $R^{9c}$ is independently selected from hydrogen, halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C═O)R⁵, —(C1-C6 alkyl)-(C═O)OR⁵, —(C1-C6 alkyl)-S(O)ₘR⁵, —(C═O)R⁵, —(C═O)OR⁵, —S(O)ₘR⁵, R⁶, and Ar²; wherein at least two of $R^{9a}$, $R^{9b}$, and $R^{9c}$ are hydrogen; wherein each of $R^{31a}$ and $R^{31b}$ is independently selected from hydrogen and C1-C3 alkyl; and wherein all variables are as defined herein. In a still further aspect, the compound has a structure represented by a formula listed below:

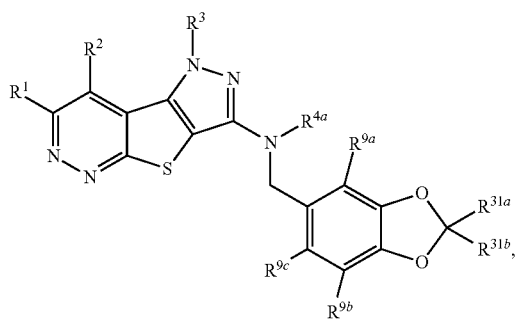

and wherein all variables are as defined herein.

In a further aspect, the compound has a structure represented by a formula listed below:

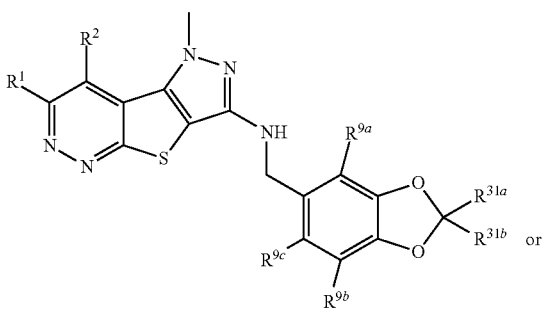

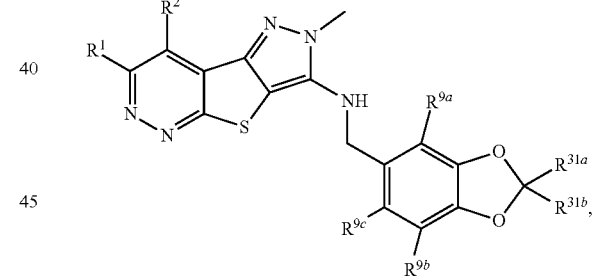

wherein R¹ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein R² is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of $R^{9a}$, $R^{9b}$, and $R^{9c}$ is independently selected from hydrogen, —F, —Cl, —Br, —NH₂, —OH, —CN, —SF₅, methyl, CH₂F, —CH₂Cl, —CHF₂, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C═O)CH₃, —(C═O)CH₃, —(CH₂)—(C═O)OCH₃, —(C═O)OCH₃, —CF(CF₃)CH₃, —C(OH)(CF₃) CH₃, —C(CF₃)(NH₂)CH₃, —C(CF₃)(CN)CH₃, —C(CF₃)₂ CH₃, —CF(OH)CH₃, —CF(NH₂)CH₃, —CF(CN)CH₃, —C(OH)(NH₂)CH₃, —C(OH)(CN)CH₃, —C(CN)(NH₂)

CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S═O)CH₃, —(S═O)CH₂F, —(S═O)CHF₂, —(S═O)CF₃, —SO₂CH₃, —SO₂CH₂F, —SO₂CHF₂, —SO₂CF₃, —SO₂-cyclopropyl, and —SO₂-phenyl; wherein at least two of $R^{9a}$, $R^{9b}$, and $R^{9c}$ are hydrogen; wherein each of $R^{31a}$ and $R^{31b}$ is independently selected from hydrogen and C1-C3 alkyl; and wherein all variables are as defined herein. In a still further aspect, the compound has a structure represented by a formula listed below:

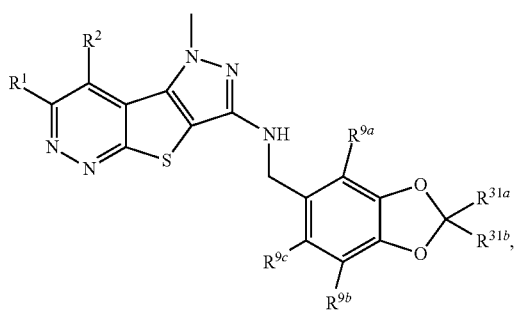

and wherein all variables are as defined herein.

In a further aspect, the compound has a structure represented by a formula listed below:

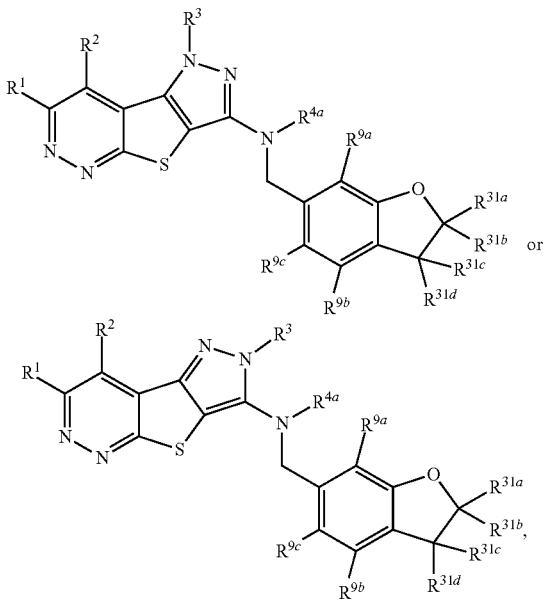

wherein each of $R^{9a}$, $R^{9b}$, and $R^{9c}$ is independently selected from hydrogen, halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C═O)R⁵, —(C1-C6 alkyl)-(C═O)OR⁵, —(C1-C6 alkyl)-S(O)ₘR⁵, —(C═O)R⁵, —(C═O)OR⁵, —S(O)ₘR⁵, R⁶, and Ar²; wherein at least two of $R^{9a}$, $R^{9b}$, and $R^{9c}$ are hydrogen; wherein each of $R^{31a}$, $R^{31b}$, $R^{31c}$, and $R^{31d}$ is independently selected from hydrogen and C1-C3 alkyl; and wherein all variables are as defined herein. In a still further aspect, the compound has a structure represented by a formula listed below:

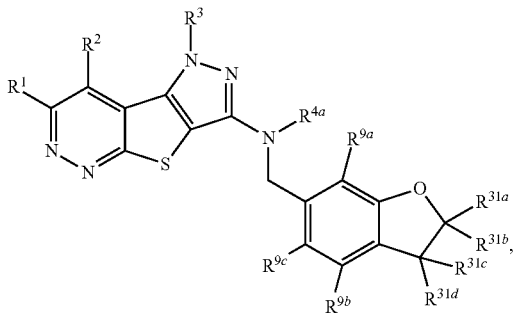

and wherein all variables are as defined herein.

In a further aspect, the compound has a structure represented by a formula listed below:

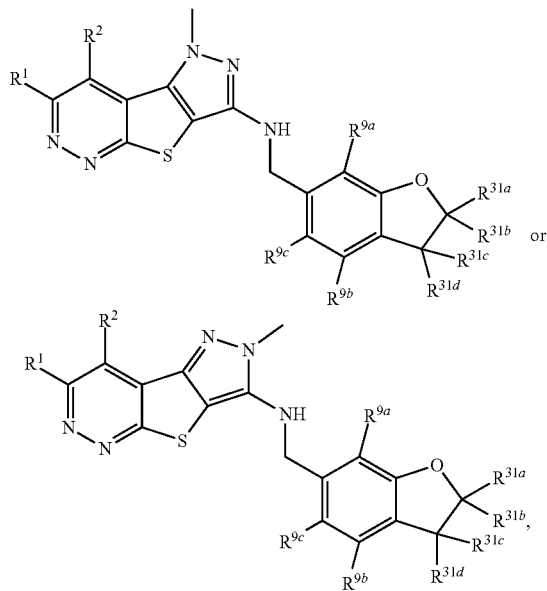

wherein $R^1$ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein $R^2$ is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of $R^{9a}$, $R^{9b}$, and $R^{9c}$ is independently selected from hydrogen, —F, —Cl, —Br, —NH₂, —OH, —CN, —SF₅, methyl, CH₂F, —CH₂Cl, —CHF, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C═O)CH₃, —(C═O)CH₃, —(CH₂)—(C═O)OCH₃, —(C═O)OCH₃, —CF(CF₃)CH₃, —C(OH)(CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH₂)CH₃, and Ar²; wherein each Ar², when present, is phenyl independently substituted with 0, 1, or 2 groups independently selected from —F, —NH₂, —OH, —CN, methyl, —CHF, —CHF₂, —CF₃, —OCH₃, —NHCH₃, —N(CH₃)₂, —SCH₃, —SCH₂F, —SCHF₂, —SCF, —(S=O)CH₃, —(S=O)CH₂F, —(S=O)CHF₂, —(S=O)CF₃, —SO₂CH₃, —SO₂CH₂F, —SO₂CHF₂, —SO₂CF₃, —SO₂-cyclopropyl, and —SO₂-phenyl; wherein at least two of R$^{9a}$, R$^{9b}$, and R$^{9c}$ are hydrogen; wherein each of R$^{31a}$, R$^{31b}$, R$^{31c}$, and R$^{31d}$ is independently selected from hydrogen and C1-C3 alkyl; and wherein all variables are as defined herein. In a still further aspect, the compound has a structure represented by a formula listed below:

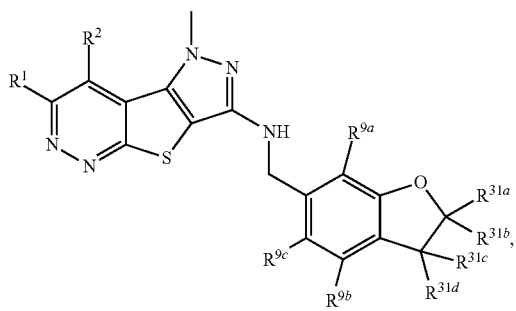

and wherein all variables are as defined herein.

In a further aspect, the compound has a structure represented by a formula listed below:

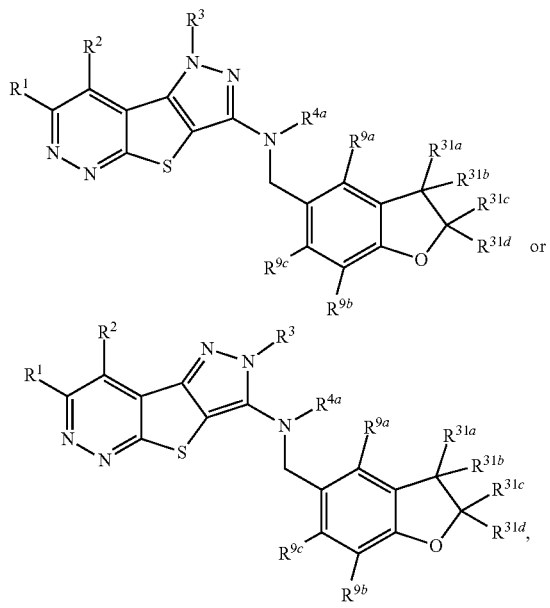

wherein each of R$^{9a}$, R$^{9b}$, and R$^{9c}$ is independently selected from hydrogen, halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R⁵, —(C1-C6 alkyl)-(C=O)OR⁵, —(C1-C6 alkyl)-S(O)$_m$R⁵, —(C=O)R⁵, —(C=O)OR⁵, —S(O)$_m$R⁵, R⁶, and Ar²; wherein at least two of R$^{9a}$, R$^{9b}$, and R$^{9c}$ are hydrogen; wherein each of R$^{31a}$, R$^{31b}$, R$^{31c}$, and R$^{31d}$ is independently selected from hydrogen and C1-C3 alkyl; and wherein all variables are as defined herein. In a still further aspect, the compound has a structure represented by a formula listed below:

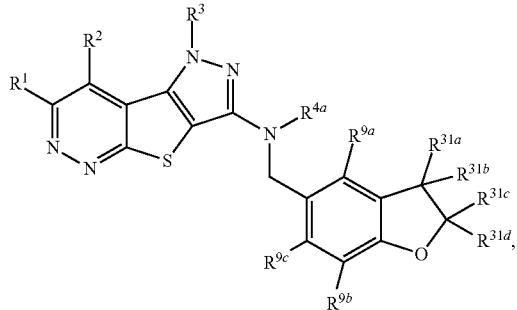

and wherein all variables are as defined herein.

In a further aspect, the compound has a structure represented by a formula listed below:

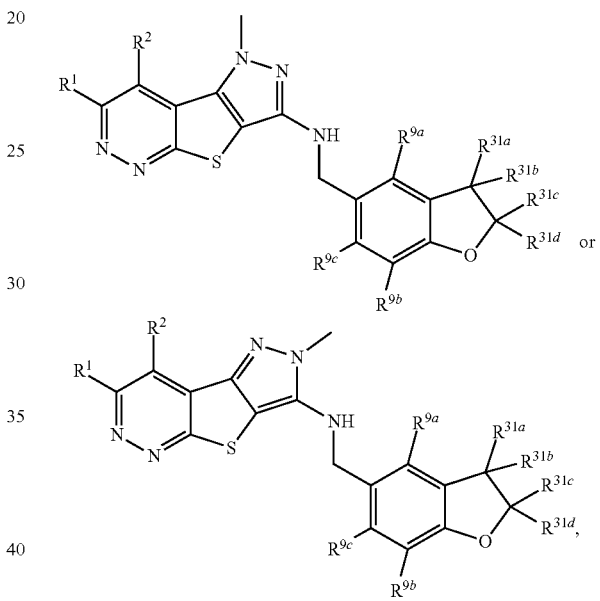

wherein R¹ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein R² is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of R$^{9a}$, R$^{9b}$, and R$^{9c}$ is independently selected from hydrogen, —F, —Cl, —Br, —NH₂, —OH, —CN, —SF₅, methyl, CH₂F, —CH₂Cl, —CHF₂, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O)OCH₃, —(C=O)OCH₃, —CF(CF₃)CH₃, —C(OH)(CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH₂)CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S=O)CH₃, —(S=O)CH₂F, —(S=O)CHF₂, —(S=O)CF₃, —SO₂CH₃, —SO₂CH₂F, —SO₂CHF₂, —SO₂CF₃, —SO₂-cyclopropyl, and —SO₂-phenyl; wherein at least two of R⁹ᵃ, R⁹ᵇ, and R⁹ᶜ are hydrogen; wherein each of R³¹ᵃ, R³¹ᵇ, R³¹ᶜ, and R³¹ᵈ is independently selected from hydrogen and C1-C3 alkyl; and wherein all variables are as defined herein. In a still further aspect, the compound has a structure represented by a formula listed below:

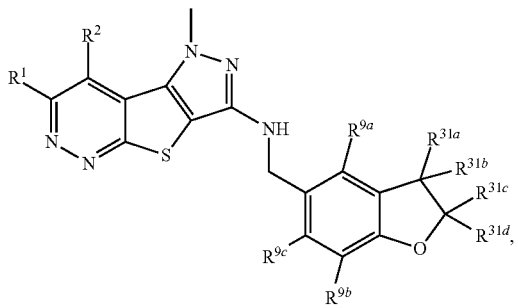

and wherein all variables are as defined herein.

In a further aspect, the compound has a structure represented by a formula listed below:

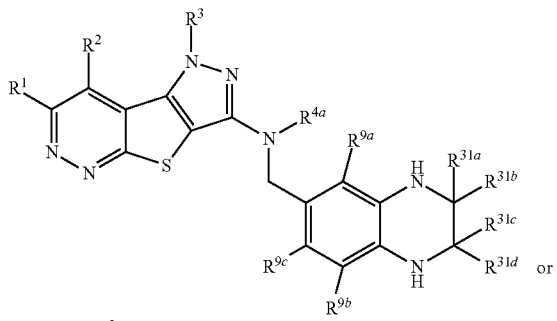

wherein each of R⁹ᵃ, R⁹ᵇ, and R⁹ᶜ is independently selected from hydrogen, halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R⁵, —(C1-C6 alkyl)-(C=O)OR⁵, —(C1-C6 alkyl)-S(O)ₘR⁵, —(C=O)R⁵, —(C=O)OR⁵, —S(O)ₘR⁵, R⁶, and Ar²; wherein at least two of R⁹ᵃ, R⁹ᵇ, and R⁹ᶜ are hydrogen; wherein each of R³¹ᵃ, R³¹ᵇ, R³¹ᶜ, and R³¹ᵈ is independently selected from hydrogen and C1-C3 alkyl; and wherein all variables are as defined herein. In a still further aspect, the compound has a structure represented by a formula listed below:

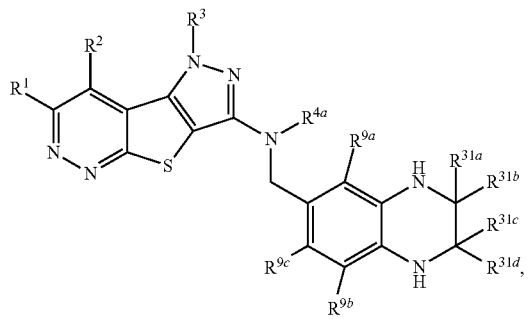

and wherein all variables are as defined herein.

In a further aspect, the compound has a structure represented by a formula listed below:

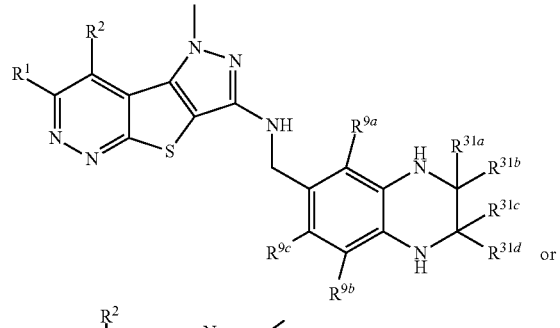

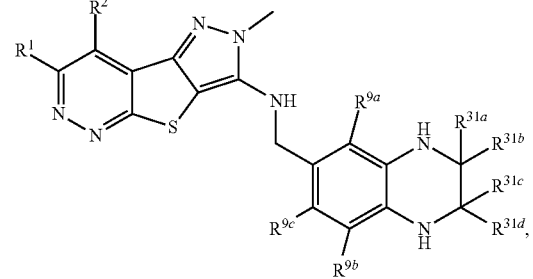

wherein R¹ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein R² is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of R⁹ᵃ, R⁹ᵇ, and R⁹ᶜ is independently selected from hydrogen, —F, —Cl, —Br, —NH₂, —OH, —CN, —SF₅, methyl, CH₂F, —CH₂Cl, —CHF₂, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O)OCH₃, —(C=O)OCH₃, —CF(CF₃)CH₃, —C(OH)(CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH₂)CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S=O)CH₃, —(S=O)CH₂F, —(S=O)CHF₂, —(S=O)CF₃, —SO₂CH₃, —SO$_2$CH$_2$F, —SO$_2$CHF$_2$, —SO$_2$CF$_3$, —SO$_2$-cyclopropyl, and —SO$_2$-phenyl; wherein at least two of R$^{9a}$, R$^{9b}$, and R$^{9c}$ are hydrogen; wherein each of R$^{31a}$, R$^{31b}$, R$^{31c}$, and R$^{31d}$ is independently selected from hydrogen and C1-C3 alkyl; and wherein all variables are as defined herein. In a still further aspect, the compound has a structure represented by a formula listed below:

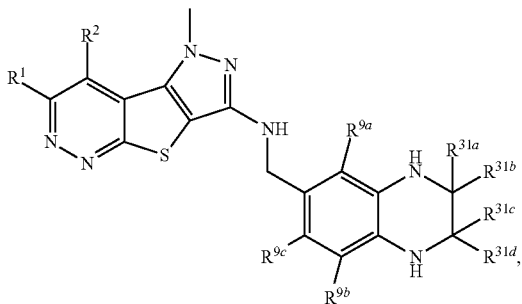

and wherein all variables are as defined herein.

In a further aspect, the compound has a structure represented by a formula listed below:

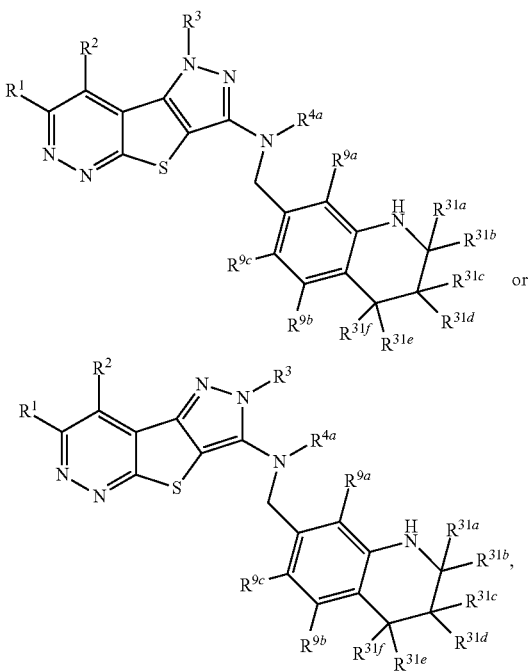

wherein each of R$^{9a}$, R$^{9b}$, and R$^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; wherein at least two of R$^{9a}$, R$^{9b}$, and R$^{9c}$ are hydrogen; wherein each of R$^{31a}$, R$^{31b}$, R$^{31c}$, R$^{31d}$, R$^{31e}$, and R$^{31f}$ is independently selected from hydrogen and C1-C3 alkyl, provided that at least two of R$^{31a}$, R$^{31b}$, R$^{31c}$, R$^{31d}$, R$^{31e}$, and R$^{31f}$ are hydrogen; and wherein all variables are as defined herein. In a still further aspect, the compound has a structure represented by a formula listed below:

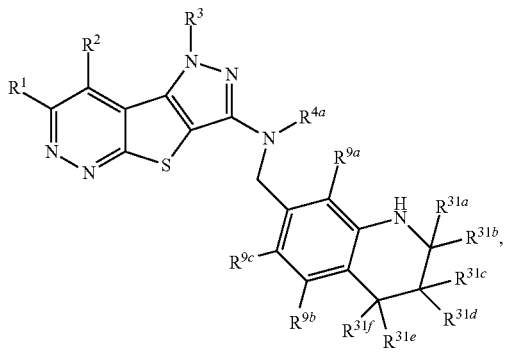

and wherein all variables are as defined herein.

In a further aspect, the compound has a structure represented by a formula listed below:

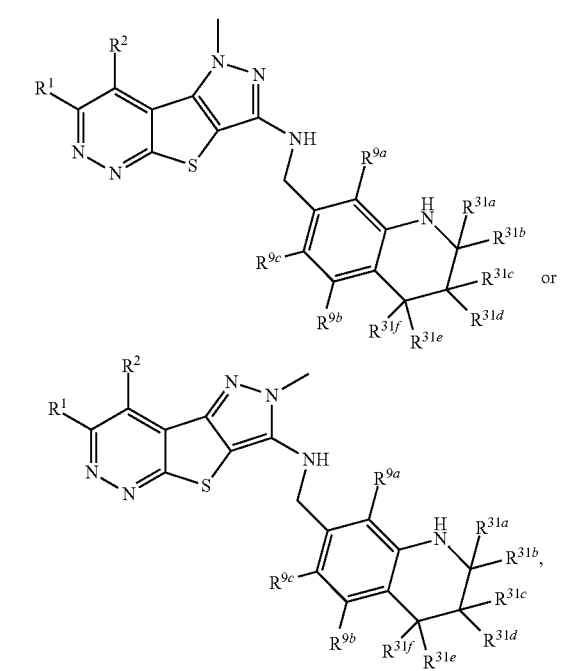

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of R$^{9a}$, R$^{9b}$, and R$^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; wherein at least two of R$^{9a}$, R$^{9b}$, and R$^{9c}$ are hydrogen; wherein each of R$^{31a}$, R$^{31b}$, R$^{31c}$, R$^{31d}$, R$^{31e}$, and R$^{31f}$ is independently selected from hydrogen and C1-C3 alkyl, provided that at least two of R$^{31a}$, R$^{31b}$, R$^{31c}$, R$^{31d}$, R$^{31e}$, and R$^{31f}$ are hydrogen; and wherein all variables are as defined herein. In a still further aspect, the compound has a structure represented by a formula listed below:

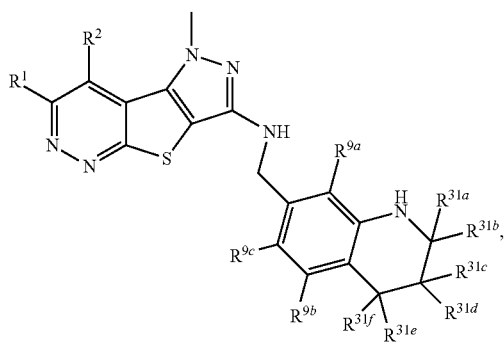

and wherein all variables are as defined herein.

In a further aspect, the compound has a structure represented by a formula listed below:

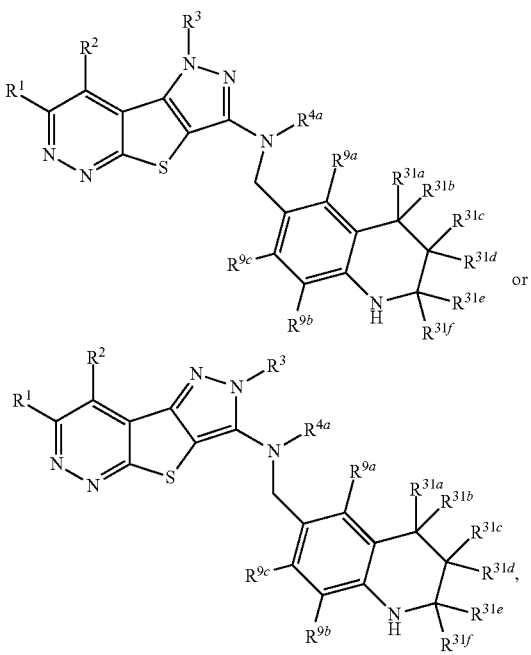

wherein each of R$^{9a}$, R$^{9b}$, and R$^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; wherein at least two of R$^{9a}$, R$^{9b}$, and R$^{9c}$ are hydrogen; wherein each of R$^{31a}$, R$^{31b}$, R$^{31c}$, R$^{31d}$, R$^{31e}$, and R$^{31f}$ is independently selected from hydrogen and C1-C3 alkyl, provided that at least two of R$^{31a}$, R$^{31b}$, R$^{31c}$, R$^{31d}$, R$^{31e}$, and R$^{31f}$ are hydrogen; and wherein all variables are as defined herein. In a still further aspect, the compound has a structure represented by a formula listed below:

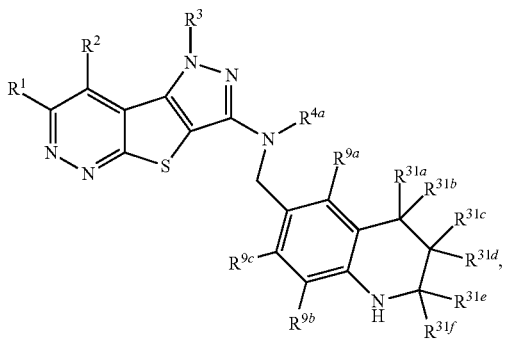

and wherein all variables are as defined herein.

In a further aspect, the compound has a structure represented by a formula listed below:

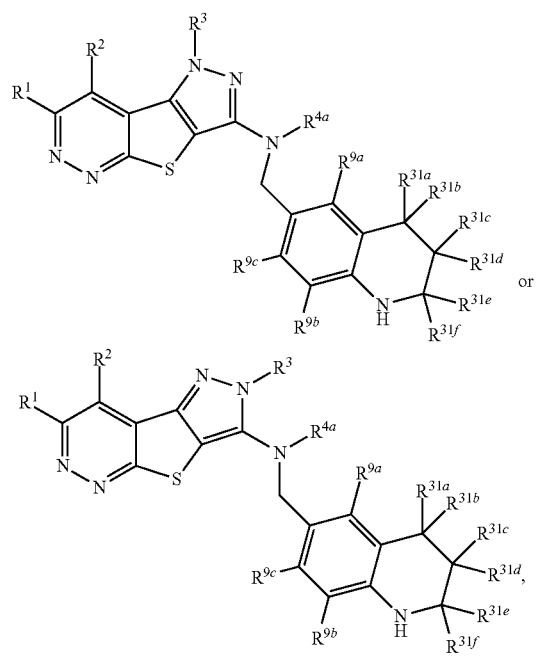

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of R$^{9a}$, R$^{9b}$, and R$^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)

CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH₂)CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S=O)CH₃, —(S=O)CH₂F, —(S=O)CHF₂, —(S=O)CF₃, —SO₂CH₃, —SO₂CH₂F, —SO₂CHF₂, —SO₂CF₃, —SO₂-cyclopropyl, and —SO₂-phenyl; wherein at least two of $R^{9a}$, $R^{9b}$, and $R^{9c}$ are hydrogen; wherein each of $R^{31a}$, $R^{31b}$, $R^{31c}$, $R^{31d}$, $R^{31e}$, and $R^{31f}$ is independently selected from hydrogen and C1-C3 alkyl, provided that at least two of $R^{31a}$, $R^{31b}$, $R^{31c}$, $R^{31d}$, $R^{31e}$, and $R^{31f}$ are hydrogen; and wherein all variables are as defined herein. In a still further aspect, the compound has a structure represented by a formula listed below:

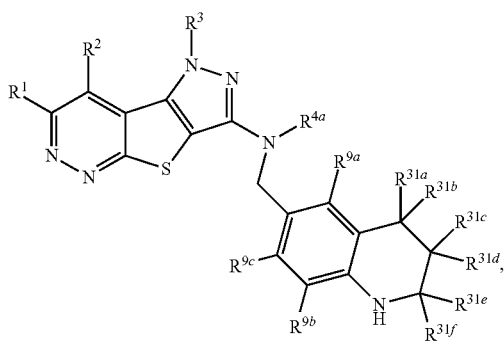

and wherein all variables are as defined herein.

In a further aspect, the compound has a structure represented by a formula listed below:

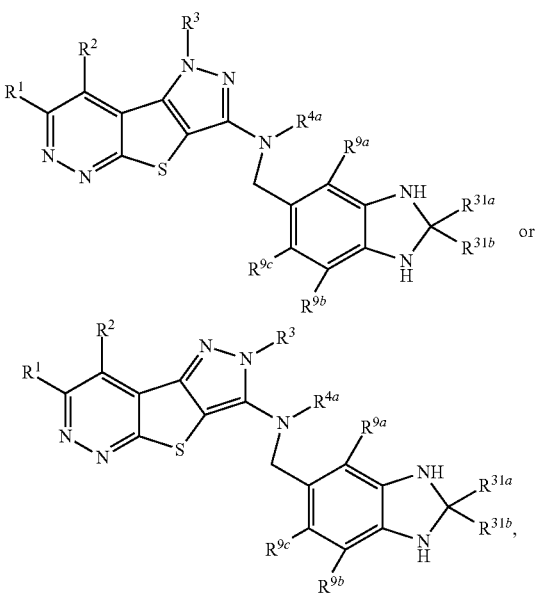

wherein each of $R^{9a}$, $R^{9b}$, and $R^{9c}$ is independently selected from hydrogen, halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R⁵, —(C1-C6 alkyl)-(C=O)OR⁵, —(C1-C6 alkyl)-S(O)ₘR⁵, —(C=O)R⁵, —(C=O)OR⁵, —S(O)ₘR⁵, R⁶, and Ar²; wherein at least two of $R^{9a}$, $R^{9b}$, and $R^{9c}$ are hydrogen; wherein each of $R^{31a}$ and $R^{31b}$ is independently selected from hydrogen and C1-C3 alkyl; and wherein all variables are as defined herein. In a still further aspect, the compound has a structure represented by a formula listed below:

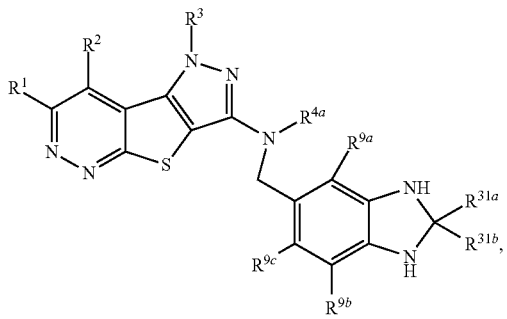

and wherein all variables are as defined herein.

In a further aspect, the compound has a structure represented by a formula listed below:

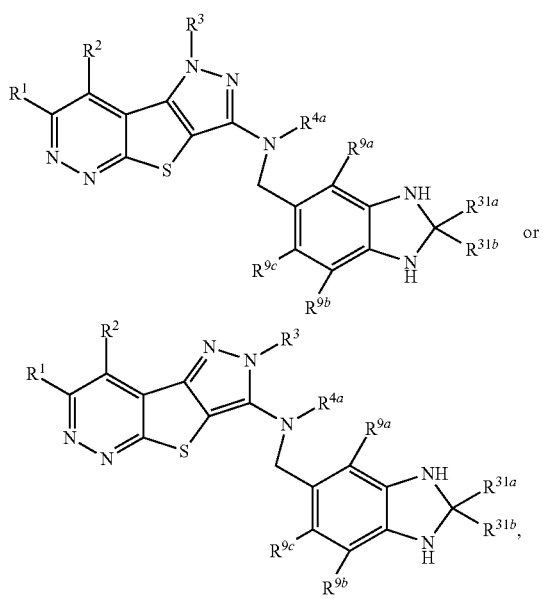

wherein $R^1$ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein $R^2$ is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of $R^{9a}$, $R^{9b}$, and $R^{9c}$ is independently selected from hydrogen, —F, —Cl, —Br, —NH₂, —OH, —CN, —SF₅, methyl, CH₂F, —CH₂Cl, —CHF₂, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O)OCH₃, —(C=O)OCH₃, —CF(CF₃)CH₃, —C(OH)(CF₃)CH₃, —C(CF₃)(NH₂)CH₃, —C(CF₃)(CN)CH₃, —C(CF₃)₂

CH₃, —CF(OH)CH₃, —CF(NH₂)CH₃, —CF(CN)CH₃, —C(OH)(NH₂)CH₃, —C(OH)(CN)CH₃, —C(CN)(NH₂) CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S=O)CH₃, —(S=O)CH₂F, —(S=O)CHF₂, —(S=O)CF₃, —SO₂CH₃, —SO₂CH₂F, —SO₂CHF₂, —SO₂CF₃, —SO₂-cyclopropyl, and —SO₂-phenyl; wherein at least two of R$^{9a}$, R$^{9b}$, and R$^{9c}$ are hydrogen; wherein each of R$^{31a}$ and R$^{31b}$ is independently selected from hydrogen and C1-C3 alkyl; and wherein all variables are as defined herein. In a still further aspect, the compound has a structure represented by a formula listed below:

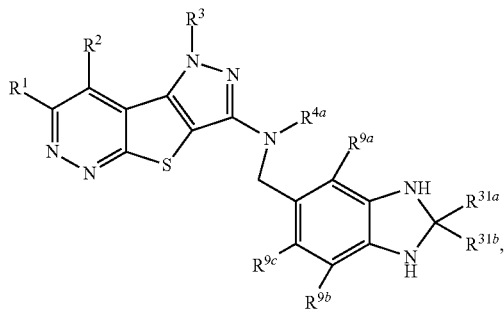

and wherein all variables are as defined herein.

In a further aspect, the compound has a structure represented by a formula listed below:

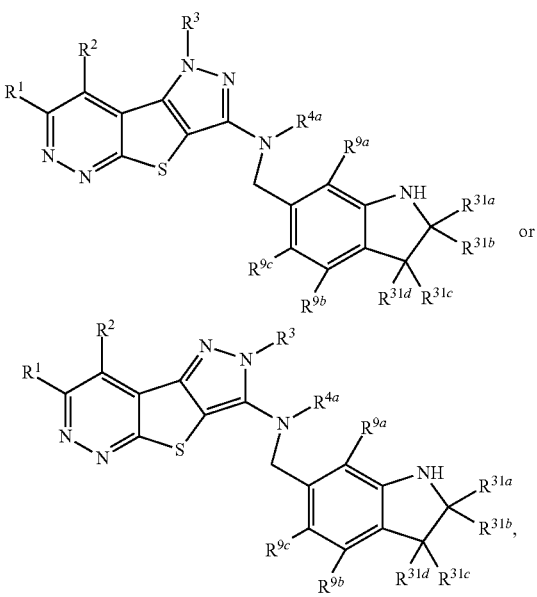

wherein each of R$^{9a}$, R$^{9b}$, and R$^{9c}$ is independently selected from hydrogen, halogen, —NH₂, —OH, —CN, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R⁵, —(C1-C6 alkyl)-(C=O)OR⁵, —(C1-C6 alkyl)-S(O)$_m$R⁵, —(C=O)R⁵, —(C=O)OR⁵, —S(O)$_m$R⁵, R⁶, and Ar²; wherein at least two of R$^{9a}$, R$^{9b}$, and R$^{9c}$ are hydrogen; wherein each of R$^{31a}$, R$^{31b}$, R$^{31c}$, and R$^{31d}$ is independently selected from hydrogen and C1-C3 alkyl; and wherein all variables are as defined herein. In a still further aspect, the compound has a structure represented by a formula listed below:

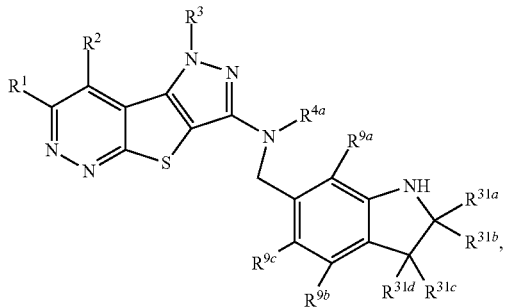

and wherein all variables are as defined herein.

In a further aspect, the compound has a structure represented by a formula listed below:

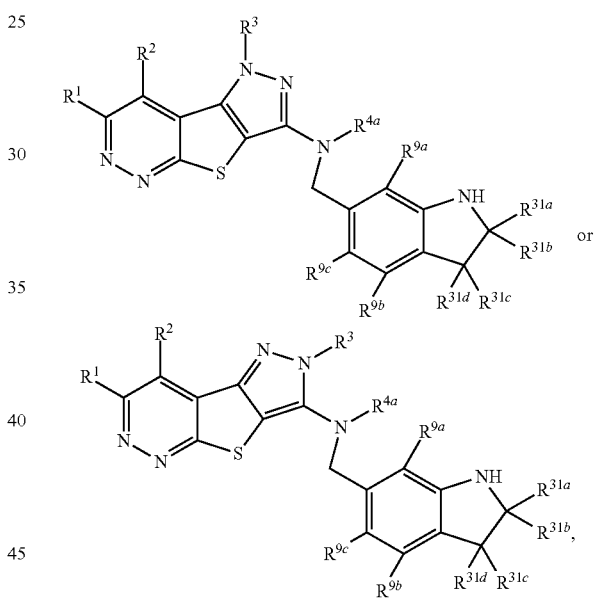

wherein R¹ is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein R² is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂; wherein each of R$^{9a}$, R$^{9b}$, and R$^{9c}$ is independently selected from hydrogen, —F, —Cl, —Br, —NH₂, —OH, —CN, —SF₅, methyl, CH₂F, —CH₂Cl, —CHF, —CF₃, —CHCl₂, —CCl₃, —OCH₃, —OCH₂CH₃, —NHCH₃, —N(CH₃)₂, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O) OCH₃, —(C=O)OCH₃, —CF(CF₃)CH₃, —C(OH)(CF₃) CH₃, —C(CF₃)(NH₂)CH₃, —C(CF₃)(CN)CH₃, —C(CF₃)₂ CH₃, —CF(OH)CH₃, —CF(NH₂)CH₃, —CF(CN)CH₃, —C(OH)(NH₂)CH₃, —C(OH)(CN)CH₃, —C(CN)(NH₂) CH₃, and Ar²; wherein each Ar², when present, is phenyl independently substituted with 0, 1, or 2 groups independently selected from —F, —NH$_2$, —OH, —CN, methyl, —CHF, —CHF$_2$, —CF$_3$, —OCH$_3$, —NHCH$_3$, —N(CH$_3$)$_2$, —SCH$_3$, —SCH$_2$F, —SCHF$_2$, —SCF, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; wherein at least two of R$^{9a}$, R$^{9b}$, and R$^{9c}$ are hydrogen; wherein each of R$^{31a}$, R$^{31b}$, R$^{31c}$, and R$^{31d}$ is independently selected from hydrogen and C1-C3 alkyl; and wherein all variables are as defined herein. In a still further aspect, the compound has a structure represented by a formula listed below:

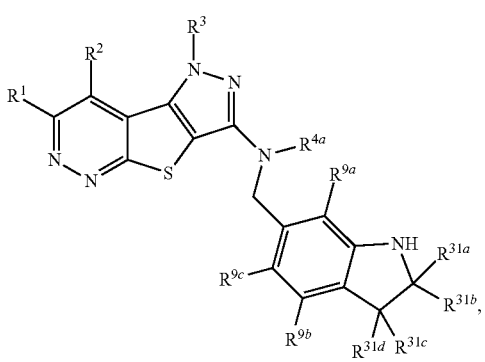

and wherein all variables are as defined herein.

In a further aspect, the compound has a structure represented by a formula listed below:

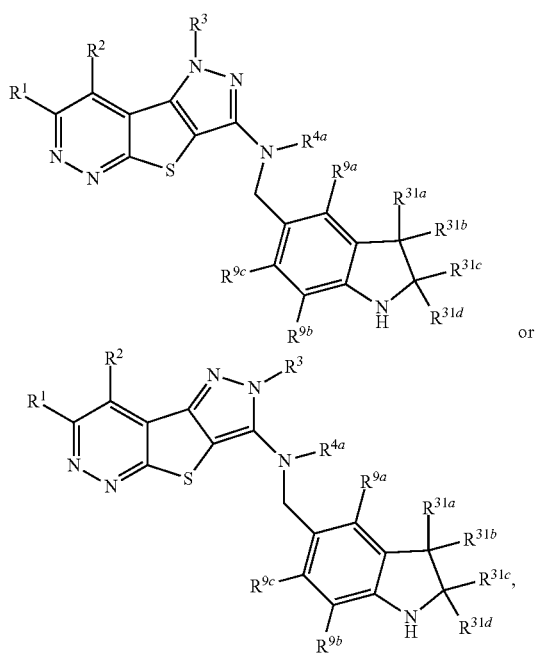

wherein each of R$^{9a}$, R$^{9b}$, and R$^{9c}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; wherein at least two of R$^{9a}$, R$^{9b}$, and R$^{9c}$ are hydrogen; wherein each of R$^{31a}$, R$^{31b}$, R$^{31c}$, and R$^{31d}$ is independently selected from hydrogen and C1-C3 alkyl; and wherein all variables are as defined herein. In a still further aspect, the compound has a structure represented by a formula listed below:

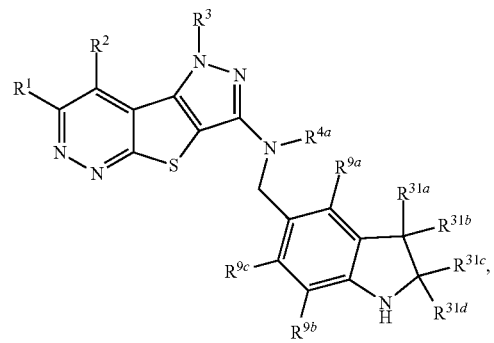

and wherein all variables are as defined herein.

In a further aspect, the compound has a structure represented by a formula listed below:

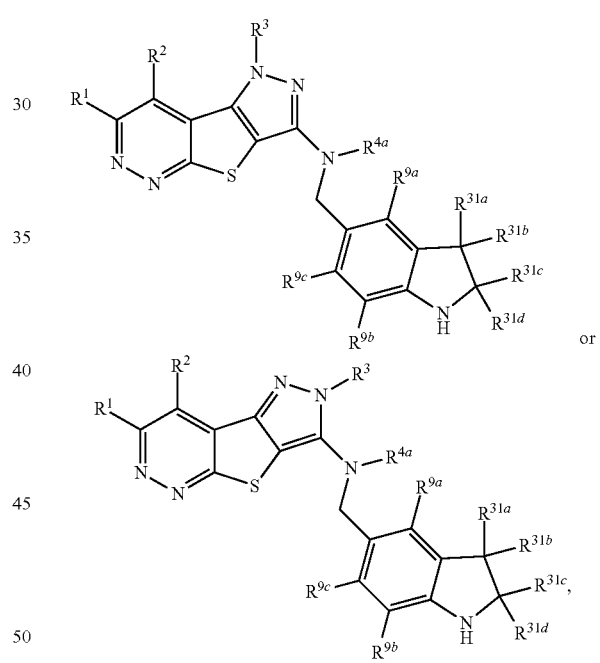

wherein R$^1$ is selected from hydrogen, —F, —Cl, methyl, —CH$_2$F, —CH$_2$Cl, —CHF, —CF$_3$, —CHCl$_2$, —CCl$_3$, —OCH$_3$, —OCH$_2$CH$_3$, —NHCH$_3$, and —N(CH$_3$)$_2$; wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$; wherein each of R$^{9a}$, R$^{9b}$, and R$^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)

CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, —C(CN)(NH₂)CH₃, and Ar²; wherein each Ar², when present, is phenyl independently substituted with 0, 1, or 2 groups independently selected from —F, —NH₂, —OH, —CN, methyl, —CH₂F, —CHF₂, —CF₃, —OCH₃, —NHCH₃, —N(CH₃)₂, —SCH₃, —SCH₂F, —SCHF₂, —SCF₃, —(S═O)CH₃, —(S═O)CH₂F, —(S═O)CHF₂, —(S═O)CF₃, —SO₂CH₃, —SO₂CH₂F, —SO₂CHF₂, —SO₂CF₃, —SO₂-cyclopropyl, and —SO₂-phenyl; wherein at least two of R$^{9a}$, R$^{9b}$, and R$^{9c}$ are hydrogen; wherein each of R$^{31a}$, R$^{31b}$, R$^{31c}$, and R$^{31d}$ is independently selected from hydrogen and C1-C3 alkyl; and wherein all variables are as defined herein. In a still further aspect, the compound has a structure represented by a formula listed below:

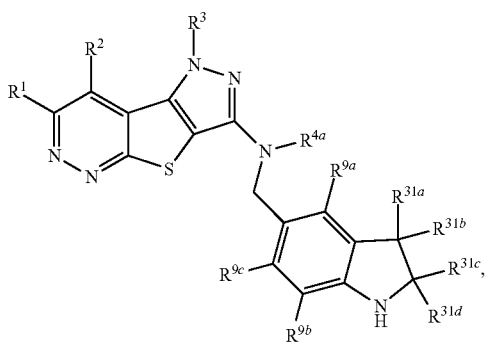

and wherein all variables are as defined herein.

Suitable substituents are described below.

a. R¹ Groups

In one aspect, R¹ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino.

In a further aspect, R¹ is selected from hydrogen, halogen, —OH, C1-C3 alkyl, C1-C3 monohaloalkyl, C1-C3 polyhaloalkyl, C1-C3 alkoxy, C1-C3 monoalkylamino, and C1-C3 dialkylamino. In a still further aspect, R¹ is selected from hydrogen, —F, —Cl, —Br, —I, —OH, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a yet further aspect, R¹ is selected from hydrogen, —F, —Cl, —OH, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, and —N(CH₂CH₃)₂. In an even further aspect, R¹ is selected from hydrogen, —F, —Cl, —OH, methyl, ethyl, propyl, isopropyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —OCH(CH₃)₂, —NHCH₃, —NHCH₂CH₃, —N(CH₃)₂, —N(CH₃)CH₂CH₃, and —N(CH₃)CH(CH₃)₂. In a still further aspect, R¹ is selected from hydrogen, —F, —Cl, —OH, methyl, —CH₂F, —CH₂Cl, —CHF₂, —CF₃, —CHCl₂, —CCl₃, —OCH₃, —OCH₂CH₃, —NHCH₃, and —N(CH₃)₂. In a yet further aspect, R¹ is selected from hydrogen, —F, —OH, methyl, —CH₂F, —CHF₂, —CF₃, —OCH₃, —NHCH₃, and —N(CH₃)₂.

In a further aspect, R¹ is selected from halogen, —OH, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R¹ is selected from halogen, —OH, C1-C3 alkyl, C1-C3 monohaloalkyl, C1-C3 polyhaloalkyl, C1-C3 alkoxy, C1-C3 monoalkylamino, and C1-C3 dialkylamino. In a yet further aspect, R¹ is selected from —F, —Cl, —Br, —I, —OH, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In an even further aspect, R¹ is selected from hydrogen, —F, —Cl, —OH, methyl, ethyl, propyl, isopropyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, —N(CH₃)CH(CH₃)₂, and —N(CH₂CH₃)₂. In a still further aspect, R¹ is selected from —F, —Cl, —OH, methyl, ethyl, propyl, isopropyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —OCH(CH₃)₂, —NHCH₃, —NHCH₂CH₃, —N(CH₃)₂, —N(CH₃)CH₂CH₃, and —N(CH₃)CH(CH₃)₂. In a yet further aspect, R¹ is selected from —F, —Cl, —OH, methyl, —CH₂F, —CH₂Cl, —CHF₂, —CF₃, —CHCl₂, —CCl₃, —OCH₃, —OCH₂CH₃, —NHCH₃, and —N(CH₃)₂. In an even further aspect, R¹ is selected from —F, —OH, methyl, —CH₂F, —CHF₂, —CF₃, —OCH₃, —NHCH₃, and —N(CH₃)₂.

In a further aspect, R¹ is selected from hydrogen, —OH, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, $R^1$ is selected from hydrogen, —OH, C1-C3 alkyl, C1-C3 monohaloalkyl, C1-C3 polyhaloalkyl, C1-C3 alkoxy, C1-C3 monoalkylamino, and C1-C3 dialkylamino. In a yet further aspect, $R^1$ is selected from hydrogen, —OH, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, $R^1$ is selected from hydrogen, —OH, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, $R^1$ is selected from hydrogen, —OH, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a yet further aspect, wherein $R^1$ is selected from hydrogen, —OH, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$. In an even further aspect, $R^1$ is selected from hydrogen, —OH, methyl, —CH$_2$F, —CHF$_2$, —CF$_3$, —OCH$_3$, —NHCH$_3$, and —N(CH$_3$)$_2$.

In a further aspect, $R^1$ is selected from hydrogen, halogen, —OH, C1-C6 alkyl, C1-C6 monohaloalkyl, and C1-C6 polyhaloalkyl. In a still further aspect, $R^1$ is selected from hydrogen, halogen, —OH, C1-C3 alkyl, C1-C3 monohaloalkyl, and C1-C3 polyhaloalkyl. In a still further aspect, $R^1$ is selected from hydrogen, —F, —Cl, —Br, —I, —OH, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a yet further aspect, $R^1$ is selected from hydrogen, —F, —Cl, —OH, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, $R^1$ is selected from hydrogen, —F, —Cl, —OH, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, $R^1$ is selected from hydrogen, —F, —Cl, —OH, methyl, —CH$_2$F, —CH$_2$Cl, —CHF$_2$, —CF$_3$, —CHCl$_2$, and —CCl$_3$. In a yet further aspect, $R^1$ is selected from hydrogen, —F, —OH, methyl, —CH$_2$F, —CHF$_2$, and —CF$_3$.

In a further aspect, $R^1$ is selected from hydrogen, halogen, —OH, C1-C6 alkoxy, C1-C6 monoalkylamino, and C1-C6 dialkylamino. In a still further aspect, $R^1$ is selected from hydrogen, halogen, —OH, C1-C3 alkoxy, C1-C3 monoalkylamino, and C1-C3 dialkylamino. In a yet further aspect, $R^1$ is selected from hydrogen, —F, —Cl, —Br, —I, —OH, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, $R^1$ is selected from hydrogen, —F, —Cl, —OH, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, $R^1$ is selected from hydrogen, —F, —Cl, —OH, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a yet further aspect, $R^1$ is selected from hydrogen, —F, —Cl, —OH, —OCH$_3$, —OCH$_2$CH$_3$, —NHCH$_3$, and —N(CH$_3$)$_2$. In an even further aspect, $R^1$ is selected from hydrogen, —F, —OH, —OCH$_3$, —NHCH$_3$, and —N(CH$_3$)$_2$.

In a further aspect, $R^1$ is selected from hydrogen, halogen, —OH, C1-C6 monohaloalkyl, C1-C6 polyhaloalkyl, C1-C6 alkoxy, C1-C6 monoalkylamino, and C1-C6 dialkylamino. In a still further aspect, $R^1$ is selected from hydrogen, halogen, —OH, C1-C3 monohaloalkyl, C1-C3 polyhaloalkyl, C1-C3 alkoxy, C1-C3 monoalkylamino, and C1-C3 dialkylamino. In a yet further aspect, $R^1$ is selected from hydrogen, —F, —Cl, —Br, —I, —OH, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, $R^1$ is selected from hydrogen, —F, —Cl, —OH, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, $R^1$ is selected from hydrogen, —F, —Cl, —OH, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a yet further aspect, R$^1$ is selected from hydrogen, —F, —Cl, —OH, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$. In an even further aspect, R$^1$ is selected from hydrogen, —F, —OH, —CH$_2$F, —CHF$_2$, —CF$_3$, —OCH$_3$, —NHCH$_3$, and —N(CH$_3$)$_2$.

In various aspects, R$^1$ is selected from —F, —Cl, —Br, —OH, methyl, ethyl, —CF$_3$, —OCH$_3$, and —NHCH$_3$. In a yet further aspect, R$^1$ is selected from —F, —Br, —OH, methyl, —CF$_3$, —OCH$_3$, and —NHCH$_3$. In an even further aspect, R$^1$ is selected from —F, —Br, and methyl. In a still further aspect, R$^1$ is selected from —F, —Cl, and —Br. In a yet further aspect, R$^1$ is selected from —F and —Br. In an even further aspect, R$^1$ is —F. In a still further aspect, R$^1$ is —Cl. In a yet further aspect, R$^1$ is —Br. In an even further aspect, R$^1$ is —OH. In a still further aspect, R$^1$ is methyl. In a yet further aspect, R$^1$ is —CF$_3$. In an even further aspect, R$^1$ is —OCH$_3$. In a still further aspect, R$^1$ is —NHCH$_3$.

In various aspects, R$^1$ and R$^2$ are optionally covalently bonded and, together with the intermediate atoms, comprise a 3- to 7-membered cycle and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a further aspect, R$^1$ and R$^2$ are optionally covalently bonded and, together with the intermediate atoms, comprise a 3- to 7-membered cycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R$^1$ and R$^2$ are optionally covalently bonded and, together with the intermediate atoms, comprise a 3- to 7-membered heterocycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a yet further aspect, R$^1$ and R$^2$ are optionally covalently bonded and, together with the intermediate atoms, comprise a 3- to 7-membered heteroaryl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino.

In a further aspect, R$^1$ and R$^2$ are optionally covalently bonded and, together with the intermediate atoms, comprise a 3- to 6-membered cycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R$^1$ and R$^2$ are optionally covalently bonded and, together with the intermediate atoms, comprise a 3- to 6-membered heterocycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a yet further aspect, R$^1$ and R$^2$ are optionally covalently bonded and, together with the intermediate atoms, comprise a 3- to 6-membered heteroaryl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino.

In a further aspect, R$^1$ and R$^2$ are optionally covalently bonded and, together with the intermediate atoms, comprise a 5- or 6-membered cycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R$^1$ and R$^2$ are optionally covalently bonded and, together with the intermediate atoms, comprise a 5- or 6-membered heterocycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a yet further aspect, R$^1$ and R$^2$ are optionally covalently bonded and, together with the intermediate atoms, comprise a 5- or 6-membered heteroaryl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino.

In a further aspect, R$^1$ and R$^2$ are optionally covalently bonded and, together with the intermediate atoms, comprise a 5-membered cycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R$^1$ and R$^2$ are optionally covalently bonded and, together with the intermediate atoms, comprise a 5-membered heterocycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a yet further aspect, R$^1$ and R$^2$ are optionally covalently bonded and, together with the intermediate atoms, comprise a 5-membered heteroaryl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino.

In a further aspect, R$^1$ and R$^2$ are optionally covalently bonded and, together with the intermediate atoms, comprise a 6-membered cycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R$^1$ and R$^2$ are optionally covalently bonded and, together with the intermediate atoms, comprise a 6-membered aryl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a further aspect, R$^1$ and R$^2$ are optionally covalently bonded and, together with the intermediate atoms, comprise a 6-membered heterocycloalkyl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a yet further aspect, R$^1$ and R$^2$ are optionally covalently bonded and, together with the intermediate atoms, comprise a 6-membered heteroaryl and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino.

b. R² Groups

In one aspect, R² is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino, or wherein R¹ and R² are optionally covalently bonded and, together with the intermediate atoms, comprise a 3- to 7-membered cycle and substituted with 0, 1 or 2 groups independently selected from halogen, —NH₂, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino. In a further aspect, R² is not hydrogen. In a still further aspect, R² is hydrogen.

In various aspects, R² is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino. In a further aspect, R² is selected from hydrogen, halogen, C1-C3 alkyl, C1-C3 monohaloalkyl, C1-C3 polyhaloalkyl, C1-C3 alkoxy, C1-C3 monoalkylamino, and C1-C3 dialkylamino. In a still further aspect, R² is selected from hydrogen, —F, —Cl, —Br, —I, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a yet further aspect, R² is selected from hydrogen, —F, —Cl, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, —N(CH₃)CH(CH₃)₂, and —N(CH₂CH₃)₂. In an even further aspect, R² is selected from hydrogen, —F, —Cl, methyl, ethyl, propyl, isopropyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —OCH(CH₃)₂, —NHCH₃, —NHCH₂CH₃, —N(CH₃)₂, —N(CH₃)CH₂CH₃, and —N(CH₃)CH(CH₃)₂. In a still further aspect, R² is selected from hydrogen, —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂. In a yet further aspect, R² is selected from hydrogen, —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂. In an even further aspect, R² is selected from hydrogen, —F, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂. In a still further aspect, R² is selected from hydrogen, —F, methyl, —CH₂F, —CHF₂, —CF₃, —OCH₃, —NHCH₃, and —N(CH₃)₂. In a yet further aspect, R² is selected from hydrogen, —Br, methyl, —CH₂F, —CHF₂, —CF₃, —OCH₃, —NHCH₃, and —N(CH₃)₂.

In a further aspect, R² is selected from halogen, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R² is selected from halogen, C1-C3 alkyl, C1-C3 monohaloalkyl, C1-C3 polyhaloalkyl, C1-C3 alkoxy, C1-C3 monoalkylamino, and C1-C3 dialkylamino. In a yet further aspect, R² is selected from —F, —Cl, —Br, —I, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In an even further aspect, R² is selected from —F, —Cl, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, —N(CH₃)CH(CH₃)₂, and —N(CH₂CH₃)₂. In a still further aspect, R² is selected from —F, —Cl, methyl, ethyl, propyl, isopropyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —OCH(CH₃)₂, —NHCH₃, —NHCH₂CH₃, —N(CH₃)₂, —N(CH₃)CH₂CH₃, and —N(CH₃)CH(CH₃)₂. In a yet further aspect, R² is selected from —F, —Cl, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂. In an even further aspect, R² is selected from —F, —Cl, methyl, —CH₂F, —CH₂Cl, —CHF₂, —CF₃, —CHCl₂, —CCl₃, —OCH₃, —OCH₂CH₃, —NHCH₃, and —N(CH₃)₂. In a still further aspect, R² is selected from —F, —Br, methyl, —CH₂F, —CH₂Cl, —CHF₂, —CF₃, —CHCl₂, —CCl₃, —OCH₃, —OCH₂CH₃, —NHCH₃, and —N(CH₃)₂. In a yet further aspect, R² is selected from —F, methyl, —CH₂F, —CHF₂, —CF₃, —OCH₃, —NHCH₃, and —N(CH₃)₂. In an even further aspect, R² is selected from —Br, methyl, —CH₂F, —CHF₂, —CF₃, —OCH₃, —NHCH₃, and —N(CH₃)₂.

In a further aspect, R² is selected from hydrogen, C1-C6 alkyl, C1-C6 monohaloalkyl, C1-C6 polyhaloalkyl, C1-C6 alkoxy, C1-C6 monoalkylamino, and C1-C6 dialkylamino. In a still further aspect, R² is selected from hydrogen, C1-C3 alkyl, C1-C3 monohaloalkyl, C1-C3 polyhaloalkyl, C1-C3 alkoxy, C1-C3 monoalkylamino, and C1-C3 dialkylamino. In a yet further aspect, R² is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH₂F, —CH₂Cl, —CH₂Br, —CH₂I, —CH₂CH₂F, —CH₂CH₂Cl, —CH₂CH₂Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, R$^2$ is selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^2$ is selected from hydrogen, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a yet further aspect, R$^2$ is selected from hydrogen, methyl, —CH$_2$F, —CH$_2$Cl, —CHF, —CF$_3$, —CHCl$_2$, —CCl$_3$, —OCH$_3$, —OCH$_2$CH$_3$, —NHCH$_3$, and —N(CH$_3$)$_2$. In an even further aspect, R$^2$ is selected from hydrogen, methyl, —CH$_2$F, —CHF$_2$, —CF$_3$, —OCH$_3$, —NHCH$_3$, and —N(CH$_3$)$_2$.

In a further aspect, R$^2$ is selected from hydrogen, halogen, C1-C6 alkyl, C1-C6 monohaloalkyl, and C1-C6 polyhaloalkyl. In a yet further aspect, R$^2$ is selected from hydrogen, halogen, C1-C3 alkyl, C1-C3 monohaloalkyl, and C1-C3 polyhaloalkyl. In a still further aspect, R$^2$ is selected from hydrogen, —F, —Cl, —Br, —I, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a yet further aspect, R$^2$ is selected from hydrogen, —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, R$^2$ is selected from hydrogen, —F, —Cl, —Br, methyl, ethyl, propyl, isopropyl, —CH$_2$F, —CH$_2$Cl, —CH$_2$CH$_2$F, —CH$_2$CH$_2$Cl, —CHF, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a still further aspect, R$^2$ is selected from hydrogen, —F, —Cl, methyl, ethyl, propyl, isopropyl, —CHF, —CH$_2$Cl, —CH$_2$CH$_2$F, —CH$_2$CH$_2$Cl, —CHF, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^2$ is selected from hydrogen, —F, —Br, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In an even further aspect, R$^2$ is selected from hydrogen, —F, —Cl, —Br, methyl, —CH$_2$F, —CH$_2$Cl, —CHF$_2$, —CF$_3$, —CHCl$_2$, and —CCl$_3$. In a still further aspect, R$^2$ is selected from hydrogen, —F, —Cl, methyl, —CHF, —CH$_2$Cl, —CHF, —CF$_3$, —CHCl$_2$, and —CCl$_3$. In a yet further aspect, R$^2$ is selected from hydrogen, —F, —Br, methyl, —CH$_2$F, —CH$_2$Cl, —CHF, —CF$_3$, —CHCl$_2$, and —CCl$_3$. In an even further, R$^2$ is selected from hydrogen, —F, methyl, —CHF, —CHF, and —CF$_3$. In a still further aspect, R$^2$ is selected from hydrogen, —Br, methyl, —CHF, —CHF, and —CF$_3$.

In a further aspect, R$^2$ is selected from hydrogen, halogen, C1-C6 alkoxy, C1-C6 monoalkylamino, and C1-C6 dialkylamino. In a still further aspect, R$^2$ is selected from hydrogen, halogen, C1-C3 alkoxy, C1-C3 monoalkylamino, and C1-C3 dialkylamino. In a yet further aspect, R$^2$ is selected from hydrogen, —F, —Cl, —Br, —I, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, R$^2$ is selected from hydrogen, —F, —Cl, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^2$ is selected from hydrogen, —F, —Cl, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a yet further aspect, R$^2$ is selected from hydrogen, —F, —Cl, —Br, —OCH$_3$, —OCH$_2$CH$_3$, —NHCH$_3$, and —N(CH$_3$)$_2$. In an even further aspect, R$^2$ is selected from hydrogen, —F, —Cl, —OCH$_3$, —OCH$_2$CH$_3$, —NHCH$_3$, and —N(CH$_3$)$_2$. In a still further aspect, R$^2$ is selected from hydrogen, —F, —Br, —OCH$_3$, —OCH$_2$CH$_3$, —NHCH$_3$, and —N(CH$_3$)$_2$. In a yet further aspect, R$^2$ is selected from hydrogen, —F, —OCH$_3$, —NHCH$_3$, and —N(CH$_3$)$_2$. In an even further aspect, R$^2$ is selected from hydrogen, —Br, —OCH$_3$, —NHCH$_3$, and —N(CH$_3$)$_2$.

In a further aspect, R$^2$ is selected from hydrogen, halogen, C1-C6 monohaloalkyl, C1-C6 polyhaloalkyl, C1-C6 alkoxy, C1-C6 monoalkylamino, and C1-C6 dialkylamino. In a still further aspect, R$^2$ is selected from hydrogen, halogen, C1-C3 monohaloalkyl, C1-C3 polyhaloalkyl, C1-C3 alkoxy, C1-C3 monoalkylamino, and C1-C3 dialkylamino. In a yet further aspect, R$^2$ is selected from hydrogen, —F, —Cl, —Br, —I, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$^2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In an even further aspect, R$^2$ is selected from hydrogen, —F, —Cl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^2$ is selected from hydrogen, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a yet further aspect, R$^2$ is selected from hydrogen, —F, —Cl, —Br, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$. In an even further aspect, R$^2$ is selected from hydrogen, —F, —Cl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$. In a still further aspect, R$^2$ is selected from hydrogen, —F, —Br, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$. In a yet further aspect, R$^2$ is selected from hydrogen, —F, —CH$_2$F, —CHF$_2$, —CF$_3$, —OCH$_3$, —NHCH$_3$, and —N(CH$_3$)$_2$. In an even further aspect, R$^2$ is selected from hydrogen, —Br, —CH$_2$F, —CHF$_2$, —CF$_3$, —OCH$_3$, —NHCH$_3$, and —N(CH$_3$)$_2$.

In a further aspect, R$^2$ is selected from hydrogen, halogen, and C1-C6 alkyl. In a still further aspect, R$^2$ is selected from hydrogen, —F, —Cl, —Br, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a yet further aspect, R$^2$ is selected from hydrogen, —F, —Cl, methyl, ethyl, propyl, isopropyl, tert-butyl, sec-butyl, and isobutyl. In an even further aspect, R$^2$ is selected from hydrogen, —F, —Cl, methyl, ethyl, propyl, and isopropyl. In a still further aspect, R$^2$ is selected from hydrogen, —F, —Cl, methyl, and ethyl. In one aspect, R$^2$ is selected from hydrogen, —F, —Cl, and methyl. In a yet further aspect, R$^2$ is selected from hydrogen, —F, —Cl, and ethyl. In an even further aspect, R$^2$ is selected from hydrogen, —F, —Br, methyl, ethyl, propyl, isopropyl, tert-butyl, sec-butyl, and isobutyl. In a still further aspect, R$^2$ is selected from hydrogen, —F, —Br, methyl, ethyl, propyl, and isopropyl. In a yet further aspect, R$^2$ is selected from hydrogen, —F, —Br, methyl and ethyl. In an even further aspect, R$^2$ is selected from hydrogen, —F, —Br, and methyl. In a still further aspect, R$^2$ is selected from hydrogen, —F, —Br, and ethyl.

In a further aspect, R$^2$ is selected from hydrogen, —F, methyl, ethyl, propyl, isopropyl, tert-butyl, sec-butyl, and isobutyl. In a still further aspect, R$^2$ is selected from hydrogen, —F, methyl, ethyl, propyl, and isopropyl. In a yet further aspect, R$^2$ is selected from hydrogen, —F, methyl, and ethyl. In an even further aspect, R$^2$ is selected from hydrogen, —F, and methyl. In a still further aspect, R$^2$ is selected from hydrogen, —F, and ethyl.

In a further aspect, R$^2$ is selected from hydrogen, —Br, methyl, ethyl, propyl, isopropyl, tert-butyl, sec-butyl, and isobutyl. In a still further aspect, R$^2$ is selected from hydrogen, —Br, methyl, ethyl, propyl, and isopropyl. In a yet further aspect, R$^2$ is selected from hydrogen, —Br, methyl, and ethyl. In an even further aspect, R$^2$ is selected from hydrogen, —Br, and methyl. In a still further aspect, R$^2$ is selected from hydrogen, —Br, and ethyl.

In a further aspect, R$^2$ is hydrogen or C1-C6 alkyl. In a still further aspect, R$^2$ is hydrogen or C1-C3 alkyl. In a yet further aspect, R$^2$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, R$^2$ is selected from hydrogen, methyl, ethyl, propyl, isopropyl, tert-butyl, sec-butyl, and isobutyl. In a still further aspect, R$^2$ is selected from hydrogen, methyl, ethyl, propyl, and isopropyl. In a yet further aspect, R$^2$ is selected from hydrogen, methyl, and ethyl. In an even further, R$^2$ is hydrogen or methyl. In a still further aspect, R$^2$ is hydrogen or ethyl.

In a further aspect, R$^2$ is selected from halogen and C1-C6 alkyl. In yet another aspect, R$^2$ is selected from —F, —Br, and methyl. In a still further aspect, R$^2$ is selected from —F, —Cl, —Br, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a yet further aspect, R$^2$ is selected from —F, —Cl, methyl, ethyl, propyl, isopropyl, tert-butyl, sec-butyl, and isobutyl. In an even further aspect, R$^2$ is selected from —F, —Cl, methyl, ethyl, propyl, and isopropyl. In a still further aspect, R$^2$ is selected from —F, —Cl, methyl, and ethyl. In a yet further aspects, R$^2$ is selected from —F, —Cl, and methyl. In an even further aspect, R$^2$ is selected from —F, —Cl, and ethyl.

In a further aspect, R$^2$ is selected from —F, methyl, ethyl, propyl, isopropyl, tert-butyl, sec-butyl, and isobutyl. In a yet further aspect, R$^2$ is selected from —F, methyl, ethyl, propyl, and isopropyl. In an even further aspect, R$^2$ is selected from —F, methyl, and ethyl. In a still further aspect, R$^2$ is selected from —F and methyl. In various further aspects, R$^2$ is selected from —F and ethyl.

In a further aspect, R$^2$ is selected from —Cl, methyl, ethyl, propyl, isopropyl, tert-butyl, sec-butyl, and isobutyl. In a yet further aspect, R$^2$ is selected from —Cl, methyl, ethyl, propyl, and isopropyl. In an even further aspect, R$^2$ is selected from —Cl, methyl, and ethyl. In a still further aspect, R$^2$ is selected from —Cl and methyl. In various further aspects, R$^2$ is selected from —Cl and ethyl.

In a further aspect, R$^2$ is selected from —Br, methyl, ethyl, propyl, isopropyl, tert-butyl, sec-butyl, and isobutyl. In a yet further aspect, R$^2$ is selected from —Br, methyl, ethyl, propyl, and isopropyl. In an even further aspect, R$^2$ is selected from —Br, methyl, and ethyl. In a still further aspect, R$^2$ is selected from —Br and methyl. In various further aspects, R$^2$ is selected from —Br and ethyl.

In a further aspect, R$^2$ is C1-C6 alkyl. In a further aspect, R$^2$ is C1-C3 alkyl. In a yet further aspect, R$^2$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, R$^2$ is selected from methyl, ethyl, propyl, isopropyl, tert-butyl, sec-butyl, and isobutyl. In a still further aspect, R$^2$ is selected from methyl, ethyl, propyl, and isopropyl. In a yet further, R$^2$ is selected from methyl and ethyl. In one aspect, R$^2$ is methyl. In a further aspect, R$^2$ is ethyl.

In various further aspects, R$^2$ is selected from —F, —Br, methyl, —CF$_3$, —OCH$_3$, and —NHCH$_3$. In a further aspect, R$^2$ is hydrogen or —CF$_3$. In a still further aspect, R$^2$ is hydrogen or —OCH$_3$. In a yet further aspect, R$^2$ is hydrogen or —NHCH$_3$. In a still further aspect, R$^2$ is —CF$_3$. In an even further aspect, R$^2$ is —OCH$_3$. In a still further aspect, R$^2$ is —NHCH$_3$.

In various further aspects, R$^2$ is hydrogen or halogen. In a still further aspect, the halogen is selected from —F, —Cl and —Br. In a yet further aspect, the halogen is selected from —F and —Cl. In an even further aspect, the halogen is selected from —F and —Br. In a still further aspect, the halogen is —F. In a yet further aspect, the halogen is —Cl. In an even further aspect, the halogen is —Br. In a still further aspect, $R^2$ is hydrogen or —F. In a yet further aspect, $R^2$ is hydrogen or —Br.

In a further aspect, $R^2$ is halogen. In still another aspect, $R^2$ is selected from —F, —Cl, and —Br. In a yet further aspect, the halogen is selected from —F, —Cl, and —Br. In an even further aspect, $R^2$ is selected from —F and —Cl. In a still further aspect, $R^2$ is selected from —F and —Br. In a yet further aspect, the halogen is —F. In an even further aspect, the halogen is —Cl. In a still further aspect, the halogen is —Br. In a yet further aspect, $R^2$ is —F. In a still further aspect, $R^2$ is —Br.

In various aspects, at least one of $R^1$ and $R^2$ is hydrogen. In a still further aspect, each of $R^1$ and $R^2$ is not hydrogen. In a yet further aspect, each of $R^1$ and $R^2$ is hydrogen. In an even further aspect, $R^1$ is not hydrogen, and $R^2$ is hydrogen. In a still further aspect, $R^1$ is hydrogen, and $R^2$ is not hydrogen.

In various aspects, at least one of $R^1$ and $R^2$ is methyl. In a still further aspect, each of $R^1$ and $R^2$ is not methyl. In a yet further aspect, each of $R^1$ and $R^2$ is methyl. In an even further aspect, $R^1$ is not methyl, and $R^2$ is methyl. In an even further aspect, $R^1$ is hydrogen, and $R^2$ is methyl. In a still further aspect, $R^1$ is methyl, and $R^2$ is hydrogen. In a yet further aspect, each of $R^1$ and $R^2$ is independently selected from hydrogen and methyl. In an even further aspect, one of $R^1$ and $R^2$ is hydrogen, and the other is methyl.

In various further aspects, $R^1$ is methyl; and $R^2$ is selected from halogen and C1-C6 alkyl. In a still further aspect, $R^1$ is methyl; and $R^2$ is selected from halogen and C1-C3 alkyl. In a yet further aspect, $R^1$ is methyl; and $R^2$ is selected from —F, —Cl, —Br, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, $R^1$ is methyl; and $R^2$ is selected from —F, —Cl, methyl, ethyl, propyl, isopropyl, tert-butyl, sec-butyl, and isobutyl. In a still further aspect, $R^1$ is methyl; and $R^2$ is selected from —F, —Cl, methyl, ethyl, propyl, and isopropyl. In a yet further aspect, $R^1$ is methyl; and $R^2$ is selected from —F, —Cl, methyl, and ethyl. In an even further aspect, $R^1$ is methyl; and $R^2$ is selected from —F, —Cl, and methyl. In a still further aspect, $R^1$ is methyl; and $R^2$ is selected from —F, —Cl, and ethyl.

In various further aspects, $R^1$ is methyl; and $R^2$ is selected from —F, methyl, ethyl, propyl, isopropyl, tert-butyl, sec-butyl, and isobutyl. In a further aspect, $R^1$ is methyl; and $R^2$ is selected from —F, methyl, ethyl, propyl, and isopropyl. In a still further aspect, $R^1$ is methyl; and $R^2$ is selected from —F, methyl, and ethyl. In a yet further aspect, $R^1$ is methyl; and $R^2$ is selected from —F and methyl. In an even further aspect, $R^1$ is methyl; and $R^2$ is selected from —F and ethyl.

In various further aspects, $R^1$ is methyl; and $R^2$ is selected from —Cl, methyl, ethyl, propyl, isopropyl, tert-butyl, sec-butyl, and isobutyl. In a further aspect, $R^1$ is methyl; and $R^2$ is selected from —Cl, methyl, ethyl, propyl, and isopropyl. In a still further aspect, $R^1$ is methyl; and $R^2$ is selected from —Cl, methyl, and ethyl. In a yet further aspect, $R^1$ is methyl; and $R^2$ is selected from —Cl and methyl. In an even further aspect, $R^1$ is methyl; and $R^2$ is selected from —Cl and ethyl.

In various further aspects, $R^1$ is methyl; and $R^2$ is selected from —Br, methyl, ethyl, propyl, isopropyl, tert-butyl, sec-butyl, and isobutyl. In a further aspect, $R^1$ is methyl; and $R^2$ is selected from —Br, methyl, ethyl, propyl, and isopropyl. In a still further aspect, $R^1$ is methyl; and $R^2$ is selected from —Br, methyl, and ethyl. In a yet further aspect, $R^1$ is methyl; and $R^2$ is selected from —Br and methyl. In an even further aspect, $R^1$ is methyl; and $R^2$ is selected from —Br and ethyl.

In a further aspect, $R^1$ is methyl; and $R^2$ is halogen. In a still further aspect, $R^1$ is methyl; and $R^2$ is selected from —F, —Cl, and —Br. In a yet further aspect, $R^1$ is methyl; and $R^2$ is selected from —F and —Cl. In an even further aspect, $R^1$ is methyl; and $R^2$ is selected from —F and —Br. In a still further aspect, $R^1$ is methyl; and wherein $R^2$ is —F. In a yet further aspect, $R^1$ is methyl; and $R^2$ is —Cl. In an even further aspect, $R^1$ is methyl; and $R^2$ is —Br.

In various further aspects, $R^1$ is methyl; and $R^2$ is C1-C6 alkyl. In a further aspect, $R^1$ is methyl; and wherein $R^2$ is C1-C3 alkyl. In a still further aspect, $R^1$ is methyl; and $R^2$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a yet further aspect, $R^1$ is methyl; hydrogen; and $R^2$ is selected from methyl, ethyl, propyl, isopropyl, tert-butyl, sec-butyl, and isobutyl. In an even further aspect, $R^1$ is methyl; and $R^2$ is selected from methyl, ethyl, propyl, and isopropyl. In a still further aspect, $R^1$ is methyl; and $R^2$ is selected from methyl and ethyl. In a yet further aspect, $R^1$ is methyl; and $R^2$ is ethyl.

In a further aspect, $R^1$ is methyl and $R^2$ is —CF$_3$. In a still further aspect, $R^1$ is methyl and $R^2$ is —OCH$_3$. In a yet further aspect, $R^1$ is methyl and $R^2$ is —NHCH$_3$. In an even further aspect, $R^1$ is methyl; and $R^2$ is —F. In a still further aspect, $R^1$ is methyl; and $R^2$ is —Br.

In various further aspects, $R^1$ is hydrogen; and $R^2$ is selected from halogen and C1-C6 alkyl. In a still further aspect, $R^1$ is hydrogen; and $R^2$ is selected from halogen and C1-C3 alkyl. In a yet further aspect, $R^1$ is hydrogen; and $R^2$ is selected from —F, —Cl, —Br, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, $R^1$ is hydrogen; and $R^2$ is selected from —F, —Cl, methyl, ethyl, propyl, isopropyl, tert-butyl, sec-butyl, and isobutyl. In a still further aspect, $R^1$ is hydrogen; and $R^2$ is selected from —F, —Cl, methyl, ethyl, propyl, and isopropyl. In a yet further aspect, $R^1$ is hydrogen; and $R^2$ is selected from —F, —Cl, methyl, and ethyl. In an even further aspect, $R^1$ is hydrogen; and $R^2$ is selected from —F, —Cl, and methyl. In a still further aspect, $R^1$ is hydrogen; and $R^2$ is selected from —F, —Cl, and ethyl.

In various further aspects, $R^1$ is hydrogen; and $R^2$ is selected from —F, methyl, ethyl, propyl, isopropyl, tert-butyl, sec-butyl, and isobutyl. In a further aspect, $R^1$ is hydrogen; and $R^2$ is selected from —F, methyl, ethyl, propyl, and isopropyl. In a still further aspect, $R^1$ is hydrogen; and $R^2$ is selected from —F, methyl, and ethyl. In a yet further aspect, $R^1$ is hydrogen; and $R^2$ is selected from —F and methyl. In an even further aspect, $R^1$ is hydrogen; and $R^2$ is selected from —F and ethyl.

In various further aspects, $R^1$ is hydrogen; and $R^2$ is selected from —Cl, methyl, ethyl, propyl, isopropyl, tert-butyl, sec-butyl, and isobutyl. In a further aspect, $R^1$ is hydrogen; and $R^2$ is selected from —Cl, methyl, ethyl, propyl, and isopropyl. In a still further aspect, $R^1$ is hydrogen; and $R^2$ is selected from —Cl, methyl, and ethyl. In a yet further aspect, $R^1$ is hydrogen; and $R^2$ is selected from —Cl and methyl. In an even further aspect, $R^1$ is hydrogen; and $R^2$ is selected from —Cl and ethyl.

In various further aspects, $R^1$ is hydrogen; and $R^2$ is selected from —Br, methyl, ethyl, propyl, isopropyl, tert-butyl, sec-butyl, and isobutyl. In a further aspect, $R^1$ is hydrogen; and $R^2$ is selected from —Br, methyl, ethyl, propyl, and isopropyl. In a still further aspect, $R^1$ is hydrogen; and $R^2$ is selected from —Br, methyl, and ethyl. In a yet further aspect, R$^1$ is hydrogen; and R$^2$ is selected from —Br and methyl. In an even further aspect, R$^1$ is hydrogen; and R$^2$ is selected from —Br and ethyl.

In a further aspect, R$^1$ is hydrogen; and R$^2$ is halogen. In a still further aspect, R$^1$ is hydrogen; and R$^2$ is selected from —F, —Cl, and —Br. In a yet further aspect, R$^1$ is hydrogen; and R$^2$ is selected from —F and —Cl. In an even further aspect, R$^1$ is hydrogen; and R$^2$ is selected from —F and —Br. In a still further aspect, R$^1$ is hydrogen; and wherein R$^2$ is —F. In a yet further aspect, R$^1$ is hydrogen; and R$^2$ is —Cl. In an even further aspect, R$^1$ is hydrogen; and R$^2$ is —Br.

In various further aspects, R$^1$ is hydrogen; and R$^2$ is C1-C6 alkyl. In a further aspect, R$^1$ is hydrogen; and wherein R$^2$ is C1-C3 alkyl. In a still further aspect, R$^1$ is hydrogen; and R$^2$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a yet further aspect, R$^1$ is hydrogen; and R$^2$ is selected from methyl, ethyl, propyl, isopropyl, tert-butyl, sec-butyl, and isobutyl. In an even further aspect, R$^1$ is hydrogen; and R$^2$ is selected from methyl, ethyl, propyl, and isopropyl. In a still further aspect, R$^1$ is hydrogen; and R$^2$ is selected from methyl and ethyl. In an even further aspect, R$^1$ is hydrogen; and R$^2$ is ethyl.

In a further aspect, R$^1$ is hydrogen; and R$^2$ is —CF$_3$. In a still further aspect, R$^1$ is hydrogen; and R$^2$ is —OCH$_3$. In a yet further aspect, R$^1$ is hydrogen; and R$^2$ is —NHCH$_3$. In an even further aspect, R$^1$ is hydrogen; and R$^2$ is —F. In a still further aspect, R$^1$ is hydrogen; and R$^2$ is —Br.

c. R$^3$ Groups

In one aspect, R$^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-. In various aspects, R$^3$ is hydrogen.

In a further aspect, R$^3$ is selected from hydrogen, C1-C8 alkyl, C1-C8 monohaloalkyl, and C1-C8 polyhaloalkyl. In a still further aspect, R$^3$ is selected from hydrogen, C1-C6 alkyl, C1-C6 monohaloalkyl, and C1-C6 polyhaloalkyl. In a yet further aspect, R$^3$ is selected from hydrogen, C1-C3 alkyl, C1-C3 monohaloalkyl, and C1-C3 polyhaloalkyl.

In a further aspect, R$^3$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, R$^3$ is selected from hydrogen, methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, R$^3$ is selected from hydrogen, methyl, ethyl, propyl, isopropyl, —CH$_2$F, —CH$_2$CH$_2$F, —CHF$_2$, —CF$_3$, —CH$_2$CHF$_2$, and —CH$_2$CF$_3$. In an even further aspect, R$^3$ is selected from hydrogen, methyl, —CH$_2$F, —CHF$_2$, and —CF$_3$. In an even further aspect, R$^3$ is selected from hydrogen, methyl, and —CF$_3$.

In various further aspects, R$^3$ is selected from C1-C8 alkyl, C1-C8 monohaloalkyl, and C1-C8 polyhaloalkyl. In a still further aspect, R$^3$ is selected from C1-C6 alkyl, C1-C6 monohaloalkyl, and C1-C6 polyhaloalkyl. In a yet further aspect, R$^3$ is selected from C1-C3 alkyl, C1-C3 monohaloalkyl, and C1-C3 polyhaloalkyl.

In a further aspect, R$^3$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, R$^3$ is selected from methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, R$^3$ is selected from methyl, ethyl, propyl, isopropyl, —CH$_2$F, —CH$_2$CH$_2$F, —CHF$_2$, —CF$_3$, —CH$_2$CHF$_2$, and —CH$_2$CF$_3$. In an even further aspect, R$^3$ is selected from methyl, —CH$_2$F, —CHF$_2$, and —CF$_3$. In an even further aspect, R$^3$ is selected from methyl and —CF$_3$.

In various further aspects, R$^3$ is selected from hydrogen and C1-C8 alkyl. In a still further aspect, R$^3$ is selected from hydrogen and C1-C6 alkyl. In a yet further aspect, R$^3$ is selected from hydrogen and C1-C3 alkyl.

In a further aspect, R$^3$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a still further aspect, R$^3$ is selected from hydrogen, methyl, ethyl, propyl, isopropyl, tert-butyl, sec-butyl, isobutyl, and tert-butyl. In a yet further aspect, R$^3$ is selected from hydrogen, methyl, ethyl, propyl, and isopropyl. In an even further aspect, R$^3$ is selected from hydrogen and methyl.

In various further aspects, R$^3$ is C1-C8 alkyl. In a still further aspect, R$^3$ is C1-C6 alkyl. In a yet further aspect, R$^3$ is C1-C3 alkyl.

In a further aspect, R$^3$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a still further aspect, R$^3$ is selected from methyl, ethyl, propyl, isopropyl, tert-butyl, sec-butyl, isobutyl, and tert-butyl. In a yet further aspect, R$^3$ is selected from methyl, ethyl, propyl, and isopropyl. In an even further aspect, R$^3$ is methyl.

In various aspects, at least one of R$^1$, R$^2$, and R$^3$ is hydrogen. In a still further aspect, each of R$^1$, R$^2$, and R$^3$ is not hydrogen. In a yet further aspect, each of R$^1$, R$^2$, and R$^3$ is hydrogen. In an even further aspect, each of R$^1$ and R$^2$ is not hydrogen, and R$^3$ is hydrogen. In a still further aspect, each of R$^1$ and R$^3$ is not hydrogen, and R$^2$ is hydrogen. In a yet further aspect, each of R$^2$ and R$^3$ is not hydrogen, and R$^1$ is hydrogen. In an even further aspect, each of R$^1$ and R$^2$ is hydrogen, and R$^3$ is not hydrogen. In a still further aspect, each of R$^1$ and R$^3$ is hydrogen, and R$^2$ is not hydrogen. In a yet further aspect, each of R$^2$ and R$^3$ is hydrogen, and R$^1$ is not hydrogen.

In various aspects, at least one of R$^1$, R$^2$, and R$^3$ is methyl. In a still further aspect, each of R$^1$, R$^2$, and R$^3$ is not methyl.

In a yet further aspect, each of $R^1$, $R^2$, and $R^3$ is methyl. In an even further aspect, $R^1$ is not methyl, and $R^2$ is methyl. In an even further aspect, $R^1$ is hydrogen, and $R^2$ is methyl. In a still further aspect, $R^1$ is methyl, and $R^2$ is hydrogen. In a yet further aspect, each of $R^1$ and $R^2$ is methyl, and $R^3$ is hydrogen. In an even further aspect, each of $R^1$ and $R^3$ is methyl, and $R^2$ is hydrogen. In a still further aspect, each of $R^2$ and $R^3$ is methyl, and $R^1$ is hydrogen. In a yet further aspect, each of $R^1$ and $R^2$ is hydrogen, and $R^3$ is methyl. In an even further aspect, each of $R^1$ and $R^3$ is hydrogen, and $R^2$ is methyl. In a still further aspect, each of $R^2$ and $R^3$ is hydrogen, and $R^1$ is methyl. In a yet further aspect, each of $R^1$, $R^2$, and $R^3$ is independently selected from hydrogen and methyl. In an even further aspect, two of $R^1$, $R^2$, and $R^3$ are hydrogen, and the other is methyl.

In various further aspects, each of $R^1$ and $R^2$ is methyl; and $R^3$ is C1-C6 alkyl. In a still further aspect, each of $R^1$ and $R^2$ is methyl; and $R^3$ is C1-C3 alkyl. In a yet further aspect, each of $R^1$ and $R^2$ is methyl; and $R^3$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, each of $R^1$ and $R^2$ is methyl; and $R^3$ is selected from methyl, ethyl, propyl, isopropyl, tert-butyl, sec-butyl, and isobutyl. In a still further aspect, each of $R^1$ and $R^2$ is methyl; and $R^3$ is selected from methyl, ethyl, propyl, and isopropyl. In a yet further aspect, each of $R^1$ and $R^2$ is methyl; and $R^3$ is selected from methyl and ethyl. In an even further aspect, each of $R^1$ and $R^2$ is methyl; and $R^3$ is ethyl.

In various further aspects, each of $R^1$ and $R^2$ is methyl; and $R^3$ is selected from hydrogen, C1-C6 alkyl, C1-C6 monohaloalkyl, and C1-C6 polyhaloalkyl. In a still further aspect, each of $R^1$ and $R^2$ is methyl; and $R^3$ is hydrogen, C1-C3 alkyl, C1-C3 monohaloalkyl, and C1-C3 polyhaloalkyl. In a yet further aspect, each of $R^1$ and $R^2$ is methyl; and $R^3$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In an even further aspect, each of $R^1$ and $R^2$ is methyl; and $R^3$ is selected from hydrogen, methyl, ethyl, propyl, isopropyl, tert-butyl, sec-butyl, isobutyl, —$CH_2F$, —$CH_2Cl$, —$CH_2CH_2F$, —$CH_2CH_2Cl$, —$CHF_2$, —$CF_3$, —$CH_2CHF_2$, and —$CH_2CF_3$. In a still further aspect, each of $R^1$ and $R^2$ is methyl; and $R^3$ is selected from hydrogen, methyl, ethyl, propyl, isopropyl, —$CH_2F$, —$CH_2CH_2F$, —$CHF_2$, —$CF_3$, —$CH_2CHF_2$, and —$CH_2CF_3$. In a yet further aspect, each of $R^1$ and $R^2$ is methyl; and $R^3$ is selected from hydrogen, methyl, ethyl, —$CH_2F$, —$CHF_2$, and —$CF_3$. In an even further aspect, each of $R^1$ and $R^2$ is methyl; and $R^3$ is selected from hydrogen, methyl and —$CF_3$.

In various further aspects, each of $R^1$ and $R^3$ is methyl; and $R^2$ is selected from halogen and C1-C6 alkyl. In a still further aspect, each of $R^1$ and $R^3$ is methyl; and $R^2$ is selected from halogen and C1-C3 alkyl. In a yet further aspect, each of $R^1$ and $R^3$ is methyl; and $R^2$ is selected from —F, —Cl, —Br, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, each of $R^1$ and $R^3$ is methyl; and $R^2$ is selected from —F, —Cl, methyl, ethyl, propyl, isopropyl, tert-butyl, sec-butyl, and isobutyl. In a still further aspect, each of $R^1$ and $R^3$ is methyl; and $R^2$ is selected from —F, —Cl, methyl, ethyl, propyl, and isopropyl. In a yet further aspect, each of $R^1$ and $R^3$ is methyl; and $R^2$ is selected from —F, —Cl, methyl, and ethyl. In an even further aspect, each of $R^1$ and $R^3$ is methyl; and $R^2$ is selected from —F, —Cl, and methyl. In a still further aspect, each of $R^1$ and $R^3$ is methyl; and $R^2$ is selected from —F, —Cl, and ethyl.

In various further aspects, each of $R^1$ and $R^3$ is methyl; and $R^2$ is selected from —F, methyl, ethyl, propyl, isopropyl, tert-butyl, sec-butyl, and isobutyl. In a further aspect, each of $R^1$ and $R^3$ is methyl; and $R^2$ is selected from —F, methyl, ethyl, propyl, and isopropyl. In a still further aspect, each of $R^1$ and $R^3$ is methyl; and $R^2$ is selected from —F, methyl, and ethyl. In a yet further aspect, each of $R^1$ and $R^3$ is methyl; and $R^2$ is selected from —F and methyl. In an even further aspect, each of $R^1$ and $R^3$ is methyl; and $R^2$ is selected from —F and ethyl.

In various further aspects, each of $R^1$ and $R^3$ is methyl; and $R^2$ is selected from —Cl, methyl, ethyl, propyl, isopropyl, tert-butyl, sec-butyl, and isobutyl. In a further aspect, each of $R^1$ and $R^3$ is methyl; and $R^2$ is selected from —Cl, methyl, ethyl, propyl, and isopropyl. In a still further aspect, each of $R^1$ and $R^3$ is methyl; and $R^2$ is selected from —Cl, methyl, and ethyl. In a yet further aspect, $R^1$ is methyl; and $R^2$ is selected from —Cl and methyl. In an even further aspect, each of $R^1$ and $R^3$ is methyl; and $R^2$ is selected from —Cl and ethyl.

In various further aspects, each of $R^1$ and $R^3$ is methyl; and $R^2$ is selected from —Br, methyl, ethyl, propyl, isopropyl, tert-butyl, sec-butyl, and isobutyl. In a further aspect, each of $R^1$ and $R^3$ is methyl; and $R^2$ is selected from —Br, methyl, ethyl, propyl, and isopropyl. In a still further aspect, each of $R^1$ and $R^3$ is methyl; and $R^2$ is selected from —Br, methyl, and ethyl. In a yet further aspect, each of $R^1$ and $R^3$ is methyl; and $R^2$ is selected from —Br and methyl. In an even further aspect, each of $R^1$ and $R^3$ is methyl; and $R^2$ is selected from —Br and ethyl.

In a further aspect, each of $R^1$ and $R^3$ is methyl; and $R^2$ is halogen. In a still further aspect, each of $R^1$ and $R^3$ is methyl; and $R^2$ is selected from —F, —Cl, and —Br. In a yet further aspect, each of $R^1$ and $R^3$ is methyl; and $R^2$ is selected from —F and —Cl. In an even further aspect, each of $R^1$ and $R^3$ is methyl; and $R^2$ is selected from —F and —Br. In a still further aspect, $R^1$ is methyl; and wherein $R^2$ is —F. In a yet further aspect, each of $R^1$ and $R^3$ is methyl; and $R^2$ is —Cl. In an even further aspect, each of $R^1$ and $R^3$ is methyl; and $R^2$ is —Br.

In various further aspects, each of $R^1$ and $R^3$ is methyl; and $R^2$ is C1-C6 alkyl. In a further aspect, each of $R^1$ and $R^3$ is methyl; and $R^2$ is C1-C3 alkyl. In a still further aspect, each of $R^1$ and $R^3$ is methyl; and $R^2$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a yet further aspect, each of $R^1$ and $R^3$ is methyl; and $R^2$ is selected from methyl, ethyl, propyl, isopropyl, tert-butyl, sec-butyl, and isobutyl. In an even further aspect, each of $R^1$ and $R^3$ is methyl; and $R^2$ is selected from methyl, ethyl, propyl, and isopropyl. In a still further aspect, each of $R^1$ and $R^3$ is methyl; and $R^2$ is selected from methyl and ethyl. In a yet further aspect, each of $R^1$ and $R^3$ is methyl; and $R^2$ is ethyl.

In a further aspect, each of $R^1$ and $R^3$ is methyl; and $R^2$ is —$CF_3$. In a still further aspect, each of $R^1$ and $R^3$ is methyl; and $R^2$ is —$OCH_3$. In a yet further aspect, each of $R^1$ and $R^3$ is methyl; and $R^2$ is —$NHCH_3$. In an even further aspect, each of $R^1$ and $R^3$ is methyl; and $R^2$ is —F. In a still further aspect, each of $R^1$ and $R^3$ is methyl; and $R^2$ is —Br.

In various further aspects, each of $R^2$ and $R^3$ is methyl; and $R^1$ is selected from halogen and C1-C6 alkyl. In a still further aspect, each of $R^2$ and $R^3$ is methyl; and $R^1$ is selected from halogen and C1-C3 alkyl. In a yet further aspect, each of $R^2$ and $R^3$ is methyl; and $R^1$ is selected from —F, —Cl, —Br, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In an even further aspect, each of $R^2$ and $R^3$ is methyl; and $R^1$ is selected from —F, —Cl, methyl, ethyl, propyl, isopropyl, tert-butyl, sec-butyl, and isobutyl. In a still further aspect, each of $R^2$ and $R^3$ is methyl; and $R^1$ is selected from —F, —Cl, methyl, ethyl, propyl, and isopropyl. In a yet further aspect, each of $R^2$ and $R^3$ is methyl; and $R^1$ is selected from —F, —Cl, methyl, and ethyl. In an even further aspect, each of $R^2$ and $R^3$ is methyl; and $R^1$ is selected from —F, —Cl, and methyl. In a still further aspect, each of $R^2$ and $R^3$ is methyl; and $R^1$ is selected from —F, —Cl, and ethyl.

In various further aspects, each of $R^2$ and $R^3$ is methyl; and $R^1$ is selected from —F, methyl, ethyl, propyl, isopropyl, tert-butyl, sec-butyl, and isobutyl. In a further aspect, each of $R^2$ and $R^3$ is methyl; and $R^1$ is selected from —F, methyl, ethyl, propyl, and isopropyl. In a still further aspect, each of $R^2$ and $R^3$ is methyl; and $R^1$ is selected from —F, methyl, and ethyl. In a yet further aspect, each of $R^2$ and $R^3$ is methyl; and $R^1$ is selected from —F and methyl. In an even further aspect, each of $R^2$ and $R^3$ is methyl; and $R^1$ is selected from —F and ethyl.

In various further aspects, each of $R^2$ and $R^3$ is methyl; and $R^1$ is selected from —Cl, methyl, ethyl, propyl, isopropyl, tert-butyl, sec-butyl, and isobutyl. In a further aspect, each of $R^2$ and $R^3$ is methyl; and $R^1$ is selected from —Cl, methyl, ethyl, propyl, and isopropyl. In a still further aspect, each of $R^2$ and $R^3$ is methyl; and $R^1$ is selected from —Cl, methyl, and ethyl. In a yet further aspect, $R^1$ is methyl; and $R^2$ is selected from —Cl and methyl. In an even further aspect, each of $R^2$ and $R^3$ is methyl; and $R^1$ is selected from —Cl and ethyl.

In various further aspects, each of $R^2$ and $R^3$ is methyl; and $R^1$ is selected from —Br, methyl, ethyl, propyl, isopropyl, tert-butyl, sec-butyl, and isobutyl. In a further aspect, each of $R^2$ and $R^3$ is methyl; and $R^1$ is selected from —Br, methyl, ethyl, propyl, and isopropyl. In a still further aspect, each of $R^2$ and $R^3$ is methyl; and $R^1$ is selected from —Br, methyl, and ethyl. In a yet further aspect, each of $R^2$ and $R^3$ is methyl; and $R^1$ is selected from —Br and methyl. In an even further aspect, each of $R^2$ and $R^3$ is methyl; and $R^1$ is selected from —Br and ethyl.

In a further aspect, each of $R^2$ and $R^3$ is methyl; and $R^1$ is halogen. In a still further aspect, each of $R^2$ and $R^3$ is methyl; and $R^1$ is selected from —F, —Cl, and —Br. In a yet further aspect, each of $R^2$ and $R^3$ is methyl; and $R^1$ is selected from —F and —Cl. In an even further aspect, each of $R^2$ and $R^3$ is methyl; and $R^1$ is selected from —F and —Br. In a still further aspect, $R^1$ is methyl; and wherein $R^2$ is —F. In a yet further aspect, each of $R^2$ and $R^3$ is methyl; and $R^1$ is —Cl. In an even further aspect, each of $R^2$ and $R^3$ is methyl; and $R^1$ is —Br.

In various further aspects, each of $R^2$ and $R^3$ is methyl; and $R^1$ is C1-C6 alkyl. In a further aspect, each of $R^2$ and $R^3$ is methyl; and $R^1$ is C1-C3 alkyl. In a still further aspect, each of $R^2$ and $R^3$ is methyl; and $R^1$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a yet further aspect, each of $R^2$ and $R^3$ is methyl; and $R^1$ is selected from methyl, ethyl, propyl, isopropyl, tert-butyl, sec-butyl, and isobutyl. In an even further aspect, each of $R^2$ and $R^3$ is methyl; and $R^1$ is selected from methyl, ethyl, propyl, and isopropyl. In a still further aspect each of $R^2$ and $R^3$ is methyl; and $R^1$ is selected from methyl and ethyl. In a yet further aspect, each of $R^2$ and $R^3$ is methyl; and $R^1$ is ethyl.

In a further aspect, each of $R^2$ and $R^3$ is methyl; and $R^1$ is —$CF_3$. In a still further aspect, each of $R^2$ and $R^3$ is methyl; and $R^1$ is —$OCH_3$. In a yet further aspect, each of $R^2$ and $R^3$ is methyl; and $R^1$ is —$NHCH_3$. In an even further aspect, each of $R^2$ and $R^3$ is methyl; and $R^1$ is —F. In a still further aspect, each of $R^2$ and $R^3$ is methyl; and $R^1$ is —Br.

In various further aspects, $R^3$ is selected from hydrogen, C1-C6 alkyl, C1-C6 monohaloalkyl, C1-C6 polyhaloalkyl, C3-C6 cycloalkyl, C2-C5 heterocycloalkyl, (C3-C6 cycloalkyl)-(C1-C6 alkyl)-, and (C2-C5 heterocycloalkyl)-(C1-C6 alkyl)-. In a further aspect, $R^3$ is selected from hydrogen, C1-C6 alkyl, C1-C6 monohaloalkyl, C1-C6 polyhaloalkyl, C3-C6 cycloalkyl, C2-C5 heterocycloalkyl, (C3-C6 cycloalkyl)-(C1-C3 alkyl)-, and (C2-C5 heterocycloalkyl)-(C1-C3 alkyl)-. In a still further aspect, $R^3$ is selected from hydrogen, C1-C3 alkyl, C1-C3 monohaloalkyl, C1-C3 polyhaloalkyl, C3-C6 cycloalkyl, C2-C5 heterocycloalkyl, (C3-C6 cycloalkyl)-(C1-C3 alkyl)-, and (C2-C5 heterocycloalkyl)-(C1-C3 alkyl)-.

In a further aspect, $R^3$ is selected from hydrogen, C1-C3 alkyl, C1-C3 monohaloalkyl, C1-C3 polyhaloalkyl, C3-C6 cycloalkyl, C2-C5 heterocycloalkyl, (C3-C6 cycloalkyl)-$(CH_2)_3$—, (C3-C6 cycloalkyl)-$(CH_2)_2$—, (C3-C6 cycloalkyl)-$CH_2$—, (C2-C5 heterocycloalkyl)-$(CH_2)_3$—, (C2-C5 heterocycloalkyl)-$(CH_2)_2$—, and (C2-C5 heterocycloalkyl)-$CH_2$—. In a still further aspect, $R^3$ is selected from hydrogen, C1-C3 alkyl, C1-C3 monohaloalkyl, C1-C3 polyhaloalkyl, C3-C6 cycloalkyl, C2-C5 heterocycloalkyl, (C3-C6 cycloalkyl)-$(CH_2)_2$—, (C3-C6 cycloalkyl)-$CH_2$—, (C2-C5 heterocycloalkyl)-$(CH_2)_2$—, and (C2-C5 heterocycloalkyl)-$CH_2$—. In a yet further aspect, $R^3$ is selected from hydrogen, C1-C3 alkyl, C1-C3 monohaloalkyl, C1-C3 polyhaloalkyl, C3-C6 cycloalkyl, C2-C5 heterocycloalkyl, (C3-C6 cycloalkyl)-$CH_2$—, and (C2-C5 heterocycloalkyl)-$CH_2$—.

In a further aspect, $R^3$ is selected from hydrogen, methyl, ethyl, propyl, isopropyl, —CHF, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —$CH_2$-cyclopropyl, —$CH_2$-cyclobutyl, —$CH_2$-cyclopentyl, —$CH_2$-cyclohexyl, —$CH_2$-pyrrolidinyl, —$CH_2$-tetrahydrofuranyl, —$CH_2$-tetrahydrothiophenyl, —$CH_2$-piperidinyl, —$CH_2$-tetrahydro-2H-pyranyl, —$CH_2$-tetrahydro-2H-thiopyranyl, —$CH_2$-azetidinyl, —$CH_2$-oxetanyl, —$CH_2$-thietanyl, —$CH_2$-aziridinyl, —$CH_2$-oxiranyl, —$CH_2$-thiiranyl, —$CH_2$-diazetidinyl, —$CH_2$-pyrazolidinyl, —$CH_2$-piperazinyl, —$CH_2$-imidazlidinyl, —$CH_2$-tetrahydropyrimidinyl, —$CH_2$-hexahydropyridazinyl, —$(CH_2)_2$-cyclopropyl, —$(CH_2)_2$-cyclobutyl, —$(CH_2)_2$-cyclopentyl, —$(CH_2)_2$-cyclohexyl, —$(CH_2)_2$-pyrrolidinyl, —$(CH_2)_2$-tetrahydrofuranyl, —$(CH_2)_2$-tetrahydrothiophenyl, —$(CH_2)_2$-piperidinyl, —$(CH_2)_2$-tetrahydro-2H-pyranyl, —$(CH_2)_2$-tetrahydro-2H-thiopyranyl, —$(CH_2)_2$-azetidinyl, —$(CH_2)_2$-oxetanyl, —$(CH_2)_2$-thietanyl, —$(CH_2)_2$-aziridinyl, —$(CH_2)_2$-oxiranyl, —$(CH_2)_2$-thiiranyl, —$(CH_2)_2$-diazetidinyl, —$(CH_2)_2$-pyrazolidinyl, —$(CH_2)_2$-piperazinyl, —$(CH_2)_2$-imidazlidinyl, —$(CH_2)_2$-tetrahydropyrimidinyl, —$(CH_2)_2$-hexahydropyridazinyl, —$(CH_2)_3$-cyclopropyl, —$(CH_2)_3$-cyclobutyl, —$(CH_2)_3$-cyclopentyl, —$(CH_2)_3$-cyclohexyl, —$(CH_2)_3$-pyrrolidinyl, —$(CH_2)_3$-tetrahydrofuranyl, —(CH$_2$)$_3$-tetrahydrothiophenyl, —(CH$_2$)$_3$-piperidinyl, —(CH$_2$)$_3$-tetrahydro-2H-pyranyl, —(CH$_2$)$_3$-tetrahydro-2H-thiopyranyl, —(CH$_2$)$_3$-azetidinyl, —(CH$_2$)$_3$-oxetanyl, —(CH$_2$)$_3$-thietanyl, —(CH$_2$)$_3$-aziridinyl, —(CH$_2$)$_3$-oxiranyl, —(CH$_2$)$_3$-thiiranyl, —(CH$_2$)$_3$-diazetidinyl, —(CH$_2$)$_3$-pyrazolidinyl, —(CH$_2$)$_3$-piperazinyl, —(CH$_2$)$_3$-imidazlidinyl, —(CH$_2$)$_3$-tetrahydropyrimidinyl, and —(CH$_2$)$_3$-hexahydropyridazinyl.

In a further aspect, R$^3$ is selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, and —(CH$_2$)$_2$-hexahydropyridazinyl.

In a further aspect, R$^3$ is selected from hydrogen, methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrrolidinyl, tetrahydrofuranyl, piperidinyl, tetrahydro-2H-pyranyl, azetidinyl, oxetanyl, aziridinyl, oxiranylpyrazolidinyl, piperazinyl, imidazlidinyl, tetrahydropyrimidinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-piperidinyl, —CH$_2$-tetrahydro-2H-pyranyl, —CH$_2$-azetidinyl, —CH$_2$-oxetanyl, —CH$_2$-aziridinyl, —CH$_2$-oxiranyl, —CH$_2$-pyrazolidinyl, —CH$_2$-piperazinyl, —CH$_2$-imidazlidinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-piperidinyl, —(CH$_2$)$_2$-tetrahydro-2H-pyranyl, —(CH$_2$)$_2$-azetidinyl, —(CH$_2$)$_2$-oxetanyl, —(CH$_2$)$_2$-aziridinyl, —(CH$_2$)$_2$-oxiranyl, —(CH$_2$)$_2$-pyrazolidinyl, —(CH$_2$)$_2$-piperazinyl, and —(CH$_2$)$_2$-imidazlidinyl.

In a further aspect, R$^3$ is selected from hydrogen, methyl, —CH$_2$F, —CHF$_2$, —CF$_3$, cyclopropyl, cyclobutyl, cyclopentyl, cyclohexyl, pyrrolidinyl, tetrahydrofuranyl, piperidinyl, tetrahydro-2H-pyranyl, azetidinyl, oxetanyl, aziridinyl, oxiranylpyrazolidinyl, piperazinyl, imidazlidinyl, tetrahydropyrimidinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-piperidinyl, —CH$_2$-tetrahydro-2H-pyranyl, —CH$_2$-azetidinyl, —CH$_2$-oxetanyl, —CH$_2$-aziridinyl, —CH$_2$-oxiranyl, —CH$_2$-pyrazolidinyl, —CH$_2$-piperazinyl, and —CH$_2$-imidazlidinyl.

In a further aspect, R$^3$ is selected from hydrogen, methyl, —CH$_2$F, —CHF$_2$, —CF$_3$, cyclopropyl, cyclobutyl, cyclopentyl, cyclohexyl, pyrrolidinyl, tetrahydrofuranyl, piperidinyl, tetrahydro-2H-pyranyl, azetidinyl, oxetanyl, aziridinyl, oxiranylpyrazolidinyl, piperazinyl, imidazlidinyl, and tetrahydropyrimidinyl.

In a further aspect, R$^3$ is selected from C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-. In a still further aspect, R$^3$ is selected from C1-C3 alkyl, C1-C3 monohaloalkyl, C1-C3 polyhaloalkyl, C3-C6 cycloalkyl, C2-C5 heterocycloalkyl, (C3-C6 cycloalkyl)-(C1-C6 alkyl)-, and (C2-C5 heterocycloalkyl)-(C1-C6 alkyl)-. In a yet further aspect, R$^3$ is selected from hydrogen, C1-C3 alkyl, C1-C3 monohaloalkyl, C1-C3 polyhaloalkyl, C3-C6 cycloalkyl, C2-C5 heterocycloalkyl, (C3-C6 cycloalkyl)-(C1-C3 alkyl)-, and (C2-C5 heterocycloalkyl)-(C1-C3 alkyl)-. In an even further aspect, R$^3$ is selected from hydrogen, C1-C3 alkyl, C1-C3 monohaloalkyl, C1-C3 polyhaloalkyl, C3-C6 cycloalkyl, C2-C5 heterocycloalkyl, (C3-C6 cycloalkyl)-CH$_2$—, and (C2-C5 heterocycloalkyl)-CH$_2$—.

In a further aspect, R$^3$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, —(CH$_2$)$_2$-hexahydropyridazinyl, —(CH$_2$)$_3$-cyclopropyl, —(CH$_2$)$_3$-cyclobutyl, —(CH$_2$)$_3$-cyclopentyl, —(CH$_2$)$_3$-cyclohexyl, —(CH$_2$)$_3$-pyrrolidinyl, —(CH$_2$)$_3$-tetrahydrofuranyl, —(CH$_2$)$_3$-tetrahydrothiophenyl, —(CH$_2$)$_3$-piperidinyl, —(CH$_2$)$_3$-tetrahydro-2H-pyranyl, —(CH$_2$)$_3$-tetrahydro-2H-thiopyranyl, —(CH$_2$)$_3$-azetidinyl, —(CH$_2$)$_3$-oxetanyl, —(CH$_2$)$_3$-thietanyl, —(CH$_2$)$_3$-aziridinyl, —(CH$_2$)$_3$-oxiranyl, —(CH$_2$)$_3$-thiiranyl, —(CH$_2$)$_3$-diazetidinyl, —(CH$_2$)$_3$- pyrazolidinyl, —(CH$_2$)$_3$-piperazinyl, —(CH$_2$)$_3$-imidazlidinyl, —(CH$_2$)$_3$-tetrahydropyrimidinyl, and —(CH$_2$)$_3$-hexahydropyridazinyl.

In a further aspect, R$^3$ is selected from methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, —(CH$_2$)$_2$-hexahydropyridazinyl, —(CH$_2$)$_3$-cyclopropyl, —(CH$_2$)$_3$-cyclobutyl, —(CH$_2$)$_3$-cyclopentyl, —(CH$_2$)$_3$-cyclohexyl, —(CH$_2$)$_3$-pyrrolidinyl, —(CH$_2$)$_3$-tetrahydrofuranyl, —(CH$_2$)$_3$-tetrahydrothiophenyl, —(CH$_2$)$_3$-piperidinyl, —(CH$_2$)$_3$-tetrahydro-2H-pyranyl, —(CH$_2$)$_3$-tetrahydro-2H-thiopyranyl, —(CH$_2$)$_3$-azetidinyl, —(CH$_2$)$_3$-oxetanyl, —(CH$_2$)$_3$-thietanyl, —(CH$_2$)$_3$-aziridinyl, —(CH$_2$)$_3$-oxiranyl, —(CH$_2$)$_3$-thiiranyl, —(CH$_2$)$_3$-diazetidinyl, —(CH$_2$)$_3$-pyrazolidinyl, —(CH$_2$)$_3$-piperazinyl, —(CH$_2$)$_3$-imidazlidinyl, —(CH$_2$)$_3$-tetrahydropyrimidinyl, and —(CH$_2$)$_3$-hexahydropyridazinyl.

In a further aspect, R$^3$ is selected from methyl, —CHF, —CH$_2$Cl, —CHF, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, —(CH$_2$)$_2$-hexahydropyridazinyl, —(CH$_2$)$_3$-cyclopropyl, —(CH$_2$)$_3$-cyclobutyl, —(CH$_2$)$_3$-cyclopentyl, —(CH$_2$)$_3$-cyclohexyl, —(CH$_2$)$_3$-pyrrolidinyl, —(CH$_2$)$_3$-tetrahydrofuranyl, —(CH$_2$)$_3$-tetrahydrothiophenyl, —(CH$_2$)$_3$-piperidinyl, —(CH$_2$)$_3$-tetrahydro-2H-pyranyl, —(CH$_2$)$_3$-tetrahydro-2H-thiopyranyl, —(CH$_2$)$_3$-azetidinyl, —(CH$_2$)$_3$-oxetanyl, —(CH$_2$)$_3$-thietanyl, —(CH$_2$)$_3$-aziridinyl, —(CH$_2$)$_3$-oxiranyl, —(CH$_2$)$_3$-thiiranyl, —(CH$_2$)$_3$-diazetidinyl, —(CH$_2$)$_3$-pyrazolidinyl, —(CH$_2$)$_3$-piperazinyl, —(CH$_2$)$_3$-imidazlidinyl, —(CH$_2$)$_3$-tetrahydropyrimidinyl, and —(CH$_2$)$_3$-hexahydropyridazinyl.

In a further aspect, R$^3$ is selected from methyl, —CH$_2$F, —CHF$_2$, —CF$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, —(CH$_2$)$_2$-hexahydropyridazinyl, —(CH$_2$)$_3$-cyclopropyl, —(CH$_2$)$_3$-cyclobutyl, —(CH$_2$)$_3$-cyclopentyl, —(CH$_2$)$_3$-cyclohexyl, —(CH$_2$)$_3$-pyrrolidinyl, —(CH$_2$)$_3$-tetrahydrofuranyl, —(CH$_2$)$_3$-tetrahydrothiophenyl, —(CH$_2$)$_3$-piperidinyl, —(CH$_2$)$_3$-tetrahydro-2H-pyranyl, —(CH$_2$)$_3$-tetrahydro-2H-thiopyranyl, —(CH$_2$)$_3$-azetidinyl, —(CH$_2$)$_3$-oxetanyl, —(CH$_2$)$_3$-thietanyl, —(CH$_2$)$_3$-aziridinyl, —(CH$_2$)$_3$-oxiranyl, —(CH$_2$)$_3$-thiiranyl, —(CH$_2$)$_3$-diazetidinyl, —(CH$_2$)$_3$-pyrazolidinyl, —(CH$_2$)$_3$-piperazinyl, —(CH$_2$)$_3$-imidazlidinyl, —(CH$_2$)$_3$-tetrahydropyrimidinyl, and —(CH$_2$)$_3$-hexahydropyridazinyl.

In a further aspect, R$^3$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro- 2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, and —(CH$_2$)$_2$-hexahydropyridazinyl.

In a further aspect, R$^3$ is selected from methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, and —(CH$_2$)$_2$-hexahydropyridazinyl.

In a further aspect, R$^3$ is selected from methyl, —CHF, —CH$_2$Cl, —CHF, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, and —(CH$_2$)$_2$-hexahydropyridazinyl.

In a further aspect, R$^3$ is selected from methyl, —CHF, —CHF, —CF$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, and —(CH$_2$)$_2$-hexahydropyridazinyl.

In a further aspect, R$^3$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, and —CH$_2$-hexahydropyridazinyl.

In a further aspect, R$^3$ is selected from methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$- tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, and —CH$_2$-hexahydropyridazinyl.

In a further aspect, R$^3$ is selected from methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, and —CH$_2$-hexahydropyridazinyl.

In a further aspect, R$^3$ is selected from methyl, —CH$_2$F, —CHF$_2$, —CF$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$-aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, and —CH$_2$-hexahydropyridazinyl.

In a further aspect, R$^3$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, and hexahydropyridazinyl.

In a further aspect, R$^3$ is selected from methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, and hexahydropyridazinyl.

In a further aspect, R$^3$ is selected from methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, and hexahydropyridazinyl.

In a further aspect, R$^3$ is selected from methyl, —CH$_2$F, —CHF$_2$, —CF$_3$, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, and hexahydropyridazinyl.

In various further aspects, R$^3$ is selected from hydrogen, C1-C6 alkyl, C1-C6 monohaloalkyl, and C1-C6 polyhaloalkyl. In a further aspect, R$^3$ is selected from hydrogen, C1-C3 alkyl, C1-C3 monohaloalkyl, and C1-C3 polyhaloalkyl. In a still further aspect, R$^3$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a yet further aspect, R$^3$ is selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, R$^3$ is selected from hydrogen, methyl, —CH$_2$F, —CH$_2$Cl, —CHF$_2$, —CF$_3$, —CHCl$_2$, and —CCl$_3$. In a still further aspect, R$^3$ is selected from hydrogen, methyl, —CH$_2$F, —CHF$_2$, and —CF$_3$. In various further aspects, R$^3$ is selected from hydrogen, methyl, and —CF$_3$.

In a further aspect, R$^3$ is selected from hydrogen, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-. In a still further aspect, R$^3$ is selected from hydrogen, C3-C6 cycloalkyl, C2-C5 heterocycloalkyl, (C3-C6 cycloalkyl)-(C1-C6 alkyl)-, and (C2-C5 heterocycloalkyl)-(C1-C6 alkyl)-. In a yet further aspect, R$^3$ is selected from hydrogen, C3-C6 cycloalkyl, C2-C5 heterocycloalkyl, (C3-C6 cycloalkyl)-(C1-C3 alkyl)-, and (C2-C5 heterocycloalkyl)-(C1-C3 alkyl)-. In a further aspect, R$^3$ is selected from hydrogen, C3-C6 cycloalkyl, C2-C5 heterocycloalkyl, (C3-C6 cycloalkyl)-CH$_2$—, and (C2-C5 heterocycloalkyl)-CH$_2$—.

In a further aspect, R$^3$ is selected from hydrogen, cyclopropyl, cyclobutyl, cyclopentyl, cyclohexyl, pyrrolidinyl, tetrahydrofuranyl, tetrahydrothiophenyl, piperidinyl, tetrahydro-2H-pyranyl, tetrahydro-2H-thiopyranyl, azetidinyl, oxetanyl, thietanyl, aziridinyl, oxiranyl, thiiranyl, diazetidinyl, pyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-tetrahydrothiophenyl, —CH$_2$-piperidinyl, —CH$_2$-tetrahydro-2H-pyranyl, —CH$_2$-tetrahydro-2H-thiopyranyl, —CH$_2$-azetidinyl, —CH$_2$-oxetanyl, —CH$_2$-thietanyl, —CH$_2$- aziridinyl, —CH$_2$-oxiranyl, —CH$_2$-thiiranyl, —CH$_2$-diazetidinyl, —CH$_2$-pyrazolidinyl, —CH$_2$-piperazinyl, —CH$_2$-imidazlidinyl, —CH$_2$-tetrahydropyrimidinyl, —CH$_2$-hexahydropyridazinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-tetrahydrothiophenyl, —(CH$_2$)$_2$-piperidinyl, —(CH$_2$)$_2$-tetrahydro-2H-pyranyl, —(CH$_2$)$_2$-tetrahydro-2H-thiopyranyl, —(CH$_2$)$_2$-azetidinyl, —(CH$_2$)$_2$-oxetanyl, —(CH$_2$)$_2$-thietanyl, —(CH$_2$)$_2$-aziridinyl, —(CH$_2$)$_2$-oxiranyl, —(CH$_2$)$_2$-thiiranyl, —(CH$_2$)$_2$-diazetidinyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, —(CH$_2$)$_2$-hexahydropyridazinyl. —(CH$_2$)$_3$-cyclopropyl, —(CH$_2$)$_3$-cyclobutyl, —(CH$_2$)$_3$-cyclopentyl, —(CH$_2$)$_3$-cyclohexyl, —(CH$_2$)$_3$-pyrrolidinyl, —(CH$_2$)$_3$-tetrahydrofuranyl, —(CH$_2$)$_3$-tetrahydrothiophenyl, —(CH$_2$)$_3$-piperidinyl, —(CH$_2$)$_3$-tetrahydro-2H-pyranyl, —(CH$_2$)$_3$-tetrahydro-2H-thiopyranyl, —(CH$_2$)$_3$-azetidinyl, —(CH$_2$)$_3$-oxetanyl, —(CH$_2$)$_3$-thietanyl, —(CH$_2$)$_3$-aziridinyl, —(CH$_2$)$_3$-oxiranyl, —(CH$_2$)$_3$-thiiranyl, —(CH$_2$)$_3$-diazetidinyl, —(CH$_2$)$_3$-pyrazolidinyl, —(CH$_2$)$_3$-piperazinyl, —(CH$_2$)$_3$-imidazlidinyl, —(CH$_2$)$_3$-tetrahydropyrimidinyl, and —(CH$_2$)$_3$-hexahydropyridazinyl.

In a yet further aspect, R$^3$ is selected from hydrogen, cyclopropyl, cyclobutyl, cyclopentyl, cyclohexyl, pyrrolidinyl, tetrahydrofuranyl, piperidinyl, tetrahydro-2H-pyranyl, azetidinyl, oxetanyl, aziridinyl, oxiranylpyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-piperidinyl, —CH$_2$-tetrahydro-2H-pyranyl, —CH$_2$-azetidinyl, —CH$_2$-oxetanyl, —CH$_2$-aziridinyl, —CH$_2$-oxiranyl, —CH$_2$-pyrazolidinyl, —CH$_2$-piperazinyl, —CH$_2$-imidazlidinyl, —(CH$_2$)$_2$-cyclopropyl, —(CH$_2$)$_2$-cyclobutyl, —(CH$_2$)$_2$-cyclopentyl, —(CH$_2$)$_2$-cyclohexyl, —(CH$_2$)$_2$-pyrrolidinyl, —(CH$_2$)$_2$-tetrahydrofuranyl, —(CH$_2$)$_2$-piperidinyl, —(CH$_2$)$_2$-tetrahydro-2H-pyranyl, —(CH$_2$)$_2$-azetidinyl, —(CH$_2$)$_2$-oxetanyl, —(CH$_2$)$_2$-aziridinyl, —(CH$_2$)$_2$-oxiranyl, —(CH$_2$)$_2$-pyrazolidinyl, —(CH$_2$)$_2$-piperazinyl, —(CH$_2$)$_2$-imidazlidinyl, —(CH$_2$)$_2$-tetrahydropyrimidinyl, and —(CH$_2$)$_2$-hexahydropyridazinyl.

In a further aspect, R$^3$ is selected from hydrogen, cyclopropyl, cyclobutyl, cyclopentyl, cyclohexyl, pyrrolidinyl, tetrahydrofuranyl, piperidinyl, tetrahydro-2H-pyranyl, azetidinyl, oxetanyl, aziridinyl, oxiranylpyrazolidinyl, piperazinyl, imidazlidinyl, tetrahydropyrimidinyl, hexahydropyridazinyl, —CH$_2$-cyclopropyl, —CH$_2$-cyclobutyl, —CH$_2$-cyclopentyl, —CH$_2$-cyclohexyl, —CH$_2$-pyrrolidinyl, —CH$_2$-tetrahydrofuranyl, —CH$_2$-piperidinyl, —CH$_2$-tetrahydro-2H-pyranyl, —CH$_2$-azetidinyl, —CH$_2$-oxetanyl, —CH$_2$-aziridinyl, —CH$_2$-oxiranyl, —CH$_2$-pyrazolidinyl, —CH$_2$-piperazinyl, and —CH$_2$-imidazlidinyl.

In a further aspect, R$^3$ is selected from hydrogen, cyclopropyl, cyclobutyl, cyclopentyl, cyclohexyl, pyrrolidinyl, tetrahydrofuranyl, piperidinyl, tetrahydro-2H-pyranyl, azetidinyl, oxetanyl, aziridinyl, oxiranylpyrazolidinyl, piperazinyl, imidazlidinyl, tetrahydropyrimidinyl, and hexahydropyridazinyl.

d. R$^{4A}$ and R$^{4B}$ Groups

In one aspect, each of R$^{4a}$ and R$^{4b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{40}$R$^{41}$, —(C1-C6 alkyl)-NR$^{40}$(C=O)R$^{41}$, —(C1-C6 alkyl)-NR$^{40}$(C=O)OR$^{41}$, —(C1-C6 alkyl)-NR$^{40}$(C=O)R$^{41}$, —(C1-C6 monohaloalkyl)-NR$^{40}$(C=O)OR$^{41}$, —(C1-C6 polyhaloalkyl)-NR$^{40}$(C=O)OR$^{41}$, —(C1-C8 alkyl)-Cy$^1$, Cy$^1$, —(C1-C8 alkyl)-Ar$^1$, —(C2-C8 alkynyl)-Ar$^1$, and Ar$^1$; and wherein R$^{4a}$ and R$^{4b}$ are not simultaneously hydrogen; or wherein R$^{4a}$ and R$^{4b}$ are optionally covalently bonded and, together with the intermediate nitrogen, comprise a 3- to 10-membered heterocycloalkyl substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C8 alkyl)-Ar$^{30}$, Ar$^{30}$, —(C1-C8 alkyl)-Cy$^{30}$, Cy$^{30}$, and R$^{57}$.

In one aspect, each of R$^{4a}$ and R$^{4b}$ is independently selected from hydrogen, C1-C6 alkyl, C1-C6 monohaloalkyl, C1-C6 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C6 alkyl)-Cy$^1$, Cy$^1$, —(C1-C6 alkyl)-Ar$^1$, —(C2-C6 alkynyl)-Ar$^1$, and Ar$^1$; and wherein R$^{4a}$ and R$^{4b}$ are not simultaneously hydrogen; or wherein R$^{4a}$ and R$^{4b}$ are optionally covalently bonded and, together with the intermediate nitrogen, comprise a 3- to 10-membered heterocycloalkyl substituted with 0, 1, 2, or 3 groups independently selected from halogen, —NH$_2$, —OH, —CN, —N$_3$, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{51}$R$^{52}$, —(C1-C3 alkyl)-NR$^{50}$(C=O)R$^{55}$, —(C1-C3 alkyl)-NR$^{50}$(C=O)OR$^{55}$, —(C1-C3 alkyl)-NR$^{50}$(C=O)R$^{55}$, —(C1-C3 alkyl)-NR$^{50}$S(O)$_m$R$^{55}$, —NR$^{50}$(C1-C3 alkyl)-(C=O)R$^{55}$, —NR$^{50}$(C1-C3 alkyl)-(C=O)OR$^{55}$, —NR$^{50}$(C1-C3 alkyl)-(C=O)R$^{55}$, —NR$^{50}$(C1-C3 alkyl)-S(O)$_m$R$^{55}$, —NR$^{50}$(C1-C3 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C3 alkyl)-(C=O)R$^{55}$, —(C1-C3 alkyl)-(C=O)OR$^{55}$, —(C1-C3 alkyl)-(C=O)R$^{55}$, —(C1-C3 alkyl)-S(O)$_m$R$^{55}$, —(C1-C3 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C6 alkyl)-Ar$^{30}$, Ar$^{30}$, —(C1-C6 alkyl)-Cy$^{30}$, Cy$^{30}$, and R$^{57}$.

In one aspect, each of R$^{4a}$ and R$^{4b}$ is independently selected from hydrogen, C1-C3 alkyl, C1-C3 monohaloalkyl, C1-C3 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C3 alkyl)-Cy$^1$, Cy$^1$, —(C1-C3 alkyl)-Ar$^1$, —(C2-C4 alkynyl)-Ar$^1$, and Ar$^1$; and wherein R$^{4a}$ and R$^{4b}$ are not simultaneously hydrogen; or wherein R$^{4a}$ and R$^{4b}$ are optionally covalently bonded and, together with the intermediate nitrogen, comprise a 3- to 10-membered heterocycloalkyl substituted with 0, 1, 2, or 3 groups independently selected from halogen, —NH$_2$, —OH, —CN, —N$_3$, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{51}$R$^{52}$, —(C1-C3 alkyl)-NR$^{50}$(C=O)R$^{55}$, —(C1-C3 alkyl)-NR$^{50}$(C=O)OR$^{55}$, —(C1-C3 alkyl)-NR$^{50}$(C=O)R$^{55}$, —(C1-C3 alkyl)-NR$^{50}$S(O)$_m$R$^{55}$, —NR$^{50}$(C1-C3 alkyl)-(C=O)R$^{55}$, —NR$^{50}$(C1-C3 alkyl)-(C=O)OR$^{55}$, —NR$^{50}$(C1-C3 alkyl)-(C=O)R$^{55}$, —NR$^{50}$(C1-C3 alkyl)-S(O)$_m$R$^{55}$, —NR$^{50}$(C1-C3 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C3 alkyl)-(C=O)R$^{55}$, —(C1-C3 alkyl)-(C=O)OR$^{55}$, —(C1-C3 alkyl)-(C=O)R$^{55}$, —(C1-C3 alkyl)-S(O)$_m$R$^{55}$, —(C1-C3 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C3 alkyl)-Ar$^{30}$, Ar$^{30}$, —(C1-C3 alkyl)-Cy$^{30}$, Cy$^{30}$, and R$^{57}$.

In a further aspect, each of R$^{4a}$ and R$^{4b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{40}$R$^{41}$, —(C1-C6 alkyl)-NR$^{40}$(C=O)R$^{41}$, —(C1-C6 alkyl)-NR$^{40}$(C=O)OR$^{41}$, —(C1-C6 alkyl)-NR$^{40}$(C=O)R$^{41}$, —(C1-C6 monohaloalkyl)-NR$^{40}$(C=O)OR$^{41}$, —(C1-C6 polyhaloalkyl)-NR$^{40}$(C=O)OR$^{41}$, —(C1-C8 alkyl)-Cy$^1$, Cy$^1$, —(C1-C8 alkyl)-Ar$^1$, —(C2-C8 alkynyl)-Ar$^1$, and Ar$^1$; and wherein R$^{4a}$ and R$^{4b}$ are not simultaneously hydrogen.

In a further aspect, each of R$^{4a}$ and R$^{4b}$ is independently selected from hydrogen, C1-C6 alkyl, C1-C6 monohaloalkyl, C1-C6 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C6 alkyl)-Cy$^1$, Cy$^1$, —(C1-C6 alkyl)-Ar$^1$, —(C2-C6 alkynyl)-Ar$^1$, and Ar$^1$; and wherein R$^{4a}$ and R$^{4b}$ are not simultaneously hydrogen.

In a further aspect, each of R$^{4a}$ and R$^{4b}$ is independently selected from hydrogen, C1-C3 alkyl, C1-C3 monohaloalkyl, C1-C3 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C3 alkyl)-Cy$^1$, Cy$^1$, —(C1-C3 alkyl)-Ar$^1$, —(C2-C4 alkynyl)-Ar$^1$, and Ar$^1$; and wherein R$^{4a}$ and R$^{4b}$ are not simultaneously hydrogen.

In a further aspect, R$^{4a}$ is hydrogen and R$^{4b}$ is selected from C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{40}$R$^{41}$, —(C1-C6 alkyl)-NR$^{40}$(C=O)R$^{41}$, —(C1-C6 alkyl)-NR$^{40}$(C=O)OR$^{41}$, —(C1-C6 alkyl)-NR$^{40}$(C=O)R$^{41}$, —(C1-C6 monohaloalkyl)-NR$^{40}$(C=O)OR$^{41}$, —(C1-C6 polyhaloalkyl)-NR$^{40}$(C=O)OR$^{41}$, —(C1-C8 alkyl)-Cy$^1$, Cy$^1$, —(C1-C8 alkyl)-Ar$^1$, —(C2-C8 alkynyl)-Ar$^1$, and Ar$^1$.

In a further aspect, R$^{4a}$ is hydrogen and R$^{4b}$ is selected from C1-C6 alkyl, C1-C6 monohaloalkyl, C1-C6 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C3 alkyl)-Cy$^1$, Cy$^1$, —(C1-C6 alkyl)-Ar$^1$, —(C2-C6 alkynyl)-Ar$^1$, and Ar$^1$.

In a further aspect, R$^{4a}$ is hydrogen and R$^{4b}$ is selected from C1-C3 alkyl, C1-C3 monohaloalkyl, C1-C3 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C3 alkyl)-Cy$^1$, Cy$^1$, —(C1-C3 alkyl)-Ar$^1$, —(C2-C4 alkynyl)-Ar$^1$, and Ar$^1$.

In a further aspect, each of R$^{4a}$ and R$^{4b}$ is independently selected from C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{40}$R$^{41}$, —(C1-C6 alkyl)-NR$^{40}$(C=O)R$^{41}$, —(C1-C6 alkyl)-NR$^{40}$(C=O)OR$^{41}$, —(C1-C6 alkyl)-NR$^{40}$(C=O)R$^{41}$, —(C1-C6 monohaloalkyl)-NR$^{40}$(C=O)OR$^{41}$, —(C1-C6 polyhaloalkyl)-NR$^{40}$(C=O)OR$^{41}$, —(C1-C8 alkyl)-Cy$^1$, Cy$^1$, —(C1-C8 alkyl)-Ar$^1$, —(C2-C8 alkynyl)-Ar$^1$, and Ar$^1$.

In a further aspect, each of R$^{4a}$ and R$^{4b}$ is independently selected from C1-C6 alkyl, C1-C6 monohaloalkyl, C1-C6 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C6 alkyl)-Cy$^1$, Cy$^1$, —(C1-C6 alkyl)-Ar$^1$, —(C2-C6 alkynyl)-Ar$^1$, and Ar$^1$.

In a further aspect, each of R$^{4a}$ and R$^{4b}$ is independently selected from C1-C3 alkyl, C1-C3 monohaloalkyl, C1-C3 polyhaloalkyl, C3-C6 hydroxyalkyl, —(C1-C3 alkyl)-O—(C1-C3 alkyl), —(C1-C3 alkyl)-O—(C1-C3 alkyl)-O—(C1-C3 alkyl), —(C1-C3 alkyl)-NR$^{40}$R$^{41}$, —(C1-C3 alkyl)-NR$^{40}$(C=O)R$^{41}$, —(C1-C3 alkyl)-NR$^{40}$(C=O)OR$^{41}$, —(C1-C3 alkyl)-NR$^{40}$(C=O)R$^{41}$, —(C1-C3 monohaloalkyl)-NR$^{40}$(C=O)OR$^{41}$, —(C1-C3 polyhaloalkyl)-NR$^{40}$(C=O)OR$^{41}$, —(C1-C3 alkyl)-Cy$^1$, Cy$^1$, —(C1-C3 alkyl)-Ar$^1$, —(C2-C4 alkynyl)-Ar$^1$, and Ar$^1$.

In a further aspect, R$^{4a}$ and R$^{4b}$ are covalently bonded and, together with the intermediate nitrogen, comprise a 3- to 10-membered heterocycloalkyl substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$ $NR^{53}R^{54}$, —(C=O)$R^{55}$, —(C=O)O$R^{55}$, —S(O)$_m R^{55}$, —S(O)$_m NR^{53}R^{54}$, —(C1-C8 alkyl)-$Ar^{30}$, $Ar^{30}$, —(C1-C8 alkyl)-$Cy^{30}$, $Cy^{30}$, and $R^{57}$.

In a further aspect, $R^{4a}$ and $R^{4b}$ are covalently bonded and, together with the intermediate nitrogen, comprise a 3- to 10-membered heterocycloalkyl substituted with 0, 1, 2, or 3 groups independently selected from halogen, —$NH_2$, —OH, —CN, —$N_3$, —$SF_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-O—(C1-C3 alkyl), —(C1-C3 alkyl)-O—(C1-C3 alkyl)-O—(C1-C3 alkyl), —(C1-C3 alkyl)-$NR^{51}R^{52}$, —(C1-C3 alkyl)-$NR^{50}$(C=O)$R^{55}$, —(C1-C3 alkyl)-$NR^{50}$(C=O)O$R^{55}$, —(C1-C3 alkyl)-$NR^{50}$(C=O)$R^{55}$, —(C1-C3 alkyl)-$NR^{50}$S(O)$_m R^{55}$, —$NR^{50}$(C1-C3 alkyl)-(C=O)$R^{55}$, —$NR^{50}$(C1-C3 alkyl)-(C=O)O$R^{55}$, —$NR^{50}$(C1-C3 alkyl)-(C=O)$R^{55}$, —$NR^{50}$(C1-C3 alkyl)-S(O)$_m R^{55}$, —$NR^{50}$(C1-C3 alkyl)-S(O)$_m NR^{53}R^{54}$, —$NR^{50}$(C=O)$R^{55}$, —$NR^{50}$(C=O)O$R^{55}$, —$NR^{50}$(C=O)$R^{55}$, —$NR^{50}$S(O)$_m R^{55}$, —(C1-C3 alkyl)-(C=O)$R^{55}$, —(C1-C3 alkyl)-(C=O)O$R^{55}$, —(C1-C3 alkyl)-(C=O)$R^{55}$, —(C1-C3 alkyl)-S(O)$_m R^{55}$, —(C1-C3 alkyl)-S(O)$_m NR^{53}R^{54}$, —(C=O)$R^{55}$, —(C=O)O$R^{55}$, —S(O)$_m R^{55}$, —S(O)$_m NR^{53}R^{54}$, —(C1-C6 alkyl)-$Ar^{30}$, $Ar^{30}$, —(C1-C6 alkyl)-$Cy^{30}$, $Cy^{30}$, and $R^{57}$.

In a further aspect, $R^{4a}$ and $R^{4b}$ are covalently bonded and, together with the intermediate nitrogen, comprise a 3- to 10-membered heterocycloalkyl substituted with 0, 1, 2, or 3 groups independently selected from halogen, —$NH_2$, —OH, —CN, —$N_3$, —$SF_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-O—(C1-C3 alkyl), —(C1-C3 alkyl)-O—(C1-C3 alkyl)-O—(C1-C3 alkyl), —(C1-C3 alkyl)-$NR^{51}R^{52}$, —(C1-C3 alkyl)-$NR^{50}$(C=O)$R^{55}$, —(C1-C3 alkyl)-$NR^{50}$(C=O)O$R^{55}$, —(C1-C3 alkyl)-$NR^{50}$(C=O)$R^{55}$, —(C1-C3 alkyl)-$NR^{50}$S(O)$_m R^{55}$, —$NR^{50}$(C1-C3 alkyl)-(C=O)$R^{55}$, —$NR^{50}$(C1-C3 alkyl)-(C=O)O$R^{55}$, —$NR^{50}$(C1-C3 alkyl)-(C=O)$R^{55}$, —$NR^{50}$(C1-C3 alkyl)-S(O)$_m R^{55}$, —$NR^{50}$(C1-C3 alkyl)-S(O)$_m NR^{53}R^{54}$, —$NR^{50}$(C=O)$R^{55}$, —$NR^{50}$(C=O)O$R^{55}$, —$NR^{50}$(C=O)$R^{55}$, —$NR^{50}$S(O)$_m R^{55}$, —(C1-C3 alkyl)-(C=O)$R^{55}$, —(C1-C3 alkyl)-(C=O)O$R^{55}$, —(C1-C3 alkyl)-(C=O)$R^{55}$, —(C1-C3 alkyl)-S(O)$_m R^{55}$, —(C1-C3 alkyl)-S(O)$_m NR^{53}R^{54}$, —(C=O)$R^{55}$, —(C=O)O$R^{55}$, —S(O)$_m R^{55}$, —S(O)$_m NR^{53}R^{54}$, —(C1-C3 alkyl)-$Ar^{30}$, $Ar^{30}$, —(C1-C3 alkyl)-$Cy^{30}$, $Cy^{30}$, and $R^{57}$.

In a further aspect, each of $R^{4a}$ and $R^{4b}$ is independently selected from hydrogen, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$(CH_2)_2CH_2OH$, —$(CH_2)_3CH_2OH$, —$(CH_2)_4CH_2OH$, —$(CH_2)_2CH(CH_3)OH$, —$CH(CH_3)(CH_2)_2CH_2OH$, —$CH(CH_3)CH_2CH_2OH$, —$CH(CH_3)CH_2OH$, —$CH_2OCH_3$, —$(CH_2)_2OCH_3$, —$(CH_2)_2OCH_2CH_3$, —$(CH_2)_3OCH_3$, —$(CH_2)_3OCH_2CH_3$, —$CH_2OCH_2OCH_3$, —$(CH_2)_2OCH_2OCH_3$, —$(CH_2)_2OCH_2OCH_2CH_3$, —$(CH_2)_3OCH_2OCH_3$, —$(CH_2)_3OCH_2OCH_2CH_3$, —$CH_2$—O—$(CH_2)_2OCH_3$, —$(CH_2)(CH_2)_2OCH_3$, —$(CH_2)_2O(CH_2)_2OCH_2CH_3$, —$(CH_2)_3O(CH_2)_2OCH_3$, —$(CH_2)_3O(CH_2)_2OCH_2CH_3$, —$CH_2NR^{40}R^{41}$, —$CH_2NHR^{41}$, —$(CH_2)_2NR^{40}R^{41}$, —$(CH_2)_2NHR^{41}$, —$(CH_2)_3NR^{40}R^{41}$, —$(CH_2)_3NHR^{41}$, —$(CH_2)_4NR^{40}R^{41}$, —$(CH_2)_4NHR^{41}$, —$CH_2NR^{40}$(C=O)$R^{41}$, —$CH_2NH$(C=O)$R^{41}$, —$(CH_2)_2NR^{40}$(C=O)$R^{41}$, —$(CH_2)_2NH$(C=O)$R^{41}$, —$(CH_2)_3NR^{40}$(C=O)$R^{41}$, —$(CH_2)_3NH$(C=O)$R^{41}$, —$(CH_2)_4NR^{40}$(C=O)$R^{41}$, —$(CH_2)_4NH$(C=O)$R^{41}$, —$CH_2NR^{40}$(C=O)O$R^{41}$, —$CH_2NH$(C=O)O$R^{41}$, —$(CH_2)_2NR^{40}$(C=O)O$R^{41}$, —$(CH_2)_2NH$(C=O)O$R^{41}$, —$(CH_2)_3NR^{40}$(C=O)O$R^{41}$, —$(CH_2)_3NH$(C=O)O$R^{41}$, —$(CH_2)_4NR^{40}$(C=O)O$R^{41}$, —$(CH_2)_4NH$(C=O)O$R^{41}$, —$CH_2NR^{40}$(C=O)NH$R^{41}$, —$CH_2NH$(C=O)NH$R^{41}$, —$(CH_2)_2NR^{40}$(C=O)NH$R^{41}$, —$(CH_2)_2NH$(C=O)NH$R^{41}$, —$(CH_2)_3NR^{40}$(C=O)NH$R^{41}$, —$(CH_2)_3NH$(C=O)NH$R^{41}$, —$(CH_2)_4NR^{40}$(C=O)NH$R^{41}$, —$(CH_2)_4NH$(C=O)NH$R^{41}$, —$CH_2$-$Cy^1$, —$(CH_2)_2$-$Cy^1$, —$(CH_2)_3$-$Cy^1$, $Cy^1$, —$(CH_2)$-$Ar^1$, —$(CH_2)_2$—$Ar^1$, —$(CH_2)_3$—$Ar^1$, $Ar^1$, —$CH_2$(CC)—$Ar^1$; and $R^{4a}$ and $R^{4b}$ are not simultaneously hydrogen.

In a further aspect, $R^{4a}$ is hydrogen; and $R^{4b}$ is selected from methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$(CH_2)_2CH_2OH$, —$(CH_2)_3CH_2OH$, —$(CH_2)_4CH_2OH$, —$(CH_2)_2CH(CH_3)OH$, —$CH(CH_3)(CH_2)_2CH_2OH$, —$CH(CH_3)CH_2CH_2OH$, —$CH(CH_3)CH_2OH$, —$CH_2OCH_3$, —$(CH_2)_2OCH_3$, —$(CH_2)_2OCH_2CH_3$, —$(CH_2)_3OCH_3$, —$(CH_2)_3OCH_2CH_3$, —$CH_2OCH_2OCH_3$, —$(CH_2)_2OCH_2OCH_3$, —$(CH_2)_2OCH_2OCH_2CH_3$, —$(CH_2)_3OCH_2OCH_3$, —$(CH_2)_3OCH_2OCH_2CH_3$, —$CH_2$—O—$(CH_2)_2OCH_3$, —$(CH_2)(CH_2)_2OCH_3$, —$(CH_2)_2O(CH_2)_2OCH_2CH_3$, —$(CH_2)_3O(CH_2)_2OCH_3$, —$(CH_2)_3O(CH_2)_2OCH_2CH_3$, —$CH_2NR^{40}R^{41}$, —$CH_2NHR^{41}$, —$(CH_2)_2NR^{40}R^{41}$, —$(CH_2)_2NHR^{41}$, —$(CH_2)_3NR^{40}R^{41}$, —$(CH_2)_3NHR^{41}$, —$(CH_2)_4NR^{40}R^{41}$, —$(CH_2)_4NHR^{41}$, —$CH_2NR^{40}$(C=O)$R^{41}$, —$CH_2NH$(C=O)$R^{41}$, —$(CH_2)_2NR^{40}$(C=O)$R^{41}$, —$(CH_2)_2NH$(C=O)$R^{41}$, —$(CH_2)_3NR^{40}$(C=O)$R^{41}$, —$(CH_2)_3NH$(C=O)$R^{41}$, —$(CH_2)_4NR^{40}$(C=O)$R^{41}$, —$(CH_2)_4NH$(C=O)$R^{41}$, —$CH_2NR^{40}$(C=O)O$R^{41}$, —$CH_2NH$(C=O)

OR$^{41}$, —(CH$_2$)$_2$NR$^{40}$(C=O)OR$^{41}$, —(CH$_2$)$_2$NH(C=O) OR$^{41}$, —(CH$_2$)$_3$NR$^{40}$(C=O)OR$^{41}$, —(CH$_2$)$_3$NH(C=O) OR$^{41}$, —(CH$_2$)$_4$NR$^{40}$(C=O)OR$^{41}$, —(CH$_2$)$_4$NH(C=O) OR$^{41}$, —CH$_2$NR$^{40}$(C=O)NHR$^{41}$, —CH$_2$NH(C=O) NHR$^{41}$, —(CH$_2$)$_2$NR$^{40}$(C=O)NHR$^{41}$, —(CH$_2$)$_2$NH(C=O) NHR$^{41}$, —(CH$_2$)$_3$NR$^{40}$(C=O)NHR$^{41}$, —(CH$_2$)$_3$NH(C=O) NHR$^{41}$, —(CH$_2$)$_4$NR$^{40}$(C=O)NHR$^{41}$, and —(CH$_2$)$_4$NH (C=O)NHR$^{41}$; and R$^{4a}$ and R$^{4b}$ are not simultaneously hydrogen.

In a further aspect, R$^{4a}$ is hydrogen; and R$^{4b}$ is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$ CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$ CH$_2$OH, —(CH$_2$)$_3$CH$_2$OH, —(CH$_2$)$_4$CH$_2$OH, —(CH$_2$)$_2$CH (CH$_3$)OH, —CH(CH$_3$)(CH$_2$)$_2$CH$_2$OH, —CH(CH$_3$) CH$_2$CH$_2$OH, —CH(CH$_3$)CH$_2$OH, —CH$_2$OCH$_3$, —(CH$_2$)$_2$ OCH$_3$, —(CH$_2$)$_2$OCH$_2$CH$_3$, —(CH$_2$)$_3$OCH$_3$, —(CH$_2$)$_3$ OCH$_2$CH$_3$, —CH$_2$OCH$_2$OCH$_3$, —(CH$_2$)$_2$OCH$_2$OCH$_3$, —(CH$_2$)$_2$OCH$_2$OCH$_2$CH$_3$, —(CH$_2$)$_3$OCH$_2$OCH$_3$, —(CH$_2$)$_3$OCH$_2$OCH$_2$CH$_3$, —CH$_2$O(CH$_2$)$_2$OCH$_3$, —(CH$_2$)$_2$(CH$_2$)$_2$OCH$_3$, —(CH$_2$)$_2$O(CH$_2$)$_2$OCH$_2$CH$_3$, —(CH$_2$)$_3$O(CH$_2$)$_2$OCH$_3$, —(CH$_2$)$_3$O(CH$_2$)$_2$OCH$_2$CH$_3$, —CH$_2$NR$^{40}$R$^{41}$, —CH$_2$NHR$^{41}$, —(CH$_2$)$_2$NR$^{40}$R$^{41}$, —(CH$_2$)$_2$NHR$^{41}$, —(CH$_2$)$_3$NR$^{40}$R$^{41}$, —(CH$_2$)$_3$NHR$^{41}$, —(CH$_2$)$_4$NR$^{40}$R$^{41}$, —(CH$_2$)$_4$NHR$^{41}$, —CH$_2$NR$^{40}$(C=O) R$^{41}$, —CH$_2$NH(C=O)R$^{41}$, —(CH$_2$)$_2$NR$^{40}$(C=O)R$^{41}$, —(CH$_2$)$_2$NH(C=O)R$^{41}$, —(CH$_2$)$_3$NR$^{40}$(C=O)R$^{41}$, —(CH$_2$)$_3$NH(C=O)R$^{41}$, —(CH$_2$)$_4$NR$^{40}$(C=O)R$^{41}$, —(CH$_2$)$_4$NH(C=O)R$^{41}$, —CH$_2$NR$^{40}$(C=O)OR$^{41}$, —CH$_2$NH(C=O)OR$^{41}$, —(CH$_2$)$_2$NR$^{40}$(C=O)OR$^{41}$, —(CH$_2$)$_2$NH(C=O)OR$^{41}$, —(CH$_2$)$_3$NR$^{40}$(C=O)OR$^{41}$, —(CH$_2$)$_3$NH(C=O)OR$^{41}$, —(CH$_2$)$_4$NR$^{40}$(C=O)OR$^{41}$, —(CH$_2$)$_4$NH(C=O)OR$^{41}$, —CH$_2$NR$^{40}$(C=O)NHR$^{41}$, —CH$_2$NH(C=O)NHR$^{41}$, —(CH$_2$)$_2$NR$^{40}$(C=O)NHR$^{41}$, —(CH$_2$)$_2$NH(C=O)NR$^{41}$, —(CH$_2$)$_3$NR$^{40}$(C=O)NHR$^{41}$, —(CH$_2$)$_3$NH(C=O)NHR$^{41}$, —(CH$_2$)$_4$NR$^{40}$(C=O)NHR$^{41}$, and —(CH$_2$)$_4$NH(C=O)NHR$^{41}$.

In a further aspect, each of R$^{4a}$ and R$^{4b}$ is independently selected from hydrogen, —CH$_2$—Cy$^1$, —(CH$_2$)$_2$—Cy$^1$, —(CH$_2$)$_3$—Cy$^1$, Cy$^1$, —(CH$_2$)—Ar$^1$, —(CH$_2$)$_2$—Ar$^1$, —(CH$_2$)$_3$—Ar$^1$, Ar$^1$, and —CH$_2$(CC)—Ar$^1$; and R$^{4a}$ and R$^{4b}$ are not simultaneously hydrogen.

In a further aspect, R$^{4a}$ is hydrogen; and R$^{4b}$ is selected from —CH$_2$—Cy$^1$, —(CH$_2$)$_2$—Cy$^1$, —(CH$_2$)$_3$—Cy$^1$, Cy$^1$, —(CH$_2$)—Ar$^1$, —(CH$_2$)$_2$—Ar$^1$, —(CH$_2$)$_3$—Ar$^1$, Ar$^1$, and —CH$_2$(CC)—Ar$^1$; and R$^{4a}$ and R$^{4b}$ are not simultaneously hydrogen.

In one aspect, each of R$^{4a}$ and R$^{4b}$ is independently selected from hydrogen, C1-C8 alkyl, C1-C8 monohaloalkyl, C1-C8 polyhaloalkyl, Cy$^1$, Cy$^1$-(C1-C6 alkyl)-, Ar$^1$, and Ar$^1$—(C1-C6 alkyl)-, wherein R$^{4a}$ and R$^{4b}$ are not both hydrogen; or R$^{4a}$ and R$^{4b}$ are optionally covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$; and wherein two of the groups are optionally covalently bonded, and together with the intermediate atoms, comprise an optionally substituted 3- to 6-membered fused ring group. In a further aspect, R$^{4a}$ is hydrogen.

In various aspects, each of R$^{4a}$ and R$^{4b}$ is independently selected from hydrogen, C1-C8 alkyl, C1-C8 monohaloalkyl, C1-C8 polyhaloalkyl, Cy$^1$, Cy$^1$-(C1-C6 alkyl)-, Ar$^1$, and Ar$^1$—(C1-C6 alkyl)-, wherein R$^{4a}$ and R$^{4b}$ are not both hydrogen. In a further aspect, R$^{4a}$ and R$^{4b}$ are covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$ R$^5$; and wherein two of the groups are optionally covalently bonded, and together with the intermediate atoms, comprise an optionally substituted 3- to 6-membered fused ring group. In a still further aspect, R$^{4a}$ and R$^{4b}$ are covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$.

In a further aspect, each of R$^{4a}$ and R$^{4b}$ is independently selected from hydrogen, C1-C6 alkyl, C1-C6 haloalkyl, C1-C6 polyhaloalkyl, Cy$^1$, Cy$^1$-(C1-C6 alkyl)-, Ar$^1$, and Ar$^1$—(C1-C6 alkyl)-; and wherein R$^{4a}$ and R$^{4b}$ are not both hydrogen. In a still further aspect, each of R$^{4a}$ and R$^{4b}$ is independently selected from hydrogen, C1-C3 alkyl, C1-C3 haloalkyl, C1-C3 polyhaloalkyl, Cy$^1$, Cy$^1$-(C1-C3 alkyl)-, Ar$^1$, and Ar$^1$—(C1-C3 alkyl)-; and wherein R$^{4a}$ and R$^{4b}$ are not both hydrogen. In a yet further aspect, each of R$^{4a}$ and R$^{4b}$ is independently selected from hydrogen, C1-C3 alkyl, C1-C3 haloalkyl, C1-C3 polyhaloalkyl, Cy$^1$, Cy$^1$-(CH$_2$)$_3$—, Cy$^1$-(CH$_2$)$_2$—, Cy$^1$-CH$_2$—, Ar$^1$, Ar$^1$—(CH$_2$)$_3$—, Ar$^1$—(CH$_2$)$_2$—, and Ar$^1$—CH$_2$—; and wherein R$^{4a}$ and R$^{4b}$ are not both hydrogen. In an even further aspect, each of R$^{4a}$ and R$^{4b}$ is independently selected from hydrogen, C1-C3 alkyl, C1-C3 haloalkyl, C1-C3 polyhaloalkyl, Cy$^1$, Cy$^1$-(CH$_2$)$_2$—, Cy$^1$-CH$_2$—, Ar$^1$, Ar$^1$—(CH$_2$)$_2$—, and Ar$^1$—CH$_2$—; and wherein R$^{4a}$ and R$^{4b}$ are not both hydrogen. In a still further aspect, each of R$^{4a}$ and R$^{4b}$ is independently selected from hydrogen, C1-C3 alkyl, C1-C3 haloalkyl, C1-C3 polyhaloalkyl, Cy$^1$, Cy$^1$-CH$_2$—, Ar$^1$, and Ar$^1$—CH$_2$—; and wherein R$^{4a}$ and R$^{4b}$ are not both hydrogen.

In a further aspect, each of R$^{4a}$ and R$^{4b}$ is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$ CHI$_2$, —(CH$_2$)$_2$CI$_3$, Cy$^1$, Cy$^1$-(CH$_2$)$_3$—, Cy$^1$-(CH$_2$)$_2$—, Cy$^1$-CH$_2$—, Ar$^1$, Ar$^1$—(CH$_2$)$_3$—, Ar$^1$—(CH$_2$)$_2$—, and Ar$^1$—CH$_2$—; and wherein R$^{4a}$ and R$^{4b}$ are not both hydrogen. In a still further aspect, each of R$^{4a}$ and R$^{4b}$ is independently selected from hydrogen, methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, $Cy^1$, $Cy^1$-$(CH_2)_3$—, $Cy^1$-$(CH_2)_2$—, $Cy^1$-$CH_2$—, $Ar^1$, $Ar^1$—$(CH_2)_3$—, $Ar^1$—$(CH_2)_2$—, and $Ar^1$—$CH_2$—; and wherein $R^{4a}$ and $R^{4b}$ are not both hydrogen. In a yet further aspect, each of $R^{4a}$ and $R^{4b}$ is independently selected from hydrogen, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, $Cy^1$, $Cy^1$-$(CH_2)_3$—, $Cy^1$-$(CH_2)_2$—, $Cy^1$-$CH_2$—, $Ar^1$, $Ar^1$—$(CH_2)_3$—, $Ar^1$—$(CH_2)_2$—, and $Ar^1$—$CH_2$—; and wherein $R^{4a}$ and $R^{4b}$ are not both hydrogen. In an even further aspect, each of $R^{4a}$ and $R^{4b}$ is independently selected from hydrogen, methyl, —$CH_2F$, —$CHF_2$, —$CF_3$, $Cy^1$, $Cy^1$-$(CH_2)_2$—, $Cy^1$-$CH_2$—, $Ar^1$, $Ar^1$—$(CH_2)_2$—, and $Ar^1$—$CH_2$—; and wherein $R^{4a}$ and $R^{4b}$ are not both hydrogen. In a still further aspect, each of $R^{4a}$ and $R^{4b}$ is independently selected from hydrogen, methyl, —$CH_2F$, —$CHF_2$, —$CF_3$, $Cy^1$, $Cy^1$-$CH_2$—, $Ar^1$, and $Ar^1$—$CH_2$—; and wherein $R^{4a}$ and $R^{4b}$ are not both hydrogen.

In a further aspect, each of $R^{4a}$ and $R^{4b}$ is independently selected from hydrogen, C1-C6 alkyl, C1-C6 haloalkyl, and C1-C6 polyhaloalkyl; and wherein $R^{4a}$ and $R^{4b}$ are not both hydrogen. In a still further aspect, each of $R^{4a}$ and $R^{4b}$ is independently selected from hydrogen, C1-C3 alkyl, C1-C3 haloalkyl, and C1-C3 polyhaloalkyl; and wherein $R^{4a}$ and $R^{4b}$ are not both hydrogen. In a yet further aspect, each of $R^{4a}$ and $R^{4b}$ is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, and —$(CH_2)_2CI_3$; and wherein $R^{4a}$ and $R^{4b}$ are not both hydrogen. In an even further aspect, each of $R^{4a}$ and $R^{4b}$ is independently selected from hydrogen, methyl, ethyl, propyl, isopropyl, tert-butyl, sec-butyl, isobutyl, tert-butyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$; and wherein $R^{4a}$ and $R^{4b}$ are not both hydrogen. In a still further aspect, each of $R^{4a}$ and $R^{4b}$ is independently selected from hydrogen, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$; and wherein $R^{4a}$ and $R^{4b}$ are not both hydrogen. In a yet further aspect, each of $R^{4a}$ and $R^{4b}$ is independently selected from hydrogen, methyl, —$CH_2F$, —$CHF_2$, and —$CF_3$; and wherein $R^{4a}$ and $R^{4b}$ are not both hydrogen. In an even further aspect, each of $R^{4a}$ and $R^{4b}$ is independently selected from hydrogen, methyl, and —$CF_3$; and wherein $R^{4a}$ and $R^{4b}$ are not both hydrogen.

In various further aspects, each of $R^{4a}$ and $R^{4b}$ is independently selected from hydrogen, $Cy^1$, $Cy^1$-(C1-C6 alkyl)-, $Ar^1$, and $Ar^1$—(C1-C6 alkyl)-; and wherein $R^{4a}$ and $R^{4b}$ are not both hydrogen. In a still further aspect, each of $R^{4a}$ and $R^{4b}$ is independently selected from hydrogen, $Cy^1$, $Cy^1$-(C1-C3 alkyl)-, $Ar^1$, and $Ar^1$—(C1-C3 alkyl)-; and wherein $R^{4a}$ and $R^{4b}$ are not both hydrogen. In a yet further aspect, each of $R^{4a}$ and $R^{4b}$ is independently selected from hydrogen, $Cy^1$, $Cy^1$-$(CH_2)_3$—, $Cy^1$-$(CH_2)_2$—, $Cy^1$-$CH_2$—, $Ar^1$, $Ar^1$—$(CH_2)_3$—, $Ar^1$—$(CH_2)_2$—, and $Ar^1$—$CH_2$—; and wherein $R^{4a}$ and $R^{4b}$ are not both hydrogen. In a yet further aspect, each of $R^{4a}$ and $R^{4b}$ is independently selected from hydrogen, $Cy^1$, $Cy^1$-$(CH_2)_2$—, $Cy^1$-$CH_2$—, $Ar^1$, $Ar^1$—$(CH_2)_2$—, and $Ar^1$—$CH_2$—; and wherein $R^{4a}$ and $R^{4b}$ are not both hydrogen. In an even further aspect, each of $R^{4a}$ and $R^{4b}$ is independently selected from hydrogen, $Cy^1$, $Cy^1$-$CH_2$—, $Ar^1$, and $Ar^1$—$CH_2$—; and wherein $R^{4a}$ and $R^{4b}$ are not both hydrogen.

In a further aspect, each of $R^{4a}$ and $R^{4b}$ is independently selected from hydrogen, $Cy^1$, and $Cy^1$-(C1-C6 alkyl)-; and wherein $R^{4a}$ and $R^{4b}$ are not both hydrogen. In a still further aspect, each of $R^{4a}$ and $R^{4b}$ is independently selected from hydrogen, $Cy^1$, and $Cy^1$-(C1-C3 alkyl)-; and wherein $R^{4a}$ and $R^{4b}$ are not both hydrogen. In a yet further aspect, each of $R^{4a}$ and $R^{4b}$ is independently selected from hydrogen, $Cy^1$, $Cy^1$-$(CH_2)_3$—, $Cy^1$-$(CH_2)_2$—, and $Cy^1$-$(CH_2)$—; and wherein $R^{4a}$ and $R^{4b}$ are not both hydrogen. In an even further aspect, each of $R^{4a}$ and $R^{4b}$ is independently selected from hydrogen, $Cy^1$, $Cy^1$-$(CH_2)_2$—, and $Cy^1$-$(CH_2)$—; and wherein $R^{4a}$ and $R^{4b}$ are not both hydrogen. In a still further aspect, each of $R^{4a}$ and $R^{4b}$ is independently selected from hydrogen, $Cy^1$, and $Cy^1$-$(CH_2)$—; and wherein $R^{4a}$ and $R^{4b}$ are not both hydrogen.

In a further aspect, each of $R^{4a}$ and $R^{4b}$ is independently selected from hydrogen, $Ar^1$, and $Ar^1$—(C1-C6 alkyl)-; and wherein $R^{4a}$ and $R^{4b}$ are not both hydrogen. In a still further aspect, each of $R^{4a}$ and $R^{4b}$ is independently selected from hydrogen, $Ar^1$, and $Ar^1$—(C1-C3 alkyl)-; and wherein $R^{4a}$ and $R^{4b}$ are not both hydrogen. In a yet further aspect, each of $R^{4a}$ and $R^{4b}$ is independently selected from hydrogen, $Ar^1$, $Ar^1$—$(CH_2)_3$—, $Ar^1$—$(CH_2)_2$—, and $Ar^1$—$(CH_2)$—; and wherein $R^{4a}$ and $R^{4b}$ are not both hydrogen. In an even further aspect, each of $R^{4a}$ and $R^{4b}$ is independently selected from hydrogen, $Ar^1$, $Ar^1$—$(CH_2)_2$—, and $Ar^1$—$(CH_2)$—; and wherein $R^{4a}$ and $R^{4b}$ are not both hydrogen. In a still further aspect, each of $R^{4a}$ and $R^{4b}$ is independently selected from hydrogen, $Ar^1$, and $Ar^1$—$(CH_2)$—; and wherein $R^{4a}$ and $R^{4b}$ are not both hydrogen.

In a further aspect, $R^{4a}$ is hydrogen and $R^{4b}$ is selected from C1-C6 alkyl, C1-C6 haloalkyl, and C1-C6 polyhaloalkyl. In a still further aspect, $R^{4a}$ is hydrogen and $R^{4b}$ is selected from C1-C3 alkyl, C1-C3 haloalkyl, and C1-C3 polyhaloalkyl. In a yet further aspect, $R^{4a}$ is hydrogen and $R^{4b}$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, and —$(CH_2)_2CI_3$. In an even further aspect, $R^{4a}$ is hydrogen and $R^{4b}$ is selected from methyl, ethyl, propyl, isopropyl, tert-butyl, sec-butyl, isobutyl, tert-butyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In a still further aspect, $R^{4a}$ is hydrogen and $R^{4b}$ is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, R$^{4a}$ is hydrogen and R$^{4b}$ is selected from methyl, —CH$_2$F, —CHF$_2$, and —CF$_3$. In an even further aspect, R$^{4a}$ is hydrogen and R$^{4b}$ is selected from methyl, and —CF$_3$.

In various further aspects, R$^{4a}$ is hydrogen and R$^{4b}$ is selected from C1-C8 alkyl, C1-C8 monohaloalkyl, C1-C8 polyhaloalkyl, Cy$^1$, Cy$^1$-(C1-C6 alkyl)-, Ar$^1$, and Ar$^1$—(C1-C6 alkyl)-. In a further aspect, R$^{4a}$ is hydrogen and R$^{4b}$ is selected from C1-C6 alkyl, C1-C6 haloalkyl, C1-C6 polyhaloalkyl, Cy$^1$, Cy$^1$-(C1-C6 alkyl)-, Ar$^1$, and Ar$^1$—(C1-C6 alkyl. In a still further aspect, R$^{4a}$ is hydrogen and R$^{4b}$ is selected from C1-C3 alkyl, C1-C3 haloalkyl, C1-C3 polyhaloalkyl, Cy$^1$, Cy$^1$-(C1-C3 alkyl)-, Ar$^1$, and Ar$^1$—(C1-C3 alkyl)-. In a yet further aspect, R$^{4a}$ is hydrogen and R$^{4b}$ is selected from C1-C3 alkyl, C1-C3 haloalkyl, C1-C3 polyhaloalkyl, Cy$^1$, Cy$^1$-(CH$_2$)$_3$—, Cy$^1$-(CH$_2$)$_2$—, Cy$^1$-CH$_2$—, Ar$^1$, Ar$^1$—(CH$_2$)$_3$—, Ar$^1$—(CH$_2$)$_2$—, and Ar$^1$—CH$_2$—. In an even further aspect, R$^{4a}$ is hydrogen and R$^{4b}$ is selected from C1-C3 alkyl, C1-C3 haloalkyl, C1-C3 polyhaloalkyl, Cy$^1$, Cy$^1$-(CH$_2$)$_2$—, Cy$^1$-CH$_2$—, Ar$^1$, Ar$^1$—(CH$_2$)$_2$—, and Ar$^1$—CH$_2$—. In a still further aspect, R$^{4a}$ is hydrogen and R$^{4b}$ is selected from C1-C3 alkyl, C1-C3 haloalkyl, C1-C3 polyhaloalkyl, Cy$^1$, Cy$^1$-CH$_2$—, Ar$^1$, and Ar$^1$—CH$_2$—.

In a further aspect, R$^{4a}$ is hydrogen and R$^{4b}$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, Cy$^1$, Cy$^1$-(CH$_2$)$_3$—, Cy$^1$-(CH$_2$)$_2$—, Cy$^1$-CH$_2$—, Ar$^1$, Ar$^1$—(CH$_2$)$_3$—, Ar$^1$—(CH$_2$)$_2$—, and Ar$^1$—CH$_2$—. In a still further aspect R$^{4a}$ is hydrogen and R$^{4b}$ is selected from methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, Cy$^1$, Cy$^1$-(CH$_2$)$_3$—, Cy$^1$-(CH$_2$)$_2$—, Cy$^1$-CH$_2$—, Ar$^1$, Ar$^1$—(CH$_2$)$_3$—, Ar$^1$—(CH$_2$)$_2$—, and Ar$^1$—CH$_2$—. In an even further aspect, R$^{4a}$ is hydrogen and R$^{4b}$ is selected from methyl, —CH$_2$F, —CHF$_2$, —CF$_3$, Cy$^1$, Cy$^1$-(CH$_2$)$_2$—, Cy$^1$-CH$_2$—, Ar$^1$, Ar$^1$—(CH$_2$)$_2$—, and Ar$^1$—CH$_2$—. In a still further aspect, R$^{4a}$ is hydrogen and R$^{4b}$ is selected from methyl, —CH$_2$F, —CHF$_2$, —CF$_3$, Cy$^1$, Cy$^1$-CH$_2$—, Ar$^1$, and Ar$^1$—CH$_2$—.

In a further aspect, R$^{4a}$ is hydrogen and R$^{4b}$ is selected from C1-C6 alkyl, C1-C6 haloalkyl, and C1-C6 polyhaloalkyl. In a still further aspect, R$^{4a}$ is hydrogen and R$^{4b}$ is selected from C1-C3 alkyl, C1-C3 haloalkyl, and C1-C3 polyhaloalkyl. In a yet further aspect, R$^{4a}$ is hydrogen and R$^{4b}$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In an even further aspect, R$^{4a}$ is hydrogen and R$^{4b}$ is selected from methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, R$^{4a}$ is hydrogen and R$^{4b}$ is selected from methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, R$^{4a}$ is hydrogen and R$^{4b}$ is selected from methyl, —CH$_2$F, —CHF$_2$, and —CF$_3$. In an even further aspect, R$^{4a}$ is hydrogen and R$^{4b}$ is selected from methyl, and —CF$_3$.

In various further aspects, R$^{4a}$ is hydrogen and R$^{4b}$ is selected from hydrogen, Cy$^1$, Cy$^1$-(C1-C6 alkyl)-, Ar$^1$, and Ar$^1$—(C1-C6 alkyl)-. In a still further aspect, R$^{4a}$ is hydrogen and R$^{4b}$ is selected from hydrogen, Cy$^1$, Cy$^1$-(C1-C3 alkyl)-, Ar$^1$, and Ar$^1$—(C1-C3 alkyl)-. In a yet further aspect, R$^{4a}$ is hydrogen and R$^{4b}$ is selected from hydrogen, Cy$^1$, Cy$^1$-(CH$_2$)$_3$—, Cy$^1$-(CH$_2$)$_2$—, Cy$^1$-CH$_2$—, Ar$^1$, Ar$^1$—(CH$_2$)$_3$—, Ar$^1$—(CH$_2$)$_2$—, and Ar$^1$—CH$_2$—. In a yet further aspect, R$^{4a}$ is hydrogen and R$^{4b}$ is selected from hydrogen, Cy$^1$, Cy$^1$-(CH$_2$)$_2$—, Cy$^1$-CH$_2$—, Ar$^1$, Ar$^1$—(CH$_2$)$_2$—, and Ar$^1$—CH$_2$—. In an even further aspect, R$^{4a}$ is hydrogen and R$^{4b}$ is selected from hydrogen, Cy$^1$, Cy$^1$-CH$_2$—, Ar$^1$, and Ar$^1$—CH$_2$—.

In a further aspect, R$^{4a}$ is hydrogen and R$^{4b}$ is selected from Cy$^1$, and Cy$^1$-(C1-C6 alkyl)-. In a still further aspect, R$^{4a}$ is hydrogen and R$^{4b}$ is selected from Cy$^1$, and Cy$^1$-(C1-C3 alkyl)-. In a yet further aspect, R$^{4a}$ is hydrogen and R$^{4b}$ is selected from Cy$^1$, Cy$^1$-(CH$_2$)$_3$—, Cy$^1$-(CH$_2$)$_2$—, and Cy$^1$-(CH$_2$)—. In an even further aspect, R$^{4a}$ is hydrogen and R$^{4b}$ is selected from Cy$^1$, Cy$^1$-(CH$_2$)$_2$—, and Cy$^1$-(CH$_2$)—. In a still further aspect, R$^{4a}$ is hydrogen and R$^{4b}$ is selected from Cy$^1$, and Cy$^1$-(CH$_2$)—.

In a further aspect, R$^{4a}$ is hydrogen and R$^{4b}$ is selected from Ar$^1$, and Ar$^1$—(C1-C6 alkyl)-. In a still further aspect, R$^{4a}$ is hydrogen and R$^{4b}$ is selected from Ar$^1$, and Ar$^1$—(C1-C3 alkyl)-. In a yet further aspect, R$^{4a}$ is hydrogen and R$^{4b}$ is selected from Ar$^1$, Ar$^1$—(CH$_2$)$_3$—, Ar$^1$—(CH$_2$)$_2$—, and Ar$^1$—(CH$_2$)—. In an even further aspect, R$^{4a}$ is hydrogen and R$^{4b}$ is selected from Ar$^1$, Ar$^1$—(CH$_2$)$_2$—, and Ar$^1$—(CH$_2$)—. In a still further aspect R$^{4a}$ is hydrogen and R$^{4b}$ is selected from Ar$^1$, and Ar$^1$—(CH$_2$)—.

In various aspects, R$^{4a}$ is hydrogen and R$^{4b}$ is Cy$^1$. In a further aspect, R$^{4a}$ is hydrogen and R$^{4b}$ is Cy$^1$. In a still further aspect, R$^{4a}$ is hydrogen and wherein R$^{4b}$ is C2-C7 heterocycloalkyl. In a yet further aspect, R$^{4a}$ is hydrogen and R$^{4b}$ is C3 heterocycloalkyl.

In an even further aspect, $R^{4a}$ is hydrogen and $R^{4b}$ is C3-C8 cycloalkyl. In a still further aspect, $R^{4a}$ is hydrogen and $R^{4b}$ is C3 cycloalkyl. In a yet further aspect, $R^{4a}$ is hydrogen and $R^{4b}$ is C3 cycloalkyl substituted with 1 group. In a still further aspect, $R^{4a}$ is hydrogen and $R^{4b}$ is C3 cycloalkyl substituted with $Ar^2$. In a yet further aspect, $R^{4a}$ is hydrogen and $R^{4b}$ is C3 cycloalkyl substituted with a substituted phenyl. In an even further aspect, $R^{4a}$ is hydrogen and $R^{4b}$ is C3 cycloalkyl substituted with a substituted phenyl, wherein the phenyl is substituted with C1-C8 alkoxy.

In a further aspect, $R^{4a}$ is hydrogen and $R^{4b}$ is $Cy^1$-(C1-C6 alkyl)-. In a yet further aspect, $R^{4a}$ is hydrogen and $R^{4b}$ is $Cy^1$-(C1-C3 alkyl)-. In an even further aspect, $R^{4a}$ is hydrogen and $R^{4b}$ is $Cy^1$—$(CH_2)_3$—. In a still further aspect, $R^{4a}$ is hydrogen and $R^{4b}$ is $Cy^1$-$(CH_2)_2$—. In a yet further aspect, $R^{4a}$ is hydrogen and $R^{4b}$ is $Cy^1$-$CH_2$—.

In a further aspect, $R^{4a}$ is hydrogen and $R^{4b}$ is $Ar^1$. In a still further aspect, $R^{4a}$ is hydrogen and $R^{4b}$ is $Ar^1$—(C1-C6 alkyl)-. In a yet further aspect, $R^{4a}$ is hydrogen and $R^{4b}$ is $Ar^1$—(C1-C3 alkyl)-. In an even further aspect, $R^{4a}$ is hydrogen and $R^{4b}$ is $Ar^1$—$(CH_2)_3$—. In a still further aspect, $R^{4a}$ is hydrogen and $R^{4b}$ is $Ar^1$—$(CH_2)_2$—. In a yet further aspect, $R^{4a}$ is hydrogen and $R^{4b}$ is $Ar^1$—$CH_2$—.

In a further aspect, $R^{4a}$ is hydrogen and $R^{4b}$ is phenyl substituted with 1, 2, or 3 groups. In a still further aspect, $R^{4a}$ is hydrogen and $R^{4b}$ is phenyl substituted with 1, 2, or 3 groups independently selected from halogen, C1-C8 alkoxy, and —$S(O)_mR^5$.

In a further aspect, $R^{4a}$ and $R^{4b}$ are covalently bonded and, together with the intermediate nitrogen, comprise a substituted 3- to 7-membered heterocycloalkyl. In a still further aspect, $R^{4a}$ and $R^{4b}$ are covalently bonded and, together with the intermediate nitrogen, comprise a substituted 3- to 6-membered heterocycloalkyl. In a yet further aspect, $R^{4a}$ and $R^{4b}$ are covalently bonded and, together with the intermediate nitrogen, comprise a substituted 3- to 5-membered heterocycloalkyl.

In a further aspect, $R^{4a}$ and $R^{4b}$ are covalently bonded and, together with the intermediate nitrogen, comprise a 3-membered heterocycloalkyl substituted with 0, 1 or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)O$R^5$, —(C1-C6 alkyl)-S(O)$_mR^5$, —(C=O)$R^5$, —(C=O)O$R^5$, and —$S(O)_mR^5$. In a still further aspect, $R^{4a}$ and $R^{4b}$ are covalently bonded and, together with the intermediate nitrogen, comprise a 3-membered heterocycloalkyl substituted with 0, 1 or 2 groups independently selected from —F, —Cl, —$NH_2$, —OH, —CN, methyl, —$CH_2F$, —$CHF_2$, and —$CF_3$.

In a further aspect, $R^{4a}$ and $R^{4b}$ are covalently bonded and, together with the intermediate nitrogen, comprise a 4-membered heterocycloalkyl substituted with 0, 1 or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)O$R^5$, —(C1-C6 alkyl)-S(O)$_mR^5$, —(C=O)$R^5$, —(C=O)O$R^5$, and —$S(O)_mR^5$. In a still further aspect, $R^{4a}$ and $R^{4b}$ are covalently bonded and, together with the intermediate nitrogen, comprise a 4-membered heterocycloalkyl substituted with 0, 1 or 2 groups independently selected from —F, —Cl, —$NH_2$, —OH, —CN, methyl, —$CH_2F$, —$CHF_2$, and —$CF_3$.

In a further aspect, $R^{4a}$ and $R^{4b}$ are covalently bonded and, together with the intermediate nitrogen, comprise a 5-membered heterocycloalkyl substituted with 0, 1 or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)O$R^5$, —(C1-C6 alkyl)-S(O)$_mR^5$, —(C=O)$R^5$, —(C=O)O$R^5$, and —$S(O)_mR^5$. In a further aspect, $R^{4a}$ and $R^{4b}$ are covalently bonded and, together with the intermediate nitrogen, comprise a 5-membered heterocycloalkyl substituted with 0, 1 or 2 groups independently selected from —F, —Cl, —$NH_2$, —OH, —CN, methyl, —$CH_2F$, —$CHF_2$, and —$CF_3$.

In a further aspect, $R^{4a}$ and $R^{4b}$ are covalently bonded and, together with the intermediate nitrogen, comprise a 6-membered heterocycloalkyl substituted with 0, 1 or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)O$R^5$, —(C1-C6 alkyl)-S(O)$_mR^5$, —(C=O)$R^5$, —(C=O)O$R^5$, and —$S(O)_mR^5$. In a still further aspect, $R^{4a}$ and $R^{4b}$ are covalently bonded and, together with the intermediate nitrogen, comprise a 6-membered heterocycloalkyl substituted with 0, 1 or 2 groups independently selected from —F, —Cl, —$NH_2$, —OH, —CN, methyl, —$CH_2F$, —$CHF_2$, and —$CF_3$.

In a further aspect, $R^{4a}$ and $R^{4b}$ are covalently bonded and, together with the intermediate nitrogen, comprise a 7-membered heterocycloalkyl substituted with 0, 1 or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)O$R^5$, —(C1-C6 alkyl)-S(O)$_mR^5$, —(C=O)$R^5$, —(C=O)O$R^5$, and —$S(O)_mR^5$. In a still further aspect, $R^{4a}$ and $R^{4b}$ are covalently bonded and, together with the intermediate nitrogen, comprise a 7-membered heterocycloalkyl substituted with 0, 1 or 2 groups independently selected from —F, —Cl, —$NH_2$, —OH, —CN, methyl, —$CH_2F$, —$CHF_2$, and —$CF_3$.

In a further aspect, $R^{4a}$ and $R^{4b}$ are covalently bonded and, together with the intermediate nitrogen, comprise a pyrrolidinyl group substituted with 0 or 1 group independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)O$R^5$, —(C1-C6 alkyl)-S(O)$_mR^5$, —(C=O)$R^5$, —(C=O)O$R^5$, and —$S(O)_mR^5$. In a still further aspect, $R^{4a}$ and $R^{4b}$ are covalently bonded and, together with the intermediate nitrogen, comprise a pyrrolidinyl group substituted with 0 or 1 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C6 alkyl)-(C=O)$R^5$, —(C1-C6 alkyl)-(C=O)O$R^5$, —(C1-C6 alkyl)-S(O)$_mR^5$, —(C=O)$R^5$, —(C=O)O$R^5$, and —$S(O)_mR^5$. In a yet further aspect, $R^{4a}$ and $R^{4b}$ are covalently bonded and, together with the intermediate nitrogen, comprise a pyrrolidinyl group substituted with 0 or 1 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C3 alkyl)-(C=O)$R^5$, —(C1-C3 alkyl)-(C=O)O$R^5$, —(C1-C3 alkyl)-S(O)$_mR^5$, —(C=O)$R^5$, —(C=O)O$R^5$, and —$S(O)_mR^5$. In an even further aspect, $R^{4a}$ and $R^{4b}$ are covalently bonded and, together with the intermediate nitrogen, comprise a pyrrolidinyl group substituted with 0 or 1 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$.

In a further aspect, R$^{4a}$ and R$^{4b}$ are covalently bonded and, together with the intermediate nitrogen, comprise a pyrrolidinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a still further aspect, R$^{4a}$ and R$^{4b}$ are covalently bonded and, together with the intermediate nitrogen, comprise a pyrrolidinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a yet further aspect, R$^{4a}$ and R$^{4b}$ are covalently bonded and, together with the intermediate nitrogen, comprise a pyrrolidinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, and —SO$_2$R$^5$.

In a further aspect, R$^{4a}$ and R$^{4b}$ are covalently bonded and, together with the intermediate nitrogen, comprise a pyrrolidinyl group substituted with 0 or 1 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, R$^{4a}$ and R$^{4b}$ are covalently bonded and, together with the intermediate nitrogen, comprise a pyrrolidinyl group substituted with 0 or 1 groups independently selected from —F, —NH$_2$, —OH, —CN, methyl, —CH$_2$F, —CH$_2$Cl, —CHF$_2$, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, R$^{4a}$ and R$^{4b}$ are covalently bonded and, together with the intermediate nitrogen, comprise a pyrrolidinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R$^{4a}$ and R$^{4b}$ are covalently bonded and, together with the intermediate nitrogen, comprise a pyrrolidinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, R$^{4a}$ and R$^{4b}$ are covalently bonded and, together with the intermediate nitrogen, comprise a pyrrolidinyl group substituted with 0 or 1 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, R$^{4a}$ and R$^{4b}$ are covalently bonded and, together with the intermediate nitrogen, comprise a pyrrolidinyl group substituted with 0 or 1 group independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, R$^{4a}$ and R$^{4b}$ are covalently bonded and, together with the intermediate nitrogen, comprise a pyrrolidinyl group substituted with 0 or 1 group independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, R$^{4a}$ and R$^{4b}$ are covalently bonded and, together with the intermediate nitrogen, comprise a pyrrolidinyl group substituted with 0 or 1 group independently selected from —F, —Cl, —NH$_2$, —OH, —CN, methyl, —CH$_2$F, —CHF$_2$, and —CF$_3$. In an even further aspect, R$^{4a}$ and R$^{4b}$ are covalently bonded and, together with the intermediate nitrogen, comprise a pyrrolidinyl group substituted with 0 or 1 group independently selected from —F, methyl, and —CF$_3$.

In a further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a still further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a yet further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$. In an even further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$.

In a further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a still further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a yet further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, and —SO$_2$R$^5$.

In a further aspect, R$^{4a}$ and R$^{4b}$ are covalently bonded and, together with the intermediate nitrogen, comprise a pyrrolidinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, R$^{4a}$ and R$^{4b}$ are covalently bonded and, together with the intermediate nitrogen, comprise a pyrrolidinyl group substituted with 0, 1, or 2 groups independently selected from —F, —NH$_2$, —OH, —CN, methyl, —CH$_2$F, —CH$_2$Cl, —CHF$_2$, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, R$^{4a}$ and R$^{4b}$ are covalently bonded and, together with the intermediate nitrogen, comprise a pyrrolidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, R$^{4a}$ and R$^{4b}$ are covalently bonded and, together with the intermediate nitrogen, comprise a pyrrolidinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, R$^{4a}$ and R$^{4b}$ are covalently bonded and, together with the intermediate nitrogen, comprise a pyrrolidinyl group substituted with 0, 1, or 2 groups independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, R$^{4a}$ and R$^{4b}$ are covalently bonded and, together with the intermediate nitrogen, comprise a pyrrolidinyl group substituted with 0, 1, or 2 groups independently selected from —F, —Cl, —NH$_2$, —OH, —CN, methyl, —CH$_2$F, —CHF$_2$, and —CF$_3$. In an even further aspect, R$^{4a}$ and R$^{4b}$ are covalently bonded and, together with the intermediate nitrogen, comprise a pyrrolidinyl group substituted with 0, 1, or 2 groups independently selected from —F, methyl, and —CF$_3$.

In a still further aspect, R$^{4a}$ and R$^{4b}$ are covalently bonded and, together with the intermediate nitrogen, comprise an unsubstituted pyrrolidinyl group.

In a further aspect, R$^{4a}$ and R$^{4b}$ are covalently bonded and, together with the intermediate nitrogen, comprise a piperidinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a still further aspect, R$^{4a}$ and R$^{4b}$ are covalently bonded and, together with the intermediate nitrogen, comprise a piperidinyl group substituted with 0 or 1 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar², —(C1-C6 alkyl)-(C=O)R⁵, —(C1-C6 alkyl)-(C=O)OR⁵, —(C1-C6 alkyl)-S(O)ₘR⁵, —(C=O)R⁵, —(C=O)OR⁵, and —S(O)ₘR⁵. In a yet further aspect, R⁴ᵃ and R⁴ᵇ are covalently bonded and, together with the intermediate nitrogen, comprise a piperidinyl group substituted with 0 or 1 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar², —(C1-C3 alkyl)-(C=O)R⁵, —(C1-C3 alkyl)-(C=O)OR⁵, —(C1-C3 alkyl)-S(O)ₘR⁵, —(C=O)R⁵, —(C=O)OR⁵, and —S(O)ₘR⁵. In an even further aspect, R⁴ᵃ and R⁴ᵇ are covalently bonded and, together with the intermediate nitrogen, comprise a piperidinyl group substituted with 0 or 1 groups independently selected from halogen, —NH₂, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar², —(C1-C3 alkyl)-(C=O)R⁵, —(C1-C3 alkyl)-(C=O)OR⁵, —(C1-C3 alkyl)-S(O)ₘR⁵, —(C=O) R⁵, —(C=O)OR⁵, and —S(O)ₘR⁵.

In a further aspect, R⁴ᵃ and R⁴ᵇ are covalently bonded and, together with the intermediate nitrogen, comprise a piperidinyl group substituted with 0 or 1 groups independently selected from halogen, —NH₂, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar², —(CH₂)₃—(C=O)R⁵, —(CH₂)₂—(C=O)R⁵, —CH₂—(C=O)R⁵, —(CH₂)₃—(C=O)OR⁵, —(CH₂)₂—(C=O)OR⁵, —CH₂—(C=O)OR⁵, —(CH₂)₃—(S=O)R⁵, —(CH₂)₂—(S=O)R⁵, —CH₂—(S=O)R⁵, —(CH₂)₃—SO₂R⁵, —(CH₂)₂—SO₂R⁵, —CH₂—SO₂R⁵, —(C=O)R⁵, —(C=O)OR⁵, —(S=O)R⁵, and —SO₂R⁵. In a still further aspect, R⁴ᵃ and R⁴ᵇ are covalently bonded and, together with the intermediate nitrogen, comprise a piperidinyl group substituted with 0 or 1 groups independently selected from halogen, —NH₂, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar², —(CH₂)₂—(C=O)R⁵, —CH₂—(C=O)R⁵, —(CH₂)₂—(C=O)OR⁵, —CH₂—(C=O)OR⁵, —(CH₂)₂—(S=O)R⁵, —CH₂—(S=O)R⁵, —(CH₂)₂—SO₂R⁵, —CH₂—SO₂R⁵, —(C=O) R⁵, —(C=O)OR⁵, —(S=O)R⁵, and —SO₂R⁵. In a yet further aspect, R⁴ᵃ and R⁴ᵇ are covalently bonded and, together with the intermediate nitrogen, comprise a piperidinyl group substituted with 0 or 1 groups independently selected from halogen, —NH₂, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar², —CH₂—(C=O)R⁵, —CH₂—(C=O)OR⁵, —CH₂—(S=O)R⁵, —CH₂—SO₂R⁵, —(C=O)R⁵, —(C=O)OR⁵, —(S=O)R⁵, and —SO₂R⁵.

In a further aspect, R⁴ᵃ and R⁴ᵇ are covalently bonded and, together with the intermediate nitrogen, comprise a piperidinyl group substituted with 0 or 1 groups independently selected from —F, —Cl, —NH₂, —OH, —CN, methyl, ethyl, propyl, isopropyl, —CHF, —CH₂Cl, —CH₂CH₂F, —CH₂CH₂Cl, —(CH₂)₂CH₂F, —(CH₂)₂CH₂Cl, —CHF, —CF₃, —CHCl₂, —CCl₃, —CH₂CHF₂, —CH₂CF₃, —CH₂CHCl₂, —CH₂CCl₃, —NH(CH₃), —N(CH₃)₂, cyclopropyl, cyclobutyl, cyclopentyl, cyclohexyl, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O) OCH₃, —(C=O)OCH₃, and Ar²; and wherein Ar², when present, is substituted with 0, 1, 2, or 3 groups selected from —F, —Cl, —Br, —NH₂, —OH, —CN, methyl, CH₂F, —CH₂Cl, —CHF₂, —CF₃, —CHCl₂, —CCl₃, —OCH₃, —OCH₂CH₃, —NHCH₃, —N(CH₃)₂, —SCH₃, —SOCH₃, and —SO₂CH₃. In a still further aspect, R⁴ᵃ and R⁴ᵇ are covalently bonded and, together with the intermediate nitrogen, comprise a piperidinyl group substituted with 0 or 1 groups independently selected from —F, —NH₂, —OH, —CN, methyl, —CHF, —CH₂Cl, —CHF, —CF₃, —CHCl₂, —CCl₃, —NH(CH₃), —N(CH₃)₂, cyclopropyl, —(CH₂)—SCH₃, —(CH₂)—SOCH₃, —(CH₂)—SO₂CH₃, —SCH₃, —SOCH₃, —SO₂CH₃, —(CH₂)—SCF₃, —(CH₂)—SOCF₃, —(CH₂)—SO₂CF₃, —SCF₃, —SOCF₃, —SO₂CF₃, —(CH₂)—(C=O)CH₃, —(C=O)CH₃, —(CH₂)—(C=O) OCH₃, —(C=O)OCH₃, and phenyl; and wherein phenyl, when present, is substituted with 0, 1, 2, or 3 groups selected from —F, —Cl, —Br, —NH₂, —OH, —CN, methyl, CH₂F, —CH₂Cl, —CHF₂, —CF₃, —CHCl₂, —CCl₃, —OCH₃, —OCH₂CH₃, —NHCH₃, —N(CH₃)₂, —SCH₃, —SOCH₃, and —SO₂CH₃.

In a further aspect, R⁴ᵃ and R⁴ᵇ are covalently bonded and, together with the intermediate nitrogen, comprise a piperidinyl group substituted with 0 or 1 group independently selected from halogen, —NH₂, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R⁴ᵃ and R⁴ᵇ are covalently bonded and, together with the intermediate nitrogen, comprise a piperidinyl group substituted with 0 or 1 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, R⁴ᵃ and R⁴ᵇ are covalently bonded and, together with the intermediate nitrogen, comprise a piperidinyl group substituted with 0 or 1 groups independently selected from halogen, —NH₂, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, R⁴ᵃ and R⁴ᵇ are covalently bonded and, together with the intermediate nitrogen, comprise a piperidinyl group substituted with 0 or 1 group independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —NH(CH₃), —N(CH₃)₂, cyclopropyl, cyclobutyl, cyclopentyl, and cyclohexyl. In a still further aspect, R⁴ᵃ and R⁴ᵇ are covalently bonded and, together with the intermediate nitrogen, comprise a piperidinyl group substituted with 0 or 1 group independently selected from —F, —Cl, —NH₂, —OH, —CN, methyl, —CH₂F, —CHF₂, —CF₃, —NH(CH₃), —N(CH₃)₂, and cyclopropyl. In yet further aspect, R⁴ᵃ and R⁴ᵇ are covalently bonded and, together with the intermediate nitrogen, comprise a piperidinyl group substituted with 0 or 1 group independently selected from —F, —Cl, —NH₂, —OH, —CN, methyl, —CH₂F, —CHF₂, and —CF₃. In an even further aspect, R⁴ᵃ and R⁴ᵇ are covalently bonded and, together with the intermediate nitrogen, comprise a piperidinyl group substituted with 0 or 1 group independently selected from —F, methyl, and —CF₃.

In a further aspect, R⁴ᵃ and R⁴ᵇ are covalently bonded and, together with the intermediate nitrogen, comprise a piperidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a still further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a yet further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$. In an even further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$.

In a further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a still further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a yet further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, and —SO$_2$R$^5$.

In a further aspect, R$^{4a}$ and R$^{4b}$ are covalently bonded and, together with the intermediate nitrogen, comprise a piperidinyl group substituted with 0, 1, or 2 groups independently selected from —F, —Cl, —NH$_2$, —OH, —CN, methyl, ethyl, propyl, isopropyl, —CHF$_2$, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, R$^{4a}$ and R$^{4b}$ are covalently bonded and, together with the intermediate nitrogen, comprise a piperidinyl group substituted with 0, 1, or 2 groups independently selected from —F, —NH$_2$, —OH, —CN, methyl, —CHF$_2$, —CH$_2$Cl, —CHF$_2$, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, R$^{4a}$ and R$^{4b}$ are covalently bonded and, together with the intermediate nitrogen, comprise a piperidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, R$^{4a}$ and R$^{4b}$ are covalently bonded and, together with the intermediate nitrogen, comprise a piperidinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, R$^{4a}$ and R$^{4b}$ are covalently bonded and, together with the intermediate nitrogen, comprise a piperidinyl group substituted with 0, 1, or 2 groups independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, R$^{4a}$ and R$^{4b}$ are covalently bonded and, together with the intermediate nitrogen, comprise a piperidinyl group substituted with 0, 1, or 2 groups independently selected from —F, —Cl, —NH$_2$, —OH, —CN, methyl, —CH$_2$F, —CHF$_2$, and —CF$_3$. In an even further aspect, $R^{4a}$ and $R^{4b}$ are covalently bonded and, together with the intermediate nitrogen, comprise a piperidinyl group substituted with 0, 1, or 2 groups independently selected from —F, methyl, and —CF$_3$.

In a still further aspect, $R^{4a}$ and $R^{4b}$ are covalently bonded and, together with the intermediate nitrogen, comprise an unsubstituted piperidinyl group.

In a further aspect, $R^{4a}$ and $R^{4b}$ are covalently bonded and, together with the intermediate nitrogen, comprise an azetidinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a still further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a yet further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$. In an even further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$.

In a further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a still further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a yet further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, and —SO$_2$R$^5$.

In a further aspect, $R^{4a}$ and $R^{4b}$ are covalently bonded and, together with the intermediate nitrogen, comprise an azetidinyl group substituted with 0 or 1 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, $R^{4a}$ and $R^{4b}$ are covalently bonded and, together with the intermediate nitrogen, comprise an azetidinyl group substituted with 0 or 1 groups independently selected from —F, —NH$_2$, —OH, —CN, methyl, —CHF, —CH$_2$Cl, —CHF$_2$, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, $R^{4a}$ and $R^{4b}$ are covalently bonded and, together with the intermediate nitrogen, comprise an azetidinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, $R^{4a}$ and $R^{4b}$ are covalently bonded and, together with the intermediate nitrogen, comprise an azetidinyl group substituted with 0 or 1 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, $R^{4a}$ and $R^{4b}$ are covalently bonded and, together with the intermediate nitrogen, comprise an azetidinyl group substituted with 0 or 1 group independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, $R^{4a}$ and $R^{4b}$ are covalently bonded and, together with the intermediate nitrogen, comprise an azetidinyl group substituted with 0 or 1 group independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, $R^{4a}$ and $R^{4b}$ are covalently bonded and, together with the intermediate nitrogen, comprise an azetidinyl group substituted with 0 or 1 group independently selected from —F, —Cl, —NH$_2$, —OH, —CN, methyl, —CH$_2$F, —CHF$_2$, and —CF$_3$. In an even further aspect, $R^{4a}$ and $R^{4b}$ are covalently bonded and, together with the intermediate nitrogen, comprise an azetidinyl group substituted with 0 or 1 group independently selected from —F, methyl, and —CF$_3$.

In a further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, and —S(O)$_m$R$^5$. In a still further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, and —S(O)$_m$R$^5$. In a yet further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C3 alkyl)-(C═O)R$^5$, —(C1-C3 alkyl)-(C═O)OR$^5$, —(C1-C3 alkyl)-S(O)$_m$R$^5$, —(C═O)R$^5$, —(C═O)OR$^5$, and —S(O)$_m$R$^5$. In an even further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C═O)R$^5$, —(C1-C3 alkyl)-(C═O)OR$^5$, —(C1-C3 alkyl)-S(O)$_m$R$^5$, —(C═O)R$^5$, —(C═O)OR$^5$, and —S(O)$_m$R$^5$.

In a further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C═O)R$^5$, —(CH$_2$)$_2$—(C═O)R$^5$, —CH$_2$—(C═O)R$^5$, —(CH$_2$)$_3$—(C═O)OR$^5$, —(CH$_2$)$_2$—(C═O)OR$^5$, —CH$_2$—(C═O)OR$^5$, —(CH$_2$)$_3$—(S═O)R$^5$, —(CH$_2$)$_2$—(S═O)R$^5$, —CH$_2$—(S═O)R$^5$, —(CH$_2$)$_3$—SO$_2$R$^5$, —(CH$_2$)$_2$—SO$_2$R$^5$, —CH$_2$—SO$_2$R$^5$, —(C═O)R$^5$, —(C═O)OR$^5$, —(S═O)R$^5$, and —SO$_2$R$^5$. In a still further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C═O)R$^5$, —CH$_2$—(C═O)R$^5$, —(CH$_2$)$_2$—(C═O)OR$^5$, —CH$_2$—(C═O)OR$^5$, —(CH$_2$)$_2$—(S═O)R$^5$, —CH$_2$—(S═O)R$^5$, —(CH$_2$)$_2$—SO$_2$R$^5$, —CH$_2$—SO$_2$R$^5$, —(C═O)R$^5$, —(C═O)OR$^5$, —(S═O)R$^5$, and —SO$_2$R$^5$. In a yet further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C═O)R$^5$, —CH$_2$—(C═O)OR$^5$, —CH$_2$—(S═O)R$^5$, —CH$_2$—SO$_2$R$^5$, —(C═O)R$^5$, —(C═O)OR$^5$, —(S═O)R$^5$, and —SO$_2$R$^5$.

In a further aspect, $R^{4a}$ and $R^{4b}$ are covalently bonded and, together with the intermediate nitrogen, comprise an azetidinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C═O)CH$_3$, —(C═O)CH$_3$, —(CH$_2$)—(C═O)OCH$_3$, —(C═O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, $R^{4a}$ and $R^{4b}$ are covalently bonded and, together with the intermediate nitrogen, comprise an azetidinyl group substituted with 0, 1, or 2 groups independently selected from —F, —NH$_2$, —OH, —CN, methyl, —CH$_2$F, —CH$_2$Cl, —CHF$_2$, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C═O)CH$_3$, —(C═O)CH$_3$, —(CH$_2$)—(C═O)OCH$_3$, —(C═O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, $R^{4a}$ and $R^{4b}$ are covalently bonded and, together with the intermediate nitrogen, comprise an azetidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, $R^{4a}$ and $R^{4b}$ are covalently bonded and, together with the intermediate nitrogen, comprise an azetidinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, R$^{4a}$ and R$^{4b}$ are covalently bonded and, together with the intermediate nitrogen, comprise an azetidinyl group substituted with 0, 1, or 2 groups independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, R$^{4a}$ and R$^{4b}$ are covalently bonded and, together with the intermediate nitrogen, comprise an azetidinyl group substituted with 0, 1, or 2 groups independently selected from —F, —Cl, —NH$_2$, —OH, —CN, methyl, —CH$_2$F, —CHF$_2$, and —CF$_3$. In an even further aspect, R$^{4a}$ and R$^{4b}$ are covalently bonded and, together with the intermediate nitrogen, comprise an azetidinyl group substituted with 0, 1, or 2 groups independently selected from —F, methyl, and —CF$_3$.

In a still further aspect, R$^{4a}$ and R$^{4b}$ are covalently bonded and, together with the intermediate nitrogen, comprise an unsubstituted azetidinyl group.

In a further aspect, R$^{4a}$ and R$^{4b}$ are covalently bonded and, together with the intermediate nitrogen, comprise an aziridinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a still further aspect, R$^{4a}$ and R$^{4b}$ are covalently bonded and, together with the intermediate nitrogen, comprise an aziridinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a yet further aspect, R$^{4a}$ and R$^{4b}$ are covalently bonded and, together with the intermediate nitrogen, comprise an aziridinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$. In an even further aspect, R$^{4a}$ and R$^{4b}$ are covalently bonded and, together with the intermediate nitrogen, comprise an aziridinyl group substituted with 0 or 1 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O) R$^5$, —(C=O)OR$^5$, and —S(O)$_m$R$^5$.

In a further aspect, R$^{4a}$ and R$^{4b}$ are covalently bonded and, together with the intermediate nitrogen, comprise an aziridinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a still further aspect, R$^{4a}$ and R$^{4b}$ are covalently bonded and, together with the intermediate nitrogen, comprise an aziridinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O) R$^5$, —(C=O)OR$^5$, —(S=O)R$^5$, and —SO$_2$R$^5$. In a yet further aspect, R$^{4a}$ and R$^{4b}$ are covalently bonded and, together with the intermediate nitrogen, comprise an aziridinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, and —SO$_2$R$^5$.

In a further aspect, R$^{4a}$ and R$^{4b}$ are covalently bonded and, together with the intermediate nitrogen, comprise an aziridinyl group substituted with 0 or 1 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O) OCH$_3$, —(C=O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, R$^{4a}$ and R$^{4b}$ are covalently bonded and, together with the intermediate nitrogen, comprise an aziridinyl group substituted with 0 or 1 groups independently selected from —F, —NH$_2$, —OH, —CN, methyl, —CHF, —CH$_2$Cl, —CHF, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O) OCH$_3$, —(C=O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, R$^{4a}$ and R$^{4b}$ are covalently bonded and, together with the intermediate nitrogen, comprise an aziridinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R$^{4a}$ and R$^{4b}$ are covalently bonded and, together with the intermediate nitrogen, comprise an aziridinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, $R^{4a}$ and $R^{4b}$ are covalently bonded and, together with the intermediate nitrogen, comprise an aziridinyl group substituted with 0 or 1 groups independently selected from halogen, —$NH_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, $R^{4a}$ and $R^{4b}$ are covalently bonded and, together with the intermediate nitrogen, comprise an aziridinyl group substituted with 0 or 1 group independently selected from —F, —Cl, —$NH_2$, —OH, —CN, methyl, ethyl, propyl, isopropyl, —CHF, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NH(CH_3)$, —$N(CH_3)_2$, cyclopropyl, cyclobutyl, cyclopentyl, and cyclohexyl. In a still further aspect, $R^{4a}$ and $R^{4b}$ are covalently bonded and, together with the intermediate nitrogen, comprise an aziridinyl group substituted with 0 or 1 group independently selected from —F, —Cl, —$NH_2$, —OH, —CN, methyl, —$CH_2F$, —$CHF_2$, —$CF_3$, —$NH(CH_3)$, —$N(CH_3)_2$, and cyclopropyl. In yet further aspect, $R^{4a}$ and $R^{4b}$ are covalently bonded and, together with the intermediate nitrogen, comprise an aziridinyl group substituted with 0 or 1 group independently selected from —F, —Cl, —$NH_2$, —OH, —CN, methyl, —CHF, —$CHF_2$, and —$CF_3$. In an even further aspect, $R^{4a}$ and $R^{4b}$ are covalently bonded and, together with the intermediate nitrogen, comprise an aziridinyl group substituted with 0 or 1 group independently selected from —F, methyl, and —$CF_3$.

In a further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)$OR^5$, —(C1-C6 alkyl)-S(O)$_mR^5$, —(C=O)$R^5$, —(C=O)$OR^5$, and —S(O)$_mR^5$. In a still further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C6 alkyl)-(C=O)$R^5$, —(C1-C6 alkyl)-(C=O)$OR^5$, —(C1-C6 alkyl)-S(O)$_mR^5$, —(C=O)$R^5$, —(C=O)$OR^5$, and —S(O)$_mR^5$. In a yet further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C3 alkyl)-(C=O)$R^5$, —(C1-C3 alkyl)-(C=O)$OR^5$, —(C1-C3 alkyl)-S(O)$_mR^5$, —(C=O)$R^5$, —(C=O)$OR^5$, and —S(O)$_mR^5$. In an even further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, $Ar^2$, —(C1-C3 alkyl)-(C=O)$R^5$, —(C1-C3 alkyl)-(C=O)$OR^5$, —(C1-C3 alkyl)-S(O)$_mR^5$, —(C=O)$R^5$, —(C=O)$OR^5$, and —S(O)$_mR^5$.

In a further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$(CH_2)_3$—(C=O)$R^5$, —$(CH_2)_2$—(C=O)$R^5$, —$CH_2$—(C=O)$R^5$, —$(CH_2)_3$—(C=O)$OR^5$, —$(CH_2)_2$—(C=O)$OR^5$, —$CH_2$—(C=O)$OR^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —(C=O)$R^5$, —(C=O)$OR^5$, —(S=O)$R^5$, and —$SO_2R^5$. In a still further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$(CH_2)_2$—(C=O)$R^5$, —$CH_2$—(C=O)$R^5$, —$(CH_2)_2$—(C=O)$OR^5$, —$CH_2$—(C=O)$OR^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)$OR^5$, —(S=O)$R^5$, and —$SO_2R^5$. In a yet further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$CH_2$—(C=O)$R^5$, —$CH_2$—(C=O)$OR^5$, —$CH_2$—(S=O)$R^5$, —$CH_2$—$SO_2R^5$, —(C=O)$R^5$, —(C=O)$OR^5$, —(S=O)$R^5$, and —$SO_2R^5$.

In a further aspect, $R^{4a}$ and $R^{4b}$ are covalently bonded and, together with the intermediate nitrogen, comprise an aziridinyl group substituted with 0, 1, or 2 groups independently selected from —F, —Cl, —$NH_2$, —OH, —CN, methyl, ethyl, propyl, isopropyl, —CHF, —$CH_2Cl$, —$CH_2CH_2F$, —$CH_2CH_2Cl$, —$(CH_2)_2CH_2F$, —$(CH_2)_2CH_2Cl$, —CHF, —$CF_3$, —$CHCl_2$, —$CCl_3$, —$CH_2CHF_2$, —$CH_2CF_3$, —$CH_2CHCl_2$, —$CH_2CCl_3$, —$NH(CH_3)$, —$N(CH_3)_2$, cyclopropyl, cyclobutyl, cyclopentyl, cyclohexyl, —$(CH_2)$—$SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—(C=O)$CH_3$, —(C=O)$CH_3$, —$(CH_2)$—(C=O)$OCH_3$, —(C=O)$OCH_3$, and $Ar^2$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —CHF, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$; In a still further aspect, $R^{4a}$ and $R^{4b}$ are covalently bonded and, together with the intermediate nitrogen, comprise an aziridinyl group substituted with 0, 1, or 2 groups independently selected from —F, —$NH_2$, —OH, —CN, methyl, —$CH_2F$, —$CH_2Cl$, —CHF, —$CF_3$, —$CHCl_2$, —$CCl_3$, —$NH(CH_3)$, —$N(CH_3)_2$, cyclopropyl, —$(CH_2)$—$SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—(C=O)$CH_3$, —(C=O)$CH_3$, —$(CH_2)$—(C=O)$OCH_3$, —(C=O)$OCH_3$, and phenyl; and wherein phenyl, when present, is substituted with 0, 1, 2, or 3 groups selected from —F, —Cl, —Br, —$NH_2$, —OH, —CN, methyl, $CH_2F$, —$CH_2Cl$, —CHF, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$.

In a further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, $R^{4a}$ and $R^{4b}$ are covalently bonded and, together with the intermediate nitrogen, comprise an aziridinyl group substituted with 0, 1, or 2 groups independently selected from halogen, —$NH_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, $R^{4a}$ and $R^{4b}$ are covalently bonded and, together with the intermediate nitrogen, comprise an aziridinyl group substituted with 0, 1, or 2 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NH(CH_3)$, —$N(CH_3)_2$, cyclopropyl, cyclobutyl, cyclopentyl, and cyclohexyl. In a still further aspect, $R^{4a}$ and $R^{4b}$ are covalently bonded and, together with the intermediate nitrogen, comprise an aziridinyl group substituted with 0, 1, or 2 groups independently selected from —F, —Cl, —$NH_2$, —OH, —CN, methyl, —$CH_2F$, —$CHF_2$, —$CF_3$, —$NH(CH_3)$, —$N(CH_3)_2$, and cyclopropyl. In yet further aspect, $R^{4a}$ and $R^{4b}$ are covalently bonded and, together with the intermediate nitrogen, comprise an aziridinyl group substituted with 0, 1, or 2 groups independently selected from —F, —Cl, —$NH_2$, —OH, —CN, methyl, —$CH_2F$, —$CHF_2$, and —$CF_3$. In an even further aspect, $R^{4a}$ and $R^{4b}$ are covalently bonded and, together with the intermediate nitrogen, comprise an aziridinyl group substituted with 0, 1, or 2 groups independently selected from —F, methyl, and —$CF_3$.

In a still further aspect, $R^{4a}$ and $R^{4b}$ are covalently bonded and, together with the intermediate nitrogen, comprise an unsubstituted aziridinyl group.

In a further aspect, $R^{4a}$ and $R^{4b}$ are covalently bonded and, together with the intermediate nitrogen, comprise an imidazolidinyl group substituted with 0 or 1 group independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)$OR^5$, —(C1-C6 alkyl)-S(O)$_mR^5$, —(C=O)$R^5$, —(C=O)$OR^5$, and —S(O)$_mR^5$. In a still further aspect, $R^{4a}$ and $R^{4b}$ are covalently bonded and, together with the intermediate nitrogen, comprise an imidazolidinyl group substituted with 0 or 1 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C6 alkyl)-(C=O)$R^5$, —(C1-C6 alkyl)-(C=O)$OR^5$, —(C1-C6 alkyl)-S(O)$_mR^5$, —(C=O)$R^5$, —(C=O)$OR^5$, and —S(O)$_mR^5$. In a yet further aspect, $R^{4a}$ and $R^{4b}$ are covalently bonded and, together with the intermediate nitrogen, comprise an imidazolidinyl group substituted with 0 or 1 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C3 alkyl)-(C=O)$R^5$, —(C1-C3 alkyl)-(C=O)$OR^5$, —(C1-C3 alkyl)-S(O)$_mR^5$, —(C=O)$R^5$, —(C=O)$OR^5$, and —S(O)$_mR^5$. In an even further aspect, $R^{4a}$ and $R^{4b}$ are covalently bonded and, together with the intermediate nitrogen, comprise an imidazolidinyl group substituted with 0 or 1 groups independently selected from halogen, —$NH_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, $Ar^2$, —(C1-C3 alkyl)-(C=O)$R^5$, —(C1-C3 alkyl)-S(O)$_mR^5$, —(C=O)$R^5$, —(C=O)$OR^5$, and —S(O)$_mR^5$.

In a further aspect, $R^{4a}$ and $R^{4b}$ are covalently bonded and, together with the intermediate nitrogen, comprise an imidazolidinyl group substituted with 0 or 1 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$(CH_2)_3$—(C=O)$R^5$, —$(CH_2)_2$—(C=O)$R^5$, —$CH_2$—(C=O)$R^5$, —$(CH_2)_3$—(C=O)$OR^5$, —$(CH_2)_2$—(C=O)$OR^5$, —$CH_2$—(C=O)$OR^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —(C=O)$R^5$, —(C=O)$OR^5$, —(S=O)$R^5$, and —$SO_2R^5$. In a still further aspect, $R^{4a}$ and $R^{4b}$ are covalently bonded and, together with the intermediate nitrogen, comprise an imidazolidinyl group substituted with 0 or 1 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$(CH_2)_2$—(C=O)$R^5$, —$CH_2$—(C=O)$R^5$, —$(CH_2)_2$—(C=O)$OR^5$, —$CH_2$—(C=O)$OR^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)$OR^5$, —(S=O)$R^5$, and —$SO_2R^5$. In a yet further aspect, $R^{4a}$ and $R^{4b}$ are covalently bonded and, together with the intermediate nitrogen, comprise an imidazolidinyl group substituted with 0 or 1 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$CH_2$—(C=O)$R^5$, —$CH_2$—(C=O)$OR^5$, —$CH_2$—(S=O)$R^5$, —$CH_2$—$SO_2R^5$, —(C=O)$R^5$, —(C=O)$OR^5$, —(S=O)$R^5$, and —$SO_2R^5$.

In a further aspect, $R^{4a}$ and $R^{4b}$ are covalently bonded and, together with the intermediate nitrogen, comprise an imidazolidinyl group substituted with 0 or 1 groups independently selected from —F, —Cl, —$NH_2$, —OH, —CN, methyl, ethyl, propyl, isopropyl, —CHF, —$CH_2Cl$, —$CH_2CH_2F$, —$CH_2CH_2Cl$, —$(CH_2)_2CH_2F$, —$(CH_2)_2CH_2Cl$, —CHF, —$CF_3$, —$CHCl_2$, —$CCl_3$, —$CH_2CHF_2$, —$CH_2CF_3$, —$CH_2CHCl_2$, —$CH_2CCl_3$, —$NH(CH_3)$, $N(CH_3)_2$, cyclopropyl, cyclobutyl, cyclopentyl, cyclohexyl, —$(CH_2)$—$SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—(C=O)$CH_3$, —(C=O)$CH_3$, —$(CH_2)$—(C=O)$OCH_3$, —(C=O)$OCH_3$, and $Ar^2$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —CHF, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a still further aspect, $R^{4a}$ and $R^{4b}$ are covalently bonded and, together with the intermediate nitrogen, comprise an imidazolidinyl group substituted with 0 or 1 groups independently selected from —F, —$NH_2$, —OH, —CN, methyl, —CHF, —$CH_2Cl$, —CHF, —$CF_3$, —$CHCl_2$, —$CCl_3$, —$NH(CH_3)$, —$N(CH_3)_2$, cyclopropyl, —$(CH_2)$—$SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—(C=O)$CH_3$, —(C=O)$CH_3$, —$(CH_2)$—(C=O)

OCH$_3$, —(C=O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, R$^{4a}$ and R$^{4b}$ are covalently bonded and, together with the intermediate nitrogen, comprise an imidazolidinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R$^{4a}$ and R$^{4b}$ are covalently bonded and, together with the intermediate nitrogen, comprise an imidazolidinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, R$^{4a}$ and R$^{4b}$ are covalently bonded and, together with the intermediate nitrogen, comprise an imidazolidinyl group substituted with 0 or 1 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, R$^{4a}$ and R$^{4b}$ are covalently bonded and, together with the intermediate nitrogen, comprise an imidazolidinyl group substituted with 0 or 1 group independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, R$^{4a}$ and R$^{4b}$ are covalently bonded and, together with the intermediate nitrogen, comprise an imidazolidinyl group substituted with 0 or 1 group independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, R$^{4a}$ and R$^{4b}$ are covalently bonded and, together with the intermediate nitrogen, comprise an imidazolidinyl group substituted with 0 or 1 group independently selected from —F, —Cl, —NH$_2$, —OH, —CN, methyl, —CH$_2$F, —CHF$_2$, and —CF$_3$. In an even further aspect, R$^{4a}$ and R$^{4b}$ are covalently bonded and, together with the intermediate nitrogen, comprise an imidazolidinyl group substituted with 0 or 1 group independently selected from —F, methyl, and —CF$_3$.

In a further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a still further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a yet further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$. In an even further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$.

In a further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a still further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a yet further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, and —SO$_2$R$^5$.

In a further aspect, R$^{4a}$ and R$^{4b}$ are covalently bonded and, together with the intermediate nitrogen, comprise an imidazolidinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, R$^{4a}$ and R$^{4b}$ are covalently bonded and, together with the intermediate nitrogen, comprise an imidazolidinyl group substituted with 0, 1, or 2 groups independently selected from —F, —NH$_2$, —OH, —CN, methyl, —CHF, —CH$_2$Cl, —CHF, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, R$^{4a}$ and R$^{4b}$ are covalently bonded and, together with the intermediate nitrogen, comprise an imidazolidinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, R$^{4a}$ and R$^{4b}$ are covalently bonded and, together with the intermediate nitrogen, comprise an imidazolidinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, R$^{4a}$ and R$^{4b}$ are covalently bonded and, together with the intermediate nitrogen, comprise an imidazolidinyl group substituted with 0, 1, or 2 groups independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, R$^{4a}$ and R$^{4b}$ are covalently bonded and, together with the intermediate nitrogen, comprise an imidazolidinyl group substituted with 0, 1, or 2 groups independently selected from —F, —Cl, —NH$_2$, —OH, —CN, methyl, —CH$_2$F, —CHF$_2$, and —CF$_3$. In an even further aspect, R$^{4a}$ and R$^{4b}$ are covalently bonded and, together with the intermediate nitrogen, comprise an imidazolidinyl group substituted with 0, 1, or 2 groups independently selected from —F, methyl, and —CF$_3$.

In a still further aspect, R$^{4a}$ and R$^{4b}$ are covalently bonded and, together with the intermediate nitrogen, comprise an unsubstituted imidazolidinyl group.

In a further aspect, R$^{4a}$ and R$^{4b}$ are covalently bonded and, together with the intermediate nitrogen, comprise an piperazinyl group substituted with 0 or 1 group independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a still further aspect, R$^{4a}$ and R$^{4b}$ are covalently bonded and, together with the intermediate nitrogen, comprise an piperazinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, and —S(O)$_m$R$^5$. In a yet further aspect, R$^{4a}$ and R$^{4b}$ are covalently bonded and, together with the intermediate nitrogen, comprise an piperazinyl group substituted with 0 or 1 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$. In an even further aspect, R$^{4a}$ and R$^{4b}$ are covalently bonded and, together with the intermediate nitrogen, comprise an piperazinyl group substituted with 0 or 1 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, Ar$^2$, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, and —S(O)$_m$R$^5$.

In a further aspect, R$^{4a}$ and R$^{4b}$ are covalently bonded and, together with the intermediate nitrogen, comprise an piperazinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a still further aspect, R$^{4a}$ and R$^{4b}$ are covalently bonded and, together with the intermediate nitrogen, comprise an piperazinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —(S=O)R$^5$, and —SO$_2$R$^5$. In a yet further aspect, R$^{4a}$ and R$^{4b}$ are covalently bonded and, together with the intermediate nitrogen, comprise an piperazinyl group substituted with 0 or 1 groups independently selected from halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, Ar$^2$, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, and —SO$_2$R$^5$.

In a further aspect, R$^{4a}$ and R$^{4b}$ are covalently bonded and, together with the intermediate nitrogen, comprise an piperazinyl group substituted with 0 or 1 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—$(C=O)CH_3$, —$(C=O)CH_3$, —$(CH_2)$—$(C=O)OCH_3$, —$(C=O)OCH_3$, and $Ar^2$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a still further aspect, $R^{4a}$ and $R^{4b}$ are covalently bonded and, together with the intermediate nitrogen, comprise an piperazinyl group substituted with 0 or 1 groups independently selected from —F, —$NH_2$, —OH, —CN, methyl, —$CH_2F$, —$CH_2Cl$, —$CHF_2$, —$CF_3$, —$CHCl_2$, —$CCl_3$, —$NH(CH_3)$, —$N(CH_3)_2$, cyclopropyl, —$(CH_2)$—$SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—$(C=O)CH_3$, —$(C=O)CH_3$, —$(CH_2)$—$(C=O)OCH_3$, —$(C=O)OCH_3$, and phenyl; and wherein phenyl, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$.

In a further aspect, $R^{4a}$ and $R^{4b}$ are covalently bonded and, together with the intermediate nitrogen, comprise a piperazinyl group substituted with 0 or 1 group independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, $R^{4a}$ and $R^{4b}$ are covalently bonded and, together with the intermediate nitrogen, comprise a piperazinyl group substituted with 0 or 1 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, $R^{4a}$ and $R^{4b}$ are covalently bonded and, together with the intermediate nitrogen, comprise an piperazinyl group substituted with 0 or 1 groups independently selected from halogen, —$NH_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, $R^{4a}$ and $R^{4b}$ are covalently bonded and, together with the intermediate nitrogen, comprise an piperazinyl group substituted with 0 or 1 group independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NH(CH_3)$, —$N(CH_3)_2$, cyclopropyl, cyclobutyl, cyclopentyl, and cyclohexyl. In a still further aspect, $R^{4a}$ and $R^{4b}$ are covalently bonded and, together with the intermediate nitrogen, comprise an piperazinyl group substituted with 0 or 1 group independently selected from —F, —Cl, —$NH_2$, —OH, —CN, methyl, —$CH_2F$, —$CHF_2$, —$CF_3$, —$NH(CH_3)$, —$N(CH_3)_2$, and cyclopropyl. In yet further aspect, $R^{4a}$ and $R^{4b}$ are covalently bonded and, together with the intermediate nitrogen, comprise a piperazinyl group substituted with 0 or 1 group independently selected from —F, —Cl, —$NH_2$, —OH, —CN, methyl, —$CH_2F$, —$CHF_2$, and —$CF_3$. In an even further aspect, $R^{4a}$ and $R^{4b}$ are covalently bonded and, together with the intermediate nitrogen, comprise a piperazinyl group substituted with 0 or 1 group independently selected from —F, methyl, and —$CF_3$.

In a further aspect, $R^{4a}$ and $R^{4b}$ are covalently bonded and, together with the intermediate nitrogen, comprise an piperazinyl group substituted with 0, 1, or 2 groups independently selected from halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, $Ar^2$, —(C1-C6 alkyl)-(C=O)$R^5$, —(C1-C6 alkyl)-(C=O)$OR^5$, —(C1-C6 alkyl)-S(O)$_m R^5$, —(C=O)$R^5$, —(C=O)$OR^5$, and —S(O)$_m R^5$. In a still further aspect, $R^{4a}$ and $R^{4b}$ are covalently bonded and, together with the intermediate nitrogen, comprise an piperazinyl group substituted with 0, 1, or 2 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C6 alkyl)-(C=O)$R^5$, —(C1-C6 alkyl)-(C=O)$OR^5$, —(C1-C6 alkyl)-S(O)$_m R^5$, —(C=O)$R^5$, —(C=O)$OR^5$, and —S(O)$_m R^5$. In a yet further aspect, $R^{4a}$ and $R^{4b}$ are covalently bonded and, together with the intermediate nitrogen, comprise an piperazinyl group substituted with 0, 1, or 2 groups independently selected from halogen, —$NH_2$, —OH, —CN, C1-C6 alkyl, C1-C6 haloalkyl, C1-C6 polyhaloalkyl, C1-C6 alkoxy, C1-C6 alkylamino, C1-C6 dialkylamino, C3-C6 cycloalkyl, $Ar^2$, —(C1-C3 alkyl)-(C=O)$R^5$, —(C1-C3 alkyl)-(C=O)$OR^5$, —(C1-C3 alkyl)-S(O)$_m R^5$, —(C=O)$R^5$, —(C=O)$OR^5$, and —S(O)$_m R^5$. In an even further aspect, $R^{4a}$ and $R^{4b}$ are covalently bonded and, together with the intermediate nitrogen, comprise an piperazinyl group substituted with 0, 1, or 2 groups independently selected from halogen, —$NH_2$, —OH, —CN, C1-C6 alkyl, C1-C6 haloalkyl, C1-C3 polyhaloalkyl, C1-C3 alkoxy, C1-C3 alkylamino, C1-C3 dialkylamino, C3-C6 cycloalkyl, $Ar^2$, —(C1-C3 alkyl)-(C=O)$R^5$, —(C1-C3 alkyl)-(C=O)$OR^5$, —(C1-C3 alkyl)-S(O)$_m R^5$, —(C=O)$R^5$, —(C=O)$OR^5$, and —S(O)$_m R^5$.

In a further aspect, $R^{4a}$ and $R^{4b}$ are covalently bonded and, together with the intermediate nitrogen, comprise an piperazinyl group substituted with 0, 1, or 2 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$(CH_2)_3$—$(C=O)R^5$, —$(CH_2)_2$—$(C=O)R^5$, —$CH_2$—$(C=O)R^5$, —$(CH_2)_3$—$(C=O)OR^5$, —$(CH_2)_2$—$(C=O)OR^5$, —$CH_2$—$(C=O)OR^5$, —$(CH_2)_3$—$(S=O)R^5$, —$(CH_2)_2$—$(S=O)R^5$, —$CH_2$—$(S=O)R^5$, —$(CH_2)_3$—$SO_2R^5$, —$(CH_2)_2$—$SO_2R^5$, —$CH_2$—$SO_2R^5$, —$(CH_2)_2$—$R^5$, —$(C=O)R^5$, —$(C=O)OR^5$, —$(S=O)R^5$, and —$SO_2R^5$. In a still further aspect, $R^{4a}$ and $R^{4b}$ are covalently bonded and, together with the intermediate nitrogen, comprise an piperazinyl group substituted with 0, 1, or 2 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$(CH_2)_2$—$(C=O)R^5$, —$CH_2$—$(C=O)R^5$, —$(CH_2)_2$—$(C=O)OR^5$, —$CH_2$—$(C=O)OR^5$, —$(CH_2)_2$—$(S=O)R^5$, —$CH_2$—$(S=O)R^5$, —$(CH_2)_2$—$SO_2R^5$, —$CH_2$—$SO_2R^5$, —$(C=O)R^5$, —$(C=O)OR^5$, —$(S=O)R^5$, and —$SO_2R^5$. In a yet further aspect, $R^{4a}$ and $R^{4b}$ are covalently bonded and, together with the intermediate nitrogen, comprise an piperazinyl group substituted with 0, 1, or 2 groups independently selected from halogen, —$NH_2$, —OH, —CN, C1-C3 alkyl, C1-C3 haloalkyl, C1-C3 polyhaloalkyl, C1-C3 alkoxy, C1-C3 alkylamino, C1-C3 dialkylamino, C3-C6 cycloalkyl, $Ar^2$, —$CH_2$—$(C=O)R^5$, —$CH_2$—$(C=O)OR^5$, —$CH_2$—$(S=O)R^5$, —$CH_2$—$SO_2R^5$, —$(C=O)R^5$, —$(C=O)OR^5$, —$(S=O)R^5$, and —$SO_2R^5$.

In a further aspect, $R^{4a}$ and $R^{4b}$ are covalently bonded and, together with the intermediate nitrogen, comprise an piperazinyl group substituted with 0, 1, or 2 groups independently selected from —F, —Cl, —NH$_2$, —OH, —CN, methyl, ethyl, propyl, isopropyl, —CHF, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, cyclohexyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C═O)CH$_3$, —(C═O)CH$_3$, —(CH$_2$)—(C═O)OCH$_3$, —(C═O)OCH$_3$, and Ar$^2$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, R$^{4a}$ and R$^{4b}$ are covalently bonded and, together with the intermediate nitrogen, comprise an piperazinyl group substituted with 0, 1, or 2 groups independently selected from —F, —NH$_2$, —OH, —CN, methyl, —CHF, —CH$_2$Cl, —CHF, —CF$_3$, —CHCl$_2$, —CCl$_3$, —NH(CH$_3$), —N(CH$_3$)$_2$, cyclopropyl, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C═O)CH$_3$, —(C═O)CH$_3$, —(CH$_2$)—(C═O)OCH$_3$, —(C═O)OCH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, R$^{4a}$ and R$^{4b}$ are covalently bonded and, together with the intermediate nitrogen, comprise an piperazinyl group substituted with 0, 1, or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and C3-C8 cycloalkyl. In a still further aspect, R$^{4a}$ and R$^{4b}$ are covalently bonded and, together with the intermediate nitrogen, comprise an piperazinyl group substituted with 0, 1, or 2 groups independently selected from halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and C3-C6 cycloalkyl. In a yet further aspect, R$^{4a}$ and R$^{4b}$ are covalently bonded and, together with the intermediate nitrogen, comprise an piperazinyl group substituted with 0, 1, or 2 groups independently selected from halogen, —NH$_2$, —OH, —CN, C1-C6 alkyl, C1-C6 haloalkyl, C1-C3 polyhaloalkyl, C1-C3 alkoxy, C1-C3 alkylamino, C1-C3 dialkylamino, and C3-C6 cycloalkyl.

In a further aspect, R$^{4a}$ and R$^{4b}$ are covalently bonded and, together with the intermediate nitrogen, comprise an piperazinyl group substituted with 0, 1, or 2 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NH(CH$_3$), —N(CH$_3$)$_2$, cyclopropyl, cyclobutyl, cyclopentyl, and cyclohexyl. In a still further aspect, R$^{4a}$ and R$^{4b}$ are covalently bonded and, together with the intermediate nitrogen, comprise an piperazinyl group substituted with 0, 1, or 2 groups independently selected from —F, —Cl, —NH$_2$, —OH, —CN, methyl, —CH$_2$F, —CHF$_2$, —CF$_3$, —NH(CH$_3$), —N(CH$_3$)$_2$, and cyclopropyl. In yet further aspect, R$^{4a}$ and R$^{4b}$ are covalently bonded and, together with the intermediate nitrogen, comprise an piperazinyl group substituted with 0, 1, or 2 groups independently selected from —F, —Cl, —NH$_2$, —OH, —CN, methyl, —CH$_2$F, —CHF$_2$, and —CF$_3$. In an even further aspect, R$^{4a}$ and R$^{4b}$ are covalently bonded and, together with the intermediate nitrogen, comprise a piperazinyl group substituted with 0, 1, or 2 groups independently selected from —F, methyl, and —CF$_3$.

In a still further aspect, R$^{4a}$ and R$^{4b}$ are covalently bonded and, together with the intermediate nitrogen, comprise an unsubstituted piperazinyl group.

e. R$^5$ Groups

In one aspect, each R$^5$, when present, is independently selected from hydrogen, C1-C8 alkyl, C3-C8 cycloalkyl, C1-C8 monohaloalkyl, C1-C8 polyhaloalkyl, —(C1-C3)-Ar$^2$, and Ar$^2$.

In a further aspect, each R$^5$, when present, is independently selected from hydrogen, C1-C8 alkyl, C1-C8 monohaloalkyl, C1-C8 polyhaloalkyl, and C3-C8 cycloalkyl. In a still further aspect, each R$^5$, when present, is independently selected from hydrogen, C1-C6 alkyl, C1-C6 monohaloalkyl, C1-C6 polyhaloalkyl, and C3-C6 cycloalkyl. In a yet further aspect, each R$^5$, when present, is independently selected from hydrogen, C1-C3 alkyl, C1-C3 monohaloalkyl, C1-C3 polyhaloalkyl, and C3-C6 cycloalkyl. In a yet further aspect, each R$^5$, when present, is independently selected from hydrogen, methyl, ethyl, propyl, isopropyl, tert-butyl, sec-butyl, isobutyl, tert-butyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, and cyclohexyl. In an even further aspect, each R$^5$, when present, is independently selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, cyclopropyl, cyclobutyl, cyclopentyl, and cyclohexyl. In a still further aspect, each R$^5$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, cyclobutyl, cyclopentyl, and cyclohexyl. In a yet further aspect, each R$^5$, when present, is independently selected from hydrogen, methyl, —CH$_2$F, —CH$_2$Cl, —CHF$_2$, —CF$_3$, —CHCl$_2$, —CCl$_3$, cyclopropyl, cyclobutyl, cyclopentyl, and cyclohexyl. In an even further aspect, each R$^5$, when present, is independently selected from hydrogen, methyl, —CH$_2$F, —CHF$_2$, —CF$_3$, cyclopropyl, cyclobutyl, cyclopentyl, and cyclohexyl. In a still further aspect, each R$^5$, when present, is independently selected from hydrogen, methyl, —CH$_2$F, —CHF$_2$, and —CF$_3$.

In a further aspect, each R$^5$ is independently selected from hydrogen, C1-C6 alkyl, C1-C6 monohaloalkyl, C1-C6 polyhaloalkyl, C3-C6 cycloalkyl, —(C1-C3)-Ar$^2$, and Ar$^2$. In a still further aspect, each R$^5$ is independently selected from hydrogen, C1-C3 alkyl, C1-C3 monohaloalkyl, C1-C3 polyhaloalkyl, C3-C6 cycloalkyl, —(C1-C3)-Ar$^2$, and Ar$^2$. In a yet further aspect, each R$^5$ is independently selected from hydrogen, C1-C3 alkyl, C1-C3 monohaloalkyl, C1-C3 polyhaloalkyl, C3-C6 cycloalkyl, —(CH$_2$)$_3$—Ar$^2$, —(CH$_2$)$_2$—Ar$^2$, —CH$_2$—Ar$^2$, and Ar$^2$. In an even further aspect, each R$^5$ is independently selected from hydrogen, C1-C3 alkyl, C1-C3 monohaloalkyl, C1-C3 polyhaloalkyl, C3-C6 cycloalkyl, —(CH$_2$)$_2$—Ar$^2$, —CH$_2$—Ar$^2$, and Ar$^2$. In a still further aspect, each R$^5$ is independently selected from hydrogen, C1-C3 alkyl, C1-C3 monohaloalkyl, C1-C3 polyhaloalkyl, C3-C6 cycloalkyl, —(CH$_2$)$_3$—Ar$^2$, —CH$_2$—Ar$^2$, and Ar$^2$.

In a further aspect, each R$^5$, when present, is independently selected from hydrogen, methyl, ethyl, propyl, isopropyl, tert-butyl, sec-butyl, isobutyl, tert-butyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, cyclopropyl, cyclobutyl, cyclopentyl, cyclohexyl, —(CH$_2$)—Ar$^2$, —(CH$_2$)$_2$—Ar$^2$, —(CH$_2$)$_3$—Ar$^2$, and Ar$^2$. In a still further aspect, each R$^5$, when present, is independently selected from hydrogen, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, cyclopropyl, cyclobutyl, cyclopentyl, cyclohexyl, —(CH$_2$)-Ar$^2$, —(CH$_2$)$_2$—Ar$^2$, —(CH$_2$)$_3$—Ar$^2$, and Ar$^2$. In a yet further aspect, each R$^5$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, cyclobutyl, cyclopentyl, cyclohexyl, —(CH$_2$)—Ar$^2$, and Ar$^2$. In an even further aspect, each R$^5$, when present, is independently selected from hydrogen, methyl, —CH$_2$F, —CH$_2$Cl, —CHF$_2$, —CF$_3$, —CHCl$_2$, —CCl$_3$, cyclopropyl, cyclobutyl, cyclopentyl, cyclohexyl, —(CH$_2$)—Ar$^2$, and Ar$^2$. In a still further aspect, each R$^5$, when present, is independently selected from hydrogen, methyl, —CH$_2$F, —CHF$_2$, —CF$_3$, cyclopropyl, cyclobutyl, cyclopentyl, cyclohexyl, —(CH$_2$)—Ar$^2$, and Ar$^2$.

f. R$^6$ Groups

In one aspect, each R$^6$, when present, is selected from C1-C4 alkyl, C1-C4 alkoxy, C1-C4 monoalkylamino, or C1-C4 dialkylamino substituted with 1 or 2 groups selected from fluoro, trifluoromethyl, methyl, —OH, —NH$_2$, and —CN.

In a further aspect, each R$^6$, when present, is selected from C1-C3 alkyl, C1-C3 alkoxy, C1-C3 monoalkylamino, and C1-C3 dialkylamino substituted with 1 or 2 groups independently selected from methyl, —CF$_3$, —F, —OH, —NH$_2$, and —CN.

In a further aspect, each R$^6$, when present, is selected from —CH$_2$R$^{21}$, —CHR$^{21}$R$^{22}$, —CHR$^{21}$CH$_2$R$^{22}$, —CR$^{21}$R$^{22}$CH$_3$, and —CH$_2$CHR$^{21}$R$^{22}$; and wherein each of R$^{21}$ and R$^{22}$, when present, is independently selected from methyl, —CF$_3$, —F, —OH, —NH$_2$, and —CN. In a still further aspect, each R$^6$, when present, is selected from —CH$_2$R$^{21}$ and —CHR$^{21}$R$^{22}$; and wherein each of R$^{21}$ and R$^{22}$, when present, is independently selected from methyl, —CF$_3$, —F, —OH, —NH$_2$, and —CN. In a yet further aspect, each R$^6$ when present, is —CH$_2$R$^{21}$; and R$^{21}$ is selected from methyl, —CF$_3$, —F, —OH, —NH$_2$, and —CN. In an even further aspect, each R$^6$, when present, is selected from —CH$_2$CF$_3$, —CH$_2$CH$_3$, —CH$_2$F, —CH$_2$OH, —CH$_2$NH$_2$, and —CH$_2$CN. In a further aspect, each R$^6$, when present, is selected from —CH$_2$CF$_3$, —CH$_2$F, —CH$_2$OH, —CH$_2$NH$_2$, and —CH$_2$CN.

In a further aspect, each R$^6$, when present, is —CHR$^{21}$R$^{22}$; and wherein each of R$^{21}$ and R$^{22}$, when present, is independently selected from methyl, —CF$_3$, —F, —OH, —NH$_2$, and —CN. In a still further aspect, each R$^6$, when present, is —CHR$^{21}$CH$_2$R$^{22}$; and wherein each of R$^{21}$ and R$^{22}$, when present, is independently selected from methyl, —CF$_3$, —F, —OH, —NH$_2$, and —CN. In a yet further aspect, each R$^6$, when present, is —CH$_2$CHR$^{21}$R$^{22}$; and wherein each of R$^{21}$ and R$^{22}$, when present, is independently selected from methyl, —CF$_3$, —F, —OH, —NH$_2$, and —CN. In an even further aspect, each R$^6$, when present, is —CR$^{21}$R$^{22}$CH$_3$; and wherein each of R$^{21}$ and R$^{22}$, when present, is independently selected from methyl, —CF$_3$, —F, —OH, —NH$_2$, and —CN.

In a further aspect, each R$^6$, when present, is selected from —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, each R$^6$, when present, is —CH$_2$CF$_3$. In a yet further aspect, each R$^6$, when present, is —CH$_2$F. In an even further aspect, each R$^6$, when present, is —CH$_2$OH. In a still further aspect, each R$^6$, when present, is —CH$_2$NH$_2$. In a yet further aspect, each R$^6$, when present, is —CH$_2$CN.

g. R$^{7A}$, R$^{7B}$, R$^{7C}$, R$^{7D}$, R$^{7E}$, R$^{7G}$, and R$^{7H}$ Groups In one aspect, each of R$^{7a}$, R$^{7b}$, R$^{7c}$, R$^{7d}$, R$^{7e}$, R$^{7g}$, and R$^{7h}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, —S(O)$_m$R$^5$, and Ar$^2$, provided that at least four of R$^{7a}$, R$^{7b}$, R$^{7c}$, R$^{7d}$, R$^{7e}$, R$^{7g}$, and R$^{7h}$ are hydrogen.

In a further aspect, each of R$^{7a}$, R$^{7b}$, R$^{7c}$, R$^{7d}$, R$^{7e}$, R$^{7g}$, and R$^{7h}$ is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, —(C1-C6 alkyl)-(C═O)R$^5$, —(C1-C6 alkyl)-(C═O)OR$^5$, —(C1-C6 alkyl)-S(O)$_m$R$^5$, —(C═O)R$^5$, —(C═O)OR$^5$, —S(O)$_m$R$^5$, and Ar$^2$, provided that at least four of R$^{7a}$, R$^{7b}$, R$^{7c}$, R$^{7d}$, R$^{7e}$, R$^{7g}$, and R$^{7h}$ are hydrogen. In a still further aspect, each of R$^{7a}$, R$^{7b}$, R$^{7c}$, R$^{7d}$, R$^{7e}$, R$^{7g}$, and R$^{7h}$ is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-(C═O)R$^5$, —(C1-C3 alkyl)-(C═O)OR$^5$, —(C1-C3 alkyl)-S(O)$_m$R$^5$, —(C═O)R$^5$, —(C═O)OR$^5$, —S(O)$_m$R$^5$, and Ar$^2$, provided that at least four of R$^{7a}$, R$^{7b}$, R$^{7c}$, R$^{7d}$, R$^{7e}$, R$^{7g}$, and R$^{7h}$ are hydrogen. In a yet further aspect, each of R$^{7a}$, R$^{7b}$, R$^{7c}$, R$^{7d}$, R$^{7e}$, R$^{7g}$, and R$^{7h}$ is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, —(C1-C3 alkyl)-(C═O)R$^5$, —(C1-C3 alkyl)-(C═O)OR$^5$, —(C1-C3 alkyl)-S(O)$_m$R$^5$, —(C═O)R$^5$, —(C═O)OR$^5$, —S(O)$_m$R$^5$, and Ar$^2$, provided that at least four of R$^{7a}$, R$^{7b}$, R$^{7c}$, R$^{7d}$, R$^{7e}$, R$^{7g}$, and R$^{7h}$ are hydrogen. In an even further aspect, each of R$^{7a}$, R$^{7b}$, R$^{7c}$, R$^{7d}$, R$^{7e}$, R$^{7g}$, and R$^{7h}$ is independently selected from hydrogen, halogen, —NH$_2$, —OH, —CN, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C═O)R$^5$, —(C1-C3 alkyl)-(C═O)OR$^5$, —(C1-C3 alkyl)-(S═O)R$^5$, —(C1-C3 alkyl)-SO$_2$R$^5$, —(C═O)R$^5$, —(C═O)OR$^5$, —(S═O)R$^5$, —SO$_2$R$^5$, R$^6$, and Ar$^2$, provided that at least four of R$^{7a}$, R$^{7b}$, R$^{7c}$, R$^{7d}$, R$^{7e}$, R$^{7g}$, and R$^{7h}$ are hydrogen.

In a further aspect, each of R$^{7a}$, R$^{7b}$, R$^{7c}$, R$^{7d}$, R$^{7e}$, R$^{7g}$, and R$^{7h}$ is independently selected from hydrogen, —F, —Cl, —NH$_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$, provided that at least four of R$^{7a}$, R$^{7b}$, R$^{7c}$, R$^{7d}$, R$^{7e}$, R$^{7g}$, and R$^{7h}$ are hydrogen. In a still further aspect, each of R$^{7a}$, R$^{7b}$, R$^{7c}$, R$^{7d}$, R$^{7e}$, R$^{7g}$, and R$^{7h}$ is independently selected from hydrogen, —F, —Cl, —NH$_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$, provided that at least four of R$^{7a}$, R$^{7b}$, R$^{7c}$, R$^{7d}$, R$^{7e}$, R$^{7g}$, and R$^{7h}$ are hydrogen. In a yet further aspect, each of R$^{7a}$, R$^{7b}$, R$^{7c}$, R$^{7d}$, R$^{7e}$, R$^{7g}$, and R$^{7h}$ is independently selected from hydrogen, —F, —Cl, —NH$_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$, provided that at least four of R$^{7a}$, R$^{7b}$, R$^{7c}$, R$^{7d}$, R$^{7e}$, R$^{7g}$, and R$^{7h}$ are hydrogen. In an even further aspect, each of R$^{7a}$, R$^{7b}$, R$^{7c}$, R$^{7d}$, R$^{7e}$, R$^{7g}$, and R$^{7h}$ is independently selected from hydrogen, —F, —Cl, —NH$_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, —SO$_2$R$^5$, R$^6$, and Ar$^2$, provided that at least four of R$^{7a}$, R$^{7b}$, R$^{7c}$, R$^{7d}$, R$^{7e}$, R$^{7g}$, and R$^{7h}$ are hydrogen.

In a further aspect, each of R$^{7a}$, R$^{7b}$, R$^{7c}$, R$^{7d}$, R$^{7e}$, R$^{7g}$, and R$^{7h}$ is independently selected from hydrogen, —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl, provided that at least four of R$^{7a}$, R$^{7b}$, R$^{7c}$, R$^{7d}$, R$^{7e}$, R$^{7g}$, and R$^{7h}$ are hydrogen.

In a further aspect, each of R$^{7a}$, R$^{7b}$, R$^{7c}$, R$^{7d}$, R$^{7e}$, R$^{7g}$, and R$^{7h}$ is independently selected from hydrogen, —F, —NH$_2$, —OH, —CN, methyl, —CH$_2$F, —CHF$_2$, —CF$_3$, —OCH$_3$, —NHCH$_3$, —N(CH$_3$)$_2$, —(CH$_2$)—(C=O)CH$_3$, —(CH$_2$)—(C=O)OCH$_3$, —(CH$_2$)—S—CH$_3$, —(CH$_2$)—(S=O)CH$_3$, —(CH$_2$)—SO$_2$CH$_3$, —(C=O)CH$_3$, —(C=O)OCH$_3$, —S—CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$, provided that at least four of R$^{7a}$, R$^{7b}$, R$^{7c}$, R$^{7d}$, R$^{7e}$, R$^{7g}$, and R$^{7h}$ are hydrogen.

In one aspect, each of R$^{7a}$, R$^{7b}$, R$^{7c}$, R$^{7d}$, and R$^{7e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$, provided that at least one of R$^{7a}$, R$^{7b}$, R$^{7c}$, R$^{7d}$, and R$^{7e}$ is hydrogen.

In a further aspect, each of R$^{7a}$, R$^{7b}$, R$^{7c}$, R$^{7d}$, and R$^{7e}$ is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$, provided that at least one of R$^{7a}$, R$^{7b}$, R$^{7c}$, R$^{7d}$, and R$^{7e}$ is hydrogen. In a still further aspect, each of R$^{7a}$, R$^{7b}$, R$^{7c}$, R$^{7d}$, and R$^{7e}$ is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, —S(O)$_m$R$^5$, R$^6$, and Ar$^2$, provided that at least one of R$^{7a}$, R$^{7b}$, R$^{7c}$, R$^{7d}$, and R$^{7e}$ is hydrogen. In a yet further aspect, each of R$^{7a}$, R$^{7b}$, R$^{7c}$, R$^{7d}$, and R$^{7e}$ is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, —(C1-C3 alkyl)-(C=O)R$^5$, —(C1-C3 alkyl)-(C=O)OR$^5$, —(C1-C3 alkyl)-S(O)$_m$R$^5$, —(C=O)R$^5$, —(C=O)OR$^5$, —S(O)$_m$R$^5$, R$^6$, and Ar$^2$, provided that at least one of R$^{7a}$, R$^{7b}$, R$^{7c}$, R$^{7d}$, and R$^{7e}$ is hydrogen. In an even further aspect, each of R$^{7a}$, R$^{7b}$, R$^{7c}$, R$^{7d}$, and R$^{7e}$ is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S(O)$_m$R$^5$, R$^6$, and Ar$^2$, provided that at least one of R$^{7a}$, R$^{7b}$, R$^{7c}$, R$^{7d}$, and R$^{7e}$ is hydrogen.

In a further aspect, each of R$^{7a}$, R$^{7b}$, R$^{7c}$, R$^{7d}$, and R$^{7e}$ is independently selected from hydrogen, —F, —Cl, —NH$_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$, provided that at least one of R$^{7a}$, R$^{7b}$, R$^{7c}$, R$^{7d}$, and R$^{7e}$ is hydrogen. In a still further aspect, each of R$^{7a}$, R$^{7b}$, R$^{7c}$, R$^{7d}$, and R$^{7e}$ is independently selected from hydrogen, —F, —Cl, —NH$_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—(C=O)R$^5$, —$CH_2$—(C=O)$R^5$, —$(CH_2)_2$—(C=O)$OR^5$, —$CH_2$—(C=O)$OR^5$, —$(CH_2)_2$—S—$R^5$, —$CH_2$—S—$R^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)$OR^5$, —S—$R^5$, —(S=O)$R^5$, —$SO_2R^5$, $R^6$, and $Ar^2$, provided that at least one of $R^{7a}$, $R^{7b}$, $R^{7c}$, $R^{7d}$, and $R^{7e}$ is hydrogen. In a yet further aspect, each of $R^{7a}$, $R^{7b}$, $R^{7c}$, $R^{7d}$, and $R^{7e}$ is independently selected from hydrogen, —F, —Cl, —$NH_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)$OR^5$, —$CH_2$—S—$R^5$, —$CH_2$—(S=O)$R^5$, —$CH_2$—$SO_2R^5$, —(C=O)$R^5$, —(C=O)$OR^5$, —S—$R^5$, —(S=O)$R^5$, —$SO_2R^5$, $R^6$, and $Ar^2$, provided that at least one of $R^{7a}$, $R^{7b}$, $R^{7c}$, $R^{7d}$, and $R^{7e}$ is hydrogen. In an even further aspect, each of $R^{7a}$, $R^{7b}$, $R^{7c}$, $R^{7d}$, and $R^{7e}$ is independently selected from hydrogen, —F, —Cl, —$NH_2$, —OH, —CN, C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)$OR^5$, —$CH_2$—(S=O)$R^5$, —$CH_2$—$SO_2R^5$, —(C=O)$R^5$, —(C=O)$OR^5$, —(S=O)$R^5$, —$SO_2R^5$, $R^6$, and $Ar^2$, provided that at least one of $R^{7a}$, $R^{7b}$, $R^{7c}$, $R^{7d}$, and $R^{7e}$ is hydrogen.

In a further aspect, each of $R^{7a}$, $R^{7b}$, $R^{7c}$, $R^{7d}$, and $R^{7e}$ is independently selected from hydrogen, —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$(CH_2)$—$SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—(C=O)$CH_3$, —(C=O)$CH_3$, —$(CH_2)$—(C=O)$OCH_3$, —(C=O)$OCH_3$, —$CF(CF_3)CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, —$C(CN)(NH_2)CH_3$, and $Ar^2$; wherein each $Ar^2$, when present, is phenyl independently substituted with 0, 1, or 2 groups independently selected from —F, —$NH_2$, —OH, —CN, methyl, —$CH_2F$, —$CHF_2$, —$CF_3$, —$OCH_3$, —$NHCH_3$, —$N(CH_3)_2$, —$SCH_3$, —$SCH_2F$, —$SCHF_2$, —$SCF_3$, —(S=O)$CH_3$, —(S=O)$CH_2F$, —(S=O)$CHF_2$, —(S=O)$CF_3$, —$SO_2CH_3$, —$SO_2CH_2F$, —$SO_2CHF_2$, —$SO_2CF_3$, —$SO_2$-cyclopropyl, and —$SO_2$-phenyl; and wherein at least two of $R^{7a}$, $R^{7b}$, $R^{7c}$, $R^{7d}$, and $R^{7e}$ are hydrogen.

In a further aspect, each of $R^{7a}$, $R^{7b}$, $R^{7c}$, $R^{7d}$, and $R^{7e}$ is independently selected from hydrogen, —F, —$NH_2$, —OH, —CN, methyl, —$CH_2F$, —$CHF_2$, —$CF_3$, —$OCH_3$, —$NHCH_3$, —$N(CH_3)_2$, —$(CH_2)$—(C=O)$CH_3$, —$(CH_2)$—(C=O)$OCH_3$, —$(CH_2)$—S—$CH_3$, —$(CH_2)$—(S=O)$CH_3$, —$(CH_2)$—$SO_2CH_3$, —(C=O)$CH_3$, —(C=O)$OCH_3$, —S—$CH_3$, —(S=O)$CH_3$, —$SO_2CH_3$, —$CF(CF_3)CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, and —$C(CN)(NH_2)CH_3$, provided that at least one of $R^{7a}$, $R^{7b}$, $R^{7c}$, $R^{7d}$, and $R^{7e}$ is hydrogen.

h. $R^{9A}$, $R^{9B}$, $R^{9C}$, $R^{9D}$, and $R^{9E}$ Groups

In one aspect, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)$R^5$, —(C1-C6 alkyl)-(C=O)$OR^5$, —(C1-C6 alkyl)-S—$R^5$, —(C1-C6 alkyl)-(S=O)$R^5$, —(C1-C6 alkyl)-$SO_2R^5$, —(C=O)$R^5$, —(C=O)$OR^5$, —S—$R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen.

In a further aspect, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)$R^5$, —(C1-C6 alkyl)-(C=O)$OR^5$, —(C1-C6 alkyl)-S—$R^5$, —(C1-C6 alkyl)-(S=O)$R^5$, —(C1-C6 alkyl)-$SO_2R^5$, —(C=O)$R^5$, —(C=O)$OR^5$, —S—$R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)$R^5$, —(C1-C3 alkyl)-(C=O)$OR^5$, —(C1-C3 alkyl)-S—$R^5$, —(C1-C3 alkyl)-(S=O)$R^5$, —(C1-C3 alkyl)-$SO_2R^5$, —(C=O)$R^5$, —(C=O)$OR^5$, —S—$R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(S=O)$R^5$, —(C1-C3 alkyl)-$SO_2R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is independently selected from hydrogen, halogen, —$NH_2$, —OH, —CN, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)$R^5$, —(C1-C3 alkyl)-(C=O)$OR^5$, —(C1-C3 alkyl)-(S=O)$R^5$, —(C1-C3 alkyl)-$SO_2R^5$, —(C=O)$R^5$, —(C=O)$OR^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen.

In a further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$(CH_2)_3$—(C=O)$R^5$, —$(CH_2)_2$—(C=O)$R^5$, —$CH_2$—(C=O)$R^5$, —$(CH_2)_3$—(C=O)$OR^5$, —$(CH_2)_2$—(C=O)$OR^5$, —$CH_2$—(C=O)$OR^5$, —$(CH_2)_3$—S—$R^5$, —$(CH_2)_2$—S—$R^5$, —$CH_2$—S—$R^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —(C=O)$R^5$, —(C=O)$OR^5$, —S—$R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$(CH_2)_2$—(C=O)$R^5$, —$CH_2$—(C=O)$R^5$, —$(CH_2)_2$—(C=O)$OR^5$, —$CH_2$—(C=O)$OR^5$, —$(CH_2)_2$—S—$R^5$, —$CH_2$—S—$R^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)$OR^5$, —S—$R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)$OR^5$, —$CH_2$—S—$R^5$, —$CH_2$—(S=O)$R^5$, —$CH_2$—$SO_2R^5$, —(C=O)$R^5$, —(C=O)$OR^5$, —S—$R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)O$R^5$, —$CH_2$—(S=O)$R^5$, —$CH_2$—$SO_2R^5$, —(C=O)$R^5$, —(C=O)O$R^5$, —(S=O)$R^5$, —$SO_2R^5$, $R^6$, and $Ar^2$, provided that at least two of $R^{9a}$, $R^{9b}$, $R^{9c}$, $R^{9d}$, and $R^{9e}$ are hydrogen.

In a further aspect, each of $R^{9a}$, $R^{9b}$, $R^{9c}$, $R^{9d}$, and $R^{9e}$ is independently selected from hydrogen, —F, —Cl, —Br, —$NH_2$, —OH, —CN, —$SF_5$, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$(CH_2)$—$SCH_3$, —$(CH_2)$—$SOCH_3$, —$(CH_2)$—$SO_2CH_3$, —$SCH_3$, —$SOCH_3$, —$SO_2CH_3$, —$(CH_2)$—$SCF_3$, —$(CH_2)$—$SOCF_3$, —$(CH_2)$—$SO_2CF_3$, —$SCF_3$, —$SOCF_3$, —$SO_2CF_3$, —$(CH_2)$—(C=O)$CH_3$, —(C=O)$CH_3$, —$(CH_2)$—(C=O)$OCH_3$, —(C=O)$OCH_3$, —$CF(CF_3)CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, —$C(CN)(NH_2)CH_3$, and $Ar^2$; wherein each $Ar^2$, when present, is phenyl independently substituted with 0, 1, or 2 groups independently selected from —F, —$NH_2$, —OH, —CN, methyl, —$CH_2F$, —$CHF_2$, —$CF_3$, —$OCH_3$, —$NHCH_3$, —$N(CH_3)_2$, —$SCH_3$, —$SCH_2F$, —$SCHF_2$, —$SCF_3$, —(S=O)$CH_3$, —(S=O)$CH_2F$, —(S=O)$CHF_2$, —(S=O)$CF_3$, —$SO_2CH_3$, —$SO_2CH_2F$, —$SO_2CHF_2$, —$SO_2CF_3$, —$SO_2$-cyclopropyl, and —$SO_2$-phenyl; and wherein at least two of $R^{9a}$, $R^{9b}$, $R^{9c}$, $R^{9d}$, and $R^{9e}$ are hydrogen.

In various aspects, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)$R^5$, —(C1-C6 alkyl)-(C=O)O$R^5$, —(C1-C6 alkyl)-S—$R^5$, —(C1-C6 alkyl)-(S=O)$R^5$, —(C1-C6 alkyl)-$SO_2R^5$, —(C=O)$R^5$, —(C=O)O$R^5$, —S—$R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)$R^5$, —(C1-C3 alkyl)-(C=O)O$R^5$, —(C1-C3 alkyl)-S—$R^5$, —(C1-C3 alkyl)-(S=O)$R^5$, —(C1-C3 alkyl)-$SO_2R^5$, —(C=O)$R^5$, —(C=O)O$R^5$, —S—$R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(S=O)$R^5$, —(C1-C3 alkyl)-$SO_2R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is independently selected from hydrogen, halogen, —$NH_2$, —OH, —CN, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)$R^5$, —(C1-C3 alkyl)-(C=O)O$R^5$, —(C1-C3 alkyl)-(S=O)$R^5$, —(C1-C3 alkyl)-$SO_2R^5$, —(C=O)$R^5$, —(C=O)O$R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen.

In a further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$(CH_2)_3$—(C=O)$R^5$, —$(CH_2)_2$—(C=O)$R^5$, —$CH_2$—(C=O)$R^5$, —$(CH_2)_3$—(C=O)O$R^5$, —$(CH_2)_2$—(C=O)O$R^5$, —$CH_2$—(C=O)O$R^5$, —$(CH_2)_3$—S—$R^5$, —$(CH_2)_2$—S—$R^5$, —$CH_2$—S—$R^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —(C=O)$R^5$, —(C=O)O$R^5$, —S—$R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$(CH_2)_2$—(C=O)$R^5$, —$CH_2$—(C=O)$R^5$, —$(CH_2)_2$—(C=O)O$R^5$, —$CH_2$—(C=O)O$R^5$, —$(CH_2)_2$—S—$R^5$, —$CH_2$—S—$R^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)O$R^5$, —S—$R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)O$R^5$, —$CH_2$—S—$R^5$, —$CH_2$—(S=O)$R^5$, —$CH_2$—$SO_2R^5$, —(C=O)$R^5$, —(C=O)O$R^5$, —S—$R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is independently selected from hydrogen, —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)O$R^5$, —$CH_2$—(S=O)$R^5$, —$CH_2$—$SO_2R^5$, —(C=O)$R^5$, —(C=O)O$R^5$, —(S=O)$R^5$, —$SO_2R^5$, and $R^6$, provided that at least two of $R^{9a}$, $R^{9b}$, $R^{9c}$, $R^{9d}$, and $R^{9e}$ are hydrogen.

In a further aspect, each of $R^{9a}$, $R^{9b}$, $R^{9c}$, $R^{9d}$, and $R^{9e}$ is independently selected from hydrogen, —F, —$NH_2$, —OH, —CN, —$SF_5$, methyl, —$CH_2F$, —$CHF_2$, —$CF_3$, —$OCH_3$, —$NHCH_3$, —$N(CH_3)_2$, —$CH_2$—(C=O)$CH_3$, —$CH_2$—(C=O)$OCH_3$, —$CH_2$—S—$CH_3$, —$CH_2$—(S=O)$CH_3$, —$CH_2$—$SO_2CH_3$, —(C=O)$CH_3$, —(C=O)$OCH_3$, —S—$CH_3$, —(S=O)$CH_3$, —$SO_2CH_3$, —$CF(CF_3)CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, and —$C(CN)(NH_2)CH_3$, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, —F, —$NH_2$, —OH, —CN, —$SF_5$, methyl, —$CH_2F$, —$CHF_2$, —$CF_3$, —$OCH_3$, —$NHCH_3$, —$N(CH_3)_2$, —$CH_2$—(S=O)$CH_3$, —$CH_2$—$SO_2CH_3$, —(S=O)$CH_3$, —$SO_2CH_3$, —$CF(CF_3)CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, and —$C(CN)(NH_2)CH_3$, provided that at least two of $R^{9a}$, $R^{9b}$, $R^{9c}$, $R^{9d}$, and $R^{9e}$ are hydrogen.

In a further aspect, each of $R^{9a}$, $R^{9b}$, $R^{9c}$, $R^{9d}$, and $R^{9e}$ is independently selected from hydrogen, halogen, —$NH_2$, —OH, —CN, —$SF_5$, C1-C8 alkyl, C1-C8 haloalkyl, C1-C8 polyhaloalkyl, C1-C8 alkoxy, C1-C8 alkylamino, and C1-C8 dialkylamino, provided that at least two of $R^{9a}$, $R^{9b}$, $R^{9c}$, $R^{9d}$, and $R^{9e}$ are hydrogen, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, and C1-C6 dialkylamino, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, and C1-C3 dialkylamino, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is independently selected from hydrogen, —F, —NH$_2$, —OH, —CN, —SF$_5$, methyl, —CH$_2$F, —CHF$_2$, —CF$_3$, —OCH$_3$, —NHCH$_3$, and —N(CH$_3$)$_2$, provided that at least two of $R^{9a}$, $R^{9b}$, $R^{9c}$, $R^{9d}$, and $R^{9e}$ are hydrogen.

In one aspect, each of $R^{9a}$, $R^{9b}$, and $R^{9c}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$.

In a further aspect, each of $R^{9a}$, $R^{9b}$, and $R^{9c}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$. In a still further aspect, each of $R^{9a}$, $R^{9b}$, and $R^{9c}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$. In a yet further aspect, each of $R^{9a}$, $R^{9b}$, and $R^{9c}$ is independently selected from hydrogen, halogen, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(S=O)R$^5$, —(C1-C3 alkyl)-SO$_2$R$^5$, —(S=O)R$^5$, —SO$_2$R$^5$, R$^6$, and Ar$^2$. In an even further aspect, each of $R^{9a}$, $R^{9b}$, and $R^{9c}$ is independently selected from hydrogen, halogen, —NH$_2$, —OH, —CN, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-(S=O)R$^5$, —(C1-C3 alkyl)-SO$_2$R$^5$, —(C=O)R$^5$, —(C=O)OR$^5$, —(S=O)R$^5$, —SO$_2$R$^5$, R$^6$, and Ar$^2$.

In a further aspect, each of $R^{9a}$, $R^{9b}$, and $R^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In a still further aspect, each of $R^{9a}$, $R^{9b}$, and $R^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In a yet further aspect, each of $R^{9a}$, $R^{9b}$, and $R^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In an even further aspect, each of $R^{9a}$, $R^{9b}$, and $R^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$.

In a further aspect, each of $R^{9a}$, $R^{9b}$, and $R^{9c}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl.

In various aspects, each of $R^{9a}$, $R^{9b}$, and $R^{9c}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, and R$^6$. In a still further aspect, each of $R^{9a}$, $R^{9b}$, and $R^{9c}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, and R$^6$. In a yet further aspect, each of $R^{9a}$, $R^{9b}$, and $R^{9c}$ is independently selected from hydrogen, halogen, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(S=O)R$^5$, —(C1-C3 alkyl)-SO$_2$R$^5$, —(S=O)R$^5$, —SO$_2$R$^5$, and R$^6$. In an even further aspect, each of $R^{9a}$, $R^{9b}$, and $R^{9c}$ is independently selected from hydrogen, halogen, —NH$_2$, —OH, —CN, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-(S=O)R$^5$, —(C1-C3 alkyl)-SO$_2$R$^5$, —(C=O)R$^5$, —(C=O)OR$^5$, —(S=O)R$^5$, —SO$_2$R$^5$, and R$^6$.

In a further aspect, each of R$^{9a}$, R$^{9b}$, and R$^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a still further aspect, each of R$^{9a}$, R$^{9b}$, and R$^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a yet further aspect, each of R$^{9a}$, R$^{9b}$, and R$^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In an even further aspect, each of R$^{9a}$, R$^{9b}$, and R$^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, —SO$_2$R$^5$, and R$^6$.

In a further aspect, each of R$^{9a}$, R$^{9b}$, and R$^{9c}$ is independently selected from hydrogen, —F, —NH$_2$, —OH, —CN, —SF$_5$, methyl, —CH$_2$F, —CHF$_2$, —CF$_3$, —OCH$_3$, —NHCH$_3$, —N(CH$_3$)$_2$, —CH$_2$—(C=O)CH$_3$, —CH$_2$—(C=O)OCH$_3$, —CH$_2$—S—CH$_3$, —CH$_2$—(S=O)CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, each of R$^{9a}$, R$^{9b}$, and R$^{9c}$ is independently selected from hydrogen, —F, —NH$_2$, —OH, —CN, —SF$_5$, methyl, —CH$_2$F, —CHF$_2$, —CF$_3$, —OCH$_3$, —NHCH$_3$, —N(CH$_3$)$_2$, —CH$_2$—(S=O)CH$_3$, —CH$_2$—SO$_2$CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$.

In a further aspect, each of R$^{9a}$, R$^{9b}$, and R$^{9c}$ is independently selected from hydrogen, halogen, —NH$_2$, —OH, —CN, —SF$_5$, C1-C8 alkyl, C1-C8 haloalkyl, C1-C8 polyhaloalkyl, C1-C8 alkoxy, C1-C8 alkylamino, and C1-C8 dialkylamino. In a still further aspect, each of R$^{9a}$, R$^{9b}$, and R$^{9c}$ is independently selected from hydrogen, halogen, —NH$_2$, —OH, —CN, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each of R$^{9a}$, R$^{9b}$, and R$^{9c}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each of R$^{9a}$, R$^{9b}$, and R$^{9c}$ is independently selected from hydrogen, —F, —NH$_2$, —OH, —CN, —SF$_5$, methyl, —CH$_2$F, —CHF$_2$, —CF$_3$, —OCH$_3$, —NHCH$_3$, and —N(CH$_3$)$_2$.

In one aspect, each of R$^{9a}$ and R$^{9b}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$.

In a further aspect, each of R$^{9a}$ and R$^{9b}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$. In a still further aspect, each of R$^{9a}$ and R$^{9b}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$. In a yet further aspect, each of R$^{9a}$ and R$^{9b}$ is independently selected from hydrogen, halogen, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(S=O)R$^5$, —(C1-C3 alkyl)-SO$_2$R$^5$, —(S=O)R$^5$, —SO$_2$R$^5$, R$^6$, and Ar$^2$. In an even further aspect, each of R$^{9a}$ and R$^{9b}$ is independently selected from hydrogen, halogen, —NH$_2$, —OH, —CN, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-(S=O)R$^5$, —(C1-C3 alkyl)-SO$_2$R$^5$, —(C=O)R$^5$, —(C=O)OR$^5$, —(S=O)R$^5$, —SO$_2$R$^5$, R$^6$, and Ar$^2$.

In a further aspect, each of R$^{9a}$ and R$^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In a still further aspect, each of R$^{9a}$ and R$^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and $Ar^2$. In a yet further aspect, each of $R^{9a}$ and $R^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In an even further aspect, each of $R^{9a}$ and $R^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, —SO$_2$R$^5$, R$^6$, and Ar$^2$.

In a further aspect, each of $R^{9a}$ and $R^{9b}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl.

In various aspects, each of $R^{9a}$ and $R^{9b}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, and R$^6$. In a still further aspect, each of $R^{9a}$ and $R^{9b}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, and R$^6$. In a yet further aspect, each of $R^{9a}$ and $R^{9b}$ is independently selected from hydrogen, halogen, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(S=O)R$^5$, —(C1-C3 alkyl)-SO$_2$R$^5$, —(S=O)R$^5$, —SO$_2$R$^5$, and R$^6$. In an even further aspect, each of $R^{9a}$ and $R^{9b}$ is independently selected from hydrogen, halogen, —NH$_2$, —OH, —CN, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-(S=O)R$^5$, —(C1-C3 alkyl)-SO$_2$R$^5$, —(C=O)R$^5$, —(C=O)OR$^5$, —(S=O)R$^5$, —SO$_2$R$^5$, and R$^6$.

In a further aspect, each of $R^{9a}$ and $R^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a still further aspect, each of $R^{9a}$ and $R^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a yet further aspect, each of $R^{9a}$ and $R^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In an even further aspect, each of $R^{9a}$ and $R^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, —SO$_2$R$^5$, and R$^6$.

In a further aspect, each of $R^{9a}$ and $R^{9b}$ is independently selected from hydrogen, —F, —NH$_2$, —OH, —CN, —SF$_5$, methyl, —CH$_2$F, —CHF$_2$, —CF$_3$, —OCH$_3$, —NHCH$_3$, —N(CH$_3$)$_2$, —CH$_2$—(C=O)CH$_3$, —CH$_2$—(C=O)OCH$_3$, —CH$_2$—S—CH$_3$, —CH$_2$—(S=O)CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, each of $R^{9a}$ and $R^{9b}$ is independently selected from hydrogen, —F, —NH$_2$, —OH, —CN, —SF$_5$, methyl, —CH$_2$F, —CHF$_2$, —CF$_3$, —OCH$_3$, —NHCH$_3$, —N(CH$_3$)$_2$, —CH$_2$—(S=O)CH$_3$, —CH$_2$—SO$_2$CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$.

In a further aspect, each of $R^{9a}$ and $R^{9b}$ is independently selected from hydrogen, halogen, —NH$_2$, —OH, —CN, —SF$_5$, C1-C8 alkyl, C1-C8 haloalkyl, C1-C8 polyhaloalkyl, C1-C8 alkoxy, C1-C8 alkylamino, and C1-C8 dialkylamino. In a still further aspect, each of $R^{9a}$ and $R^{9b}$ is independently selected from hydrogen, halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each of $R^{9a}$ and $R^{9b}$ is independently selected from hydrogen, —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each of $R^{9a}$ and $R^{9b}$ is independently selected from hydrogen, —F, —NH$_2$, —OH, —CN, —SF$_5$, methyl, —CH$_2$F, —CHF$_2$, —CF$_3$, —OCH$_3$, —NHCH$_3$, and —N(CH$_3$)$_2$.

i. $R^{14a}$, $R^{14b}$, $R^{14b}$, $R^{14b}$, and $R^{14e}$ Groups

In one aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^5$. In a further aspect, each of $R^{14a}$, $R^{14b}$, $R^{14c}$, $R^{14d}$, and $R^{14e}$, when present, is hydrogen.

In a further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)$_m$R$^5$. In a still further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, and —S(O)$_m$R$^5$. In a yet further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_m$R$^5$. In an even further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_m$R$^5$. In a still further aspect, wherein each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, and —S(O)$_m$R$^5$. In a yet further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, —CF$_3$, —CCl$_3$, —OCH$_3$, —NHCH$_3$, and —S(O)$_m$R$^5$. In an even further aspect, each of $R^{14a}$, $R^{14b}$, $R^{14c}$, $R^{14d}$, and $R^{14e}$, when present, is independently selected from hydrogen, —F, —Cl, methyl, —CH$_2$F, —CH$_2$Cl, —CHF$_2$, —CF$_3$, —CHCl$_2$, —CCl$_3$, and —S(O)$_m$R$^5$.

In various aspects, each of $R^{14a}$, $R^{14b}$, $R^{14c}$, $R^{14d}$, and $R^{14e}$, when present, is independently selected from hydrogen, halogen, —NH$_2$, —OH, —CN, C1-C8 alkyl, C1-C8 haloalkyl, and C1-C8 polyhaloalkyl. In a further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C6 alkyl, C1-C6 haloalkyl, and C1-C6 polyhaloalkyl. In a still further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C3 alkyl, C1-C3 haloalkyl, and C1-C3 polyhaloalkyl. In an even further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, —CH$_2$F, —CH$_2$Cl, —CHF$_2$, —CF$_3$, —CHCl$_2$, and —CCl$_3$. In an even further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, methyl, —CF$_3$, and —CCl$_3$.

In various aspects, each of $R^{14a}$, $R^{14b}$, $R^{14c}$, $R^{14d}$, and $R^{14e}$, when present, is independently selected from hydrogen, halogen, C1-C8 alkyl, C1-C8 haloalkyl, and C1-C8 polyhaloalkyl. In a further aspect, each of $R^{14a}$, $R^{14b}$, $R^{14c}$, $R^{14d}$, and $R^{14e}$, when present, is independently selected from hydrogen, halogen, C1-C6 alkyl, C1-C6 haloalkyl, and C1-C6 polyhaloalkyl. In a still further aspect, each of $R^{14a}$, $R^{14b}$, $R^{14c}$, $R^{14d}$, and $R^{14e}$, when present, is independently selected from hydrogen, halogen, C1-C3 alkyl, C1-C3 haloalkyl, and C1-C3 polyhaloalkyl. In an even further aspect, each of $R^{14a}$, $R^{14b}$, $R^{14c}$, $R^{14d}$, and $R^{14e}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of $R^{14a}$, $R^{14b}$, $R^{14c}$, $R^{14d}$, and $R^{14e}$, when present, is independently selected from hydrogen, —F, —Cl, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of $R^{14a}$, $R^{14b}$, $R^{14c}$, $R^{14d}$, and $R^{14e}$, when present, is independently selected from hydrogen, —F, —Cl, methyl, —CH$_2$F, —CH$_2$Cl, —CHF$_2$, —CF$_3$, —CHCl$_2$, and —CCl$_3$. In an even further aspect, each of $R^{14}$, $R^{14b}$, $R^{14c}$, $R^{14d}$, and $R^{14e}$, when present, is independently selected from hydrogen, —F, —Cl, methyl, —CF$_3$, and —CCl$_3$.

In various aspects, each of $R^{14a}$, $R^{14b}$, $R^{14c}$, $R^{14d}$, and $R^{14e}$, when present, is independently selected from hydrogen, halogen, —NH$_2$, —OH, —CN, C1-C8 haloalkyl, and C1-C8 polyhaloalkyl. In a further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C6 haloalkyl, and C1-C6 polyhaloalkyl. In a still further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C3 haloalkyl, and C1-C3 polyhaloalkyl. In an even further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, —CH$_2$F, —CH$_2$Cl, —CHF$_2$, —CF$_3$, —CHCl$_2$, and —CCl$_3$. In an even further aspect, each of $R^{14a}$, $R^{14b}$, $R^{14c}$, $R^{14d}$, and $R^{14e}$, when present, is independently selected from hydrogen, —F, —Cl, —NH$_2$, —OH, —CN, —CF$_3$, and —CCl$_3$. In a still further aspect, each of $R^{14a}$, $R^{14b}$, $R^{14c}$, $R^{14d}$, and $R^{14e}$, when present, is independently selected from hydrogen, —F, —Cl, —CH$_2$F, —CH$_2$Cl, —CHF$_2$, —CF$_3$, —CHCl$_2$, and —CCl$_3$.

In various aspects, each of $R^{14a}$, $R^{14b}$, $R^{14c}$, $R^{14d}$, and $R^{14e}$, when present, is independently selected from hydrogen, halogen, and C1-C8 alkyl. In a further aspect, each of $R^{14a}$, $R^{14b}$, $R^{14c}$, $R^{14d}$, and $R^{14e}$, when present, is independently selected from hydrogen, halogen, and C1-C6 alkyl. In a still further aspect, each of $R^{14a}$, $R^{14b}$, $R^{14c}$, $R^{14d}$ and $R^{14e}$, when present, is independently selected from hydrogen, halogen, and C1-C3 alkyl. In an even further aspect, each of $R^{14a}$, $R^{14b}$, $R^{14c}$, $R^{14d}$, and $R^{14e}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, and tert-pentyl. In a still further aspect, each of $R^{14a}$, $R^{14b}$, $R^{14c}$, $R^{14d}$, and $R^{14e}$, when present, is independently selected from hydrogen, —F, —Cl, methyl, ethyl, propyl, and isopropyl. In a yet further aspect, each of $R^{14a}$, $R^{14b}$, $R^{14c}$, $R^{14d}$, and $R^{14e}$, when present, is independently selected from hydrogen, —F, —Cl, and methyl.

In various aspects, each of $R^{14a}$, $R^{14b}$, $R^{14c}$, $R^{14d}$ and $R^{14e}$, when present, is independently selected from hydrogen and C1-C8 alkyl. In a further aspect, each of $R^{14a}$, $R^{14b}$, $R^{14c}$, $R^{14d}$, and $R^{14e}$, when present, is independently selected from hydrogen and C1-C6 alkyl. In a still further aspect, each of $R^{14a}$, $R^{14b}$, $R^{14c}$, $R^{14d}$, and $R^{14e}$, when present, is independently selected from hydrogen and C1-C3 alkyl. In an even further aspect, each of $R^{14a}$, $R^{14b}$, $R^{14c}$, $R^{14d}$, and $R^{14e}$, when present, is independently selected from hydrogen, methyl, ethyl, propyl, isopropyl, tert-butyl, sec-butyl, isobutyl, tert-butyl, neopentyl, isopentyl, sec-pentyl, and tert-pentyl. In a still further aspect, each of $R^{14a}$, $R^{14b}$, $R^{14c}$, $R^{14d}$, and $R^{14e}$, when present, is independently selected from hydrogen, methyl, ethyl, propyl, and isopropyl. In a yet further aspect, each of $R^{14a}$, $R^{14b}$, $R^{14c}$, $R^{14d}$, and $R^{14e}$, when present, is independently selected from hydrogen and methyl.

In various aspects, each of $R^{14a}$, $R^{14b}$, $R^{14c}$, $R^{14d}$, and $R^{14e}$, when present, is independently selected from hydrogen, halogen, —NH$_2$, —OH, —CN, C1-C8 alkoxy, C1-C8 alkylamino, C1-C8 dialkylamino, and —S(O)$_m$R$^5$. In a further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C6 alkoxy, C1-C6 alkylamino, C1-C6 dialkylamino, and —S(O)$_m$R$^5$. In a still further aspect, each of $R^{14a}$, $R^{14b}$, $R^{14c}$, $R^{14d}$, and $R^{14e}$, when present, is independently selected from hydrogen, halogen, —NH$_2$, —OH, —CN, C1-C3 alkoxy, C1-C3 alkylamino, C1-C3 dialkylamino, and —S(O)$_m$R$^5$. In an even further aspect, each of $R^{14a}$, $R^{14b}$, $R^{14c}$, $R^{14d}$, and $R^{14e}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_m$R$^5$. In a still further aspect, each of $R^{14a}$, $R^{14b}$, $R^{14c}$, $R^{14d}$, and $R^{14e}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$^2$, —N(CH$_2$CH$_3$)$_2$, and —S(O)$_m$R$^5$.

In a yet further aspect, each of $R^{14a}$, $R^{14b}$, $R^{14c}$, $R^{14d}$, and $R^{14e}$, when present, is independently selected from hydrogen, —NH$_2$, —OH, —CN, —OCH$_3$, —NHCH$_3$, —N(CH$_3$)$_2$, and —S(O)$_m$R$^5$. In an even further aspect, each of $R^{14a}$, $R^{14b}$, $R^{14c}$, $R^{14d}$, and $R^{14e}$, when present, is independently selected from hydrogen, —NH$_2$, —OH, —CN, —OCH$_3$, —NHCH$_3$, and —S(O)$_m$R$^5$.

In a further aspect, each of $R^{14a}$, $R^{14b}$, $R^{14c}$, $R^{14d}$, and $R^{14e}$, when present, is independently selected from hydrogen and —S(O)$_m$R$^5$.

j. $R^{15a}$, $R^{15b}$, $R^{15c}$, and $R^{15d}$ Groups

In one aspect, each of $R^{15a}$, $R^{15b}$, $R^{15c}$, and $R^{15d}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^5$. In a further aspect, each of $R^{15a}$, $R^{15b}$, $R^{15c}$, and $R^{15d}$, when present, is hydrogen.

In a further aspect, each of $R^{15a}$, $R^{15b}$, $R^{15c}$, and $R^{15d}$, when present, is independently selected from hydrogen, halogen, —NH$_2$, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)$_m$R$^5$. In a still further aspect, each of $R^{15a}$, $R^{15b}$, $R^{15c}$, and $R^{15d}$, when present, is independently selected from hydrogen, halogen, —NH$_2$, —OH, —CN, C1-C3 alkyl, C1-C3 haloalkyl, C1-C3 polyhaloalkyl, C1-C3 alkoxy, C1-C3 alkylamino, C1-C3 dialkylamino, and —S(O)$_m$R$^5$. In a yet further aspect, each of $R^{15a}$, $R^{15b}$, $R^{15c}$, and $R^{15d}$, when present, is independently selected from hydrogen, —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), and —S(O)$_m$R⁵. In an even further aspect, each of R¹⁵ᵃ, R¹⁵ᵇ, R¹⁵ᶜ, and R¹⁵ᵈ, when present, is independently selected from hydrogen, —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, and —S(O)$_m$R⁵. In a still further aspect, wherein each of R¹⁵ᵃ, R¹⁵ᵇ, R¹⁵ᶜ, and R¹⁵ᵈ, when present, is independently selected from hydrogen, —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, and —S(O)$_m$R⁵. In a yet further aspect, each of R¹⁵ᵃ, R¹⁵ᵇ, R¹⁵ᶜ, and R¹⁵ᵈ, when present, is independently selected from hydrogen, —F, —Cl, —NH₂, —OH, —CN, methyl, —CF₃, —CCl₃, —OCH₃, —NHCH₃, and —S(O)$_m$R⁵. In an even further aspect, each of R¹⁵ᵃ, R¹⁵ᵇ, R¹⁵ᶜ, and R¹⁵ᵈ, when present, is independently selected from hydrogen, —F, —Cl, methyl, —CH₂F, —CH₂Cl, —CHF₂, —CF₃, —CHCl₂, —CCl₃, and —S(O)$_m$R⁵.

In various aspects, each of R¹⁵ᵃ and R¹⁵ᵇ, R¹⁵ᶜ, R¹⁵ᵈ, when present, is independently selected from hydrogen, halogen, —NH₂, —OH, —CN, C1-C8 alkyl, C1-C8 haloalkyl, and C1-C8 polyhaloalkyl. In a further aspect, each of R¹⁵ᵃ, R¹⁵ᵇ, R¹⁵ᶜ, and R¹⁵ᵈ, when present, is independently selected from hydrogen, halogen, —NH₂, —OH, —CN, C1-C6 alkyl, C1-C6 haloalkyl, and C1-C6 polyhaloalkyl. In a still further aspect, each of R¹⁵ᵃ, R¹⁵ᵇ, R¹⁵ᶜ, and R¹⁵ᵈ, when present, is independently selected from hydrogen, halogen, —NH₂, —OH, —CN, C1-C3 alkyl, C1-C3 haloalkyl, and C1-C3 polyhaloalkyl. In an even further aspect each of R¹⁵ᵃ, R¹⁵ᵇ, R¹⁵ᶜ, and R¹⁵ᵈ, when present, is independently selected from hydrogen, —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, and —(CH₂)₂CI₃. In a still further aspect each of R¹⁵ᵃ, R¹⁵ᵇ, R¹⁵ᶜ, and R¹⁵ᵈ, when present, is independently selected from hydrogen, —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —CH₂CHCl₂, —CH₂CCl₃, —(CH₂)₂CHF₂, —(CH₂)₂CF₃, —(CH₂)₂CHCl₂, and —(CH₂)₂CCl₃. In a yet further aspect, each of R¹⁵ᵃ, R¹⁵ᵇ, R¹⁵ᶜ, and R¹⁵ᵈ, when present, is independently selected from hydrogen, —F, —Cl, —NH₂, —OH, —CN, methyl, —CH₂F, —CH₂Cl, —CHF₂, —CF₃, —CHCl₂, and —CCl₃. In an even further aspect, each of R¹⁵ᵃ, R¹⁵ᵇ, R¹⁵ᶜ, and R¹⁵ᵈ, when present, is independently selected from hydrogen, —F, —Cl, —NH₂, —OH, —CN, methyl, —CF₃, and —CCl₃.

In various aspects, each of R¹⁵ᵃ, R¹⁵ᵇ, R¹⁵ᶜ, R¹⁵ᵈ, when present, is independently selected from hydrogen, halogen, C1-C8 alkyl, C1-C8 haloalkyl, and C1-C8 polyhaloalkyl. In a further aspect, each of R¹⁵ᵃ, R¹⁵ᵇ, R¹⁵ᶜ, and R¹⁵ᵈ, when present, is independently selected from hydrogen, halogen, C1-C6 alkyl, C1-C6 haloalkyl, and C1-C6 polyhaloalkyl. In a still further aspect, each of R¹⁵ᵃ, R¹⁵ᵇ, R¹⁵ᶜ, and R¹⁵ᵈ, when present, is independently selected from hydrogen, halogen, C1-C3 alkyl, C1-C3 haloalkyl, and C1-C3 polyhaloalkyl. In an even further aspect, each of R¹⁵ᵃ, R¹⁵ᵇ, R¹⁵ᶜ, and R¹⁵ᵈ, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, and —(CH₂)₂CI₃. In a still further aspect, each of R¹⁵ᵃ, R¹⁵ᵇ, R¹⁵ᶜ, and R¹⁵ᵈ, when present, is independently selected from hydrogen, —F, —Cl, —NH₂, —OH, —CN, —CH₂F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each of R$^{15a}$, R$^{15b}$, R$^{15c}$, and R$^{15d}$, when present, is independently selected from hydrogen, —F, —Cl, —NH$_2$, —OH, —CN, —CH$_2$F, —CH$_2$Cl, —CHF$_2$, —CF$_3$, —CHCl$_2$, and —CCl$_3$. In an even further aspect, each of R$^{15a}$, R$^{15b}$, R$^{15c}$, and R$^{15d}$, when present, is independently selected from hydrogen, —F, —Cl, —NH$_2$, —OH, —CN, —CF$_3$, and —CCl$_3$. In a still further aspect, each of R$^{15a}$, R$^{15b}$, R$^{15c}$, and R$^{15d}$, when present, is independently selected from hydrogen, —F, —Cl, —CH$_2$F, —CH$_2$Cl, —CHF$_2$, —CF$_3$, —CHCl$_2$, and —CCl$_3$.

In various aspects, each of R$^{15a}$, R$^{15b}$, R$^{15c}$, and R$^{15d}$, when present, is independently selected from hydrogen, halogen, and C1-C8 alkyl. In a further aspect, each of R$^{15a}$, R$^{15b}$, R$^{15c}$, and R$^{15d}$, when present, is independently selected from hydrogen, halogen, and C1-C6 alkyl. In a still further aspect, each of R$^{15a}$, R$^{15b}$, R$^{15c}$, and R$^{15d}$, when present, is independently selected from hydrogen, halogen, and C1-C3 alkyl. In an even further aspect, each of R$^{15a}$, R$^{15b}$, R$^{15c}$, and R$^{15d}$, when present, is independently selected from hydrogen, —F, —Cl, methyl, ethyl, propyl, isopropyl, tert-butyl, sec-butyl, isobutyl, tert-butyl, neopentyl, isopentyl, sec-pentyl, and tert-pentyl. In a still further aspect, each of R$^{15a}$, R$^{15b}$, R$^{15c}$, and R$^{15d}$, when present, is independently selected from hydrogen, —F, —Cl, methyl, ethyl, propyl, and isopropyl. In a yet further aspect, each of R$^{15a}$, R$^{15b}$, R$^{15c}$, and R$^{15d}$, when present, is independently selected from hydrogen, —F, —Cl, and methyl.

In various aspects, each of R$^{15a}$, R$^{15b}$, R$^{15c}$, and R$^{15d}$, when present, is independently selected from hydrogen and C1-C8 alkyl. In a further aspect, each of R$^{15a}$, R$^{15b}$, R$^{15c}$, and R$^{15d}$, when present, is independently selected from hydrogen and C1-C6 alkyl. In a still further aspect, each of R$^{15a}$, R$^{15b}$, R$^{15c}$, and R$^{15d}$, when present, is independently selected from hydrogen and C1-C3 alkyl. In an even further aspect, each of R$^{15a}$, R$^{15b}$, R$^{15c}$, and R$^{15d}$, when present, is independently selected from hydrogen, methyl, ethyl, propyl, isopropyl, tert-butyl, sec-butyl, isobutyl, tert-butyl, neopentyl, isopentyl, sec-pentyl, and tert-pentyl. In a still further aspect, each of R$^{15a}$, R$^{15b}$, R$^{15c}$, and R$^{15d}$, when present, is independently selected from hydrogen, methyl, ethyl, propyl, and isopropyl. In a yet further aspect each of R$^{15a}$, R$^{15b}$, R$^{15c}$, and R$^{15d}$ when present, is independently selected from hydrogen and methyl.

In various aspects, each of R$^{15a}$, R$^{15b}$, R$^{15c}$, and R$^{15d}$, when present, is independently selected from hydrogen, halogen, —NH$_2$, —OH, —CN, C1-C8 alkoxy, C1-C8 alkylamino, C1-C8 dialkylamino, and —S(O)$_m$R$^5$. In a further aspect, each of R$^{15a}$, R$^{15b}$, R$^{15c}$, and R$^{15d}$, when present, is independently selected from hydrogen, halogen, —NH$_2$, —OH, —CN, C1-C6 alkoxy, C1-C6 alkylamino, C1-C6 dialkylamino, and —S(O)$_m$R$^5$. In a still further aspect, each of R$^{15a}$, R$^{15b}$, R$^{15c}$, and R$^{15d}$, when present, is independently selected from hydrogen, halogen, —NH$_2$, —OH, —CN, C1-C3 alkoxy, C1-C3 alkylamino, C1-C3 dialkylamino, and —S(O)$_m$R$^5$. In an even further aspect, each of R$^{15a}$, R$^{15b}$, R$^{15c}$, and R$^{15d}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), and —S(O)$_m$R$^5$. In a still further aspect, each of R$^{15a}$, R$^{15b}$, R$^{15c}$, and R$^{15d}$, when present, is independently selected from hydrogen, —NH$_2$, —OH, —CN, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, and —S(O)$_m$R$^5$. In a yet further aspect, each of R$^{15a}$, R$^{15b}$, R$^{15c}$, and R$^{15d}$, when present, is independently selected from hydrogen, —NH$_2$, —OH, —CN, —OCH$_3$, —NHCH$_3$, —N(CH$_3$)$_2$, and —S(O)$_m$R$^5$. In an even further aspect, each of R$^{15a}$, R$^{15b}$, R$^{15c}$, and R$^{15d}$, when present, is independently selected from hydrogen, —NH$_2$, —OH, —CN, —OCH$_3$, —NHCH$_3$, and —S(O)$_m$R$^5$.

In a further aspect, each of R$^{15a}$, R$^{15b}$, R$^{15c}$, and R$^{15d}$, when present, is independently selected from hydrogen and —S(O)$_m$R$^5$.

k. R$^{16}$ Groups

In one aspect, R$^{16}$, when present, is selected from hydrogen and C1-C8 alkyl. In a further aspect, R$^{16}$, when present, is selected from hydrogen and C1-C6 alkyl. In a still further aspect, R$^{16}$, when present, is selected from hydrogen and C1-C3 alkyl. In a yet further aspect, R$^{16}$, when present, is selected from hydrogen, methyl, ethyl, propyl, isopropyl, tert-butyl, sec-butyl, isobutyl, tert-butyl, neopentyl, isopentyl, sec-pentyl, and tert-pentyl. In an even further aspect, R$^{16}$, when present, is selected from hydrogen, methyl, ethyl, propyl, and isopropyl. In a still further aspect, R$^{16}$, when present, is selected from hydrogen, methyl, and ethyl. In a yet further aspect, R$^{16}$, when present, is selected from hydrogen and methyl. In an even further aspect, R$^{16}$, when present, is hydrogen. In a still further aspect, R$^{16}$, when present, is methyl. In a yet further aspect, R$^{16}$, when present, is ethyl.

l. R$^{20}$ Groups

In one aspect, R$^{20}$ is selected from hydrogen, C1-C8 alkyl, C1-C8 monohaloalkyl, C1-C8 polyhaloalkyl, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein that at least three of R$^{7a}$, R$^{7b}$, R$^{7c}$, R$^{7d}$, R$^{7e}$, and R$^{20}$ are hydrogen. In various further aspects, R$^{20}$ is selected from hydrogen, C1-C8 alkyl, C1-C8 monohaloalkyl, C1-C8 polyhaloalkyl, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$.

In a further aspect, R$^{20}$ is selected from hydrogen, C1-C6 alkyl, C1-C6 monohaloalkyl, C1-C6 polyhaloalkyl, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$. In a still further aspect, R$^{20}$ is selected from hydrogen, C1-C6 alkyl, C1-C6 monohaloalkyl, C1-C6 polyhaloalkyl, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, R$^6$, and Ar$^2$. In a yet further aspect, R$^{20}$ is selected from hydrogen, C1-C3 alkyl, C1-C3 monohaloalkyl, C1-C3 polyhaloalkyl, —(C1-C3 alkyl)-(S=O)R$^5$, —(C1-C3 alkyl)-SO$_2$R$^5$, —(S=O)R$^5$, —SO$_2$R$^5$, R$^6$, and Ar$^2$. In an even further aspect, R$^{20}$ is selected from hydrogen, C1-C6 alkyl, C1-C6 monohaloalkyl, C1-C6 polyhaloalkyl, —(C1-C3 alkyl)-(C=O)R$^5$, —(C1-C3 alkyl)-(C=O)OR$^5$, —(C1-C3 alkyl)-(S=O)R$^5$, —(C1-C3 alkyl)-SO$_2$R$^5$, —(C=O)R$^5$, —(C=O)OR$^5$, —(S=O)R$^5$, —SO$_2$R$^5$, R$^6$, and Ar$^2$.

In a further aspect, R$^{20}$ is selected from hydrogen, —F, —Cl, —NH$_2$, —OH, —CN, C1-C3 alkyl, C1-C3 monohaloalkyl, C1-C3 polyhaloalkyl, —(CH$_2$)$_3$—(C=O)R$^5$, —(CH$_2$)$_2$—(C=O)R$^5$, —CH$_2$—(C=O)R$^5$, —(CH$_2$)$_3$—

(C=O)OR$^5$, —(CH$_2$)$_2$—(C=O)OR$^5$, —CH$_2$—(C=O) OR$^5$, —(CH$_2$)$_3$—S—R$^5$, —(CH$_2$)$_2$—S—R$^5$, —CH$_2$—S— R$^5$, —(CH$_2$)$_3$—(S=O)R$^5$, —(CH$_2$)$_2$—(S=O)R$^5$, —CH$_2$— (S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In a still further aspect, R$^{20}$ is selected from hydrogen, —F, —Cl, —NH$_2$, —OH, —CN, C1-C3 alkyl, C1-C3 monohaloalkyl, C1-C3 polyhaloalkyl, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In a yet further aspect, R$^{20}$ is selected from hydrogen, —F, —Cl, —NH$_2$, —OH, —CN, C1-C3 alkyl, C1-C3 monohaloalkyl, C1-C3 polyhaloalkyl, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, R$^6$, and Ar$^2$. In an even further aspect, R$^{20}$ is selected from hydrogen, —F, —Cl, —NH$_2$, —OH, —CN, C1-C3 alkyl, C1-C3 monohaloalkyl, C1-C3 polyhaloalkyl, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, —SO$_2$R$^5$, R$^6$, and Ar$^2$.

In a further aspect, R$^{20}$ is selected from hydrogen, methyl, CH$_2$F, —CH$_2$Cl, —CHF$_2$, —CF$_3$, —CHCl$_2$, —CCl$_3$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl.

In various aspects, R$^{20}$ is selected from hydrogen, C1-C6 alkyl, C1-C6 monohaloalkyl, C1-C6 polyhaloalkyl, —(C1-C6 alkyl)-(C=O)R$^5$, —(C1-C6 alkyl)-(C=O)OR$^5$, —(C1-C6 alkyl)-S—R$^5$, —(C1-C6 alkyl)-(S=O)R$^5$, —(C1-C6 alkyl)-SO$_2$R$^5$, —(C=O)R$^5$, —(C=O)OR$^5$, —S—R$^5$, —(S=O)R$^5$, —SO$_2$R$^5$, and R$^6$. In a still further aspect, R$^{20}$ is selected from hydrogen, C1-C6 alkyl, C1-C6 monohaloalkyl, C1-C6 polyhaloalkyl, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, and R$^6$. In a yet further aspect, R$^{20}$ is selected from hydrogen, C1-C3 alkyl, C1-C3 monohaloalkyl, C1-C3 polyhaloalkyl, —(C1-C3 alkyl)-(S=O)R$^5$, —(C1-C3 alkyl)-SO$_2$R$^5$, —(S=O)R$^5$, —SO$_2$R$^5$, and R$^6$. In an even further aspect, R$^{20}$ is selected from hydrogen, C1-C6 alkyl, C1-C6 monohaloalkyl, C1-C6 polyhaloalkyl, —(C1-C3 alkyl)-(C=O)R$^5$, —(C1-C3 alkyl)-(C=O)OR$^5$, —(C1-C3 alkyl)-(S=O)R$^5$, —(C1-C3 alkyl)-SO$_2$R$^5$, —(C=O)R$^5$, —(C=O)OR$^5$, —(S=O)R$^5$, —SO$_2$R$^5$, and R$^6$.

In a further aspect, R$^{20}$ is selected from hydrogen, C1-C3 alkyl, C1-C3 monohaloalkyl, C1-C3 polyhaloalkyl, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O) OR$^5$, —CH$_2$—(C=O)OR$^5$, —(CH$_2$)$_3$—S—R$^5$, —(CH$_2$)$_2$— S—R$^5$, —CH$_2$—S—R$^5$, —(CH$_2$)$_3$—(S=O)R$^5$, —(CH$_2$)$_2$— (S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a still further aspect, R$^{20}$ is selected from hydrogen, C1-C3 alkyl, C1-C3 monohaloalkyl, C1-C3 polyhaloalkyl, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a yet further aspect, R$^{20}$ is selected from hydrogen, C1-C3 alkyl, C1-C3 monohaloalkyl, C1-C3 polyhaloalkyl, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In an even further aspect, R$^{20}$ is selected from hydrogen, C1-C3 alkyl, C1-C3 monohaloalkyl, C1-C3 polyhaloalkyl, —CH$_2$—(C=O)R$^5$, —CH$_2$—(C=O)OR$^5$, —CH$_2$—(S=O)R$^5$, —CH$_2$—SO$_2$R$^5$, —(C=O)R$^5$, —(C=O)OR$^5$, —(S=O)R$^5$, —SO$_2$R$^5$, and R$^6$.

In a further aspect, R$^{20}$ is selected from hydrogen, methyl, —CH$_2$F, —CHF$_2$, —CF$_3$, —CH$_2$—(C=O)CH$_3$, —CH$_2$—(C=O)OCH$_3$, —CH$_2$—S—CH$_3$, —CH$_2$—(S=O)CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, R$^{20}$ is selected from hydrogen, methyl, —CH$_2$F, —CHF$_2$, —CF$_3$, —CH$_2$—(S=O)CH$_3$, —CH$_2$—SO$_2$CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$.

In a further aspect, R$^{20}$ is selected from hydrogen, C1-C8 alkyl, C1-C8 haloalkyl, And C1-C8 polyhaloalkyl. In a still further aspect, R$^{20}$ is selected from hydrogen, C1-C6 alkyl, C1-C6 monohaloalkyl, and C1-C6 polyhaloalkyl. In a yet further aspect, R$^{20}$ is selected from hydrogen, C1-C3 alkyl, C1-C3 monohaloalkyl, and C1-C3 polyhaloalkyl. In an even further aspect, R$^{20}$ is selected from hydrogen, methyl, —CH$_2$F, —CHF$_2$, and —CF$_3$.

m. R$^{31A}$, R$^{31B}$, R$^{31c}$, R$^{31D}$, R$^{31D}$, and R$^{31F}$ Groups

In one aspect, each of R$^{31a}$, R$^{31b}$, R$^{31c}$, R$^{31d}$, R$^{31e}$, and R$^{31f}$ is independently selected from hydrogen and C1-C3 alkyl, provided that at least two of R$^{31a}$, R$^{31b}$, R$^{31c}$, R$^{31d}$, R$^{31e}$, and R$^{31f}$ are hydrogen. In a still further aspect, each of R$^{31a}$, R$^{31b}$, R$^{31c}$, R$^{31d}$, R$^{31e}$, and R$^{31f}$ is independently selected from hydrogen, methyl, ethyl, propyl, and isopropyl, provided that at least two of R$^{31a}$, R$^{31b}$, R$^{31c}$, R$^{31d}$, R$^{31e}$, and R$^{31f}$ are hydrogen. In a yet further aspect, each of R$^{31a}$, R$^{31b}$, R$^{31c}$, R$^{31d}$, R$^{31e}$, and R$^{31f}$ is independently selected from hydrogen, methyl, and ethyl, provided that at least two of R$^{31a}$, R$^{31b}$, R$^{31c}$, R$^{31d}$, R$^{31e}$, and R$^{31f}$ are hydrogen. In an even further aspect, each of R$^{31a}$, R$^{31b}$, R$^{31c}$, R$^{31d}$, R$^{31e}$, and R$^{31f}$ is independently selected from hydrogen and methyl, provided that at least two of R$^{31a}$, R$^{31b}$, R$^{31c}$, R$^{31d}$, R$^{31e}$, and R$^{31f}$ are hydrogen. In a still further aspect, each of R$^{31a}$, R$^{31b}$, R$^{31c}$, R$^{31d}$, R$^{31e}$, and R$^{31f}$ is hydrogen.

In various aspects, each of R$^{31a}$, R$^{31b}$, R$^{31c}$, and R$^{31d}$ is independently selected from hydrogen and C1-C3 alkyl. In a still further aspect, each of R$^{31a}$, R$^{31b}$, R$^{31c}$, and R$^{31d}$ is independently selected from hydrogen, methyl, ethyl, propyl, and isopropyl. In a yet further aspect, each of R$^{31a}$, R$^{31b}$, R$^{31c}$, and R$^{31d}$ is independently selected from hydrogen, methyl, and ethyl. In an even further aspect, each of $R^{31a}$, $R^{31b}$, $R^{31c}$, and $R^{31d}$ is independently selected from hydrogen and methyl. In a still further aspect, each of $R^{31a}$, $R^{31b}$, $R^{31c}$, and $R^{31d}$ is hydrogen.

In various further aspects, each of $R^{31a}$ and $R^{31b}$ is independently selected from hydrogen and C1-C3 alkyl. In a still further aspect, each of $R^{31a}$ and $R^{31b}$ is independently selected from hydrogen, methyl, ethyl, propyl, and isopropyl. In a yet further aspect, each of $R^{31a}$ and $R^{31b}$ is independently selected from hydrogen, methyl, and ethyl. In an even further aspect, each of $R^{31a}$ and $R^{31b}$ is independently selected from hydrogen and methyl. In a still further aspect, each of $R^{31a}$ and $R^{31b}$ is hydrogen.

n. $R^{40}$ Groups

In one aspect, each $R^{40}$, when present, is independently selected from hydrogen and C1-C8 alkyl. In a further aspect, each $R^{40}$, when present, is hydrogen. In a still further aspect, each $R^{40}$, when present, is methyl.

In various aspects, each $R^{40}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{40}$, when present, is independently selected from hydrogen, methyl, ethyl, propyl, isopropyl, tert-butyl, sec-butyl, and isobutyl. In a still further aspect, each $R^{40}$, when present, is independently selected from hydrogen, methyl, ethyl, propyl, and isopropyl. In a yet further aspect, each $R^{40}$, when present, is independently selected from hydrogen, methyl, and ethyl. In an even further aspect, each $R^{40}$, when present, is independently selected from hydrogen and methyl.

o. $R^{41}$ Groups

In one aspect, each $R^{41}$, when present, is independently selected from hydrogen, C1-C8 alkyl, C1-C8 monohaloalkyl, C1-C8 polyhaloalkyl, —(C1-C8 alkyl)-$Cy^1$, $Cy^1$, —(C1-C8 alkyl)-$Ar^1$, and $Ar^1$. In a further aspect, each $R^{41}$, when present, is hydrogen.

In various aspects, each $R^{41}$, when present, is independently selected from hydrogen, C1-C8 alkyl, C1-C8 monohaloalkyl, and C1-C8 polyhaloalkyl.

In various aspects, each $R^{41}$, when present, is independently selected from hydrogen, C1-C8 alkyl, —(C1-C8 alkyl)-$Cy^1$, $Cy^1$, —(C1-C8 alkyl)-$Ar^1$, and $Ar^1$.

In various aspects, each $R^{41}$, when present, is independently selected from —(C1-C8 alkyl)-$Cy^1$, $Cy^1$, —(C1-C8 alkyl)-$Ar^1$, and $Ar^1$.

p. $R^{50}$ Groups

In one aspect, each $R^{50}$, when present, is independently selected from hydrogen and C1-C8 alkyl. In a further aspect, each $R^{50}$, when present, is hydrogen. In a still further aspect, each $R^{50}$, when present, is methyl.

In various aspects, each $R^{50}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{50}$, when present, is independently selected from hydrogen, methyl, ethyl, propyl, isopropyl, tert-butyl, sec-butyl, and isobutyl. In a still further aspect, each $R^{50}$, when present, is independently selected from hydrogen, methyl, ethyl, propyl, and isopropyl. In a yet further aspect, each $R^{50}$, when present, is independently selected from hydrogen, methyl, and ethyl. In an even further aspect, each $R^{50}$, when present, is independently selected from hydrogen and methyl.

q. $R^{51}$ Groups

In one aspect, each $R^{51}$, when present, is independently selected from hydrogen and C1-C8 alkyl. In a further aspect, each $R^{51}$, when present, is hydrogen. In a still further aspect, each $R^{51}$, when present, is methyl.

In various aspects, each $R^{51}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{51}$, when present, is independently selected from hydrogen, methyl, ethyl, propyl, isopropyl, tert-butyl, sec-butyl, and isobutyl. In a still further aspect, each $R^{51}$, when present, is independently selected from hydrogen, methyl, ethyl, propyl, and isopropyl. In a yet further aspect, each $R^{51}$, when present, is independently selected from hydrogen, methyl, and ethyl. In an even further aspect, each $R^{51}$, when present, is independently selected from hydrogen and methyl.

r. $R^{52}$ Groups

In one aspect, each $R^{52}$, when present, is independently selected from hydrogen and C1-C8 alkyl. In a further aspect, each $R^{52}$, when present, is hydrogen. In a still further aspect, each $R^{52}$, when present, is methyl.

In various aspects, each $R^{52}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{52}$, when present, is independently selected from hydrogen, methyl, ethyl, propyl, isopropyl, tert-butyl, sec-butyl, and isobutyl. In a still further aspect, each $R^{52}$, when present, is independently selected from hydrogen, methyl, ethyl, propyl, and isopropyl. In a yet further aspect, each $R^{52}$, when present, is independently selected from hydrogen, methyl, and ethyl. In an even further aspect, each $R^{52}$, when present, is independently selected from hydrogen and methyl.

s. $R^{53}$ Groups

In one aspect, each $R^{53}$, when present, is independently selected from hydrogen and C1-C8 alkyl. In a further aspect, each $R^{53}$, when present, is hydrogen. In a still further aspect, each $R^{53}$, when present, is methyl.

In various aspects, each $R^{53}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a further aspect, each $R^{53}$, when present, is independently selected from hydrogen, methyl, ethyl, propyl, isopropyl, tert-butyl, sec-butyl, and isobutyl. In a still further aspect, each $R^{53}$, when present, is independently selected from hydrogen, methyl, ethyl, propyl, and isopropyl. In a yet further aspect, each $R^{53}$, when present, is independently selected from hydrogen, methyl, and ethyl. In an even further aspect, each $R^{53}$, when present, is independently selected from hydrogen and methyl.

t. $R^{54}$ Groups

In one aspect, each $R^{54}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-$Ar^{21}$, and $Ar^{21}$. In a further aspect, each $R^{54}$, when present, is hydrogen.

In a further aspect, each $R^{54}$, when present, is independently selected from hydrogen, C1-C6 alkyl, C1-C6 monohaloalkyl, C1-C6 polyhaloalkyl, C3-C6 cycloalkyl, C2-C5 heterocycloalkyl, —(C1-C6)-$Ar^{21}$, and $Ar^{21}$. In a still further aspect, each $R^{54}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, —(C1-C6)-$Ar^{21}$, and $Ar^{21}$.

In a further aspect, each $R^{54}$, when present, is independently selected from hydrogen, —(C1-C6)-$Ar^{21}$, and $Ar^{21}$. In a still further aspect, each $R^{54}$, when present, is independently selected from hydrogen, —(CH$_2$)—Ar$^{21}$, —(CH$_2$)$_2$—Ar$^{21}$, —(CH$_2$)$_3$—Ar$^{21}$, —(CH(CH$_3$)CH$_2$)—Ar$^{21}$, and Ar$^{21}$. In a yet further aspect, each $R^{54}$, when present, is independently selected from hydrogen, —(CH$_2$)—Ar$^{21}$, —(CH$_2$)$_2$—Ar$^{21}$, and Ar$^{21}$. In an even further aspect, each $R^{54}$, when present, is independently selected from hydrogen, —(CH$_2$)—Ar$^{21}$, and Ar$^{21}$. In various further aspects, each Ar$^{21}$ can be substituted with 0-3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino In a yet further aspect, each Ar$^{21}$ can be substituted with 0-3 groups independently selected from —F, —Cl, —NH$_2$, —OH, —CN, —CH$_3$, —CF$_3$, —CHF$_2$, —CH$_2$F, —OCH$_3$, N(CH$_3$)$_2$, and —NHCH$_3$.

In a further aspect, each $R^{54}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{54}$, when present, is independently selected from hydrogen, C1-C8 alkyl, C1-C8 monohaloalkyl, and C1-C8 polyhaloalkyl. In a still further aspect, each $R^{54}$, when present, is independently selected from hydrogen, C1-C6 alkyl, C1-C6 monohaloalkyl, and C1-C6 polyhaloalkyl. In a yet further aspect, each $R^{54}$, when present, is independently selected from hydrogen, C1-C3 alkyl, C1-C3 monohaloalkyl, and C1-C8 polyhaloalkyl.

In a further aspect, each $R^{54}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, each $R^{54}$, when present, is independently selected from hydrogen, methyl, ethyl, propyl, isopropyl, tert-butyl, sec-butyl, isobutyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each $R^{54}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each $R^{54}$, when present, is independently selected from hydrogen, methyl, —CH$_2$F, —CHF$_2$, and —CF$_3$.

u. $R^{55}$ Groups

In one aspect, each $R^{55}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{22}$, and Ar$^{22}$. In a further aspect, each $R^{55}$, when present, is hydrogen.

In a further aspect, each $R^{55}$, when present, is independently selected from hydrogen, C1-C6 alkyl, C1-C6 monohaloalkyl, C1-C6 polyhaloalkyl, C3-C6 cycloalkyl, C2-C5 heterocycloalkyl, —(C1-C6)-Ar$^{22}$, and Ar$^{22}$. In a still further aspect, each $R^{55}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, —(C1-C6)-Ar$^{22}$, and Ar$^{22}$.

In a further aspect, each $R^{55}$, when present, is independently selected from hydrogen, —(C1-C6)-Ar$^{22}$, and Ar$^{22}$. In a still further aspect, each $R^{55}$, when present, is independently selected from hydrogen, —(CH$_2$)—Ar$^{22}$, —(CH$_2$)$_2$—Ar$^{22}$, —(CH$_2$)$_3$—Ar$^{22}$, —(CH(CH$_3$)CH$_2$)—Ar$^{22}$, and Ar$^{22}$. In a yet further aspect, each $R^{55}$, when present, is independently selected from hydrogen, —(CH$_2$)—Ar$^{22}$, —(CH$_2$)$_2$—Ar$^{22}$, and Ar$^{22}$. In an even further aspect, each $R^{55}$, when present, is independently selected from hydrogen, —(CH$_2$)—Ar$^{22}$, and Ar$^{22}$. In various further aspects, each Ar$^{22}$ can be substituted with 0-3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino In a yet further aspect, each Ar$^{22}$ can be substituted with 0-3 groups independently selected from —F, —Cl, —NH$_2$, —OH, —CN, —CH$_3$, —CF$_3$, —CHF$_2$, —CH$_2$F, —OCH$_3$, —N(CH$_3$)$_2$, and —NHCH$_3$.

In a further aspect, each $R^{55}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{55}$, when present, is independently selected from hydrogen, C1-C8 alkyl, C1-C8 monohaloalkyl, and C1-C8 polyhaloalkyl. In a still further aspect, each $R^{55}$, when present, is independently selected from hydrogen, C1-C6 alkyl, C1-C6 monohaloalkyl, and C1-C6 polyhaloalkyl. In a yet further aspect, each $R^{55}$, when present, is independently selected from hydrogen, C1-C3 alkyl, C1-C3 monohaloalkyl, and C1-C8 polyhaloalkyl.

In a further aspect, each $R^{55}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, each $R^{55}$, when present, is independently selected from hydrogen, methyl, ethyl, propyl, isopropyl, tert-butyl, sec-butyl, isobutyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each $R^{55}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each $R^{55}$, when present, is independently selected from hydrogen, methyl, —CH$_2$F, —CHF$_2$, and —CF$_3$.

v. $R^{50}$ Groups

In one aspect, each $R^{50}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{23}$, and Ar$^{23}$. In a further aspect, each $R^{50}$, when present, is hydrogen.

In a further aspect, each $R^{50}$, when present, is independently selected from hydrogen, C1-C6 alkyl, C1-C6 monohaloalkyl, C1-C6 polyhaloalkyl, C3-C6 cycloalkyl, C2-C5 heterocycloalkyl, —(C1-C6)-Ar$^{23}$, and Ar$^{23}$. In a still further aspect, each $R^{50}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, —(C1-C6)-Ar$^{23}$, and Ar$^{23}$.

In a further aspect, each $R^{50}$, when present, is independently selected from hydrogen, —(C1-C6)-Ar$^{23}$, and Ar$^{23}$. In a still further aspect, each $R^{50}$, when present, is independently selected from hydrogen, —(CH$_2$)—Ar$^{23}$, —(CH$_2$)$_2$—Ar$^{23}$, —(CH$_2$)$_3$—Ar$^{23}$, —(CH(CH$_3$)CH$_2$)—Ar$^{23}$, and Ar$^{23}$. In a yet further aspect, each $R^{50}$, when present, is independently selected from hydrogen, —(CH$_2$)—Ar$^{23}$, —(CH$_2$)$_2$—Ar$^{23}$, and Ar$^{23}$. In an even further aspect, each $R^{50}$, when present, is independently selected from hydrogen, —(CH$_2$)—Ar$^{23}$, and Ar$^{23}$. In various further aspects, each Ar$^{23}$ can be substituted with 0-3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino In a yet further aspect, each Ar$^{23}$ can be substituted with 0-3 groups independently selected from —F, —Cl, —NH$_2$, —OH, —CN, —CH$_3$, —CF$_3$, —CHF$_2$, —CH$_2$F, —OCH$_3$, —N(CH$_3$)$_2$, and —NHCH$_3$.

In a further aspect, each $R^{50}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3] heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{50}$, when present, is independently selected from hydrogen, C1-C8 alkyl, C1-C8 monohaloalkyl, and C1-C8 polyhaloalkyl. In a still further aspect, each $R^{50}$, when present, is independently selected from hydrogen, C1-C6 alkyl, C1-C6 monohaloalkyl, and C1-C6 polyhaloalkyl. In a yet further aspect, each $R^{50}$, when present, is independently selected from hydrogen, C1-C3 alkyl, C1-C3 monohaloalkyl, and C1-C8 polyhaloalkyl.

In a further aspect, each $R^{50}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$.

In a further aspect, each $R^{50}$, when present, is independently selected from hydrogen, methyl, ethyl, propyl, isopropyl, tert-butyl, sec-butyl, isobutyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, each $R^{50}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each $R^{50}$, when present, is independently selected from hydrogen, methyl, —CH$_2$F, —CHF$_2$, and —CF$_3$.

w. $R^{57}$ Groups

In one aspect, each $R^{57}$, when present, is independently selected from C1-C4 alkyl, C1-C4 alkoxy, C1-C4 monoalkylamino, or C1-C4 dialkylamino substituted with 1 or 2 groups selected from —F, —CH$_3$, —CF$_3$, —OH, —NH$_2$, and —CN.

In one aspect, each $R^{57}$, when present, is independently selected from C1-C4 alkyl, C1-C4 alkoxy, C1-C4 monoalkylamino, or C1-C4 dialkylamino substituted with 1 or 2 groups selected from —CH$_3$, —CF$_3$, —F, —OH, —NH$_2$, and —CN.

In a further aspect, each $R^{57}$, when present, is independently selected from C1-C3 alkyl, C1-C3 alkoxy, C1-C3 monoalkylamino, and C1-C3 dialkylamino substituted with 1 or 2 groups independently selected from —CH$_3$, —CF$_3$, —F, —OH, —NH$_2$, and —CN.

In a further aspect, each $R^{57}$, when present, is independently selected from —CH$_2$R$^{58}$, —CHR$^{58}$R$^{59}$, —CHR$^{58}$CH$_2$R$^{59}$, —CR$^{58}$R$^{59}$CH$_3$, and —CH$_2$CHR$^{58}$R$^{59}$; and wherein each of $R^{58}$ and $R^{59}$, when present, is independently selected from —CH$_3$, —CF$_3$, —F, —OH, —NH$_2$, and —CN. In a still further aspect, each $R^{57}$, when present, is independently selected from —CH$_2$R$^{58}$ and —CHR$^{58}$R$^{59}$; and wherein each of $R^{58}$ and $R^{59}$, when present, is independently selected from —CH$_3$, —CF$_3$, —F, —OH, —NH$_2$, and —CN. In a yet further aspect, each $R^{57}$, when present, is —CH$_2$R$^{58}$; and each $R^{58}$ is independently selected from —CH$_3$, —CF$_3$, —F, —OH, —NH$_2$, and —CN. In an even further aspect, each $R^{57}$, when present, is independently selected from —CH$_2$CF$_3$, —CH$_2$CH$_3$, —CH$_2$F, —CH$_2$OH, —CH$_2$NH$_2$, and —CH$_2$CN. In a yet further aspect, each $R^{57}$, when present, is independently selected from —CH$_2$CF$_3$, —CH$_2$F, —CH$_2$OH, —CH$_2$NH$_2$, and —CH$_2$CN. In a still further aspect, each $R^{57}$, when present, is —CHR$^{58}$R$^{59}$; and each of $R^{58}$ and $R^{59}$, when present, is independently selected from —CH$_3$, —CF$_3$, —F, —OH, —NH$_2$, and —CN.

In a further aspect, each $R^{57}$, when present, is —CHR$^{58}$CH$_2$R$^{59}$; and each of $R^{58}$ and $R^{59}$, when present, is independently selected from —CH$_3$, —CF$_3$, —F, —OH, —NH$_2$, and —CN. In a yet further aspect, each $R^{57}$, when present, is —CH$_2$CHR$^{58}$R$^{59}$; and each of $R^{58}$ and $R^{59}$, when present, is independently selected from —CH$_3$, —CF$_3$, —F, —OH, —NH$_2$, and —CN. In an even further aspect, each $R^{57}$, when present, is —CR$^{58}$R$^{59}$CH$_3$; and each of $R^{58}$ and $R^{59}$, when present, is independently selected from —CH$_3$, —CF$_3$, —F, —OH, —NH$_2$, and —CN.

In a further aspect, each $R^{57}$, when present, is independently selected from —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, each $R^{57}$, when present, is —CH$_2$CF$_3$. In a yet further aspect, each $R^{57}$, when present, is —CH$_2$F. In an even further aspect, each $R^{57}$, when present, is —CH$_2$OH. In a still further aspect, each $R^{57}$, when present, is —CH$_2$NH$_2$. In a yet further aspect, each $R^{57}$, when present, is —CH$_2$CN.

x. $R^{58}$ Groups

In one aspect, each $R^{58}$, when present, is independently selected from —CH$_3$, —CF$_3$, —F, —OH, —NH$_2$, and —CN. In a further aspect, each $R^{58}$, when present, is independently selected from —CF$_3$, —F, —OH, —NH$_2$, and —CN. In a still further aspect, each $R^{58}$, when present, is independently selected from —CH$_3$, —F, —OH, —NH$_2$, and —CN. In a yet further aspect, each $R^{58}$, when present, is independently selected from —CH$_3$, —CF$_3$, —OH, —NH$_2$, and —CN. In an even further aspect, each $R^{58}$, when present, is independently selected from —CH$_3$, —CF$_3$, —F, —NH$_2$, and —CN. In a still further aspect, each $R^{58}$, when present, is independently selected from —CH$_3$, —CF$_3$, —F, —OH, and —CN. In a yet further aspect, each $R^{58}$, when present, is independently selected from —CH$_3$, —CF$_3$, —F, —OH, and —NH$_2$.

In a further aspect, each $R^{58}$, when present, is —CH$_3$. In a still further aspect, each $R^{58}$, when present, is —CF$_3$. In a yet further aspect, each $R^{58}$, when present, is —F. In an even further aspect, each $R^{58}$, when present, is —OH. In a still further aspect, each $R^{58}$, when present, is —NH$_2$. In a yet further aspect, each $R^{58}$, when present, is —CN.

y. $R^{59}$ Groups

In one aspect, each $R^{59}$, when present, is independently selected from —CH$_3$, —CF$_3$, —F, —OH, —NH$_2$, and —CN. In a further aspect, each $R^{59}$, when present, is independently selected from —CF$_3$, —F, —OH, —NH$_2$, and —CN. In a still further aspect, each $R^{59}$, when present, is independently selected from —CH$_3$, —F, —OH, —NH$_2$, and —CN. In a yet further aspect, each $R^{59}$, when present, is independently selected from —CH$_3$, —CF$_3$, —OH, —NH$_2$, and —CN. In an even further aspect, each $R^{59}$, when present, is independently selected from —CH$_3$, —CF$_3$, —F, —NH$_2$, and —CN. In a still further aspect, each $R^{59}$, when present, is independently selected from —CH$_3$, —CF$_3$, —F, —OH, and —CN. In a yet further aspect, each $R^{59}$, when present, is independently selected from —CH$_3$, —CF$_3$, —F, —OH, and —NH$_2$.

In a further aspect, each $R^{59}$, when present, is —CH$_3$. In a still further aspect, each $R^{59}$, when present, is —CF$_3$. In a yet further aspect, each $R^{59}$, when present, is —F. In an even further aspect, each $R^{59}$, when present, is —OH. In a still further aspect, each $R^{59}$, when present, is —NH$_2$. In a yet further aspect, each $R^{59}$, when present, is —CN.

z. $R^{65}$ Groups

In one aspect, each $R^{65}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl. In a further aspect, each $R^{65}$, when present, is hydrogen.

In a further aspect, each $R^{65}$, when present, is independently selected from hydrogen, C1-C6 alkyl, C1-C6 hydroxyalkyl, C1-C6 monohaloalkyl, C1-C6 polyhaloalkyl, C3-C6 cycloalkyl, C2-C5 heterocycloalkyl, phenyl, and monocyclic heteroaryl. In a still further aspect, each $R^{65}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, phenyl, and monocyclic heteroaryl.

In a further aspect, each $R^{65}$, when present, is independently selected from hydrogen, substituted phenyl, and substituted monocyclic heteroaryl. In a still further aspect, each phenyl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a yet further aspect, each phenyl can be substituted with 0-3 groups independently selected from —F, —Cl, —NH$_2$, —OH, —CN, —CH$_3$, —CF$_3$, —CHF$_2$, —CH$_2$F, and —OCH$_3$. In an even further aspect, each monocyclic heteroaryl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, each monocyclic heteroaryl can be substituted with 0-3 groups independently selected from —F, —Cl, —NH$_2$, —OH, —CN, —CH$_3$, —CF$_3$, —CHF$_2$, —CH$_2$F, and —OCH$_3$. In various further aspects, each monocyclic heteroaryl is independently selected from pyridine, pyrimidine, and pyradazine, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, each monocyclic heteroaryl is independently selected from pyridine, pyrimidine, and pyradazine, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{65}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{65}$, when present, is independently selected from hydrogen, C1-C8 alkyl, C1-C8 hydroxyalkyl, C1-C8 monohaloalkyl, and C1-C8 polyhaloalkyl. In a still further aspect, each $R^{65}$, when present, is independently selected from hydrogen, C1-C6 alkyl, C1-C6 hydroxyalkyl, C1-C6 monohaloalkyl, and C1-C6 polyhaloalkyl. In a yet further aspect, each $R^{65}$, when present, is independently selected from hydrogen, C1-C3 alkyl, C1-C3 hydroxyalkyl, C1-C3 monohaloalkyl, and C1-C8 polyhaloalkyl.

In a further aspect, each $R^{65}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, 1-hydroxyethyl, 2-hydroxyethyl, 1-hydroxypropyl, 2-hydroxypropyl, 3 hydroxypropyl, 1-hydroxybutyl, 2-hydroxybutyl, 3-hydroxybutyl, and 4-hydroxybutyl.

aa. $R^{66}$ Groups

In one aspect, each $R^{66}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl. In a further aspect, each $R^{66}$, when present, is hydrogen.

In a further aspect, each $R^{66}$, when present, is independently selected from hydrogen, C1-C6 alkyl, C1-C6 hydroxyalkyl, C1-C6 monohaloalkyl, C1-C6 polyhaloalkyl, C3-C6 cycloalkyl, C2-C5 heterocycloalkyl, phenyl, and monocyclic heteroaryl. In a still further aspect, each $R^{66}$, when present, is independently selected from hydrogen, C1-C3 alkyl, C1-C3 hydroxyalkyl, C1-C3 monohaloalkyl, C1-C3 polyhaloalkyl, C3-C6 cycloalkyl, C2-C5 heterocycloalkyl, phenyl, and monocyclic heteroaryl.

In a further aspect, each $R^{66}$, when present, is independently selected from hydrogen, substituted phenyl, and substituted monocyclic heteroaryl. In a still further aspect, each phenyl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a yet further aspect, each phenyl can be substituted with 0-3 groups independently selected from —F, —Cl, —NH$_2$, —OH, —CN, —CH$_3$, —CF$_3$, —CHF$_2$, —CH$_2$F, and —OCH$_3$. In an even further aspect, each monocyclic heteroaryl can be substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, each monocyclic heteroaryl can be substituted with 0-3 groups independently selected from —F, —Cl, —NH$_2$, —OH, —CN, —CH$_3$, —CF$_3$, —CHF$_2$, —CH$_2$F, and —OCH$_3$. In various further aspects, each monocyclic heteroaryl is independently selected from pyridine, pyrimidine, and pyradazine, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, each monocyclic heteroaryl is independently selected from pyridine, pyrimidine, and pyradazine, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{66}$, when present, is independently selected from hydrogen, C1-C8 alkyl, C3-C9 cycloalkyl, and C2-C7 heterocycloalkyl. In a further aspect, the C3-C9 cycloalkyl is substituted with 0-3 groups selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is substituted with 0-3 groups selected from —F, —Cl, —NH$_2$, —OH, —CN, —CH$_3$, —CF$_3$, —CHF$_2$, —CH$_2$F, and —OCH$_3$. In a further aspect, the C2-C7 heterocycloalkyl is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C2-C7 heterocycloalkyl is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl. In a further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a still further aspect, the C3-C9 cycloalkyl is selected from cyclopropyl, cyclobutyl, cyclopentyl, cyclohexyl, cycloheptyl, norbornyl, bicyclo[1.1.1]pentanyl, and adamantanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In various further aspects, the C2-C7 heterocycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from halogen, —NH$_2$, —OH, —CN, C1-C6 alkyl, C1-C6 monohaloalkyl, C1-C6 polyhaloalkyl, and C1-C6 alkoxy. In a further aspect, the C3-C9 cycloalkyl is selected from azetidinyl, pyrrolidinyl, piperidinyl, azepanyl, diazetidinyl, imidazolidinyl, pyrazolidinyl, piperazinyl, 2,5-diazabicyclo[2.2.1]heptanyl, hexahydropyrrolo[3,4-c]pyrrolyl, and 2,6-diazaspiro[3.3]heptanyl, and is substituted with 0-3 groups independently selected from —F, —Cl, —NH$_2$, —OH, —CN, —CH$_3$, —CF$_3$, —CHF$_2$, —CH$_2$F, and —OCH$_3$.

In a further aspect, each $R^{66}$, when present, is independently selected from hydrogen, C1-C8 alkyl, C1-C8 hydroxyalkyl, C1-C8 monohaloalkyl, and C1-C8 polyhaloalkyl. In a still further aspect, each $R^{66}$, when present, is independently selected from hydrogen, C1-C6 alkyl, C1-C6 hydroxyalkyl, C1-C6 monohaloalkyl, and C1-C6 polyhaloalkyl. In a yet further aspect, each $R^{66}$, when present, is independently selected from hydrogen, C1-C3 alkyl, C1-C3 hydroxyalkyl, C1-C3 monohaloalkyl, and C1-C8 polyhaloalkyl.

In a further aspect, each $R^{66}$, when present, is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, 1-hydroxyethyl, 2-hydroxyethyl, 1-hydroxypropyl, 2-hydroxypropyl, 3 hydroxypropyl, 1-hydroxybutyl, 2-hydroxybutyl, 3-hydroxybutyl, and 4-hydroxybutyl.

bb. $Ar^1$ Groups

In one aspect, each $Ar^1$, when present, is independently selected from phenyl, naphthyl, and heteroaryl, and wherein each $Ar^1$ is independently substituted with 0, 1, 2, or 3 groups independently selected from halogen, —$NH_2$, —OH, —CN, —$N_3$, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-$NR^{51}R^{52}$, —(C1-C6 alkyl)-$NR^{50}(C=O)R^{55}$, —(C1-C6 alkyl)-$NR^{50}(C=O)OR^{55}$, —(C1-C6 alkyl)-$NR^{50}(C=O)R^{55}$, —(C1-C6 alkyl)-$NR^{50}S(O)_mR^{55}$, —$NR^{50}$(C1-C6 alkyl)-(C=O)$R^{55}$, —$NR^{50}$(C1-C6 alkyl)-(C=O)$OR^{55}$, —$NR^{50}$(C1-C6 alkyl)-(C=O)$R^{55}$, —$NR^{50}$(C1-C6 alkyl)-S(O)$_mR^{55}$, —$NR^{50}$(C1-C6 alkyl)-S(O)$_mNR^{53}R^{54}$, —$NR^{50}$(C=O)$R^{55}$, —$NR^{50}$(C=O)$OR^{55}$, —$NR^{50}$(C=O)$R^{55}$, —$NR^{50}S(O)_mR^{55}$, —(C1-C6 alkyl)-(C=O)$R^{55}$, —(C1-C6 alkyl)-(C=O)$OR^{55}$, —(C1-C6 alkyl)-(C=O)$R^{55}$, —(C1-C6 alkyl)-S(O)$_mR^{55}$, —(C1-C6 alkyl)-S(O)$_mNR^{53}R^{54}$, —(C=O)$R^{55}$, —(C=O)$OR^{55}$, —S(O)$_mR^{55}$, —S(O)$_mNR^{53}R^{54}$, —(C1-C8 alkyl)-$Ar^{20}$, $Ar^{20}$, —(C1-C8 alkyl)-$Cy^{20}$, $Cy^{20}$, and $R^{57}$.

In one aspect, each $Ar^1$, when present, is independently selected from phenyl and heteroaryl, and wherein each $Ar^1$ is independently substituted with 0, 1, 2, or 3 groups independently selected from halogen, —$NH_2$, —OH, —CN, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)$R^5$, —(C1-C6 alkyl)-(C=O)$OR^5$, —(C1-C6 alkyl)-S(O)$_mR^5$, —(C=O)$R^5$, —(C=O)$OR^5$, —S(O)$_mR^5$, $R^6$, and $Ar^2$; and wherein two of the groups are optionally covalently bonded, and together with the intermediate atoms, comprise an optionally substituted 3- to 6-membered fused ring group.

In various further aspects, each $Ar^1$, when present, is independently substituted with 0, 1, or 2 groups. In a still further aspect, each $Ar^1$, when present, is independently substituted with 1, 2, or 3 groups. In a yet further aspect, each $Ar^1$, when present, is independently substituted with 0 or 1 groups. In an even further aspect, each $Ar^1$, when present, is independently substituted with 0 or 2 groups. In a still further aspect, each $Ar^1$, when present, is independently substituted with 0 or 3 groups. In a yet further aspect, each $Ar^1$, when present, is independently substituted with 2 or 3 groups. In an even further aspect, each $Ar^1$, when present, is independently substituted with 1 or 3 groups. In a still further aspect, each $Ar^1$, when present, is independently substituted with 2 or 3 groups. In a yet further aspect, each $Ar^1$, when present, is independently monosubstituted. In an even further aspect, each $Ar^1$, when present, is independently substituted with two groups. In a still further aspect, each $Ar^1$, when present, is independently substituted with three groups.

In a further aspect, each $Ar^1$, when present, is independently selected from phenyl and heteroaryl, and wherein $Ar^1$ is unsubstituted. In a yet further aspect, each $Ar^1$, when present, is independently selected from phenyl, pyridinyl, pyrimidinyl, pyridazinyl, and pyrazinyl, and wherein $Ar^1$ is unsubstituted.

In a further aspect, each $Ar^1$, when present, is independently selected from phenyl, pyridinyl, pyrimidinyl, pyridazinyl, and pyrazinyl.

In a further aspect, each $Ar^1$, when present, is independently selected from pyridinyl, pyrimidinyl, and pyrazinyl. In a further aspect, each $Ar^1$, when present, is independently selected from pyridinyl, pyrimidinyl, pyridazinyl, and pyrazinyl, and wherein $Ar^1$ is unsubstituted.

In various further aspects, each $Ar^1$, when present, is phenyl. In an even further aspect, each $Ar^1$ is unsubstituted phenyl.

In a further aspect, each $Ar^1$, when present, is independently selected from phenyl and heteroaryl, and each $Ar^1$ is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, $Ar^2$, —$(CH_2)_3$—(C=O)$R^5$, —$(CH_2)_2$—(C=O)$R^5$, —$CH_2$—(C=O)$R^5$, —$(CH_2)_3$—(C=O)$OR^5$, —$(CH_2)_2$—(C=O)$OR^5$, —$CH_2$—(C=O)$OR^5$, —$(CH_2)_3$—S—$R^5$, —$(CH_2)_2$—S—$R^5$, —$CH_2$—S—$R^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —(C=O)$R^5$, —(C=O)$OR^5$, —S—$R^5$, —(S=O)$R^5$, —$SO_2R^5$, and $R^6$. In a still further aspect, each $Ar^1$, when present, is independently selected from phenyl and heteroaryl, and each $Ar^1$ is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, $Ar^2$, —$(CH_2)_2$—(C=O)$R^5$, —$CH_2$—(C=O)$R^5$, —$(CH_2)_2$—(C=O)$OR^5$, —$CH_2$—(C=O)$OR^5$, —$(CH_2)_2$—S—$R^5$, —$CH_2$—S—$R^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)$OR^5$, —S—$R^5$, —(S=O)$R^5$, —$SO_2R^5$, and $R^6$. In a yet further aspect, each $Ar^1$, when present, is independently selected from phenyl and heteroaryl, and each $Ar^1$ is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, $Ar^2$, —$CH_2$—(C=O)$R^5$, —$CH_2$—(C=O)$OR^5$, —$CH_2$—S—$R^5$, —$CH_2$—(S=O)$R^5$, —$CH_2$—$SO_2R^5$, —(C=O)$R^5$, —(C=O)$OR^5$, —S—$R^5$, —(S=O)$R^5$, —$SO_2R^5$, and $R^6$.

In a further aspect, each $Ar^1$, when present, is independently selected from phenyl and heteroaryl, and each $Ar^1$ is independently substituted with 0, 1, 2, or 3 groups independently selected from —F, —Cl, —$NH_2$, —OH, —CN, —$SF_5$, C1-C8 alkyl, C1-C8 monohaloalkyl, C1-C8 polyhaloalkyl, C1-C8 alkoxy, C1-C8 alkylamino, C1-C8 dialkylamino, $Ar^2$, —$CH_2$—(C=O)$R^5$, —$CH_2$—(C=O)$OR^5$, —$CH_2$—S—$R^5$, —$CH_2$—(S=O)$R^5$, —$CH_2$—$SO_2R^5$, —(C=O)$R^5$, —(C=O)$OR^5$, —S—$R^5$, —(S=O)$R^5$, —$SO_2R^5$, and $R^6$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a still further aspect, each $Ar^1$, when present, is independently selected from phenyl and heteroaryl, and each $Ar^1$ is independently substituted with 0, 1, 2, or 3 groups independently selected from —F, —Cl, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, $Ar^2$, —$CH_2$—(C=O)$R^5$, —$CH_2$—(C=O)$OR^5$, —$CH_2$—S—$R^5$, —$CH_2$—(S=O)$R^5$, —$CH_2$—$SO_2R^5$, —(C=O)$R^5$, —(C=O)$OR^5$, —S—$R^5$, —(S=O)$R^5$, —$SO_2R^5$, and $R^6$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a yet further aspect, each $Ar^1$, when present, is independently selected from phenyl and heteroaryl, and each $Ar^1$ is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, $Ar^2$, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$; and wherein $Ar^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, each $Ar^1$, when present, is independently selected from phenyl and heteroaryl, and each $Ar^1$ is independently substituted with 0, 1, 2, or 3 groups independently selected from —F, —Cl, —NH$_2$, —OH, —CN, —SF$_5$, methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(CH$_2$)$_3$—(C=O)CH$_3$, —(CH$_2$)$_2$—(C=O)CH$_3$, —CH$_2$—(C=O)CH$_3$, —(CH$_2$)$_3$—(C=O)OCH$_3$, —(CH$_2$)$_2$—(C=O)OCH$_3$, —CH$_2$—(C=O)OCH$_3$, —(CH$_2$)$_3$—S—CH$_3$, —(CH$_2$)$_2$—S—CH$_3$, —CH$_2$—S—CH$_3$, —(CH$_2$)$_3$—(S=O)CH$_3$, —(CH$_2$)$_2$—(S=O)CH$_3$, —CH$_2$—(S=O)CH$_3$, —(CH$_2$)$_3$—SO$_2$CH$_3$, —(CH$_2$)$_2$—SO$_2$CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, each $Ar^1$, when present, is independently selected from phenyl and heteroaryl, and each $Ar^1$ is independently substituted with 0, 1, 2, or 3 groups independently selected from —F, —Cl, —NH$_2$, —OH, —CN, —SF$_5$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_2$CH$_3$)$_2$, —(CH$_2$)$_2$—(C=O)CH$_3$, —CH$_2$—(C=O)CH$_3$, —(CH$_2$)$_2$—(C=O)OCH$_3$, —CH$_2$—(C=O)OCH$_3$, —(CH$_2$)$_2$—S—CH$_3$, —CH$_2$—S—CH$_3$, —(CH$_2$)$_2$—(S=O)CH$_3$, —CH$_2$—(S=O)CH$_3$, —(CH$_2$)$_2$—SO$_2$CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a yet further aspect, each $Ar^1$, when present, is independently selected from phenyl and heteroaryl, and each $Ar^1$ is independently substituted with 0, 1, 2, or 3 groups independently selected from —F, —Cl, —NH$_2$, —OH, —CN, —SF$_5$, methyl, ethyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —CH$_2$—(C=O)CH$_3$, —CH$_2$—(C=O)OCH$_3$, —CH$_2$—S—CH$_3$, —CH$_2$—(S=O)CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In an even further aspect, each $Ar^1$, when present, is independently selected from phenyl and heteroaryl, and each $Ar^1$ is independently substituted with 0, 1, 2, or 3 groups independently selected from —F, —NH$_2$, —OH, —CN, —SF$_5$, methyl, —CH$_2$F, —CHF$_2$, —CF$_3$, —OCH$_3$, —NHCH$_3$, —N(CH$_3$)$_2$, —(CH$_2$)—(C=O)CH$_3$, —(CH$_2$)—(C=O)OCH$_3$, —(CH$_2$)—S—CH$_3$, —(CH$_2$)—(S=O)CH$_3$, —(CH$_2$)—SO$_2$CH$_3$, —(C=O)CH$_3$, —(C=O)OCH$_3$, —S—CH$_3$, —(S=O)CH$_3$, —SO$_2$CH$_3$, —C(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In various aspects, each $Ar^1$, when present, is independently selected from phenyl and heteroaryl, and independently substituted with 0, 1, 2, or 3 groups independently selected from halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, and R$^6$. In a further aspect, each $Ar^1$, when present, is independently selected from phenyl and heteroaryl, and each $Ar^1$ is independently substituted with 0, 1, 2, or 3 groups independently selected from halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, and R$^6$. In a still further aspect, each $Ar^1$, when present, is independently selected from phenyl and heteroaryl, and each $Ar^1$ is independently substituted with 0, 1, 2, or 3 groups independently selected from halogen, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, and R$^6$.

In a further aspect, each $Ar^1$, when present, is independently selected from phenyl and heteroaryl, and each $Ar^1$ is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_2$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a still further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a yet further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$.

In a further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(CH$_2$)$_3$—(C=O)CH$_3$, —(CH$_2$)$_2$—(C=O)CH$_3$, —CH$_2$—(C=O)CH$_3$, —(CH$_2$)$_3$—(C=O)OCH$_3$, —(CH$_2$)$_2$—(C=O)OCH$_3$, —CH$_2$—(C=O)OCH$_3$, —(CH$_2$)$_3$—S—CH$_3$, —(CH$_2$)$_2$—S—CH$_3$, —CH$_2$—S—CH$_3$, —(CH$_2$)$_3$—(S=O)CH$_3$, —(CH$_2$)$_2$—(S=O)CH$_3$, —CH$_2$—(S=O)CH$_3$, —(CH$_2$)$_3$—SO$_2$CH$_3$, —(CH$_2$)$_2$—SO$_2$CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_2$CH$_3$)$_2$, —(CH$_2$)$_2$—(C=O)CH$_3$, —CH$_2$—(C=O)CH$_3$, —(CH$_2$)$_2$—(C=O)OCH$_3$, —CH$_2$—(C=O)OCH$_3$, —(CH$_2$)$_2$—S—CH$_3$, —CH$_2$—S—CH$_3$, —(CH$_2$)$_2$—(S=O)CH$_3$, —CH$_2$—(S=O)CH$_3$, —(CH$_2$)$_2$—SO$_2$CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$ In a yet further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, methyl, ethyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —CH$_2$—(C=O)CH$_3$, —CH$_2$—(C=O)OCH$_3$, —CH$_2$—S—CH$_3$, —CH$_2$—(S=O)CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In an even further aspect, each Ar$^1$, when present, is independently selected from phenyl and heteroaryl, and each Ar$^1$ is independently substituted with 0, 1, 2, or 3 groups independently selected from —F, —NH$_2$, —OH, —CN, —SF$_5$, methyl, —CH$_2$F, —CHF$_2$, —CF$_3$, —OCH$_3$, —NHCH$_3$, —N(CH$_3$)$_2$, —(CH$_2$)—(C=O)CH$_3$, —(CH$_2$)—(C=O)OCH$_3$, —(CH$_2$)—(S=O)CH$_3$, —(CH$_2$)—SO$_2$CH$_3$, —(C=O)CH$_3$, —(C=O)OCH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$, and phenyl.

In various aspects, each Ar$^1$, when present, is independently selected from phenyl and heteroaryl, and each Ar$^1$ is independently substituted with 0, 1, 2, or 3 groups independently selected from halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, and C1-C8 dialkylamino, —(C1-C6 alkyl)-S(O)$_m$R$^5$, —S(O)$_m$R$^5$, and R$^6$. In a further aspect, each Ar$^1$, when present, is independently selected from phenyl and heteroaryl, and each Ar$^1$ is independently substituted with 0, 1, 2, or 3 groups independently selected from halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-S—R$^5$, —(C1-C3 alkyl)-(S=O)R$^5$, —(C1-C3 alkyl)-SO$_2$R$^5$, —S—R$^5$, —(S=O)R$^5$, —SO$_2$R$^5$, and R$^6$. In a still further aspect, each Ar$^1$, when present, is independently selected from phenyl and heteroaryl, and each Ar$^1$ is independently substituted with 0, 1, 2, or 3 groups independently selected from halogen, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-S—R$^5$, —(C1-C3 alkyl)-(S=O)R$^5$, —(C1-C3 alkyl)-SO$_2$R$^5$, —S—R$^5$, —(S=O)R$^5$, —SO$_2$R$^5$, and R$^6$.

In a further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —S—R$^5$, —(S=O)R$^5$, —SO$_2$R$^5$, and R$^6$. In a still further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —S—R$^5$, —(S=O)R$^5$, —SO$_2$R$^5$, and R$^6$. In a yet further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, —CH$_2$—S—R$^5$, —CH$_2$—(S=O)R$^5$, —CH$_2$—SO$_2$R$^5$, —S—R$^5$, —(S=O)R$^5$, —SO$_2$R$^5$, and R$^6$.

In a further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(CH$_2$)$_3$—S—CH$_3$, —(CH$_2$)$_2$—S—CH$_3$, —CH$_2$—S—CH$_3$, —(CH$_2$)$_3$—(S=O)CH$_3$, —(CH$_2$)$_2$—(S=O)CH$_3$, —CH$_2$—(S=O)CH$_3$, —(CH$_2$)$_3$—SO$_2$CH$_3$, —(CH$_2$)$_2$—SO$_2$CH$_3$, —CH$_2$—SO$_2$CH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In a still further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_2$CH$_3$)$_2$, —(CH$_2$)$_2$—S—CH$_3$, —CH$_2$—S—CH$_3$, —(CH$_2$)$_2$—(S=O)CH$_3$, —CH$_2$—(S=O)CH$_3$, —(CH$_2$)$_2$—SO$_2$CH$_3$, —CH$_2$—SO$_2$CH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$ In a yet further aspect, each Ar$^1$, when present, is independently selected from phenyl and heteroaryl, and each Ar$^1$ is independently substituted with 0, 1, 2, or 3 groups independently selected from —F, —Cl, —NH$_2$, —OH, —CN, —SF$_5$, methyl, ethyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —CH$_2$—S—CH$_3$, —CH$_2$—(S=O)CH$_3$, —CH$_2$—SO$_2$CH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$. In an even further aspect, each Ar$^1$, when present, is independently selected from phenyl and heteroaryl, and each Ar$^1$ is independently substituted with 0, 1, 2, or 3 groups independently selected from —F, —NH$_2$, —OH, —CN, —SF$_5$, methyl, —CH$_2$F, —CHF$_2$, —CF$_3$, —OCH$_3$, —NHCH$_3$, —N(CH$_3$)$_2$, —CH$_2$—(S=O)CH$_3$, —CH$_2$—SO$_2$CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, and —C(CN)(NH$_2$)CH$_3$.

In various aspects, each Ar$^1$, when present, is phenyl, and each phenyl is independently substituted with 0, 1, 2, or 3 groups independently selected from halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, Ar$^2$, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, and R$^6$. In a further aspect, each Ar$^1$, when present, is phenyl, and each phenyl is independently substituted with 0, 1, 2, or 3 groups independently selected from halogen, —NH$_2$, —OH, —CN, —SF$_5$, C1-C6 alkyl, C1-C6 monohaloalkyl, C1-C6 polyhaloalkyl, C1-C6 alkoxy, C1-C6 alkylamino, C1-C6 dialkylamino, Ar$^2$, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, and R$^6$. In a still further aspect, each Ar$^1$, when present, is phenyl, and each phenyl is independently substituted with 0, 1, 2, or 3 groups independently selected from halogen, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, Ar$^2$, —(C1-C3 alkyl)-(C=O)R$^5$, —(C1-C3 alkyl)-(C=O)OR$^5$, —(C1-C3 alkyl)-S—R$^5$, —(C1-C3 alkyl)-(S=O)R$^5$, —(C1-C3 alkyl)-SO$_2$R$^5$, —(C=O)R$^5$, —(C=O)OR$^5$, —S—R$^5$, —(S=O)R$^5$, —SO$_2$R$^5$, and R$^6$.

In a further aspect, each Ar$^1$, when present, is phenyl, and each phenyl is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, Ar$^2$, —(CH$_2$)$_3$—(C=O)R$^5$, —(CH$_2$)$_2$—(C=O)R$^5$, —CH$_2$—(C=O)R$^5$, —(CH$_2$)$_3$—(C=O)OR$^5$, —(CH$_2$)$_2$—(C=O)OR$^5$, —CH$_2$—(C=O)OR$^5$, —(CH$_2$)$_3$—S—R$^5$, —(CH$_2$)$_2$—S—R$^5$, —CH$_2$—S—R$^5$, —(CH$_2$)$_3$—(S=O)R$^5$, —(CH$_2$)$_2$—(S=O)R$^5$, —CH$_2$—(S=O)R$^5$, —(CH$_2$)$_3$—SO$_2$R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a still further aspect, each Ar$^1$, when present, is phenyl, and each phenyl is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, Ar$^2$, —(CH$_2$)$_2$—(C=O)R$^5$, —CH$_2$—(C=O)R$^5$, —(CH$_2$)$_2$—(C=O)OR$^5$, —CH$_2$—(C=O)OR$^5$, —(CH$_2$)$_2$—S—R$^5$, —CH$_2$—S—R$^5$, —(CH$_2$)$_2$—(S=O)R$^5$, —CH$_2$—(S=O)R$^5$, —(CH$_2$)$_2$—SO$_2$R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$. In a yet further aspect, each Ar$^1$, when present, is phenyl, and each phenyl is independently substituted with 0, 1, 2, or 3 groups independently selected from —F, —Cl, —NH$_2$, —OH, —CN, —SF$_5$, C1-C3 alkyl, C1-C3 monohaloalkyl, C1-C3 polyhaloalkyl, C1-C3 alkoxy, C1-C3 alkylamino, C1-C3 dialkylamino, Ar$^2$, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$.

In a further aspect, each Ar$^1$, when present, is phenyl, and each phenyl is independently substituted with 0, 1, 2, or 3 groups independently selected from —F, —Cl, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, Ar$^2$, —CH$_2$—(C=O)R$^5$, —CH$_2$—(C=O)OR$^5$, —CH$_2$—S—R$^5$, —CH$_2$—(S=O)R$^5$, —CH$_2$—

$SO_2R^5$, —(C=O)$R^5$, —(C=O)O$R^5$, —S—$R^5$, —(S=O)$R^5$, —$SO_2R^5$, and $R^6$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a still further aspect, each $Ar^1$, when present, is phenyl, and each phenyl is independently substituted with 0, 1, 2, or 3 groups independently selected from —F, —Cl, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, $Ar^2$, —$CH_2$—(C=O)$R^5$, —$CH_2$—(C=O)O$R^5$, —$CH_2$—S—$R^5$, —$CH_2$—(S=O)$R^5$, —$CH_2$—$SO_2R^5$, —(C=O)$R^5$, —(C=O)O$R^5$, —S—$R^5$, —(S=O)$R^5$, —$SO_2R^5$, and $R^6$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a yet further aspect, each $Ar^1$, when present, is phenyl, and each phenyl is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, $Ar^2$, —$CH_2$—(C=O)$R^5$, —$CH_2$—(C=O)O$R^5$, —$CH_2$—S—$R^5$, —$CH_2$—(S=O)$R^5$, —$CH_2$—$SO_2R^5$, —(C=O)$R^5$, —(C=O)O$R^5$, —S—$R^5$, —(S=O)$R^5$, —$SO_2R^5$, and $R^6$; and wherein $Ar^2$, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$.

In a further aspect, each $Ar^1$, when present, is phenyl, and each phenyl is independently substituted with 0, 1, 2, or 3 groups independently selected from —F, —Cl, —$NH_2$, —OH, —CN, —$SF_5$, methyl, ethyl, propyl, isopropyl, tert-butyl, sec-butyl, isobutyl, tert-butyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$OCH(CH_2CH_3)(CH_3)$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$(CH_2)_3$—(C=O)$CH_3$, —$(CH_2)_2$—(C=O)$CH_3$, —$CH_2$—(C=O)$CH_3$, —$(CH_2)_3$—(C=O)O$CH_3$, —$(CH_2)_2$—(C=O)O$CH_3$, —$CH_2$—(C=O)O$CH_3$, —$(CH_2)_3$—S—$CH_3$, —$(CH_2)_2$—S—$CH_3$, —$CH_2$—S—$CH_3$, —$(CH_2)_3$—(S=O)$CH_3$, —$(CH_2)_2$—(S=O)$CH_3$, —$CH_2$—(S=O)$CH_3$, —$(CH_2)_3$—$SO_2CH_3$, —$(CH_2)_2$—$SO_2CH_3$, —$CH_2$—$SO_2CH_3$, —(C=O)$CH_3$, —(C=O)O$CH_3$, —S—$CH_3$, —(S=O)$CH_3$, —$SO_2CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, —$C(CN)(NH_2)CH_3$, and phenyl; and wherein phenyl, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a still further aspect, each $Ar^1$, when present, is phenyl, and each phenyl is independently substituted with 0, 1, 2, or 3 groups independently selected from —F, —Cl, —$NH_2$, —OH, —CN, —$SF_5$, methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_2CH_3)_2$, —$(CH_2)_2$—(C=O)$CH_3$, —$CH_2$—(C=O)$CH_3$, —$(CH_2)_2$—(C=O)O$CH_3$, —$CH_2$—(C=O)O$CH_3$, —$(CH_2)_2$—S—$CH_3$, —$CH_2$—S—$CH_3$, —$(CH_2)_2$—(S=O)$CH_3$, —$CH_2$—(S=O)$CH_3$, —$(CH_2)_2$—$SO_2CH_3$, —$CH_2$—$SO_2CH_3$, —(C=O)$CH_3$, —(C=O)O$CH_3$, —S—$CH_3$, —(S=O)$CH_3$, —$SO_2CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, —$C(CN)(NH_2)CH_3$, and phenyl; and wherein phenyl, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In a yet further aspect, each $Ar^1$, when present, is phenyl, and each phenyl is independently substituted with 0, 1, 2, or 3 groups independently selected from —F, —Cl, —$NH_2$, —OH, —CN, —$SF_5$, methyl, ethyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$CH_2$—(C=O)$CH_3$, —$CH_2$—(C=O)O$CH_3$, —$CH_2$—S—$CH_3$, —$CH_2$—(S=O)$CH_3$, —$CH_2$—$SO_2CH_3$, —(C=O)$CH_3$, —(C=O)O$CH_3$, —S—$CH_3$, —(S=O)$CH_3$, —$SO_2CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, —$C(CN)(NH_2)CH_3$, and phenyl; and wherein phenyl, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$. In an even further aspect, each $Ar^1$, when present, is phenyl, and each phenyl is independently substituted with 0, 1, 2, or 3 groups independently selected from —F, —$NH_2$, —OH, —CN, —$SF_5$, methyl, —$CH_2F$, —$CHF_2$, —$CF_3$, —$OCH_3$, —$NHCH_3$, —$N(CH_3)_2$, —$(CH_2)$—(C=O)$CH_3$, —$(CH_2)$—(C=O)O$CH_3$, —$(CH_2)$—S—$CH_3$, —$(CH_2)$—(S=O)$CH_3$, —$(CH_2)$—$SO_2CH_3$, —(C=O)$CH_3$, —(C=O)O$CH_3$, —S—$CH_3$, —(S=O)$CH_3$, —$SO_2CH_3$, —$CF(CF_3)CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, —$C(CN)(NH_2)CH_3$, and phenyl; and wherein phenyl, when present, is substituted with 0, 1, 2, or 3 groups selected from —F, —Cl, —Br, —$NH_2$, —OH, —CN, methyl, $CH_2F$, —$CH_2Cl$, —$CHF_2$, —$CF_3$, —$CHCl_2$, —$CCl_3$, —$OCH_3$, —$OCH_2CH_3$, —$NHCH_3$, —$N(CH_3)_2$, —$SCH_3$, —$SOCH_3$, and —$SO_2CH_3$.

In various aspects, each $Ar^1$, when present, is phenyl, and each phenyl is independently substituted with 0, 1, 2, or 3 groups independently selected from halogen, —$NH_2$, —OH, —CN, —$SF_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)$R^5$, —(C1-C6 alkyl)-(C=O)O$R^5$, —(C1-C6 alkyl)-S(O)$_m$$R^5$, —(C=O)$R^5$, —(C=O)O$R^5$, —S(O)$_m$$R^5$, and $R^6$. In a further aspect, each $Ar^1$, when present, is phenyl, and each phenyl is independently substituted with 0, 1, 2, or 3 groups independently selected from halogen, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)$R^5$, —(C1-C3 alkyl)-(C=O)O$R^5$, —(C1-C3 alkyl)-S—$R^5$, —(C1-C3 alkyl)-(S=O)$R^5$, —(C1-C3 alkyl)-$SO_2R^5$, —(C=O)$R^5$, —(C=O)O$R^5$, —S—$R^5$, —(S=O)

$R^5$, —$SO_2R^5$, and $R^6$. In a still further aspect, each $Ar^1$, when present, is phenyl, and each phenyl is independently substituted with 0, 1, 2, or 3 groups independently selected from halogen, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(C=O)$R^5$, —(C1-C3 alkyl)-(C=O)O$R^5$, —(C1-C3 alkyl)-S—$R^5$, —(C1-C3 alkyl)-(S=O)$R^5$, —(C1-C3 alkyl)-$SO_2R^5$, —(C=O)$R^5$, —(C=O)O$R^5$, —S—$R^5$, —(S=O)$R^5$, —$SO_2R^5$, and $R^6$.

In a further aspect, each $Ar^1$, when present, is phenyl, and each phenyl is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$(CH_2)_3$—(C=O)$R^5$, —$(CH_2)_2$—(C=O)$R^5$, —$CH_2$—(C=O)$R^5$, —$(CH_2)_3$—(C=O)O$R^5$, —$(CH_2)_2$—(C=O)O$R^5$, —$CH_2$—(C=O)O$R^5$, —$(CH_2)_3$—S—$R^5$, —$(CH_2)_2$—S—$R^5$, —$CH_2$—S—$R^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —(C=O)$R^5$, —(C=O)O$R^5$, —S—$R^5$, —(S=O)$R^5$, —$SO_2R^5$, and $R^6$. In a still further aspect, each $Ar^1$, when present, is phenyl, and each phenyl is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$(CH_2)_2$—(C=O)$R^5$, —$CH_2$—(C=O)$R^5$, —$(CH_2)_2$—(C=O)O$R^5$, —$CH_2$—(C=O)O$R^5$, —$(CH_2)_2$—S—$R^5$, —$CH_2$—S—$R^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)O$R^5$, —S—$R^5$, —(S=O)$R^5$, —$SO_2R^5$, and $R^6$. In a yet further aspect, each $Ar^1$, when present, is phenyl, and each phenyl is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)O$R^5$, —$CH_2$—S—$R^5$, —$CH_2$—(S=O)$R^5$, —$CH_2$—$SO_2R^5$, —(C=O)$R^5$, —(C=O)O$R^5$, —S—$R^5$, —(S=O)$R^5$, —$SO_2R^5$, and $R^6$.

In a further aspect, each $Ar^1$, when present, is phenyl, and each phenyl is independently substituted with 0, 1, 2, or 3 groups independently selected from —F, —Cl, —$NH_2$, —OH, —CN, —$SF_5$, methyl, ethyl, propyl, isopropyl, tert-butyl, sec-butyl, isobutyl, tert-butyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$OCH(CH_2CH_3)(CH_3)$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$(CH_2)_3$—(C=O)$CH_3$, —$(CH_2)_2$—(C=O)$CH_3$, —$CH_2$—(C=O)$CH_3$, —$(CH_2)_3$—(C=O)$OCH_3$, —$(CH_2)_2$—(C=O)$OCH_3$, —$CH_2$—(C=O)$OCH_3$, —$(CH_2)_3$—S—$CH_3$, —$(CH_2)_2$—S—$CH_3$, —$CH_2$—S—$CH_3$, —$(CH_2)_3$—(S=O)$CH_3$, —$(CH_2)_2$—(S=O)$CH_3$, —$CH_2$—(S=O)$CH_3$, —$(CH_2)_3$—$SO_2CH_3$, —$(CH_2)_2$—$SO_2CH_3$, —$CH_2$—$SO_2CH_3$, —(C=O)$CH_3$, —(C=O)$OCH_3$, —S—$CH_3$, —(S=O)$CH_3$, —$SO_2CH_3$, —C(OH)($CF_3$)$CH_3$, —C($CF_3$)($NH_2$)$CH_3$, —C($CF_3$)($CN$)$CH_3$, —C($CF_3$)$_2CH_3$, —CF(OH)$CH_3$, —CF($NH_2$)$CH_3$, —CF($CN$)$CH_3$, —C(OH)($NH_2$)$CH_3$, —C(OH)($CN$)$CH_3$, and —C($CN$)($NH_2$)$CH_3$. In a still further aspect, each $Ar^1$, when present, is phenyl, and each phenyl is independently substituted with 0, 1, 2, or 3 groups independently selected from —F, —Cl, —$NH_2$, —OH, —CN, —$SF_5$, methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_2CH_3)_2$, —$(CH_2)_2$—(C=O)$CH_3$, —$CH_2$—(C=O)$CH_3$, —$(CH_2)_2$—(C=O)$OCH_3$, —$CH_2$—(C=O)$OCH_3$, —$(CH_2)_2$—S—$CH_3$, —$CH_2$—S—$CH_3$, —$(CH_2)_2$—(S=O)$CH_3$, —$CH_2$—(S=C)$CH_3$, —$(CH_2)_2$—$SO_2CH_3$, —$CH_2$—$SO_2CH_3$, —(C=O)$CH_3$, —(C=O)$OCH_3$, —S—$CH_3$, —(S=O)$CH_3$, —$SO_2CH_3$, —C(OH)($CF_3$)$CH_3$, —C($CF_3$)($NH_2$)$CH_3$, —C($CF_3$)($CN$)$CH_3$, —C($CF_3$)$_2CH_3$, —CF(OH)$CH_3$, —CF($NH_2$)$CH_3$, —CF($CN$)$CH_3$, —C(OH)($NH_2$)$CH_3$, —C(OH)($CN$)$CH_3$, and —C($CN$)($NH_2$)$CH_3$ In a yet further aspect, each $Ar^1$, when present, is phenyl, and each phenyl is independently substituted with 0, 1, 2, or 3 groups independently selected from —F, —Cl, —$NH_2$, —OH, —CN, —$SF_5$, methyl, ethyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$CH_2$—(C=O)$CH_3$, —$CH_2$—(C=O)$OCH_3$, —$CH_2$—S—$CH_3$, —$CH_2$—(S=O)$CH_3$, —$CH_2$—$SO_2CH_3$, —(C=O)$CH_3$, —(C=O)$OCH_3$, —S—$CH_3$, —(S=O)$CH_3$, —$SO_2CH_3$, —C(OH)($CF_3$)$CH_3$, —C($CF_3$)($NH_2$)$CH_3$, —C($CF_3$)($CN$)$CH_3$, —C($CF_3$)$_2CH_3$, —CF(OH)$CH_3$, —CF($NH_2$)$CH_3$, —CF($CN$)$CH_3$, —C(OH)($NH_2$)$CH_3$, —C(OH)($CN$)$CH_3$, and —C($CN$)($NH_2$)$CH_3$. In an even further aspect, each $Ar^1$, when present, is phenyl, and each phenyl is independently substituted with 0, 1, 2, or 3 groups independently selected from —F, —$NH_2$, —OH, —CN, —$SF_5$, methyl, —$CH_2F$, —$CHF_2$, —$CF_3$, —$OCH_3$, —$NHCH_3$, —$N(CH_3)_2$, —$(CH_2)$—(C=O)$CH_3$, —$(CH_2)$—(C=O)$OCH_3$, —$(CH_2)$—(S=O)$CH_3$, —$(CH_2)$—$SO_2CH_3$, —(C=O)$CH_3$, —(C=O)$OCH_3$, —(S=O)$CH_3$, —$SO_2CH_3$, —CF($CF_3$)$CH_3$, —C(OH)($CF_3$)$CH_3$, —C($CF_3$)($NH_2$)$CH_3$, —C($CF_3$)($CN$)$CH_3$, —C($CF_3$)$_2CH_3$, —CF(OH)$CH_3$, —CF($NH_2$)$CH_3$, —CF($CN$)$CH_3$, —C(OH)($NH_2$)$CH_3$, —C(OH)($CN$)$CH_3$, and —C($CN$)($NH_2$)$CH_3$, and phenyl.

In various aspects, each $Ar^1$, when present, is phenyl, and each phenyl is independently substituted with 0, 1, 2, or 3 groups independently selected from halogen, —$NH_2$, —OH, —CN, —$SF_5$, C1-C8 alkyl, C1-C8 monohaloalkyl, C1-C8 polyhaloalkyl, C1-C8 alkoxy, C1-C8 alkylamino, and C1-C8 dialkylamino, —(C1-C6 alkyl)-S(O)$_mR^5$, —S(O)$_mR^5$, and $R^6$. In a further aspect, each $Ar^1$, when present, is phenyl, and each phenyl is independently substituted with 0, 1, 2, or 3 groups independently selected from halogen, —$NH_2$, —OH, —CN, —$SF_5$, C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-S—$R^5$, —(C1-C3 alkyl)-(S=O)$R^5$, —(C1-C3 alkyl)-$SO_2R^5$, —S—$R^5$, —(S=O)$R^5$, —$SO_2R^5$, and $R^6$. In a still further aspect, each $Ar^1$, when present, is phenyl, and each phenyl is independently substituted with 0, 1, 2, or 3 groups independently selected from halogen, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-S—$R^5$, —(C1-C3 alkyl)-(S=O)$R^5$, —(C1-C3 alkyl)-$SO_2R^5$, —S—$R^5$, —(S=O)$R^5$, —$SO_2R^5$, and $R^6$.

In a further aspect, each $Ar^1$, when present, is phenyl, and each phenyl is independently substituted with 0, 1, 2, or 3 groups independently selected from —F, —Cl, —$NH_2$, —OH, —CN, —$SF_5$, C1-C3 alkyl, C1-C3 monohaloalkyl, C1-C3 polyhaloalkyl, C1-C3 alkoxy, C1-C3 alkylamino, C1-C3 dialkylamino, —$(CH_2)_3$—S—$R^5$, —$(CH_2)_2$—$R^5$, —$CH_2$—S—$R^5$, —$(CH_2)_3$—(S=O)$R^5$, —$(CH_2)_2$—

(S=O)R⁵, —CH₂—(S=O)R⁵, —(CH₂)₃—SO₂R⁵, —(CH₂)₂—SO₂R⁵, —CH₂—SO₂R⁵, —S—R⁵, —(S=O) R⁵, —SO₂R⁵, and R⁶. In a still further aspect, each Ar¹, when present, is phenyl, and each phenyl is independently substituted with 0, 1, 2, or 3 groups independently selected from —F, —Cl, —NH₂, —OH, —CN, —SF₅, C1-C3 alkyl, C1-C3 monohaloalkyl, C1-C3 polyhaloalkyl, C1-C3 alkoxy, C1-C3 alkylamino, C1-C3 dialkylamino, —(CH₂)₂—S—R⁵, —CH₂—S—R⁵, —(CH₂)₂—(S=O)R⁵, —CH₂—(S=O) R⁵, —(CH₂)₂—SO₂R⁵, —CH₂—SO₂R⁵, —S—R⁵, —(S=O)R⁵, —SO₂R⁵, and R⁶. In a yet further aspect, each Ar¹, when present, is phenyl, and each phenyl is independently substituted with 0, 1, 2, or 3 groups independently selected from —F, —Cl, —NH₂, —OH, —CN, —SF₅, C1-C3 alkyl, C1-C3 monohaloalkyl, C1-C3 polyhaloalkyl, C1-C3 alkoxy, C1-C3 alkylamino, C1-C3 dialkylamino, —CH₂—S—R⁵, —CH₂—(S=O)R⁵, —CH₂—SO₂R⁵, —S—R⁵, —(S=O)R⁵, —SO₂R⁵, and R⁶.

In a further aspect, each Ar¹, when present, is phenyl, and each phenyl is independently substituted with 0, 1, 2, or 3 groups independently selected from —F, —Cl, —NH₂, —OH, —CN, —SF₅, methyl, ethyl, propyl, isopropyl, tert-butyl, sec-butyl, isobutyl, tert-butyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —OCH(CH₂CH₃)(CH₃), —NHCH₃, —NHCH₂CH₃, —NH(CH₂)₂CH₃, —NHCH(CH₃)₂, —N(CH₃)₂, —N(CH₃)CH₂CH₃, —N(CH₃)(CH₂)₂CH₃, —N(CH₃)CH(CH₃)₂, —N(CH₂CH₃)₂, —(CH₂)₃—S—CH₃, —(CH₂)₂—S—CH₃, —CH₂—S—CH₃, —(CH₂)₃—(S=O)CH₃, —(CH₂)₂—(S=O)CH₃, —CH₂—(S=O)CH₃, —(CH₂)₃—SO₂CH₃, —(CH₂)₂—SO₂CH₃, —CH₂—SO₂CH₃, —S—CH₃, —(S=O)CH₃, —SO₂CH₃, —C(OH)(CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, and —C(CN)(NH₂)CH₃. In a still further aspect, each Ar¹, when present, is phenyl, and each phenyl is independently substituted with 0, 1, 2, or 3 groups independently selected from —F, —Cl, —NH₂, —OH, —CN, —SF₅, methyl, ethyl, propyl, isopropyl, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —OCH₃, —OCH₂CH₃, —NHCH₃, —NHCH₂CH₃, —NH(CH₂)₂CH₃, —NHCH(CH₃)₂, —N(CH₃)₂, —N(CH₃)CH₂CH₃, —N(CH₂CH₃)₂, —(CH₂)₂—S—CH₃, —CH₂—S—CH₃, —(CH₂)₂—(S=O)CH₃, —CH₂—(S=O)CH₃, —(CH₂)₂—SO₂CH₃, —CH₂—SO₂CH₃, —S—CH₃, —(S=O)CH₃, —SO₂CH₃, —C(OH) (CF₃)CH₃, —C(CF₃)(NH₂)CH₃, —C(CF₃)(CN)CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, and —C(CN)(NH₂)CH₃ In a yet further aspect, each Ar¹, when present, is phenyl, and each phenyl is independently substituted with 0, 1, 2, or 3 groups independently selected from —F, —Cl, —NH₂, —OH, —CN, —SF₅, methyl, ethyl, —CH₂F, —CH₂Cl, —CHF₂, —CF₃, —CHCl₂, —CCl₃, —OCH₃, —NHCH₃, —N(CH₃)₂, —CH₂—S—CH₃, —CH₂—(S=O)CH₃, —CH₂—SO₂CH₃, —S—CH₃, —(S=O)CH₃, —SO₂CH₃, —C(OH)(CF₃)CH₃, —C(CF₃) (NH₂)CH₃, —C(CF₃)(CN)CH₃, —C(CF₃)₂CH₃, —CF(OH) CH₃, —CF(NH₂)CH₃, —CF(CN)CH₃, —C(OH)(NH₂)CH₃, —C(OH)(CN)CH₃, and —C(CN)(NH₂)CH₃. In an even further aspect, each Ar¹, when present, is phenyl, and each phenyl is independently substituted with 0, 1, 2, or 3 groups independently selected from —F, —NH₂, —OH, —CN, —SF₅, methyl, —CH₂F, —CHF₂, —CF₃, —OCH₃, —NHCH₃, —N(CH₃)₂, —CH₂—(S=O)CH₃, —CH₂—SO₂CH₃, —(S=O)CH₃, —SO₂CH₃, —CF(CF₃)CH₃, —C(OH)(CF₃)CH₃, —C(CF₃)(NH₂)CH₃, —C(CF₃)(CN) CH₃, —C(CF₃)₂CH₃, —CF(OH)CH₃, —CF(NH₂)CH₃, —CF(CN)CH₃, —C(OH)(NH₂)CH₃, —C(OH)(CN)CH₃, and —C(CN)(NH₂)CH₃.

In one aspect, each Ar¹, when present, is a heteroaryl, and wherein each Ar¹ is independently substituted with 0, 1, 2, or 3 groups independently selected from halogen, —NH₂, —OH, —CN, —N₃, —SF₅, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR⁵¹R⁵², —(C1-C6 alkyl)-NR⁵⁰ (C=O)R⁵⁵, —(C1-C6 alkyl)-NR⁵⁰(C=O)OR⁵⁵, —(C1-C6 alkyl)-NR⁵⁰(C=O)R⁵⁵, —(C1-C6 alkyl)-NR⁵⁰S(O)ₘR⁵⁵, —NR⁵⁰(C1-C6 alkyl)-(C=O)R⁵⁵, —NR⁵⁰(C1-C6 alkyl)-(C=O)OR⁵⁵, —NR⁵⁰(C1-C6 alkyl)-(C=O)R⁵⁵, —NR⁵⁰ (C1-C6 alkyl)-S(O)ₘR⁵⁵, —NR⁵⁰(C1-C6 alkyl)-S(O)ₘ NR⁵³R⁵⁴, —NR⁵⁰(C=O)R⁵⁵, —NR⁵⁰(C=O)OR⁵⁵, —NR⁵⁰(C=O)R⁵⁵, —NR⁵⁰S(O)ₘR⁵⁵, —(C1-C6 alkyl)-(C=O)R⁵⁵, —(C1-C6 alkyl)-(C=O)OR⁵⁵, —(C1-C6 alkyl)-(C=O)R⁵⁵, —(C1-C6 alkyl)-S(O)ₘR⁵⁵, —(C1-C6 alkyl)-S(O)ₘNR⁵³R⁵⁴, —(C=O)R⁵⁵, —(C=O)OR⁵⁵, —S(O)ₘR⁵⁵, —S(O)ₘNR⁵³R⁵⁴, —(C1-C8 alkyl)-Ar²⁰, Ar²⁰, —(C1-C8 alkyl)-Cy²⁰, Cy²⁰, and R⁵⁷.

In a further aspect, Ar¹ is heteroaryl substituted with 0, 1, or 2 groups independently selected from halogen, —NH₂, —OH, —CN, C1-C6 alkyl, C1-C6 haloalkyl, C1-C6 polyhaloalkyl, C1-C6 alkoxy, C1-C6 alkylamino, C1-C6 dialkylamino, and —S(O)ₘR⁵⁵. In a yet further aspect, Ar¹ is heteroaryl substituted with 0, 1, or 2 groups independently selected from halogen, —NH₂, —OH, —CN, C1-C6 alkyl, C1-C3 haloalkyl, C1-C3 polyhaloalkyl, C1-C3 alkoxy, C1-C3 alkylamino, C1-C3 dialkylamino, and —S(O)ₘR⁵⁵. In an even further aspect, Ar¹ is heteroaryl substituted with 0, 1, or 2 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, Ar¹ is heteroaryl substituted with 0, 1, or 2 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$.

In a further aspect, Ar$^1$ is heteroaryl substituted with 0, 1, or 2 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In a still further aspect, Ar$^1$ is heteroaryl substituted with 0, 1, or 2 groups independently selected from —F, —Cl, —NH$_2$, —OH, —CN, methyl, —CHF$_2$, and —CF$_3$. In a yet further aspect, Ar$^1$ is heteroaryl substituted with 0-2 —F groups. In an even further aspect, Ar$^1$ is heteroaryl substituted with 0-2 —Cl groups. In a still further aspect, Ar$^1$ is heteroaryl substituted with 0-2 methyl groups. In a yet further aspect, Ar$^1$ is heteroaryl substituted with 0-2 —CF$_3$ groups. In an even further aspect, Ar$^1$ is heteroaryl substituted with 0-2 —NH$_2$ groups. In a still further aspect, Ar$^1$ is heteroaryl substituted with 0-2 —OH groups. In a yet further aspect, Ar$^1$ is heteroaryl substituted with 0-2 —CN groups.

In a further aspect, Ar$^1$ is heteroaryl substituted with 0, 1, or 2 groups independently selected from —F, —Cl, —NH$_2$, —OH, —CN, methyl, —CF$_3$, —CCl$_3$, —OCH$_3$, and —NHCH$_3$. In a yet further aspect, Ar$^1$ is heteroaryl substituted with 0-1 groups selected from —F, —Cl, —NH$_2$, —OH, —CN, methyl, —CF$_3$, —CCl$_3$, —OCH$_3$, and —NHCH$_3$. In a still further aspect, Ar$^1$ is heteroaryl substituted with 1-2 groups independently selected from —F, —Cl, —NH$_2$, —OH, —CN, methyl, —CF$_3$, —CCl$_3$, —OCH$_3$, and —NHCH$_3$. In a yet further aspect, Ar$^1$ is heteroaryl substituted with 1-2 groups independently selected from —F, —Cl, methyl, —CH$_2$F, —CH$_2$Cl, —CHF$_2$, —CF$_3$, —CHCl$_2$, and —CCl$_3$. In an even further aspect, Ar$^1$ is heteroaryl monosubstituted with a group selected from —F, —Cl, methyl, —CH$_2$F, —CH$_2$Cl, —CHF$_2$, —CF$_3$, —CHCl$_2$, and —CCl$_3$.

In a further aspect, Ar$^1$ has a structure represented by a formula selected from:

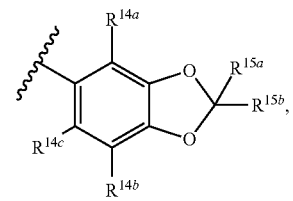
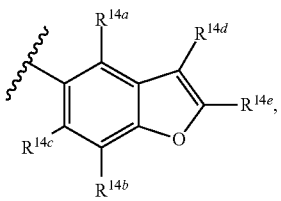
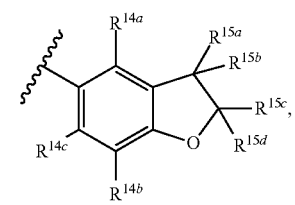
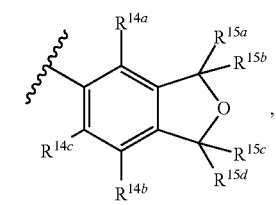
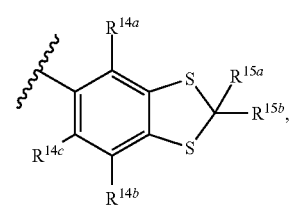
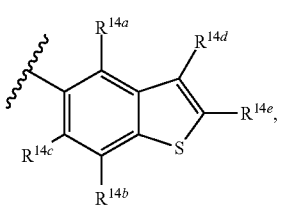

-continued

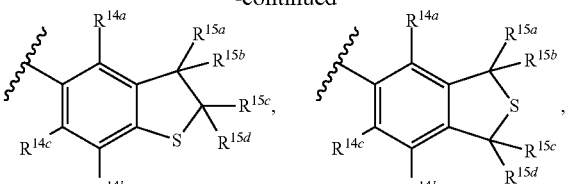
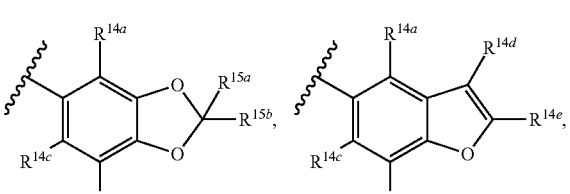
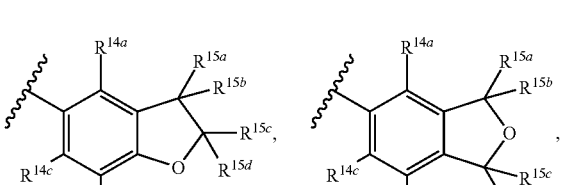
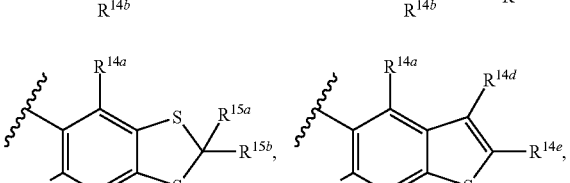
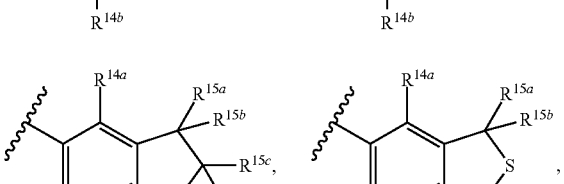
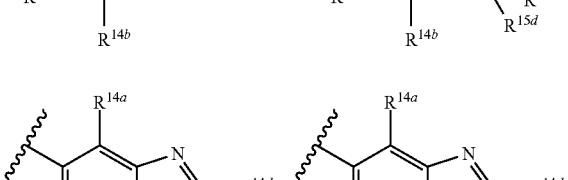
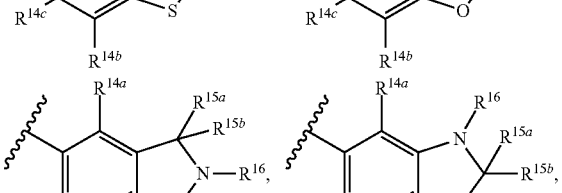

-continued

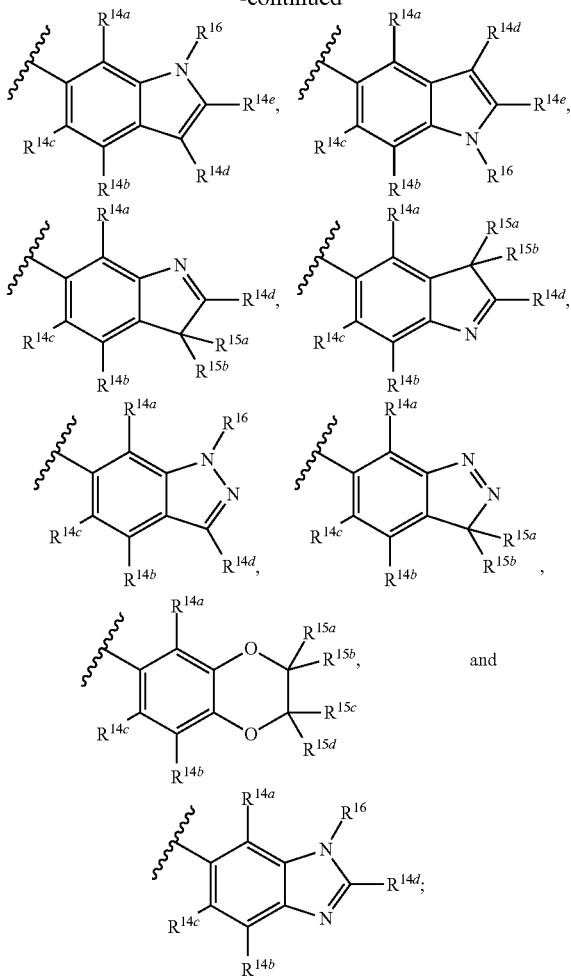

wherein each of $R^{14a}$, $R^{14b}$, $R^{14c}$, $R^{14d}$, and $R^{14e}$, when present, is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; each of $R^{15a}$, $R^{15b}$, $R^{15c}$, and $R^{15d}$, when present is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; wherein $R^{16}$, when present, is selected from hydrogen and C1-C8 alkyl; and wherein all variables are as defined herein.

In a further aspect, $Ar^1$ has a structure represented by a formula selected from:

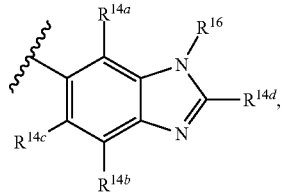

wherein each of $R^{14a}$, $R^{14b}$, $R^{14c}$, and $R^{14d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; wherein $R^{16}$ is selected from hydrogen and C1-C8 alkyl; and wherein all variables are as defined herein.

In a further aspect, $Ar^1$ has a structure represented by a formula selected from:

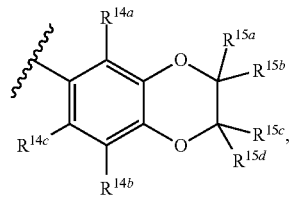

wherein each of $R^{14a}$, $R^{14b}$, and $R^{14c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; wherein each of $R^{15a}$, $R^{15b}$, $R^{15c}$, and $R^{15d}$, when present is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; and wherein all variables are as defined herein.

In a further aspect, $Ar^1$ has a structure represented by a formula selected from:

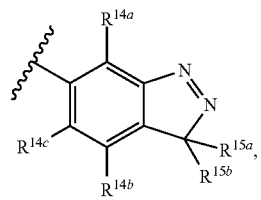

wherein each of $R^{14a}$, $R^{14b}$, and $R^{14c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; wherein each of $R^{15a}$ and $R^{15b}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; and wherein all variables are as defined herein.

In a further aspect, $Ar^1$ has a structure represented by a formula selected from:

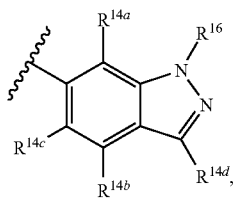

wherein each of $R^{14a}$, $R^{14b}$, and $R^{14c}$, and $R^{14d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —$S(O)_m R^{55}$; wherein $R^{16}$ is selected from hydrogen and C1-C8 alkyl; and wherein all variables are as defined herein.

In a further aspect, $Ar^1$ has a structure represented by a formula selected from:

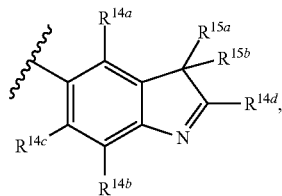

wherein each of $R^{14a}$, $R^{14b}$, $R^{14c}$, and $R^{14d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$ and $R^{15b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

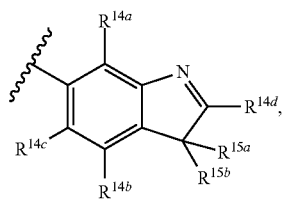

wherein each of $R^{14a}$, $R^{14b}$, $R^{14c}$, and $R^{14d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$ and $R^{15b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

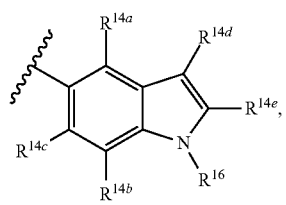

wherein each of $R^{14a}$, $R^{14b}$, $R^{14c}$, $R^{14d}$, and $R^{14e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein R$^{16}$ is selected from hydrogen and C1-C8 alkyl; and wherein all variables are as defined herein.

In a further aspect, Ar$^1$ has a structure represented by a formula selected from:

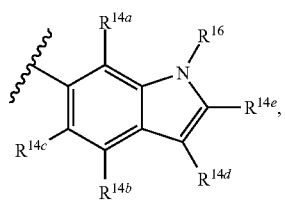

wherein each of $R^{14a}$, $R^{14b}$, $R^{14c}$, $R^{14d}$, and $R^{14e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein R$^{16}$ is selected from hydrogen and C1-C8 alkyl; and wherein all variables are as defined herein.

In a further aspect, Ar$^1$ has a structure represented by a formula selected from:

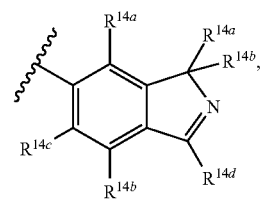

wherein each of $R^{14a}$, $R^{14b}$, $R^{14c}$, and $R^{14d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$ and $R^{15b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

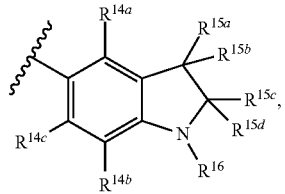

wherein each of $R^{14a}$, $R^{14b}$, and $R^{14c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$, $R^{15b}$, $R^{15c}$, and $R^{15d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein R$^{16}$ is selected from hydrogen and C1-C8 alkyl; and wherein all variables are as defined herein.

In a further aspect, Ar$^1$ has a structure represented by a formula selected from:

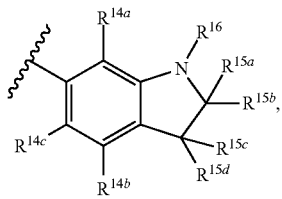

wherein each of $R^{14a}$, $R^{14b}$, and $R^{14c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; wherein each of $R^{15a}$, $R^{15b}$, $R^{15c}$, and $R^{15d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; wherein $R^{16}$ is selected from hydrogen and C1-C8 alkyl; and wherein all variables are as defined herein.

In a further aspect, $Ar^1$ has a structure represented by a formula selected from:

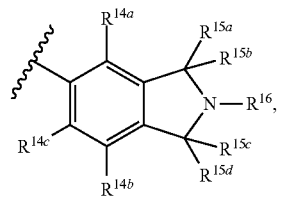

wherein each of $R^{14a}$, $R^{14b}$, and $R^{14c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; wherein each of $R^{15a}$, $R^{15b}$, $R^{15c}$, and $R^{15d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; wherein $R^{16}$ is selected from hydrogen and C1-C8 alkyl; and wherein all variables are as defined herein.

In a further aspect, $Ar^1$ has a structure represented by a formula selected from:

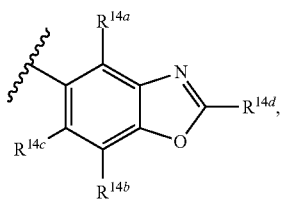

wherein each of $R^{14a}$, $R^{14b}$, $R^{14c}$, and $R^{14d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; and wherein all variables are as defined herein.

In a further aspect, $Ar^1$ has a structure represented by a formula selected from:

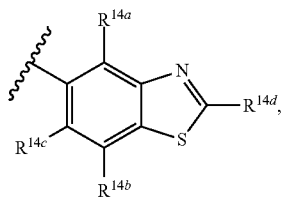

wherein each of $R^{14a}$, $R^{14b}$, $R^{14c}$, and $R^{14d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; and wherein all variables are as defined herein.

In a further aspect, $Ar^1$ has a structure represented by a formula selected from:

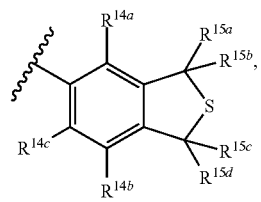

wherein each of $R^{14a}$, $R^{14b}$, and $R^{14c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; wherein each of $R^{15a}$, $R^{15b}$, $R^{15c}$, and $R^{15d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; and wherein all variables are as defined herein.

In a further aspect, $Ar^1$ has a structure represented by a formula selected from:

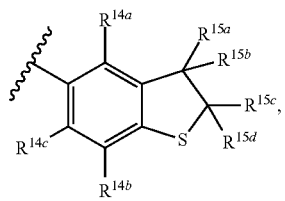

wherein each of $R^{14a}$, $R^{14b}$, and $R^{14c}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; wherein each of $R^{15a}$, $R^{15b}$, $R^{15c}$, and $R^{15d}$ is independently selected from hydrogen, halogen, —$NH_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m R^{55}$; and wherein all variables are as defined herein.

In a further aspect, $Ar^1$ has a structure represented by a formula selected from:

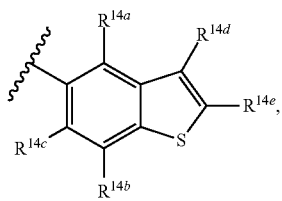

wherein each of $R^{14a}$, $R^{14b}$, $R^{14c}$, $R^{14d}$, and $R^{14e}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

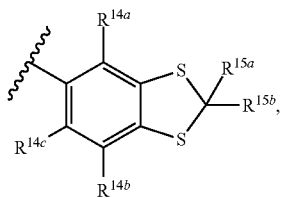

wherein each of $R^{14a}$, $R^{14b}$, and $R^{14c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$ and $R^{15b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

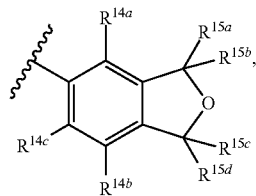

wherein each of $R^{14a}$, $R^{14b}$, and $R^{14c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$, $R^{15b}$, $R^{15c}$, and $R^{15d}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

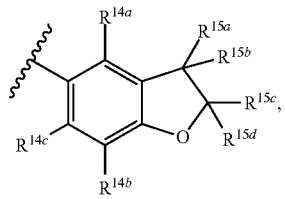

wherein each of $R^{14a}$, $R^{14b}$, and $R^{14c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$, $R^{15b}$, $R^{15c}$, and $R^{15d}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

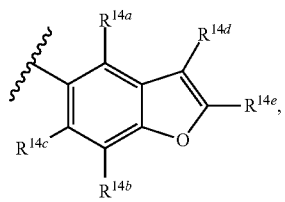

wherein each of $R^{14a}$, $R^{14b}$, $R^{14c}$, $R^{14d}$, and $R^{14e}$, when present, is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

In a further aspect, Ar$^1$ has a structure represented by a formula selected from:

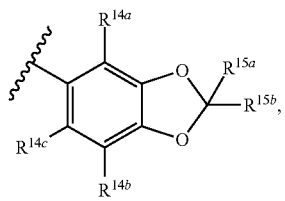

wherein each of $R^{14a}$, $R^{14b}$, and $R^{14c}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; wherein each of $R^{15a}$ and $R^{15b}$ is independently selected from hydrogen, halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, and —S(O)$_m$R$^{55}$; and wherein all variables are as defined herein.

cc. Ar$^2$ Groups

In one aspect, each Ar$^2$, when present, is independently selected from phenyl and heteroaryl, and wherein each Ar$^2$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, and —S(O)$_m$R$^5$.

In a further aspect, each Ar$^2$, when present, is independently selected from phenyl and heteroaryl, and independently substituted with 0, 1, 2, or 3 groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a still further aspect, each Ar$^2$, when present, is independently selected from phenyl and heteroaryl, and independently substituted with 0, 1, 2, or 3 groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In a yet further aspect, each Ar$^2$, when present, is independently selected from phenyl and heteroaryl, and independently substituted with 0, 1, 2, or 3 groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In an even further aspect, each Ar$^2$, when present, is independently selected from phenyl and heteroaryl, and independently substituted with 0, 1, 2, or 3 groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently substituted with 0, 1, or 2 groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each Ar$^2$, when present, is independently substituted with 0, 1, or 2 groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently substituted with 0, 1, or 2 groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently substituted with 0, 1, or 2 groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently substituted with 0, 1, or 2 groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently substituted with 1, 2 or 3 groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each Ar$^2$, when present, is independently substituted with 1, 2 or 3 groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently substituted with 1, 2 or 3 groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently substituted with 1, 2 or 3 groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently substituted with 1, 2 or 3 groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently substituted with 0 or 1 group selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each Ar$^2$, when present, is independently substituted with 0 or 1 group selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently substituted with 0 or 1 group selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently substituted with 0 or 1 group selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently substituted with 0 or 1 group selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently substituted with 1 or 2 groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each Ar$^2$, when present, is independently substituted with 1 or 2 groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently substituted with 1 or 2 groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently substituted with 1 or 2 groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently substituted with 1 or 2 groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently substituted with 2 or 3 groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further, each Ar$^2$, when present, is independently substituted with 2 or 3 groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently substituted with 2 or 3 groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently substituted with 2 or 3 groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently substituted with 2 or 3 groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently monosubstituted with a group selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each Ar$^2$, when present, is independently monosubstituted with a group selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently monosubstituted with a group selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently monosubstituted with a group selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently monosubstituted with a group selected —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently substituted with two groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each Ar$^2$, when present, is independently substituted with two groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently substituted with two groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently substituted with two groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently substituted with two groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently substituted with three groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each Ar$^2$, when present, is independently substituted with three groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each Ar$^2$, when present, is independently substituted with three groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each Ar$^2$, when present, is independently substituted with three groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each Ar$^2$, when present, is independently substituted with three groups independently selected —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each Ar$^2$, when present, is independently selected from phenyl, pyridinyl, pyrimidinyl, pyridazinyl, and pyrazinyl.

In a further aspect, each Ar$^2$, when present, is independently selected from phenyl and heteroaryl, and wherein Ar$^2$ is unsubstituted. In one aspect, each Ar$^2$ is independently selected from phenyl, pyridinyl, pyrimidinyl, pyridazinyl, and pyrazinyl, and wherein Ar$^1$ is unsubstituted.

In a further aspect, each Ar$^2$ is independently selected from pyridinyl, pyrimidinyl, pyridazinyl, and pyrazinyl. In a still further aspect, each Ar$^2$ is independently selected from pyridinyl, pyrimidinyl, pyridazinyl, and pyrazinyl, and wherein Ar$^1$ is unsubstituted.

In a further aspect, each $Ar^2$, when present, is phenyl. In a yet further aspect, each $Ar^2$, when present, is unsubstituted phenyl.

In a further aspect, each $Ar^2$, when present, is phenyl, and each phenyl is independently substituted with 0, 1, or 2 groups independently selected from halogen, —$NH_2$, —OH, —CN, —$S(O)_mR^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each $Ar^2$, when present, is phenyl, and each phenyl is independently substituted with 0, 1, or 2 groups independently selected from halogen, —$NH_2$, —OH, —CN, —$S(O)_mR^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each $Ar^2$, when present, is phenyl, and each phenyl is independently substituted with 0, 1, or 2 groups independently selected from —F, —Cl, —$NH_2$, —OH, —CN, —$S(O)_mR^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently substituted with 0, 1, or 2 groups independently selected from —F, —Cl, —$NH_2$, —OH, —CN, —$SCH_3$, —$SOCH_3$, —$SO_2CH_3$, methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CCl_3$, —$OCH_3$, —$OCH_2CH_3$, —$OCH(CH_3)_2$, —$NHCH_3$, —$NHCH_2CH_3$, —$N(CH_3)_2$, —$N(CH_3)CH_2CH_3$, and —$N(CH_3)CH(CH_3)_2$. In a still further aspect, each $Ar^2$, when present, is phenyl, and each phenyl is independently substituted with 0, 1, or 2 groups independently selected from —F, —$NH_2$, —OH, —CN, —$SCH_3$, —$SOCH_3$, —$SO_2CH_3$, methyl, —$CH_2F$, —$CHF_2$, —$CF_3$, —$OCH_3$, —$NHCH_3$, and —$N(CH_3)_2$.

In a further aspect, each $Ar^2$, when present, is phenyl, and each phenyl is independently substituted with 1, 2 or 3 groups independently selected from halogen, —$NH_2$, —OH, —CN, —$S(O)_mR^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each $Ar^2$, when present, is phenyl, and each phenyl is independently substituted with 1, 2 or 3 groups independently selected from halogen, —$NH_2$, —OH, —CN, —$S(O)_mR^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect each $Ar^2$, when present, is phenyl, and each phenyl is independently substituted with 1, 2 or 3 groups independently selected from —F, —Cl, —$NH_2$, —OH, —CN, —$S(O)_mR^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently substituted with 1, 2 or 3 groups independently selected from —F, —Cl, —$NH_2$, —OH, —CN, —$SCH_3$, —$SOCH_3$, —$SO_2CH_3$, methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$OCH(CH_3)_2$, —$NHCH_3$, —$NHCH_2CH_3$, —$N(CH_3)_2$, —$N(CH_3)CH_2CH_3$, and —$N(CH_3)CH(CH_3)_2$. In a still further aspect, each $Ar^2$, when present, is phenyl, and each phenyl is independently substituted with 1, 2 or 3 groups independently selected from —F, —$NH_2$, —OH, —CN, —$SCH_3$, —$SOCH_3$, —$SO_2CH_3$, methyl, —$CH_2F$, —$CHF_2$, —$CF_3$, —$OCH_3$, —$NHCH_3$, and —$N(CH_3)_2$.

In a further aspect, each $Ar^2$, when present, is phenyl, and each phenyl is independently substituted with 0 or 1 group selected from halogen, —$NH_2$, —OH, —CN, —$S(O)_mR^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each $Ar^2$, when present, is phenyl, and each phenyl is independently substituted with 0 or 1 group selected from halogen, —$NH_2$, —OH, —CN, —$S(O)_mR^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each $Ar^2$, when present, is phenyl, and each phenyl is independently substituted with 0 or 1 group selected from —F, —Cl, —$NH_2$, —OH, —CN, —$S(O)_mR^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently substituted with 0 or 1 group selected from —F, —Cl, —$NH_2$, —OH, —CN, —$SCH_3$, —$SOCH_3$, —$SO_2CH_3$, methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$OCH(CH_3)_2$, —$NHCH_3$, —$NHCH_2CH_3$, —$N(CH_3)_2$, —$N(CH_3)CH_2CH_3$, and —$N(CH_3)CH(CH_3)_2$. In a still further aspect, each $Ar^2$, when present, is phenyl, and each phenyl is independently substituted with 0 or 1 group selected from —F, —$NH_2$, —OH, —CN, —$SCH_3$, —$SOCH_3$, —$SO_2CH_3$, methyl, —$CH_2F$, —$CHF_2$, —$CF_3$, —$OCH_3$, —$NHCH_3$, and —$N(CH_3)_2$.

In a further aspect, each $Ar^2$, when present, is phenyl, and each phenyl is independently substituted with 1 or 2 groups independently selected from halogen, —$NH_2$, —OH, —CN, —$S(O)_mR^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each $Ar^2$, when present, is phenyl, and each phenyl is independently substituted with 1 or 2 groups independently selected from halogen, —$NH_2$, —OH, —CN, —$S(O)_mR^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each $Ar^2$, when present, is phenyl, and each phenyl is independently substituted with 1 or 2 groups independently selected from —F, —Cl, —$NH_2$, —OH, —CN, —$S(O)_mR^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently substituted with 1 or 2 groups independently selected from —F, —Cl, —$NH_2$, —OH, —CN, —$SCH_3$, —$SOCH_3$, —$SO_2CH_3$, methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$OCH(CH_3)_2$, —$NHCH_3$, —$NHCH_2CH_3$, —$N(CH_3)_2$, —$N(CH_3)CH_2CH_3$, and —$N(CH_3)CH(CH_3)_2$. In a still further aspect, each $Ar^2$, when present, is phenyl, and each phenyl is independently substituted with 1 or 2 groups independently selected from —F, —$NH_2$, —OH, —CN, —$SCH_3$, —$SOCH_3$, —$SO_2CH_3$, methyl, —$CH_2F$, —$CHF_2$, —$CF_3$, —$OCH_3$, —$NHCH_3$, and —$N(CH_3)_2$.

In a further aspect, each $Ar^2$, when present, is phenyl, and each phenyl is independently substituted with 2 or 3 groups independently selected from halogen, —$NH_2$, —OH, —CN, —$S(O)_mR^5$, C1-C8 alkyl, C1-C8 monohaloalkyl, C1-C8 polyhaloalkyl, C1-C8 alkoxy, C1-C8 alkylamino, and C1-C8 dialkylamino. In a still further, each $Ar^2$, when present, is phenyl, and each phenyl is independently substituted with 2 or 3 groups independently selected from halogen, —$NH_2$, —OH, —CN, —$S(O)_mR^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each $Ar^2$, when present, is phenyl, and each phenyl is independently substituted with 2 or 3 groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently substituted with 2 or 3 groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each $Ar^2$, when present, is phenyl, and each phenyl is independently substituted with 2 or 3 groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each $Ar^2$, when present, is phenyl, and each phenyl is independently monosubstituted with a group selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each $Ar^2$, when present, is phenyl, and each phenyl is independently monosubstituted with a group selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each $Ar^2$, when present, is phenyl, and each phenyl is independently monosubstituted with a group selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently monosubstituted with a group selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each $Ar^2$, when present, is phenyl, and each phenyl is independently monosubstituted with a group selected —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each $Ar^2$, when present, is phenyl, and each phenyl is independently substituted with two groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each $Ar^2$, when present, is phenyl, and each phenyl is independently substituted with two groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each $Ar^2$, when present, is phenyl, and each phenyl is independently substituted with two groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently substituted with two groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect each $Ar^2$, when present, is phenyl, and each phenyl is independently substituted with two groups independently selected from —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

In a further aspect, each $Ar^2$, when present, is phenyl, and each phenyl is independently substituted with three groups independently selected from halogen, —NH$_2$, —OH, —CN, —S(O)$_m$R$^5$, C1-C8 alkyl, C1-C8 monohaloalkyl, C1-C8 polyhaloalkyl, C1-C8 alkoxy, C1-C8 alkylamino, and C1-C8 dialkylamino. In a still further aspect, each $Ar^2$, when present, is phenyl, and each phenyl is independently substituted with three groups independently selected from halogen, —NH$_2$, —OH, —CN, —S(O)$_m$R$^5$, C1-C6 alkyl, C1-C6 monohaloalkyl, C1-C6 polyhaloalkyl, C1-C6 alkoxy, C1-C6 alkylamino, and C1-C6 dialkylamino. In a yet further aspect, each $Ar^2$, when present, is phenyl, and each phenyl is independently substituted with three groups independently selected from —F, —Cl, —NH$_2$, —OH, —CN, —S(O)$_m$R$^5$, C1-C3 alkyl, C1-C3 monohaloalkyl, C1-C3 polyhaloalkyl, C1-C3 alkoxy, C1-C3 alkylamino, and C1-C3 dialkylamino. In an even further aspect, each $Ar^2$, when present, is phenyl, and each phenyl is independently substituted with three groups independently selected from —F, —Cl, —NH$_2$, —OH, —CN, —SCH$_3$, —SOCH$_3$, —SO$_2$CH$_3$, methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —OCH(CH$_3$)$_2$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, each $Ar^2$, when present, is phenyl, and each phenyl is independently substituted with three groups independently selected —F, —NH$_2$, —OH, —CN, —SCH$_3$, —SOCH$_3$, —SO$_2$CH$_3$, methyl, —CH$_2$F, —CHF$_2$, —CF$_3$, —OCH$_3$, —NHCH$_3$, and —N(CH$_3$)$_2$.

dd. $Ar^{20}$ Groups

In one aspect, each $Ar^{20}$, when present, is independently selected from phenyl, naphthyl, and heteroaryl; and wherein $Ar^{20}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{20}$, when present, is independently selected from phenyl, naphthyl, and heteroaryl; and wherein $Ar^{20}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{20}$, when present, is independently selected from phenyl, naphthyl, and heteroaryl; and wherein $Ar^{20}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{20}$, when present, is selected from phenyl, naphthyl, and heteroaryl; and wherein $Ar^{20}$ is unsubstituted.

In one aspect, each $Ar^{20}$, when present, is independently selected from phenyl and monocyclic heteroaryl; and wherein $Ar^{20}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{20}$, when present, is independently selected from phenyl and monocyclic heteroaryl; and wherein $Ar^{20}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{20}$, when present, is independently selected from phenyl and monocyclic heteroaryl; and wherein $Ar^{20}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{20}$, when present, is selected from phenyl and monocyclic heteroaryl; and wherein $Ar^{20}$ is unsubstituted.

In a further aspect, each $Ar^{20}$, when present, is selected from phenyl, naphthyl, and heteroaryl; and wherein $Ar^{20}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each $Ar^{20}$, when present, is selected from phenyl, naphthyl, and heteroaryl; and wherein $Ar^{20}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each $Ar^{20}$, when present, is selected from phenyl, naphthyl, and heteroaryl; and wherein $Ar^{20}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{20}$, when present, is selected from phenyl, naphthyl, and heteroaryl; and wherein $Ar^{20}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{20}$, when present, is selected from phenyl, naphthyl, and heteroaryl; and wherein $Ar^{20}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{20}$, when present, is selected from phenyl, naphthyl, and heteroaryl; and wherein $Ar^{20}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{20}$, when present, is selected from phenyl and monocyclic heteroaryl; and wherein $Ar^{20}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{20}$, when present, is selected from phenyl, naphthyl, pyridinyl, pyrimidinyl, and pyrazinyl; and wherein $Ar^{20}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{20}$, when present, is selected from phenyl, naphthyl, pyridinyl, pyrimidinyl, and pyrazinyl; and wherein $Ar^{20}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{20}$, when present, is selected from phenyl, naphthyl, pyridinyl, pyrimidinyl, and pyrazinyl; and wherein $Ar^{20}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{20}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{20}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$) CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{20}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{20}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{20}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a yet further aspect, each $Ar^{20}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{20}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each $Ar^{20}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{20}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{20}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{20}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{20}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{20}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{20}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{20}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

ee. Ar$^{21}$ Groups

In one aspect, each Ar$^{21}$, when present, is independently selected from phenyl, naphthyl, and heteroaryl; and wherein Ar$^{21}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{21}$, when present, is independently selected from phenyl, naphthyl, and heteroaryl; and wherein Ar$^{21}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{21}$, when present, is independently selected from phenyl, naphthyl, and heteroaryl; and wherein Ar$^{21}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{21}$, when present, is selected from phenyl, naphthyl, and heteroaryl; and wherein Ar$^{21}$ is unsubstituted.

In one aspect, each Ar$^{21}$, when present, is independently selected from phenyl and monocyclic heteroaryl; and wherein Ar$^{21}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{21}$, when present, is independently selected from phenyl and monocyclic heteroaryl; and wherein Ar$^{21}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{21}$, when present, is independently selected from phenyl and monocyclic heteroaryl; and wherein Ar$^{21}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{21}$, when present, is selected from phenyl and monocyclic heteroaryl; and wherein Ar$^{21}$ is unsubstituted.

In a further aspect, each Ar$^{21}$, when present, is selected from phenyl, naphthyl, and heteroaryl; and wherein Ar$^{21}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each Ar$^{21}$, when present, is selected from phenyl, naphthyl, and heteroaryl; and wherein Ar$^{21}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each Ar$^{21}$, when present, is selected from phenyl, naphthyl, and heteroaryl; and wherein Ar$^{21}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each Ar$^{21}$, when present, is selected from phenyl, naphthyl, and heteroaryl; and wherein Ar$^{21}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each Ar$^{21}$, when present, is selected from phenyl, naphthyl, and heteroaryl; and wherein Ar$^{21}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{21}$, when present, is selected from phenyl, naphthyl, and heteroaryl; and wherein Ar$^{21}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{21}$, when present, is selected from phenyl, naphthyl, and heteroaryl; and wherein Ar$^{21}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{21}$, when present, is selected from phenyl and monocyclic heteroaryl; and wherein Ar$^{21}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{21}$, when present, is selected from phenyl, naphthyl, pyridinyl, pyrimidinyl, and pyrazinyl; and wherein $Ar^{21}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{21}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{21}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{21}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{21}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{21}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{21}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{21}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{21}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each $Ar^{21}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, each $Ar^{21}$, when present, is pyridinyl and is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each $Ar^{21}$, when present, is pyridinyl and is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each $Ar^{21}$, when present, is pyridinyl and is substituted with 0, 1, 2, or 3 groups independently selected from —F, —Cl, —NH₂, —OH, —CN, methyl, —CF₃, —CCl₃, —OCH₃, and —NHCH₃.

In various further aspects, each $Ar^{21}$, when present, is pyridinyl and is monosubstituted with a group selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), and —N(CH₂CH₃)(CH(CH₃)₂). In a still further aspect, each $Ar^{21}$, when present, is pyridinyl and is monosubstituted with a group selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, and —N(CH₂CH₃)₂. In a yet further aspect, each $Ar^{21}$, when present, is pyridinyl and is monosubstituted with a group selected from —F, —Cl, —NH₂, —OH, —CN, methyl, —CH₂F, —CH₂Cl, —CHF₂, —CF₃, —CHCl₂, —CCl₃, —OCH₃, —NHCH₃, and —N(CH₃)₂. In an even further aspect, each $Ar^{21}$, when present, is pyridinyl and is monosubstituted with a group selected from —F, —Cl, —NH₂, —OH, —CN, methyl, —CF₃, —CCl₃, —OCH₃, and —NHCH₃.

ff. $Ar^{22}$ Groups

In one aspect, each $Ar^{22}$, when present, is independently selected from phenyl, naphthyl, and heteroaryl; and wherein $Ar^{22}$ is substituted with 0, 1, 2, or 3 groups independently selected from halogen, —OH, —CN, —NH₂, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{22}$, when present, is independently selected from phenyl, naphthyl, and heteroaryl; and wherein $Ar^{22}$ is substituted with 0, 1, 2, or 3 groups independently selected from halogen, —OH, —CN, —NH₂, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{22}$, when present, is independently selected from phenyl, naphthyl, and heteroaryl; and wherein $Ar^{22}$ is substituted with 0, 1, 2, or 3 groups independently selected from halogen, —OH, —CN, —NH₂, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{22}$, when present, is selected from phenyl, naphthyl, and heteroaryl; and wherein $Ar^{22}$ is unsubstituted.

In one aspect, each $Ar^{22}$, when present, is independently selected from phenyl and monocyclic heteroaryl; and wherein $Ar^{22}$ is substituted with 0, 1, 2, or 3 groups independently selected from halogen, —OH, —CN, —NH₂, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{22}$, when present, is independently selected from phenyl and monocyclic heteroaryl; and wherein $Ar^{22}$ is substituted with 0, 1, 2, or 3 groups independently selected from halogen, —OH, —CN, —NH₂, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{22}$, when present, is independently selected from phenyl and monocyclic heteroaryl; and wherein $Ar^{22}$ is substituted with 0, 1, 2, or 3 groups independently selected from halogen, —OH, —CN, —NH₂, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{22}$, when present, is selected from phenyl and monocyclic heteroaryl; and wherein $Ar^{22}$ is unsubstituted.

In a further aspect, each $Ar^{22}$, when present, is selected from phenyl, naphthyl, and heteroaryl; and wherein $Ar^{22}$ is substituted with 0, 1, or 2 groups independently selected from halogen, —OH, —CN, —NH₂, C1-C8 alkyl, C1-C8 alkoxy, C1-C8 haloalkyl, or C1-C8 polyhaloalkyl, C1-C8 alkylamino, and C1-C8 dialkylamino. In a still further aspect, each $Ar^{22}$, when present, is selected from phenyl, naphthyl, and heteroaryl; and wherein $Ar^{22}$ is substituted with 0 or 1 group selected from halogen, —OH, —CN, —NH₂, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each $Ar^{22}$, when present, is selected from phenyl, naphthyl, and heteroaryl; and wherein $Ar^{22}$ is substituted with 1 or 2 groups independently selected from halogen, —OH, —CN, —NH₂, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{22}$, when present, is selected from phenyl, naphthyl, and heteroaryl; and wherein $Ar^{22}$ is monosubstituted with a group selected from halogen, —OH, —CN, —NH₂, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{22}$, when present, is selected from phenyl, naphthyl, and heteroaryl; and wherein $Ar^{22}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{22}$, when present, is selected from phenyl, naphthyl, and heteroaryl; and wherein $Ar^{22}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{22}$, when present, is selected from phenyl, naphthyl, and heteroaryl; and wherein $Ar^{22}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{22}$, when present, is selected from phenyl and monocyclic heteroaryl; and wherein $Ar^{22}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{22}$, when present, is selected from phenyl, naphthyl, pyridinyl, pyrimidinyl, and pyrazinyl; and wherein $Ar^{22}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{22}$, when present, is selected from phenyl, naphthyl, pyridinyl, pyrimidinyl, and pyrazinyl; and wherein $Ar^{22}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{22}$, when present, is selected from phenyl, naphthyl, pyridinyl, pyrimidinyl, and pyrazinyl; and wherein $Ar^{22}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{22}$, when present, is selected from phenyl, naphthyl, pyridinyl, pyrimidinyl, and pyrazinyl; and wherein $Ar^{22}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{22}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{22}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{22}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{22}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{22}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{22}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{22}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{22}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{22}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{22}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{22}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{22}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

gg. Ar$^{23}$ Groups

In one aspect, each Ar$^{23}$, when present, is independently selected from phenyl, naphthyl, and heteroaryl; and wherein Ar$^{23}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{23}$, when present, is independently selected from phenyl, naphthyl, and heteroaryl; and wherein Ar$^{23}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{23}$, when present, is independently selected from phenyl, naphthyl, and heteroaryl; and wherein Ar$^{23}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{23}$, when present, is selected from phenyl, naphthyl, and heteroaryl; and wherein $Ar^{23}$ is unsubstituted.

In one aspect, each $Ar^{23}$, when present, is independently selected from phenyl and monocyclic heteroaryl; and wherein $Ar^{23}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each $Ar^{23}$, when present, is independently selected from phenyl and monocyclic heteroaryl; and wherein $Ar^{23}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each $Ar^{23}$, when present, is independently selected from phenyl and monocyclic heteroaryl; and wherein $Ar^{23}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each $Ar^{23}$, when present, is selected from phenyl and monocyclic heteroaryl; and wherein $Ar^{23}$ is unsubstituted.

In a further aspect, each $Ar^{23}$, when present, is selected from phenyl, naphthyl, and heteroaryl; and wherein $Ar^{23}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each $Ar^{23}$, when present, is selected from phenyl, naphthyl, and heteroaryl; and wherein $Ar^{23}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each $Ar^{23}$, when present, is selected from phenyl, naphthyl, and heteroaryl; and wherein $Ar^{23}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each $Ar^{23}$, when present, is selected from phenyl, naphthyl, and heteroaryl; and wherein $Ar^{23}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{23}$, when present, is selected from phenyl, naphthyl, and heteroaryl; and wherein $Ar^{23}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{23}$, when present, is selected from phenyl, naphthyl, and heteroaryl; and wherein $Ar^{23}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{23}$, when present, is selected from phenyl, naphthyl, and heteroaryl; and wherein $Ar^{23}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{23}$, when present, is selected from phenyl and monocyclic heteroaryl; and wherein $Ar^{23}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{23}$, when present, is selected from phenyl, naphthyl, pyridinyl, pyrimidinyl, and pyrazinyl; and wherein $Ar^{23}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{23}$, when present, is selected from phenyl, naphthyl, pyridinyl, pyrimidinyl, and pyrazinyl; and wherein $Ar^{23}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{23}$, when present, is selected from phenyl, naphthyl, pyridinyl, pyrimidinyl, and pyrazinyl; and wherein $Ar^{23}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{23}$, when present, is selected from phenyl, naphthyl, pyridinyl, pyrimidinyl, and pyrazinyl; and wherein $Ar^{23}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{23}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{23}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, Ar$^{23}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{23}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$ CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{23}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{23}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{23}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

hh. Ar$^{30}$ Groups

In one aspect, each Ar$^{30}$, when present, is independently selected from phenyl, naphthyl, and heteroaryl; and wherein Ar$^{30}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{30}$, when present, is independently selected from phenyl, naphthyl, and heteroaryl; and wherein Ar$^{30}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{30}$, when present, is independently selected from phenyl, naphthyl, and heteroaryl; and wherein Ar$^{30}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{30}$, when present, is selected from phenyl, naphthyl, and heteroaryl; and wherein Ar$^{30}$ is unsubstituted.

In one aspect, each Ar$^{30}$, when present, is independently selected from phenyl and monocyclic heteroaryl; and wherein Ar$^{30}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{30}$, when present, is independently selected from phenyl and monocyclic heteroaryl; and wherein Ar$^{30}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{30}$, when present, is independently selected from phenyl and monocyclic heteroaryl; and wherein Ar$^{30}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{30}$, when present, is selected from phenyl and monocyclic heteroaryl; and wherein Ar$^{30}$ is unsubstituted.

In a further aspect, each Ar$^{30}$, when present, is selected from phenyl, naphthyl, and heteroaryl; and wherein Ar$^{30}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each Ar$^{30}$, when present, is selected from phenyl, naphthyl, and heteroaryl; and wherein Ar$^{30}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each Ar$^{30}$, when present, is selected from phenyl, naphthyl, and heteroaryl; and wherein Ar$^{30}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each Ar$^{30}$, when present, is selected from phenyl, naphthyl, and heteroaryl; and wherein Ar$^{30}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each Ar$^{30}$, when present, is selected from phenyl, naphthyl, and heteroaryl; and wherein Ar$^{30}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is selected from phenyl, naphthyl, and heteroaryl; and wherein Ar$^{30}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is selected from phenyl, naphthyl, and heteroaryl; and wherein Ar$^{30}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is selected from phenyl and monocyclic heteroaryl; and wherein Ar$^{30}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is selected from phenyl, naphthyl, pyridinyl, pyrimidinyl, and pyrazinyl; and wherein Ar$^{30}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is selected from phenyl, naphthyl, pyridinyl, pyrimidinyl, and pyrazinyl; and wherein Ar$^{30}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is selected from phenyl, naphthyl, pyridinyl, pyrimidinyl, and pyrazinyl; and wherein Ar$^{30}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is selected from phenyl, naphthyl, pyridinyl, pyrimidinyl, and pyrazinyl; and wherein Ar$^{30}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, Ar$^{30}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is pyridinyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is pyridinyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each Ar$^{30}$, when present, is pyridinyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{30}$, when present, is pyridinyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{30}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{30}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

ii. Ar$^{40}$ Groups

In one aspect, each Ar$^{40}$, when present, is independently selected from phenyl, naphthyl, and heteroaryl; and wherein Ar$^{40}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{40}$, when present, is independently selected from phenyl, naphthyl, and heteroaryl; and wherein Ar$^{40}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{40}$, when present, is independently selected from phenyl, naphthyl, and heteroaryl; and wherein Ar$^{40}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{40}$, when present, is selected from phenyl, naphthyl, and heteroaryl; and wherein Ar$^{40}$ is unsubstituted.

In one aspect, each Ar$^{40}$, when present, is independently selected from phenyl and monocyclic heteroaryl; and wherein Ar$^{40}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a further aspect, each Ar$^{40}$, when present, is independently selected from phenyl and monocyclic heteroaryl; and wherein Ar$^{40}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, and C1-C6 dialkylamino. In a still further aspect, each Ar$^{40}$, when present, is independently selected from phenyl and monocyclic heteroaryl; and wherein Ar$^{40}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, and C1-C3 dialkylamino. In a yet further aspect, each Ar$^{40}$, when present, is selected from phenyl and monocyclic heteroaryl; and wherein Ar$^{40}$ is unsubstituted.

In a further aspect, each Ar$^{40}$, when present, is selected from phenyl, naphthyl, and heteroaryl; and wherein Ar$^{40}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a still further aspect, each Ar$^{40}$, when present, is selected from phenyl, naphthyl, and heteroaryl; and wherein Ar$^{40}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In a yet further aspect, each Ar$^{40}$, when present, is selected from phenyl, naphthyl, and heteroaryl; and wherein Ar$^{40}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino. In an even further aspect, each Ar$^{40}$, when present, is selected from phenyl, naphthyl, and heteroaryl; and wherein Ar$^{40}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, and C1-C8 dialkylamino.

In a further aspect, each $Ar^{40}$, when present, is selected from phenyl, naphthyl, and heteroaryl; and wherein $Ar^{40}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{40}$, when present, is selected from phenyl, naphthyl, and heteroaryl; and wherein $Ar^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{40}$, when present, is selected from phenyl, naphthyl, and heteroaryl; and wherein $Ar^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{40}$, when present, is selected from phenyl and monocyclic heteroaryl; and wherein $Ar^{40}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{40}$, when present, is selected from phenyl, naphthyl, pyridinyl, pyrimidinyl, and pyrazinyl; and wherein $Ar^{40}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{40}$, when present, is selected from phenyl, naphthyl, pyridinyl, pyrimidinyl, and pyrazinyl; and wherein $Ar^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{40}$, when present, is selected from phenyl, naphthyl, pyridinyl, pyrimidinyl, and pyrazinyl; and wherein $Ar^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{40}$, when present, is selected from phenyl, naphthyl, pyridinyl, pyrimidinyl, and pyrazinyl; and wherein $Ar^{40}$ is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{40}$, when present, is phenyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each $Ar^{40}$, when present, is phenyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each $Ar^{40}$, when present, is phenyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each $Ar^{40}$, when present, is phenyl and is substituted with 0, 1, 2, or 3 groups independently selected from —F, —Cl, —NH$_2$, —OH, —CN, methyl, —CF$_3$, —CCl$_3$, —OCH$_3$, and —NHCH$_3$.

In various further aspects, each $Ar^{40}$, when present, is phenyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{40}$, when present, is phenyl and is monosubstituted with a group selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{40}$, when present, is phenyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{40}$, when present, is phenyl and is monosubstituted with a group selected from —F, —Cl, —NH$_2$, —OH, —CN, methyl, —CF$_3$, —CCl$_3$, —OCH$_3$, and —NHCH$_3$.

In various further aspects, each Ar$^{40}$, when present, is pyridinyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), and —N(CH$_2$CH$_3$)(CH(CH$_3$)$_2$). In a still further aspect, each Ar$^{40}$, when present, is pyridinyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, each Ar$^{40}$, when present, is pyridinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, and —N(CH$_3$)$_2$. In an even further aspect, each Ar$^{40}$, when present, is pyridinyl and is monosubstituted with a group selected from —F, —Cl, —NH$_2$, —OH, —CN, methyl, —CF$_3$, —CCl$_3$, —OCH$_3$, and —NHCH$_3$.

jj. Cy$^1$ Groups

In one aspect, each Cy$^1$, when present, is independently selected from C3-C8 cycloalkyl and C2-C7 heterocycloalkyl, and each Cy$^1$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and two of the groups are optionally covalently bonded, and together with the intermediate atoms, comprise an optionally substituted 3- to 6-membered fused ring group.

In various aspects, each Cy$^1$, when present, is independently selected from C3-C8 cycloalkyl and C2-C7 heterocycloalkyl, and each Cy$^1$ is independently substituted with 0, 1, 2, or 3 groups independently selected from halogen, —NH$_2$, —OH, —CN, —C1-C8 alkyl, C1-C8 monohaloalkyl, C1-C8 polyhaloalkyl, C1-C8 alkoxy, C1-C8 alkylamino, C1-C8 dialkylamino, Ar², —(C1-C6 alkyl)-(C=O)R⁵, —(C1-C6 alkyl)-(C=O)OR⁵, —(C1-C6 alkyl)-S(O)$_m$R⁵, —(C=O) R⁵, —(C=O)OR⁵, —S(O)$_m$R⁵, and R⁶. In a further aspect, each Cy¹, when present, is independently selected from C3-C8 cycloalkyl and C2-C7 heterocycloalkyl, and each Cy¹ is independently substituted with 0, 1, 2, or 3 groups independently selected from halogen, —NH₂, —OH, —CN, —C1-C6 alkyl, C1-C6 monohaloalkyl, C1-C6 polyhaloalkyl, C1-C6 alkoxy, C1-C6 alkylamino, C1-C6 dialkylamino, Ar², —(C1-C3 alkyl)-(C=O)R⁵, —(C1-C3 alkyl)-(C=O)OR⁵, —(C1-C3 alkyl)-S—R⁵, —(C1-C3 alkyl)-(S=O)R⁵, —(C1-C3 alkyl)-SO₂R⁵, —(C=O)R⁵, —(C=O)OR⁵, —S—R⁵, —(S=O)R⁵, —SO₂R⁵, and R⁶. In a still further aspect, each Cy¹, when present, is independently selected from C3-C8 cycloalkyl and C2-C7 heterocycloalkyl, and each Cy¹ is independently substituted with 0, 1, 2, or 3 groups independently selected from halogen, —NH₂, —OH, —CN, —C1-C3 alkyl, C1-C3 monohaloalkyl, C1-C3 polyhaloalkyl, C1-C3 alkoxy, C1-C3 alkylamino, C1-C3 dialkylamino, Ar², —(C1-C3 alkyl)-(C=O)R⁵, —(C1-C3 alkyl)-(C=O)OR⁵, —(C1-C3 alkyl)-S—R⁵, —(C1-C3 alkyl)-(S=O)R⁵, —(C1-C3 alkyl)-SO₂R⁵, —(C=O)R⁵, —(C=O)OR⁵, —S—R⁵, —(S=O) R⁵, —SO₂R⁵, and R⁶.

In various further aspects, each Cy¹, when present, is independently substituted with 0, 1, or 2 groups. In a still further aspect, each Cy¹, when present, is independently substituted with 1, 2, or 3 groups. In a yet further aspect, each Cy¹, when present, is independently substituted with 0 or 1 groups. In an even further aspect, each Cy¹, when present, is independently substituted with 0 or 2 groups. In a still further aspect, each Cy¹, when present, is independently substituted with 0 or 3 groups. In a yet further aspect, each Cy¹, when present, is independently substituted with 2 or 3 groups. In an even further aspect, each Cy¹, when present, is independently substituted with 1 or 3 groups. In a still further aspect, each Cy¹, when present, is independently substituted with 2 or 3 groups. In a yet further aspect, each Cy¹, when present, is independently monosubstituted. In an even further aspect, each Cy¹, when present, is independently substituted with two groups. In a still further aspect, each Cy¹, when present, is independently substituted with three groups.

In a further aspect, each Cy¹, when present, is C3-C8 cycloalkyl. In a still further aspect, each Cy¹, when present, is selected from cyclopropyl, cyclobutyl, cyclopentyl, and cyclohexyl. In a yet further aspect, each Cy¹, when present, is cyclopropyl. In an even further aspect, each Cy¹, when present, is cyclobutyl. In a still further aspect, each Cy¹, when present, is cyclopentyl. In a yet further aspect, each Cy¹, when present, is cyclohexyl. In an even further aspect, each Cy¹, when present, is C3 cycloalkyl. In a still further aspect, each Cy¹, when present, is C3 cycloalkyl and substituted with 1 group.

In a further aspect, each Cy¹, when present, is C3-C8 cycloalkyl and is unsubstituted. In a still further aspect, each Cy¹, when present, is selected from cyclopropyl, cyclobutyl, cyclopentyl, and cyclohexyl, and wherein each Cy¹, when present, is unsubstituted. In a yet further aspect, each Cy¹, when present, is unsubstituted cyclopropyl. In an even further aspect, each Cy¹, when present, is unsubstituted cyclobutyl. In an even further aspect, each Cy¹, when present, is unsubstituted cyclopentyl. In a further aspect, each Cy¹, when present, is unsubstituted cyclohexyl.

In a further aspect, each Cy¹, when present, is C2-C7 heterocycloalkyl. In a still further aspect, each Cy¹, when present, is C2 heterocycloalkyl. In a yet further aspect, each Cy¹, when present, is C3 heterocycloalkyl. In an even further aspect, each Cy¹, when present, is C2 heterocycloalkyl and substituted with 1 group. In a still further aspect, each Cy¹, when present, is C3 heterocycloalkyl and substituted with 1 group. In a yet further aspect, each Cy¹, when present, is selected from pyrrolidinyl, tetrahydrofuranyl, piperidinyl, tetrahydro-2H-pyranyl, azepanyl, oxepanyl, diazepanyl, piperazinyl, and imidazolidinyl. In an even further aspect, each Cy¹, when present, is selected from pyrrolidinyl, piperidinyl, azepanyl, diazepanyl, piperazinyl, and imidazolidinyl. In a still further aspect, each Cy¹, when present, is pyrrolidinyl. In another aspect, each Cy¹, when present, is piperidinyl.

In a further aspect, each Cy¹, when present, is C2-C7 heterocycloalkyl and is unsubstituted. In a yet further aspect, each Cy¹, when present, is selected from pyrrolidinyl, tetrahydrofuranyl, piperidinyl, tetrahydro-2H-pyranyl, azepanyl, oxepanyl, diazepanyl, piperazinyl, and imidazolidinyl, and wherein Cy¹ is unsubstituted. In an even further aspect, each Cy¹, when present, is selected from pyrrolidinyl, piperidinyl, azepanyl, diazepanyl, piperazinyl, and imidazolidinyl, and wherein Cy¹ is unsubstituted. In a still further aspect, each Cy¹, when present, is unsubstituted pyrrolidinyl. In one aspect, each Cy¹, when present, is unsubstituted piperidinyl.

In a further aspect, each Cy¹, when present, is independently selected from C3-C8 cycloalkyl and C2-C7 heterocycloalkyl, and each Cy¹ is independently substituted with 0, 1, 2, or 3 groups independently selected from —F, —Cl, —NH₂, —OH, —CN, —C1-C3 alkyl, C1-C3 monohaloalkyl, C1-C3 polyhaloalkyl, C1-C3 alkoxy, C1-C3 alkylamino, C1-C3 dialkylamino, Ar², —(CH₂)₃—(C=O)R⁵, —(CH₂)₂—(C=O)R⁵, —CH₂—(C=O)R⁵, —(CH₂)₃—(C=O)OR⁵, —(CH₂)₂—(C=O)OR⁵, —CH₂—(C=O)OR⁵, —(CH₂)₃—S—R⁵, —(CH₂)₂—S—R⁵, —CH₂—S—R⁵, —(CH₂)₃—(S=O)R⁵, —(CH₂)₂—(S=O)R⁵, —CH₂—(S=O)R⁵, —(CH₂)₃—SO₂R⁵, —(CH₂)₂—SO₂R⁵, —CH₂—SO₂R⁵, —(C=O)R⁵, —(C=O)OR⁵, —S—R⁵, —(S=O)R⁵, —SO₂R⁵, and R⁶. In a still further aspect, each Cy¹, when present, is independently selected from C3-C8 cycloalkyl and C2-C7 heterocycloalkyl, and each Cy¹ is independently substituted with 0, 1, 2, or 3 groups independently selected from —F, —Cl, —NH₂, —OH, —CN, —C1-C3 alkyl, C1-C3 monohaloalkyl, C1-C3 polyhaloalkyl, C1-C3 alkoxy, C1-C3 alkylamino, C1-C3 dialkylamino, Ar², —(CH₂)₂—(C=O)R⁵, —CH₂—(C=O)R⁵, —(CH₂)₂—(C=O)OR⁵, —CH₂—(C=O)OR⁵, —(CH₂)₂—S—R⁵, —CH₂—S—R⁵, —(CH₂)₂—(S=O)R⁵, —CH₂—(S=O)R⁵, —(CH₂)₂—SO₂R⁵, —CH₂—SO₂R⁵, —(C=O)R⁵, —(C=O)OR⁵, —S—R⁵, —(S=O)R⁵, —SO₂R⁵, and R⁶. In a yet further aspect, each Cy¹, when present, is independently selected from C3-C8 cycloalkyl and C2-C7 heterocycloalkyl, and each Cy¹ is independently substituted with 0, 1, 2, or 3 groups independently selected from —F, —Cl, —NH₂, —OH, —CN, —C1-C3 alkyl, C1-C3 monohaloalkyl, C1-C3 polyhaloalkyl, C1-C3 alkoxy, C1-C3 alkylamino, C1-C3 dialkylamino, Ar², —CH₂—(C=O)R⁵, —CH₂—(C=O)OR⁵, —CH₂—S—R⁵, —CH₂—(S=O)R⁵, —CH₂—SO₂R⁵, —(C=O)R⁵, —(C=O)OR⁵, —S—R⁵, —(S=O)R⁵, —SO₂R⁵, and R⁶.

In a further aspect, each Cy¹, when present, is independently selected from C3-C8 cycloalkyl and C2-C7 heterocycloalkyl, and each Cy¹ is independently substituted with 0, 1, 2, or 3 groups independently selected from —F, —Cl, —NH₂, —OH, —CN, —C1-C8 alkyl, C1-C8 monohaloalkyl, C1-C8 polyhaloalkyl, C1-C8 alkoxy, C1-C8 alkylamino, C1-C8 dialkylamino, Ar², —CH₂—(C=O)R⁵, —CH₂—(C=O) OR⁵, —CH₂—S—R⁵, —CH₂—(S=O)R⁵, —CH₂—SO₂R⁵, —(C=O)R⁵, —(C=O)OR⁵, —S—R⁵, —(S=O)R⁵, —SO₂R⁵, and R⁶; and wherein Ar², when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, each Cy$^1$, when present, is independently selected from C3-C8 cycloalkyl and C2-C7 heterocycloalkyl, and each Cy$^1$ is independently substituted with 0, 1, 2, or 3 groups independently selected from —F, —Cl, —NH$_2$, —OH, —CN, —C1-C6 alkyl, C1-C6 monohaloalkyl, C1-C6 polyhaloalkyl, C1-C6 alkoxy, C1-C6 alkylamino, C1-C6 dialkylamino, Ar$^2$, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a yet further aspect, each Cy$^1$, when present, is independently selected from C3-C8 cycloalkyl and C2-C7 heterocycloalkyl, and each Cy$^1$ is independently substituted with 0, 1, 2, or 3 groups independently selected from —F, —Cl, —NH$_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, Ar$^2$, —CH$_2$—(C=O)R$^5$, —CH$_2$—(C=O)OR$^5$, —CH$_2$—S—R$^5$, —CH$_2$—(S=O)R$^5$, —CH$_2$—SO$_2$R$^5$, —(C=O)R$^5$, —(C=O)OR$^5$, —S—R$^5$, —(S=O)R$^5$, —SO$_2$R$^5$, and R$^6$; and wherein Ar$^2$, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In a further aspect, each Cy$^1$, when present, is independently selected from C3-C8 cycloalkyl and C2-C7 heterocycloalkyl, and each Cy$^1$ is independently substituted with 0, 1, 2, or 3 groups independently selected from —F, —Cl, —NH$_2$, —OH, —CN, -methyl, ethyl, propyl, isopropyl, tert-butyl, sec-butyl, isobutyl, tert-butyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(CH$_2$)$_3$—(C=O)CH$_3$, —(CH$_2$)$_2$—(C=O)CH$_3$, —CH$_2$—(C=O)CH$_3$, —(CH$_2$)$_3$—(C=O)OCH$_3$, —(CH$_2$)$_2$—(C=O)OCH$_3$, —CH$_2$—(C=O)OCH$_3$, —(CH$_2$)$_3$—S—CH$_3$, —(CH$_2$)$_2$—S—CH$_3$, —CH$_2$—S—CH$_3$, —(CH$_2$)$_3$—(S=O)CH$_3$, —(CH$_2$)$_2$—(S=O)CH$_3$, —CH$_2$—(S=O)CH$_3$, —(CH$_2$)$_3$—SO$_2$CH$_3$, —(CH$_2$)$_2$—SO$_2$CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a still further aspect, each Cy$^1$, when present, is independently selected from C3-C8 cycloalkyl and C2-C7 heterocycloalkyl, and each Cy$^1$ is independently substituted with 0, 1, 2, or 3 groups independently selected from —F, —Cl, —NH$_2$, —OH, —CN, -methyl, ethyl, propyl, isopropyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —OCH$_3$, —OCH$_2$CH$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_2$CH$_3$)$_2$, —(CH$_2$)$_2$—(C=O)CH$_3$, —CH$_2$—(C=O)CH$_3$, —(CH$_2$)$_2$—(C=O)OCH$_3$, —CH$_2$—(C=O)OCH$_3$, —(CH$_2$)$_2$—S—CH$_3$, —CH$_2$—S—CH$_3$, —(CH$_2$)$_2$—(S=O)CH$_3$, —CH$_2$—(S=O)CH$_3$, —(CH$_2$)$_2$—SO$_2$CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In a yet further aspect, each Cy$^1$, when present, is independently selected from C3-C8 cycloalkyl and C2-C7 heterocycloalkyl, and each Cy$^1$ is independently substituted with 0, 1, 2, or 3 groups independently selected from —F, —Cl, —NH$_2$, —OH, —CN, -methyl, ethyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —CH$_2$—(C=O)CH$_3$, —CH$_2$—(C=O)OCH$_3$, —CH$_2$—S—CH$_3$, —CH$_2$—(S=C)CH$_3$, —CH$_2$—SO$_2$CH$_3$, —(C=O)CH$_3$, —(C=O)OCH$_3$, —S—CH$_3$, —(S=O)CH$_3$, —SO$_2$CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$. In an even further aspect, each Cy$^1$, when present, is independently selected from C3-C8 cycloalkyl and C2-C7 heterocycloalkyl, and each Cy$^1$ is independently substituted with 0, 1, 2, or 3 groups independently selected from —F, —NH$_2$, —OH, —CN, -methyl, —CH$_2$F, —CHF$_2$, —CF$_3$, —OCH$_3$, —NHCH$_3$, —N(CH$_3$)$_2$, —(CH$_2$)—(C=O)CH$_3$, —(CH$_2$)—(C=O)OCH$_3$, —(CH$_2$)—S—CH$_3$, —(CH$_2$)—(S=O)CH$_3$, —(CH$_2$)—SO$_2$CH$_3$, —(C=O)CH$_3$, —(C=O)OCH$_3$, —S—CH$_3$, —(S=O)CH$_3$, —SO$_2$CH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and phenyl; and wherein phenyl, when present, is substituted with 0, 1, 2, or 3 groups selected from —F, —Cl, —Br, —NH$_2$, —OH, —CN, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —SCH$_3$, —SOCH$_3$, and —SO$_2$CH$_3$.

In various aspects, each Cy$^1$, when present, is independently selected from C3-C8 cycloalkyl and C2-C7 heterocycloalkyl, and independently substituted with 0, 1, 2, or 3 groups independently selected from halogen, —NH$_2$, —OH, —CN, —C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, and R$^6$. In a further aspect, each Cy$^1$, when present, is independently selected from C3-C8 cycloalkyl and C2-C7 heterocycloalkyl, and each Cy$^1$ is independently substituted with 0, 1, 2, or 3 groups independently selected from halogen, —NH$_2$, —OH, —CN, —C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-(C=O)$R^5$, —(C1-C3 alkyl)-(C=O)$OR^5$, —(C1-C3 alkyl)-S—$R^5$, —(C1-C3 alkyl)-(S=O)$R^5$, —(C1-C3 alkyl)-$SO_2R^5$, —(C=O)$R^5$, —(C=O)$OR^5$, —S—$R^5$, —(S=O)$R^5$, —$SO_2R^5$, and $R^6$. In a still further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from halogen, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-(C=O)$R^5$, —(C1-C3 alkyl)-(C=O)$OR^5$, —(C1-C3 alkyl)-S—$R^5$, —(C1-C3 alkyl)-(S=O)$R^5$, —(C1-C3 alkyl)-$SO_2R^5$, —(C=O)$R^5$, —(C=O)$OR^5$, —S—$R^5$, —(S=O)$R^5$, —$SO_2R^5$, and $R^6$.

In a further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —$(CH_2)_3$—(C=O)$R^5$, —$(CH_2)_2$—(C=O)$R^5$, —$CH_2$—(C=O)$R^5$, —$(CH_2)_3$—(C=O)$OR^5$, —$(CH_2)_2$—(C=O)$OR^5$, —$CH_2$—(C=O)$OR^5$, —$(CH_2)_3$—S—$R^5$, —$(CH_2)_2$—S—$R^5$, —$CH_2$—S—$R^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —(C=O)$R^5$, —(C=O)$OR^5$, —S—$R^5$, —(S=O)$R^5$, —$SO_2R^5$, and $R^6$. In a still further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —$(CH_2)_2$—(C=O)$R^5$, —$CH_2$—(C=O)$R^5$, —$(CH_2)_2$—(C=O)$OR^5$, —$CH_2$—(C=O)$OR^5$, —$(CH_2)_2$—S—$R^5$, —$CH_2$—S—$R^5$, —$(CH_2)_2$—(S=O)$R^5$, —$CH_2$—(S=O)$R^5$, —$(CH_2)_2$—$SO_2R^5$, —$CH_2$—$SO_2R^5$, —(C=O)$R^5$, —(C=O)$OR^5$, —S—$R^5$, —(S=O)$R^5$, —$SO_2R^5$, and $R^6$. In a yet further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —$CH_2$—(C=O)$R^5$, —$CH_2$—(C=O)$OR^5$, —$CH_2$—S—$R^5$, —$CH_2$—(S=O)$R^5$, —$CH_2$—$SO_2R^5$, —(C=O)$R^5$, —(C=O)$OR^5$, —S—$R^5$, —(S=O)$R^5$, —$SO_2R^5$, and $R^6$.

In a further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, -methyl, ethyl, propyl, isopropyl, tert-butyl, sec-butyl, isobutyl, tert-butyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$OCH(CH_2CH_3)(CH_3)$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$(CH_2)_3$—(C=O)$CH_3$, —$(CH_2)_2$—(C=O)$CH_3$, —$CH_2$—(C=O)$CH_3$, —$(CH_2)_3$—(C=O)$OCH_3$, —$(CH_2)_2$—(C=O)$OCH_3$, —$CH_2$—(C=O)$OCH_3$, —$(CH_2)_3$—S—$CH_3$, —$(CH_2)_2$—S—$CH_3$, —$CH_2$—S—$CH_3$, —$(CH_2)_3$—(S=O)$CH_3$, —$(CH_2)_2$—(S=O)$CH_3$, —$CH_2$—(S=O)$CH_3$, —$(CH_2)_3$—$SO_2CH_3$, —$(CH_2)_2$—$SO_2CH_3$, —$CH_2$—$SO_2CH_3$, —(C=O)$CH_3$, —(C=O)$OCH_3$, —S—$CH_3$, —(S=O)$CH_3$, —$SO_2CH_3$, —C(OH)($CF_3$)$CH_3$, —C($CF_3$)($NH_2$)$CH_3$, —C($CF_3$)(CN)$CH_3$, —C($CF_3$)$_2CH_3$, —CF(OH)$CH_3$, —CF($NH_2$)$CH_3$, —CF(CN)$CH_3$, —C(OH)($NH_2$)$CH_3$, —C(OH)(CN)$CH_3$, and —C(CN)($NH_2$)$CH_3$. In a still further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, -methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_2CH_3)_2$, —$(CH_2)_2$—(C=O)$CH_3$, —$CH_2$—(C=O)$CH_3$, —$(CH_2)_2$—(C=O)$OCH_3$, —$CH_2$—(C=O)$OCH_3$, —$(CH_2)_2$—S—$CH_3$, —$CH_2$—S—$CH_3$, —$(CH_2)_2$—(S=O)$CH_3$, —$CH_2$—(S=O)$CH_3$, —$(CH_2)_2$—$SO_2CH_3$, —$CH_2$—$SO_2CH_3$, —(C=O)$CH_3$, —(C=O)$OCH_3$, —S—$CH_3$, —(S=O)$CH_3$, —$SO_2CH_3$, —C(OH)($CF_3$)$CH_3$, —C($CF_3$)($NH_2$)$CH_3$, —C($CF_3$)(CN)$CH_3$, —C($CF_3$)$_2CH_3$, —CF(OH)$CH_3$, —CF($NH_2$)$CH_3$, —CF(CN)$CH_3$, —C(OH)($NH_2$)$CH_3$, —C(OH)(CN)$CH_3$, and —C(CN)($NH_2$)$CH_3$ In a yet further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, -methyl, ethyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$CH_2$—(C=O)$CH_3$, —$CH_2$—(C=O)$OCH_3$, —$CH_2$—S—$CH_3$, —$CH_2$—(S=O)$CH_3$, —$CH_2$—$SO_2CH_3$, —(C=O)$CH_3$, —(C=O)$OCH_3$, —S—$CH_3$, —(S=O)$CH_3$, —$SO_2CH_3$, —C(OH)($CF_3$)$CH_3$, —C($CF_3$)($NH_2$)$CH_3$, —C($CF_3$)(CN)$CH_3$, —C($CF_3$)$_2CH_3$, —CF(OH)$CH_3$, —CF($NH_2$)$CH_3$, —CF(CN)$CH_3$, —C(OH)($NH_2$)$CH_3$, —C(OH)(CN)$CH_3$, and —C(CN)($NH_2$)$CH_3$. In an even further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —$NH_2$, —OH, —CN, -methyl, —$CH_2F$, —$CHF_2$, —$CF_3$, —$OCH_3$, —$NHCH_3$, —$N(CH_3)_2$, —$(CH_2)$—(C=O)$CH_3$, —$(CH_2)$—(C=O)$OCH_3$, —$(CH_2)$—S—$CH_3$, —$(CH_2)$—(S=O)$CH_3$, —$(CH_2)$—$SO_2CH_3$, —(C=O)$CH_3$, —(C=O)$OCH_3$, —(S=O)$CH_3$, —$SO_2CH_3$, —CF($CF_3$)$CH_3$, —C(OH)($CF_3$)$CH_3$, —C($CF_3$)($NH_2$)$CH_3$, —C($CF_3$)(CN)$CH_3$, —C($CF_3$)$_2CH_3$, —CF(OH)$CH_3$, —CF($NH_2$)$CH_3$, —CF(CN)$CH_3$, —C(OH)($NH_2$)$CH_3$, —C(OH)(CN)$CH_3$, and —C(CN)($NH_2$)$CH_3$, and phenyl.

In various aspects, each $Cy^1$, when present, is independently selected from C3-C8 cycloalkyl and C2-C7 heterocycloalkyl, and each $Cy^1$ is independently substituted with 0, 1, 2, or 3 groups independently selected from halogen, —$NH_2$, —OH, —CN, —C1-C8 alkyl, C1-C8 monohaloalkyl, C1-C8 polyhaloalkyl, C1-C8 alkoxy, C1-C8 alkylamino, and C1-C8 dialkylamino, —(C1-C6 alkyl)-S(O)$_mR^5$, —S(O)$_mR^5$, and $R^6$. In a further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from halogen, —$NH_2$, —OH, —CN, —C1-C6 alkyl, C1-C6 monohaloalkyl, C1-C6 polyhaloalkyl, C1-C6 alkoxy, C1-C6 alkylamino, C1-C6 dialkylamino, —(C1-C3 alkyl)-S—$R^5$, —(C1-C3 alkyl)-(S=O)$R^5$, —(C1-C3 alkyl)-$SO_2R^5$, —S—$R^5$, —(S=O)$R^5$, —$SO_2R^5$, and $R^6$. In a still further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from halogen, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —(C1-C3 alkyl)-S—$R^5$, —(C1-C3 alkyl)-(S=O)$R^5$, —(C1-C3 alkyl)-$SO_2R^5$, —S—$R^5$, —(S=O)$R^5$, —$SO_2R^5$, and $R^6$.

In a further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —$(CH_2)_3$—S—$R^5$, —$(CH_2)_2$—S—$R^5$, —$CH_2$—S—$R^5$, —$(CH_2)_3$—(S=O)$R^5$, —$(CH_2)_2$—(S=O)$R^5$, —$CH_2$—(S=O)$R^5$, —$(CH_2)_3$—$SO_2R^5$, —$(CH_2)_2$—$SO_2R^5$, —$CH_2$—$SO_2R^5$, —S—$R^5$, —(S=O)$R^5$, —$SO_2R^5$, and $R^6$. In a still further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —$(CH_2)_2$—S—$R^5$, —$CH_2$—S—$R^5$, —$(CH_2)_2$—(S=O)$R^5$, —$CH_2$—(S=O)$R^5$, —$(CH_2)_2$—$SO_2R^5$, —$CH_2$—$SO_2R^5$, —S—$R^5$, —(S=O)$R^5$, —$SO_2R^5$, and $R^6$. In a yet further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, —C1-C3 alkyl, C1-C3 monohaloalkyl, C1-C3 polyhaloalkyl, C1-C3 alkoxy, C1-C3 alkylamino, C1-C3 dialkylamino, —$CH_2$—S—$R^5$, —$CH_2$—(S=O)$R^5$, —$CH_2$—$SO_2R^5$, —S—$R^5$, —(S=O)$R^5$, —$SO_2R^5$, and $R^6$.

In a further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, -methyl, ethyl, propyl, isopropyl, tert-butyl, sec-butyl, isobutyl, tert-butyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$OCH(CH_2CH_3)(CH_3)$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$(CH_2)_3$—S—$CH_3$, —$(CH_2)_2$—S—$CH_3$, —$CH_2$—S—$CH_3$, —$(CH_2)_3$—(S=O)$CH_3$, —$(CH_2)_2$—(S=O)$CH_3$, —$CH_2$—(S=O)$CH_3$, —$(CH_2)_3$—$SO_2CH_3$, —$(CH_2)_2$—$SO_2CH_3$, —$CH_2$—$SO_2CH_3$, —S—$CH_3$, —(S=O)$CH_3$, —$SO_2CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, and —$C(CN)(NH_2)CH_3$. In a still further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, -methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$OCH_3$, —$OCH_2CH_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_2CH_3)_2$, —$(CH_2)_2$—S—$CH_3$, —$CH_2$—S—$CH_3$, —$(CH_2)_2$—(S=O)$CH_3$, —$CH_2$—(S=O)$CH_3$, —$(CH_2)_2$—$SO_2CH_3$, —$CH_2$—$SO_2CH_3$, —S—$CH_3$, —(S=O)$CH_3$, —$SO_2CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, and —$C(CN)(NH_2)CH_3$ In a yet further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —Cl, —$NH_2$, —OH, —CN, -methyl, ethyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$CH_2$—S—$CH_3$, —$CH_2$—(S=O)$CH_3$, —$CH_2$—$SO_2CH_3$, —S—$CH_3$, —(S=O)$CH_3$, —$SO_2CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, and —$C(CN)(NH_2)CH_3$. In an even further aspect, each $Cy^1$, when present, is independently selected from C3-C8 cycloalkyl and C2-C7 heterocycloalkyl, and each $Cy^1$ is independently substituted with 0, 1, 2, or 3 groups independently selected from —F, —$NH_2$, —OH, —CN, -methyl, —$CH_2F$, —$CHF_2$, —$CF_3$, —$OCH_3$, —$NHCH_3$, —$N(CH_3)_2$, —$CH_2$—(S=O)$CH_3$, —$CH_2$—$SO_2CH_3$, —(S=O)$CH_3$, —$SO_2CH_3$, —$CF(CF_3)CH_3$, —$C(OH)(CF_3)CH_3$, —$C(CF_3)(NH_2)CH_3$, —$C(CF_3)(CN)CH_3$, —$C(CF_3)_2CH_3$, —$CF(OH)CH_3$, —$CF(NH_2)CH_3$, —$CF(CN)CH_3$, —$C(OH)(NH_2)CH_3$, —$C(OH)(CN)CH_3$, and —$C(CN)(NH_2)CH_3$.

kk. $Cy^{20}$ Groups

In one aspect, each $Cy^{20}$, when present, is independently selected from C3-C9 cycloalkyl and C2-C7 heterocycloalkyl, and wherein each $Cy^{20}$ is substituted with 0, 1, 2, or 3 groups independently selected from halogen, —OH, —CN, —$NH_2$, C1-C8 alkyl, C1-C8 alkoxy, C1-C8 haloalkyl, or C1-C8 polyhaloalkyl, C1-C8 alkylamino, C1-C8 dialkylamino, and —$S(O)_mR^{50}$. In a further aspect, each $Cy^{20}$, when present, is independently selected from C3-C9 cycloalkyl and C2-C7 heterocycloalkyl, and wherein each $Cy^{20}$ is substituted with 0, 1, 2, or 3 groups independently selected from halogen, —OH, —CN, —$NH_2$, C1-C6 alkyl, C1-C6 alkoxy, C1-C6 haloalkyl, or C1-C6 polyhaloalkyl, C1-C6 alkylamino, C1-C6 dialkylamino, and —$S(O)_mR^{50}$. In a still further aspect, each $Cy^{20}$, when present, is independently selected from C3-C9 cycloalkyl and C2-C7 heterocycloalkyl, and wherein each $Cy^{20}$ is substituted with 0, 1, 2, or 3 groups independently selected from halogen, —OH, —CN, —$NH_2$, C1-C3 alkyl, C1-C3 alkoxy, C1-C3 haloalkyl, or C1-C3 polyhaloalkyl, C1-C3 alkylamino, C1-C3 dialkylamino, and —$S(O)_mR^{50}$. In a yet further aspect, each $Cy^{20}$, when present, is independently selected from C3-C9 cycloalkyl and C2-C7 heterocycloalkyl, and wherein each $Cy^{20}$ is unsubstituted.

In a further aspect, each $Cy^{20}$, when present, is independently selected from C3-C9 cycloalkyl and C2-C7 heterocycloalkyl, and wherein each $Cy^{20}$ is substituted with 0, 1, or 2 groups independently selected from halogen, —OH, —CN, —$NH_2$, C1-C8 alkyl, C1-C8 alkoxy, C1-C8 haloalkyl, or C1-C8 polyhaloalkyl, C1-C8 alkylamino, C1-C8 dialkylamino, and —$S(O)_mR^{50}$. In a still further aspect, each $Cy^{20}$, when present, is independently selected from C3-C9 cycloalkyl and C2-C7 heterocycloalkyl, and wherein each $Cy^{20}$ is substituted with 0 or 1 group selected from halogen, —OH, —CN, —$NH_2$, C1-C8 alkyl, C1-C8 alkoxy, C1-C8 haloalkyl, or C1-C8 polyhaloalkyl, C1-C8 alkylamino, C1-C8 dialkylamino, and —$S(O)_mR^{50}$. In a yet further aspect, each $Cy^{20}$, when present, is independently selected from C3-C9 cycloalkyl and C2-C7 heterocycloalkyl, and wherein each $Cy^{20}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_m$R$^{50}$. In an even further aspect, each $Cy^{20}$, when present, is independently selected from C3-C9 cycloalkyl and C2-C7 heterocycloalkyl, and wherein each $Cy^{20}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_m$R$^{56}$.

In a further aspect, each $Cy^{20}$, when present, is independently selected from C3-C9 cycloalkyl and C2-C7 heterocycloalkyl, and wherein each $Cy^{20}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each $Cy^{20}$, when present, is independently selected from C3-C9 cycloalkyl and C2-C7 heterocycloalkyl, and wherein each $Cy^{20}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{20}$, when present, is independently selected from C3-C9 cycloalkyl and C2-C7 heterocycloalkyl, and wherein each $Cy^{20}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{20}$, when present, is independently selected from C3-C9 cycloalkyl and C2-C7 heterocycloalkyl, and wherein each $Cy^{20}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each $Cy^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{20}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a still further aspect, each $Cy^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{20}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each $Cy^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{20}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each $Cy^{20}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{20}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each $Cy^{20}$, when present, is cyclopropyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)

$CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, —$S(=O)CH_3$, and —$SO_2CH_3$. In a still further aspect, each $Cy^{20}$, when present, is cyclopropyl and is substituted with 0, 1, 2, or 3 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$S(=O)CH_3$, and —$SO_2CH_3$. In a yet further aspect, each $Cy^{20}$, when present, is cyclopropyl and is substituted with 0, 1, 2, or 3 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$S(=O)CH_3$, and —$SO_2CH_3$. In an even further aspect, each $Cy^{20}$, when present, is cyclopropyl and is substituted with 0, 1, 2, or 3 groups independently selected from —F, —Cl, —$NH_2$, —OH, —CN, methyl, —$CF_3$, —$CCl_3$, —$OCH_3$, —$NHCH_3$, —$S(=O)CH_3$, and —$SO_2CH_3$.

In various further aspects, each $Cy^{20}$, when present, is cyclopropyl and is monosubstituted with a group selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, —$S(=O)CH_3$, and —$SO_2CH_3$. In a still further aspect, each $Cy^{20}$, when present, is cyclopropyl and is monosubstituted with a group selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, $N(CH_2CH_3)_2$, —$S(=O)CH_3$, and —$SO_2CH_3$. In a yet further aspect, each $Cy^{20}$, when present, is cyclopropyl and is monosubstituted with a group selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$S(=O)CH_3$, and —$SO_2CH_3$. In an even further aspect, each $Cy^{20}$, when present, is cyclopropyl and is monosubstituted with a group selected from —F, —Cl, —$NH_2$, —OH, —CN, methyl, —$CF_3$, —$CCl_3$, —$OCH_3$, —$NHCH_3$, —$S(=O)CH_3$, and —$SO_2CH_3$.

In various further aspects, each $Cy^{20}$, when present, is azetidinyl and is substituted with 0, 1, 2, or 3 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, —$S(=O)CH_3$, and —$SO_2CH_3$. In a still further aspect, each $Cy^{20}$, when present, is azetidinyl and is substituted with 0, 1, 2, or 3 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$S(=O)CH_3$, and —$SO_2CH_3$. In a yet further aspect, each $Cy^{20}$, when present, is azetidinyl and is substituted with 0, 1, 2, or 3 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$S(=O)CH_3$, and —$SO_2CH_3$. In an even further aspect, each $Cy^{20}$, when present, is azetidinyl and is substituted with 0, 1, 2, or 3 groups independently selected from —F, —Cl, —$NH_2$, —OH, —CN, methyl, —$CF_3$, —$CCl_3$, —$OCH_3$, —$NHCH_3$, —$S(=O)CH_3$, and —$SO_2CH_3$.

In various further aspects, each $Cy^{20}$, when present, is azetidinyl and is monosubstituted with a group selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, —$S(=O)CH_3$, and —$SO_2CH_3$. In a still further aspect, each $Cy^{20}$, when present, is azetidinyl and is monosubstituted with a group selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{20}$, when present, is azetidinyl and is monosubstituted with a group selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{20}$, when present, is azetidinyl and is monosubstituted with a group selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

ll. Cy$^{30}$ Groups

In one aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_m$R$^{65}$. In a further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from halogen, —OH, —CN, —NH$_2$, C1-C6 alkyl, C1-C6 alkoxy, C1-C6 haloalkyl, or C1-C6 polyhaloalkyl, C1-C6 alkylamino, C1-C6 dialkylamino, and —S(O)$_m$R$^{65}$. In a still further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from halogen, —OH, —CN, —NH$_2$, C1-C3 alkyl, C1-C3 alkoxy, C1-C3 haloalkyl, or C1-C3 polyhaloalkyl, C1-C3 alkylamino, C1-C3 dialkylamino, and —S(O)$_m$R$^{65}$. In a yet further aspect, each Cy$^{30}$, when present, is independently selected from C3-C9 cycloalkyl and C2-C7 heterocycloalkyl, and wherein each Cy$^{30}$ is unsubstituted.

In a further aspect, each Cy$^{30}$, when present, is independently selected from C3-C9 cycloalkyl and C2-C7 heterocycloalkyl, and wherein each Cy$^{30}$ is substituted with 0, 1, or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_m$R$^{65}$. In a still further aspect, each Cy$^{30}$, when present, is independently selected from C3-C9 cycloalkyl and C2-C7 heterocycloalkyl, and wherein each Cy$^{30}$ is substituted with 0 or 1 group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_m$R$^{65}$. In a yet further aspect, each Cy$^{30}$, when present, is independently selected from C3-C9 cycloalkyl and C2-C7 heterocycloalkyl, and wherein each Cy$^{30}$ is substituted with 1 or 2 groups independently selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_m$R$^{65}$. In an even further aspect, each Cy$^{30}$, when present, is independently selected from C3-C9 cycloalkyl and C2-C7 heterocycloalkyl, and wherein each Cy$^{30}$ is monosubstituted with a group selected from halogen, —OH, —CN, —NH$_2$, C1-C8 alkyl, C1-C8 alkoxy, C1-C8 haloalkyl, or C1-C8 polyhaloalkyl, C1-C8 alkylamino, C1-C8 dialkylamino, and —S(O)$_m$R$^{65}$.

In a further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S═O)CH$_3$, and —SO$_2$CH$_3$. In a still further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S═O)CH$_3$, and —SO$_2$CH$_3$. In a yet further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S═O)CH$_3$, and —SO$_2$CH$_3$. In an even further aspect, each Cy$^{30}$, when present, is independently selected from C3-C9 cycloalkyl and C2-C7 heterocycloalkyl, and wherein each Cy$^{30}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S═O)CH$_3$, and —SO$_2$CH$_3$.

In various further aspects, each Cy$^{30}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{30}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)

$CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, —$(S=O)CH_3$, and —$SO_2CH_3$. In a still further aspect, each $Cy^{30}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{30}$ is substituted with 0, 1, 2, or 3 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$(S=O)CH_3$, and —$SO_2CH_3$. In a yet further aspect, each $Cy^{30}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{30}$ is substituted with 0, 1, 2, or 3 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$(S=O)CH_3$, and —$SO_2CH_3$. In an even further aspect, each $Cy^{30}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein $Cy^{30}$ is substituted with 0, 1, 2, or 3 groups independently selected from —F, —Cl, —$NH_2$, —OH, —CN, methyl, —$CF_3$, —$CCl_3$, —$OCH_3$, —$NHCH_3$, —$(S=O)CH_3$, and —$SO_2CH_3$.

In various further aspects, each $Cy^{30}$, when present, is cyclopropyl and is substituted with 0, 1, 2, or 3 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, —$(S=O)CH_3$, and —$SO_2CH_3$. In a still further aspect, each $Cy^{30}$, when present, is cyclopropyl and is substituted with 0, 1, 2, or 3 groups independently selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$(S=O)CH_3$, and —$SO_2CH_3$. In a yet further aspect, each $Cy^{30}$, when present, is cyclopropyl and is substituted with 0, 1, 2, or 3 groups independently selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$(S=O)CH_3$, and —$SO_2CH_3$. In an even further aspect, each $Cy^{30}$, when present, is cyclopropyl and is substituted with 0, 1, 2, or 3 groups independently selected from —F, —Cl, —$NH_2$, —OH, —CN, methyl, —$CF_3$, —$CCl_3$, —$OCH_3$, —$NHCH_3$, —$(S=O)CH_3$, and —$SO_2CH_3$.

In various further aspects, each $Cy^{30}$, when present, is cyclopropyl and is monosubstituted with a group selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, —$N(CH_2CH_3)_2$, —$N(CH_2CH_3)((CH_2)_2CH_3)$, —$N(CH_2CH_3)(CH(CH_3)_2)$, —$(S=O)CH_3$, and —$SO_2CH_3$. In a still further aspect, each $Cy^{30}$, when present, is cyclopropyl and is monosubstituted with a group selected from —F, —Cl, —$NH_2$, —OH, —CN, methyl, ethyl, propyl, isopropyl, —$CH_2F$, —$CH_2Cl$, —$CH_2CH_2F$, —$CH_2CH_2Cl$, —$(CH_2)_2CH_2F$, —$(CH_2)_2CH_2Cl$—$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$NH(CH_2)_3CH_3$, —$N(CH_3)_2$, —$N(CH_3)CH_2CH_3$, —$N(CH_3)(CH_2)_2CH_3$, —$N(CH_3)CH(CH_3)_2$, $N(CH_2CH_3)_2$, —$(S=O)CH_3$, and —$SO_2CH_3$. In a yet further aspect, each $Cy^{30}$, when present, is cyclopropyl and is monosubstituted with a group selected from —F, —Cl, —$NH_2$, —OH, —CN, methyl, —$CH_2F$, —$CH_2Cl$, —$CHF_2$, —$CF_3$, —$CHCl_2$, —$CCl_3$, —$OCH_3$, —$NHCH_3$, —$N(CH_3)_2$, —$(S=O)CH_3$, and —$SO_2CH_3$. In an even further aspect, each $Cy^{30}$, when present, is cyclopropyl and is monosubstituted with a group selected from —F, —Cl, —$NH_2$, —OH, —CN, methyl, —$CF_3$, —$CCl_3$, —$OCH_3$, —$NHCH_3$, —$(S=O)CH_3$, and —$SO_2CH_3$.

In various further aspects, each $Cy^{30}$, when present, is azetidinyl and is substituted with 0, 1, 2, or 3 groups independently selected from —F, —Cl, —$NH_2$, —OH, —CN, methyl, ethyl, propyl, isopropyl, tert-butyl, sec-butyl, isobutyl, tert-butyl, neopentyl, isopentyl, sec-pentyl, tert-pentyl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)_2(CH_3)$, —$NHCH_3$, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃. In a still further aspect, each Cy³⁰, when present, is azetidinyl and is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, —(S=O)CH₃, and —SO₂CH₃. In a yet further aspect, each Cy³⁰, when present, is azetidinyl and is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy³⁰, when present, is azetidinyl and is substituted with 0, 1, 2, or 3 groups independently selected from —F, —Cl, —NH₂, —OH, —CN, methyl, —CF₃, —CCl₃, —OCH₃, —NHCH₃, —(S=O)CH₃, and —SO₂CH₃.

In various further aspects, each Cy³⁰, when present, is azetidinyl and is monosubstituted with a group selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃. In a still further aspect, each Cy³⁰, when present, is azetidinyl and is monosubstituted with a group selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, —(S=O)CH₃, and —SO₂CH₃. In a yet further aspect, each Cy³⁰, when present, is azetidinyl and is monosubstituted with a group selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy³⁰, when present, is azetidinyl and is monosubstituted with a group selected from —F, —Cl, —NH₂, —OH, —CN, methyl, —CF₃, —CCl₃, —OCH₃, —NHCH₃, —(S=O)CH₃, and —SO₂CH₃.

mm. Cy⁴⁰ Groups

In one aspect, each Cy⁴⁰, when present, is independently selected from C3-C9 cycloalkyl and C2-C7 heterocycloalkyl, and wherein each Cy⁴⁰ is substituted with 0, 1, 2, or 3 groups independently selected from halogen, —OH, —CN, —NH₂, C1-C8 alkyl, C1-C8 alkoxy, C1-C8 haloalkyl, or C1-C8 polyhaloalkyl, C1-C8 alkylamino, C1-C8 dialkylamino, and —S(O)ₘR⁶⁶. In a further aspect, each Cy⁴⁰, when present, is independently selected from C3-C9 cycloalkyl and C2-C7 heterocycloalkyl, and wherein each Cy⁴⁰ is substituted with 0, 1, 2, or 3 groups independently selected from halogen, —OH, —CN, —NH₂, C1-C6 alkyl, C1-C6 alkoxy, C1-C6 haloalkyl, or C1-C6 polyhaloalkyl, C1-C6 alkylamino, C1-C6 dialkylamino, and —S(O)ₘR⁶⁶. In a still further aspect, each Cy⁴⁰, when present, is independently selected from C3-C9 cycloalkyl and C2-C7 heterocycloalkyl, and wherein each Cy⁴⁰ is substituted with 0, 1, 2, or 3 groups independently selected from halogen, —OH, —CN, —NH₂, C1-C3 alkyl, C1-C3 alkoxy, C1-C3 haloalkyl, or C1-C3 polyhaloalkyl, C1-C3 alkylamino, C1-C3 dialkylamino, and —S(O)ₘR⁶⁶. In a yet further aspect, each Cy⁴⁰, when present, is independently selected from C3-C9 cycloalkyl and C2-C7 heterocycloalkyl, and wherein each Cy⁴⁰ is unsubstituted.

In a further aspect, each Cy⁴⁰, when present, is independently selected from C3-C9 cycloalkyl and C2-C7 heterocycloalkyl, and wherein each Cy⁴⁰ is substituted with 0, 1, or 2 groups independently selected from halogen, —OH, —CN, —NH₂, C1-C8 alkyl, C1-C8 alkoxy, C1-C8 haloalkyl, or C1-C8 polyhaloalkyl, C1-C8 alkylamino, C1-C8 dialkylamino, and —S(O)ₘR⁶⁶. In a still further aspect, each Cy⁴⁰, when present, is independently selected from C3-C9 cycloalkyl and C2-C7 heterocycloalkyl, and wherein each Cy⁴⁰ is substituted with 0 or 1 group selected from halogen, —OH, —CN, —NH₂, C1-C8 alkyl, C1-C8 alkoxy, C1-C8 haloalkyl, or C1-C8 polyhaloalkyl, C1-C8 alkylamino, C1-C8 dialkylamino, and —S(O)ₘR⁶⁶. In a yet further aspect, each Cy⁴⁰, when present, is independently selected from C3-C9 cycloalkyl and C2-C7 heterocycloalkyl, and wherein each Cy⁴⁰ is substituted with 1 or 2 groups independently selected from halogen, —OH, —CN, —NH₂, C1-C8 alkyl, C1-C8 alkoxy, C1-C8 haloalkyl, or C1-C8 polyhaloalkyl, C1-C8 alkylamino, C1-C8 dialkylamino, and —S(O)ₘR⁶⁶. In an even further aspect, each Cy⁴⁰, when present, is independently selected from C3-C9 cycloalkyl and C2-C7 heterocycloalkyl, and wherein each Cy⁴⁰ is monosubstituted with a group selected from halogen, —OH, —CN, —NH₂, C1-C8 alkyl, C1-C8 alkoxy, C1-C8 haloalkyl, or C1-C8 polyhaloalkyl, C1-C8 alkylamino, C1-C8 dialkylamino, and —S(O)ₘR⁶⁶.

In a further aspect, each Cy⁴⁰, when present, is independently selected from C3-C9 cycloalkyl and C2-C7 heterocycloalkyl, and wherein each Cy⁴⁰ is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each Cy$^{40}$, when present, is independently selected from C3-C9 cycloalkyl and C2-C7 heterocycloalkyl, and wherein each Cy$^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each Cy$^{40}$, when present, is independently selected from C3-C9 cycloalkyl and C2-C7 heterocycloalkyl, and wherein each Cy$^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each Cy$^{40}$, when present, is independently selected from C3-C9 cycloalkyl and C2-C7 heterocycloalkyl, and wherein each Cy$^{40}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each Cy$^{40}$, when present, is selected from cyclopropyl, cyclobutyl, cyclopentyl, cyclohexyl, azetidinyl, pyrrolidinyl, tetrahydrofuranyl, piperidinyl, azepanyl, diazetidinyl, pyrazolidinyl, imidazolidinyl, piperazinyl, and morpholinyl; and wherein Cy$^{40}$ is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each Cy$^{40}$, when present, is cyclopropyl and is substituted with 0, 1, 2, or 3 groups independently selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —N(CH$_2$CH$_3$)((CH$_2$)$_2$CH$_3$), —N(CH$_2$CH$_3$)(CH(CH$_3$)$_2$), —(S=O)CH$_3$, and —SO$_2$CH$_3$. In a still further aspect, each Cy$^{40}$, when present, is cyclopropyl and is substituted with 0, 1, 2, or 3 groups independently selected from —F, —Cl, —NH$_2$, —OH, —CN, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl—CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, —(S=O)CH$_3$, and —SO$_2$CH$_3$. In a yet further aspect, each Cy$^{40}$, when present, is cyclopropyl and is substituted with 0, 1, 2, or 3 groups independently selected from —F, —Cl, —NH$_2$, —OH, —CN, methyl, —CH$_2$F, —CH$_2$Cl, —CHF$_2$, —CF$_3$, —CHCl$_2$, —CCl$_3$, —OCH$_3$, —NHCH$_3$, —N(CH$_3$)$_2$, —(S=O)CH$_3$, and —SO$_2$CH$_3$. In an even further aspect, each Cy$^{40}$, when present, is cyclopropyl and is substituted with 0, 1, 2, or 3 groups independently selected from —F, —Cl, —NH$_2$, —OH, —CN, methyl, —CF$_3$, —CCl$_3$, —OCH$_3$, —NHCH$_3$, —(S=O)CH$_3$, and —SO$_2$CH$_3$.

In various further aspects, each Cy$^{40}$, when present, is cyclopropyl and is monosubstituted with a group selected from —F, —Cl, —NH$_2$, —OH, —CN, methyl, ethyl, propyl, isopropyl, tert-butyl, sec-butyl, isobutyl, tert-butyl, neopentyl, isopentyl, sec-pentyl, tert-pentyl, —CH$_2$F, —CH$_2$Cl, —CH$_2$Br, —CH$_2$I, —CH$_2$CH$_2$F, —CH$_2$CH$_2$Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃. In a still further aspect, each Cy⁴⁰, when present, is cyclopropyl and is monosubstituted with a group selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, N(CH₂CH₃)₂, —(S=O)CH₃, and —SO₂CH₃. In a yet further aspect, each Cy⁴⁰, when present, is cyclopropyl and is monosubstituted with a group selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy⁴⁰, when present, is cyclopropyl and is monosubstituted with a group selected from —F, —Cl, —NH₂, —OH, —CN, methyl, —CF₃, —CCl₃, —OCH₃, —NHCH₃, —(S=O)CH₃, and —SO₂CH₃.

In various further aspects, each Cy⁴⁰, when present, is azetidinyl and is substituted with 0, 1, 2, or 3 groups independently selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃. In a still further aspect, each Cy⁴⁰, when present, is azetidinyl and is substituted with 0, 1, 2, or 3 groups independently selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, —(S=O)CH₃, and —SO₂CH₃. In a yet further aspect, each Cy⁴⁰, when present, is azetidinyl and is substituted with 0, 1, 2, or 3 groups independently selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy⁴⁰, when present, is azetidinyl and is substituted with 0, 1, 2, or 3 groups independently selected from —F, —Cl, —NH₂, —OH, —CN, methyl, —CF₃, —CCl₃, —OCH₃, —NHCH₃, —(S=O)CH₃, and —SO₂CH₃.

In various further aspects, each Cy⁴⁰, when present, is azetidinyl and is monosubstituted with a group selected from —F, —Cl, —NH₂, —OH, —CN, methyl, ethyl, propyl, isopropyl, tert-butyl, sec-butyl, isobutyl, tert-butyl, neopentyl, isopentyl, sec-pentyl, tert-pentyl, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —OCH₃, —OCH₂CH₃, —O(CH₂)₂CH₃, —OCH(CH₃)₂, —OCH(CH₂CH₃)₂(CH₃), —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, —N(CH₂CH₃)((CH₂)₂CH₃), —N(CH₂CH₃)(CH(CH₃)₂), —(S=O)CH₃, and —SO₂CH₃. In a still further aspect, each Cy⁴⁰, when present, is azetidinyl and is monosubstituted with a group selected from —F, —Cl, —NH₂, —OH, —CN, methyl, ethyl, propyl, isopropyl, —CH₂F, —CH₂Cl, —CH₂CH₂F, —CH₂CH₂Cl, —(CH₂)₂CH₂F, —(CH₂)₂CH₂Cl—CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —NHCH₃, —NHCH₂CH₃, —NH(CH₂)₂CH₃, —NHCH(CH₃)₂, —NH(CH₂)₃CH₃, —N(CH₃)₂, —N(CH₃)CH₂CH₃, —N(CH₃)(CH₂)₂CH₃, —N(CH₃)CH(CH₃)₂, —N(CH₂CH₃)₂, —(S=O)CH₃, and —SO₂CH₃. In a yet further aspect, each Cy⁴⁰, when present, is azetidinyl and is monosubstituted with a group selected from —F, —Cl, —NH₂, —OH, —CN, methyl, —CH₂F, —CH₂Cl, —CHF₂, —CF₃, —CHCl₂, —CCl₃, —OCH₃, —NHCH₃, —N(CH₃)₂, —(S=O)CH₃, and —SO₂CH₃. In an even further aspect, each Cy⁴⁰, when present, is azetidinyl and is monosubstituted with a group selected from —F, —Cl, —NH₂, —OH, —CN, methyl, —CF₃, —CCl₃, —OCH₃, —NHCH₃, —(S=O)CH₃, and —SO₂CH₃.

2. Example Compounds

In one aspect, a compound can be present as one or more of the following structures:

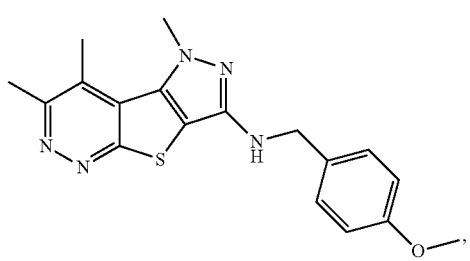

-continued
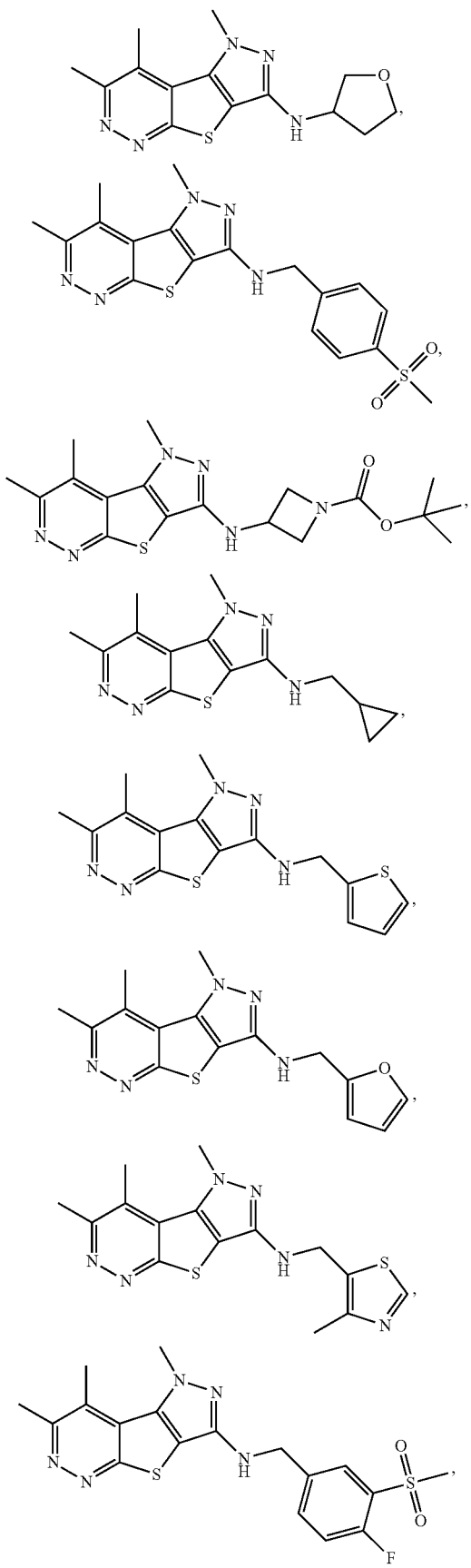
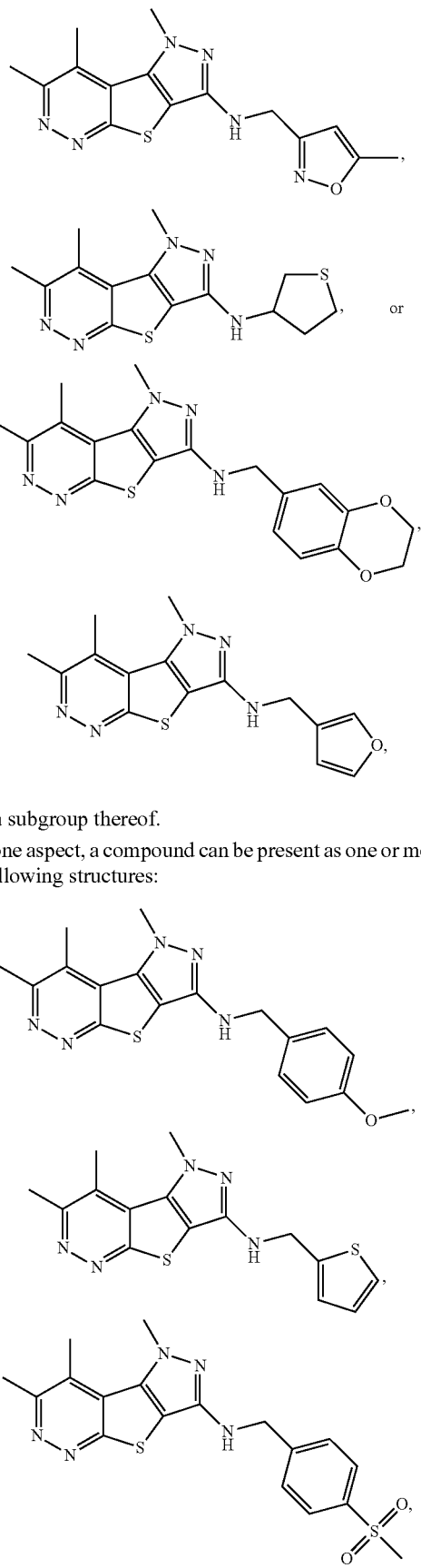
or a subgroup thereof.
In one aspect, a compound can be present as one or more of the following structures:

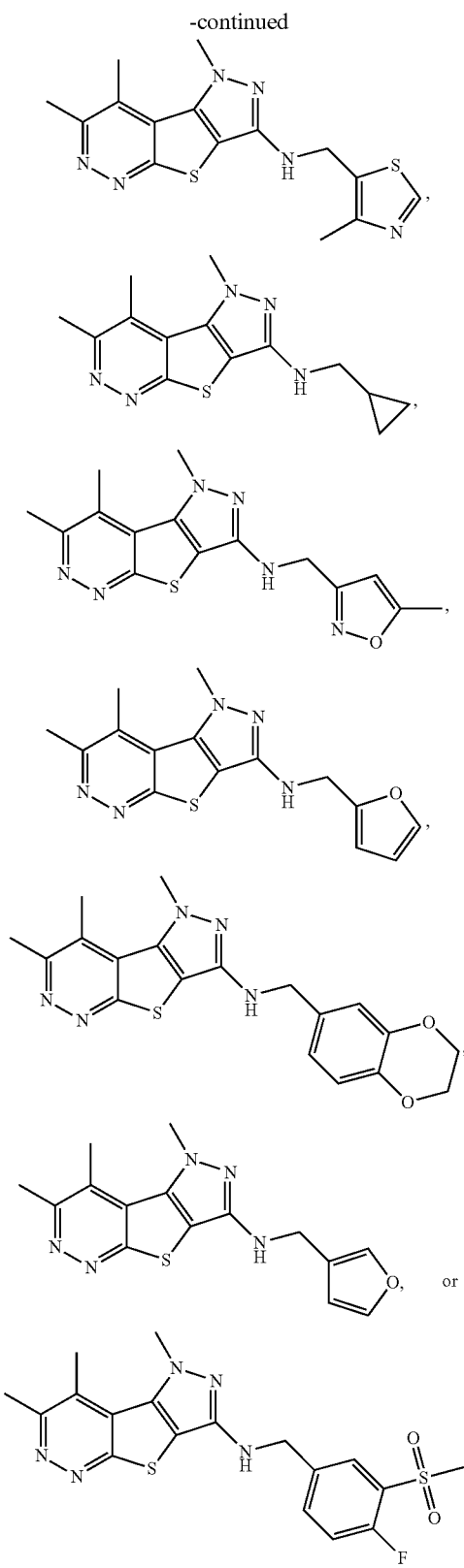
or a subgroup thereof.
In one aspect, a compound can be present as one or more of the following structures:
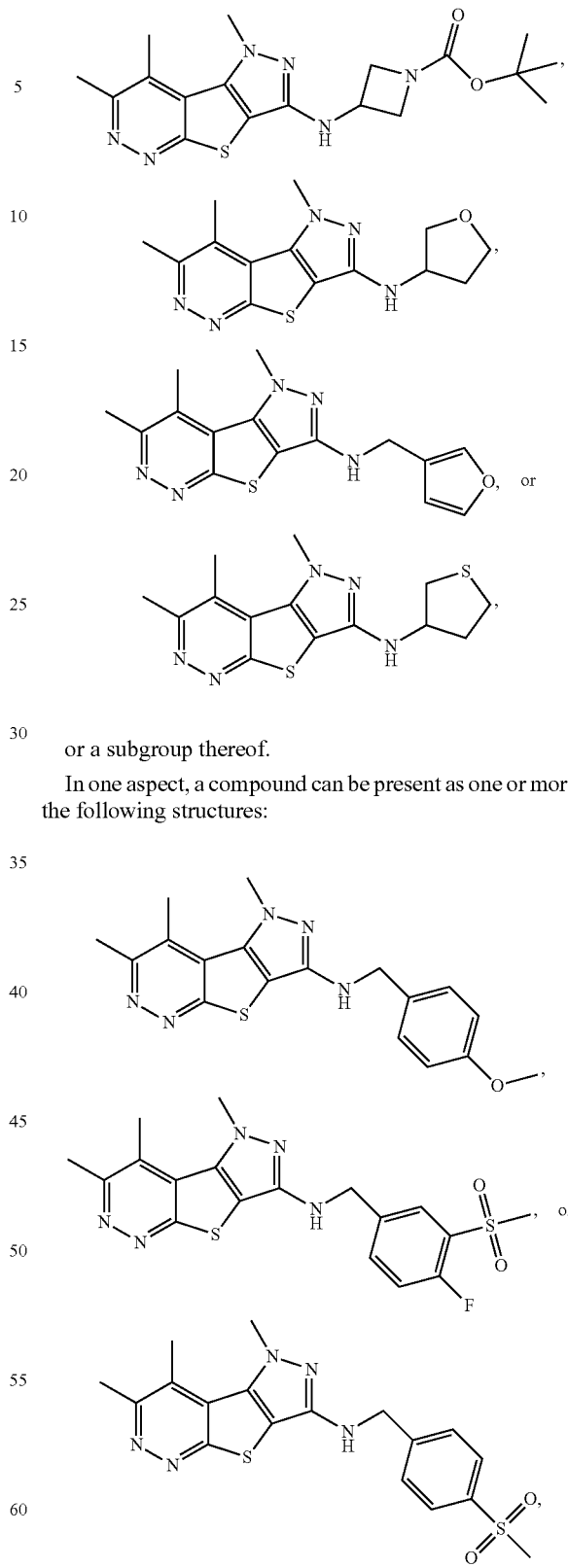
or a subgroup thereof.
In one aspect, a compound can be present as one or more of the following structures:

317
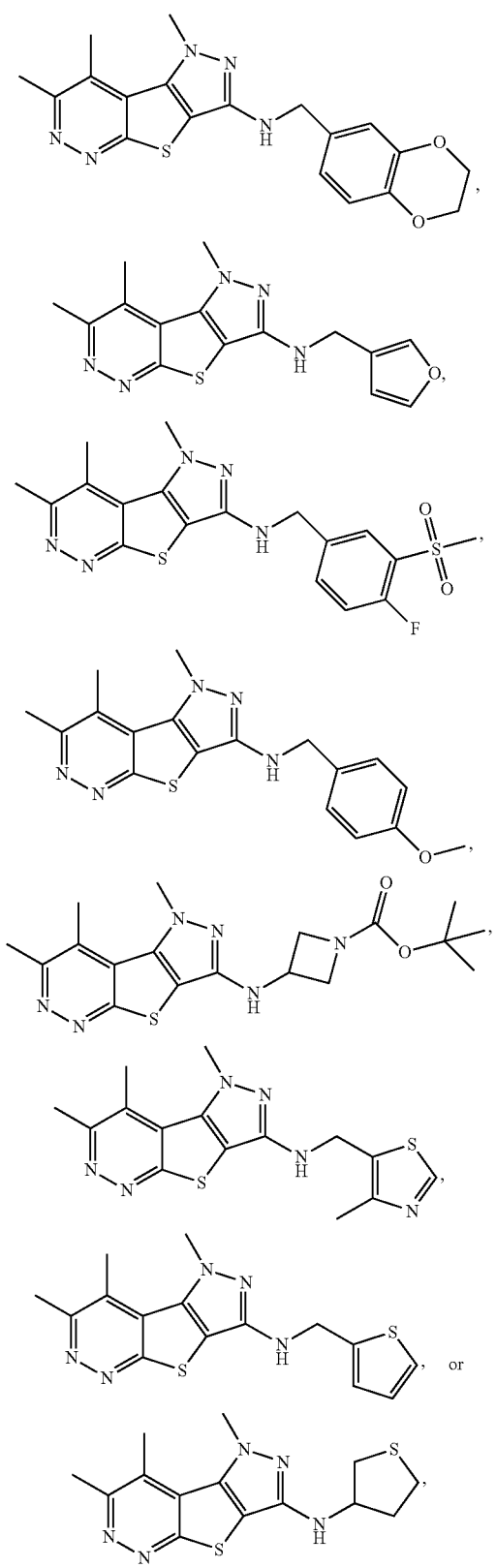
or a subgroup thereof.
In one aspect, a compound can be present as one or more of the following structures:
318
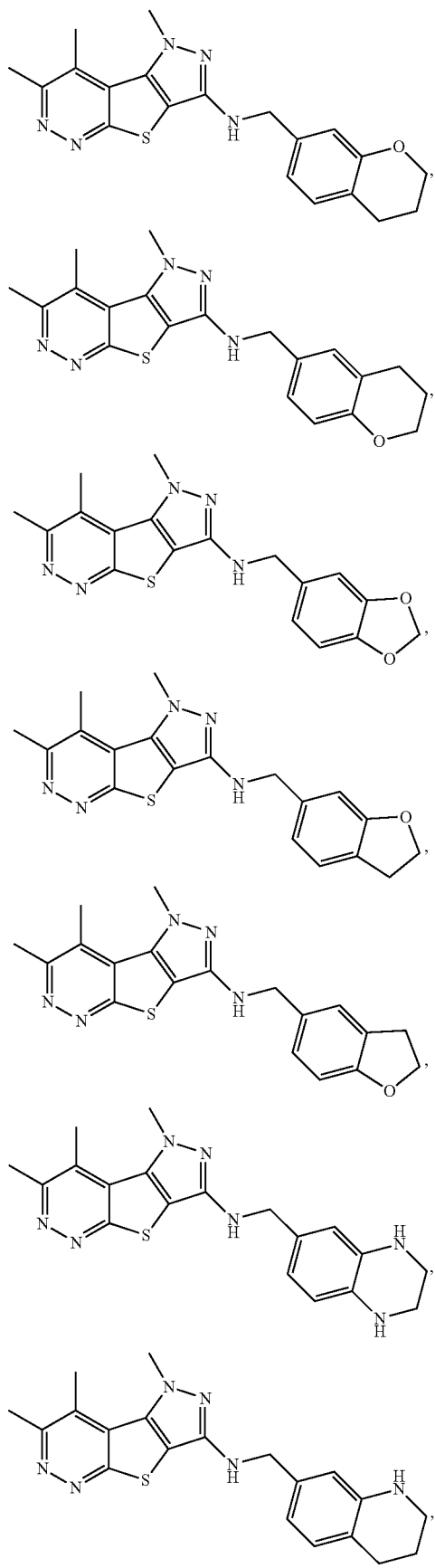

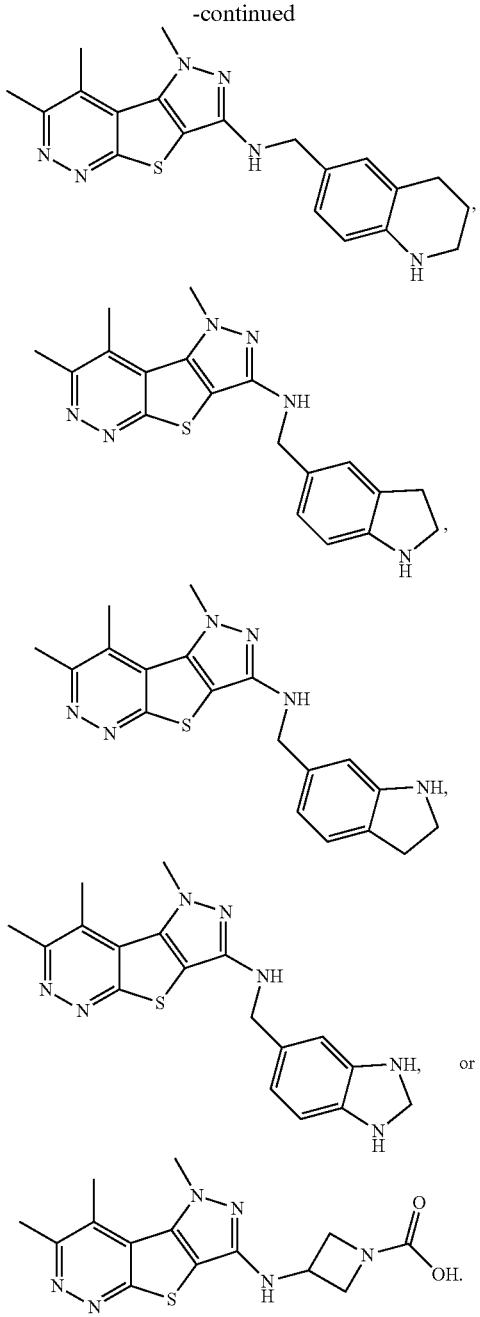

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

3. Muscarinic Acetylcholine Receptor $M_4$ Activity

The human muscarinic acetylcholine receptor $M_4$ (mAChR $M_4$) is a protein of 479 amino acids encoded by the CHRM4 gene. The molecular weight of the unglycosylated protein is about 54 kDa and it is a transmembrane GPCR. As described above, the mAChR $M_4$ is a member of the GPCR Class 1 family, or the rhodopsin-like GPCRs, which are characterized by structural features similar to rhodopsin such as seven transmembrane segments. The muscarinic acetylcholine receptors have the N-terminus oriented to the extracellular face of the membrane and the C-terminus located on the cytoplasmic face. A schematic of the structure of mAChR $M_4$ is shown in FIG. 1, with the transmembrane segments shown as cylindrical shapes (which span the lipid bilayer of the cell membrane). The orthosteric binding for natural ligand, acetylcholine, for mAChRs is within a pocket located in the transmembrane segments as depicted in FIG. 1.

In one aspect, the disclosed compounds potentiate the agonist response (e.g., acetylcholine) of mAChR $M_4$. In a further aspect, the disclosed compounds increase mAChR $M_4$ response to non-maximal concentrations of agonist in the presence of compound compared to the response to agonist in the absence of compound. The potentiation of mAChR $M_4$ activity, can be demonstrated by methodology known in the art. For example, activation of mAChR $M_4$ activity can be determined by measurement of calcium flux in response to agonist, e.g. acetylcholine, in cells loaded with a $Ca^{2+}$-sensitive fluorescent dye (e.g., Fluo-4). In a further aspect, the calcium flux was measured as an increase in fluorescent static ratio. In a yet further aspect, positive allosteric modulator activity was analyzed as a concentration-dependent increase in the $EC_{20}$ acetylcholine response (i.e. the response of mAChR $M_4$ at a concentration of acetylcholine that yields 20% of the maximal response).

In one aspect, the disclosed compounds activate mAChR $M_4$ response as an increase in calcium fluorescence in mAChR $M_4$-transfected CHO-K1 cells in the presence of the compound, compared to the response of equivalent CHO-K1 cells in the absence of the compound. In a further aspect, a disclosed compound activates the mAChR $M_4$ response with an $EC_{50}$ of less than about 10 µM, of less than about 5 µM, of less than about 1 µM, of less than about 500 nM, of less than about 100 nM, or of less than about 50 nM. In a further aspect, the mAChR $M_4$-transfected CHO-K1 cells are transfected with human mAChR $M_4$. In a still further aspect, the mAChR $M_4$-transfected CHO-K1 cells are transfected with rat mAChR $M_4$.

In one aspect, the disclosed compounds exhibit positive allosteric modulation of mAChR $M_4$ response to acetylcholine as an increase in response to non-maximal concentrations of acetylcholine in CHO-K1 cells transfected with a mAChR $M_4$ in the presence of the compound, compared to the response to acetylcholine in the absence of the compound. In a yet further aspect, the disclosed compounds exhibit positive allosteric modulation of the mAChR $M_4$ response to acetylcholine with an $EC_{50}$ of less than about 10,000 nM. In an even further aspect, the disclosed compounds exhibit positive allosteric modulation of the mAChR $M_4$ response to acetylcholine with an $EC_{50}$ of less than about 5,000 nM. In a still further aspect, the disclosed compounds exhibit positive allosteric modulation of the mAChR $M_4$ response to acetylcholine with an $EC_{50}$ of less than about 1,000 nM. In a yet further aspect, the disclosed compounds exhibit positive allosteric modulation of the mAChR $M_4$ response to acetylcholine with an $EC_{50}$ of less than about 500 nM. In an even further aspect, the disclosed compounds exhibit positive allosteric modulation of the mAChR $M_4$ response to acetylcholine with an $EC_{50}$ of less than about 100 nM. In a still further aspect, the $EC_{50}$ for positive allosteric modulation is determined in CHO-K1 cells are transfected with a mAChR $M_4$. In a yet further aspect, the mAChR $M_4$ transfected human mAChR $M_4$. In a still further aspect, the mAChR $M_4$ transfected rat mAChR $M_4$.

Without wishing to be bound by a particular theory, the disclosed compounds and products of the disclosed methods are believed to bind to an allosteric site distinct from the orthosteric binding site. Further, without wishing to be bound by particular theory, the disclosed compounds and products of the disclosed methods bind to an allosteric site that comprises portions of one or more extracellular loops and transmembrane segments distinct from the orthosteric binding site. For example, a disclosed compound can bind at the binding site as illustrated in FIG. 1.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly-conserved.

In various further aspects, the compound activates mAChR $M_4$ response in mAChR $M_4$-transfected CHO-K1 cells with an $EC_{50}$ less than the $EC_{50}$ for one or more of mAChR $M_1$, $M_2$, $M_3$ or $M_5$-transfected CHO-K1 cells That is, a disclosed compound can have selectivity for the mAChR $M_4$ receptor vis-à-vis one or more of the mAChR $M_1$, $M_2$, $M_3$ or $M_5$ receptors. For example, in one aspect, a disclosed compound can activate mAChR $M_4$ response with an $EC_{50}$ of about 5-fold less than that for mAChR $M_1$, of about 10-fold less than that for mAChR $M_1$, of about 20-fold less than that for mAChR $M_1$, of about 30-fold less than that for mAChR $M_1$, of about 50-fold less than that for mAChR $M_1$, of about 100-fold less than that for mAChR $M_1$, of about 200-fold less than that for mAChR $M_1$, of about 300-fold less than that for mAChR $M_1$, of about 400-fold less than that for mAChR $M_1$, or greater than about 500-fold less than that for mAChR $M_1$. In a further aspect, a disclosed compound can activate mAChR $M_4$ response with an $EC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, of about 50-fold less than that for mAChR $M_2$, of about 100-fold less than that for mAChR $M_2$, of about 200-fold less than that for mAChR $M_2$, of about 300-fold less than that for mAChR $M_2$, of about 400-fold less than that for mAChR $M_2$, or greater than about 500-fold less than that for mAChR $M_2$. In a further aspect, a disclosed compound can activate mAChR $M_4$ response with an $EC_{50}$ of about 5-fold less than that for mAChR $M_3$, of about 10-fold less than that for mAChR $M_3$, of about 20-fold less than that for mAChR $M_3$, of about 30-fold less than that for mAChR $M_3$, of about 50-fold less than that for mAChR $M_3$, of about 100-fold less than that for mAChR $M_3$, of about 200-fold less than that for mAChR $M_3$, of about 300-fold less than that for mAChR $M_3$, of about 400-fold less than that for mAChR $M_3$, or greater than about 500-fold less than that for mAChR $M_3$. In a further aspect, a disclosed compound can activate mAChR $M_4$ response with an $EC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, of about 50-fold less than that for mAChR $M_5$, of about 100-fold less than that for mAChR $M_5$, of about 200-fold less than that for mAChR $M_5$, of about 300-fold less than that for mAChR $M_5$, of about 400-fold less than that for mAChR $M_5$, or greater than about 500-fold less than that for mAChR $M_5$. In a further aspect, a disclosed compound can activate mAChR $M_4$ response with an $EC_{50}$ of 5-fold less than that for the mAChR $M_1$, $M_2$, $M_3$, or $M_5$ receptors, of about 10-fold less than that for the mAChR $M_1$, $M_2$, $M_3$, or $M_5$ receptors, of about 20-fold less than that for the mAChR $M_1$, $M_2$, $M_3$, or $M_5$ receptors, of about 30-fold less than that for the $M_2$-$M_5$ receptors, of about 50-fold less than that for the mAChR $M_1$, $M_2$, $M_3$, or $M_5$ receptors, of about 100-fold less than that for the mAChR $M_1$, $M_2$, $M_3$, or $M_5$ receptors, of about 200-fold less than that for the mAChR $M_1$, $M_2$, $M_3$, or $M_5$ receptors, of about 300-fold less than that for the mAChR $M_1$, $M_2$, $M_3$, or $M_5$ receptors, of about 400-fold less than that for the mAChR $M_1$, $M_2$, $M_3$, or $M_5$ receptors, or greater than about 500-fold less than that for the mAChR $M_1$, $M_2$, $M_3$, or $M_5$ receptors.

In various further aspects, the compound activates mAChR $M_4$ response in $M_1$-transfected CHO-K1 cells with an $EC_{50}$ of less than about 10 µM and exhibits a selectivity for the $M_1$ receptor vis-à-vis one or more of the mAChR $M_1$, $M_2$, $M_3$, or $M_5$ receptors. For example, in one aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_1$, of about 10-fold less than that for mAChR $M_1$, of about 20-fold less than that for mAChR $M_1$, of about 30-fold less than that for mAChR $M_1$, of about 50-fold less than that for mAChR $M_1$, of about 100-fold less than that for mAChR $M_1$, of about 200-fold less than that for mAChR $M_1$, of about 300-fold less than that for mAChR $M_1$, of about 400-fold less than that for mAChR $M_1$, or greater than about 500-fold less than that for mAChR $M_1$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, of about 50-fold less than that for mAChR $M_2$, of about 100-fold less than that for mAChR $M_2$, of about 200-fold less than that for mAChR $M_2$, of about 300-fold less than that for mAChR $M_2$, of about 400-fold less than that for mAChR $M_2$, or greater than about 500-fold less than that for mAChR $M_2$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_3$, of about 10-fold less than that for mAChR $M_3$, of about 20-fold less than that for mAChR $M_3$, of about 30-fold less than that for mAChR $M_3$, of about 50-fold less than that for mAChR $M_3$, of about 100-fold less than that for mAChR $M_3$, of about 200-fold less than that for mAChR $M_3$, of about 300-fold less than that for mAChR $M_3$, of about 400-fold less than that for mAChR $M_3$, or greater than about 500-fold less than that for mAChR $M_3$. In a further aspect, the compound can have an $EC_{50}$ of less than about 10 µM, of less than about 5 µM, of less than about 1 µM, of less than about 500 nM, of less than about 100 nM, or of less than about 50 nM; and the compound can also activate mAChR $M_4$ response with an $EC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, of about 50-fold less than that for mAChR $M_5$, of about 100-fold less than that for mAChR $M_5$, of about 200-fold less than that for mAChR $M_5$, of about 300-fold less than that for mAChR $M_5$, of about 400-fold less than that for mAChR $M_5$, or greater than about 500-fold less than that for mAChR $M_5$. In a further aspect, the compound can have an $EC_{50}$ of less than about 10 μM, of less than about 5 μM, of less than about 1 μM, of less than about 500 nM, of less than about 100 nM, or of less than about 50 nM; and the compound can also activate mAChR $M_4$ response with $EC_{50}$ of 5-fold less than that for the mAChR $M_1$, $M_2$, $M_3$, or $M_5$ receptors, of about 10-fold less than that for the mAChR $M_1$, $M_2$, $M_3$, or $M_5$ receptors, of about 20-fold less than that for the mAChR $M_1$, $M_2$, $M_3$, or $M_5$ receptors, of about 30-fold less than that for the $M_2$-$M_5$ receptors, of about 50-fold less than that for the mAChR $M_1$, $M_2$, $M_3$, or $M_5$ receptors, of about 100-fold less than that for the mAChR $M_1$, $M_2$, $M_3$, or $M_5$ receptors, of about 200-fold less than that for the mAChR $M_1$, $M_2$, $M_3$, or $M_5$ receptors, of about 300-fold less than that for the mAChR $M_1$, $M_2$, $M_3$, or $M_5$ receptors, of about 400-fold less than that for the mAChR $M_1$, $M_2$, $M_3$, or $M_5$ receptors, or greater than about 500-fold less than that for the mAChR $M_1$, $M_2$, $M_3$, or $M_5$ receptors.

In vivo efficacy for disclosed compounds can be measured in a number of preclinical rat behavioral models where known, clinically useful antipsychotics display similar positive responses. For example, disclosed compounds are anticipated to reverse amphetamine-induced hyperlocomotion in male Sprague-Dawley rats at doses ranging from 1 to 100 mg/kg p.o.

C. METHODS OF MAKING THE COMPOUNDS

In one aspect, the invention relates to methods of making compounds useful as positive allosteric activators of the mAChR $M_4$ receptor, which can be useful in the treatment neurological and psychiatric disorders associated with muscarinic acetylcholine dysfunction and other diseases in which muscarinic acetylcholine receptors are involved. In one aspect, the invention relates to the disclosed synthetic manipulations. In a further aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Tautomers and Positional Isomers

It is appreciated that certain disclosed compounds can be present as an equilibrium mixture of tautomers. For example, in certain aspects, the invention relates to compounds having structures represented by a formula:

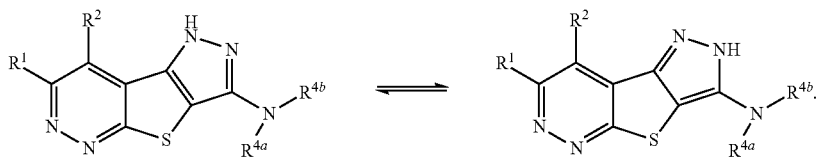

It is further appreciated that N-substitution (e.g., N-alkylation) of the equilibrium of tautomers can provide both of the corresponding N-substitution products as positional isomers:

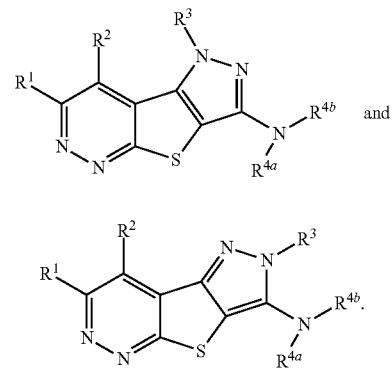

It is even further appreciated that the corresponding N-substitution products can be separated to provide either of the two corresponding N-substitution products. For example, in certain aspects, the invention relates to a compound having a structure represented by a formula:

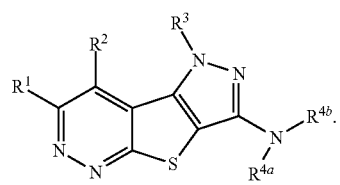

As a further example, in certain aspects, the invention relates to a compound having a structure represented by a formula:

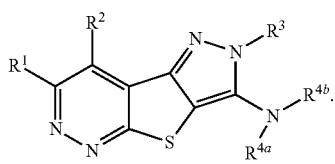

Thus, it is understood that, when a compound having the structure represented by a formula:

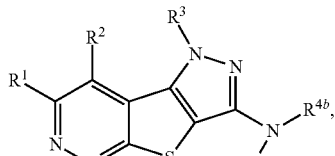

is described, the disclosed methods can, if desired, be applied to the other tautomer in order to provide a compound having a structure represented by a formula:

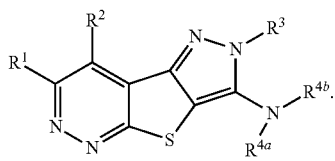

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

2. Route I

In one aspect, substituted pyrazolo[3',4':4,5]thieno[2,3-c]pyridazine-3-amine analogs of the present invention can be prepared generically by the synthetic scheme as shown below.

SCHEME 1A

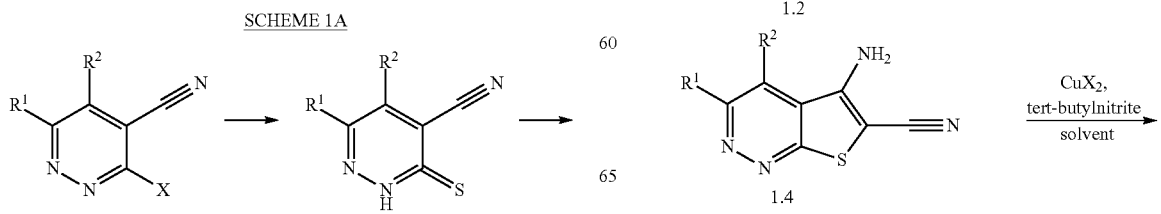

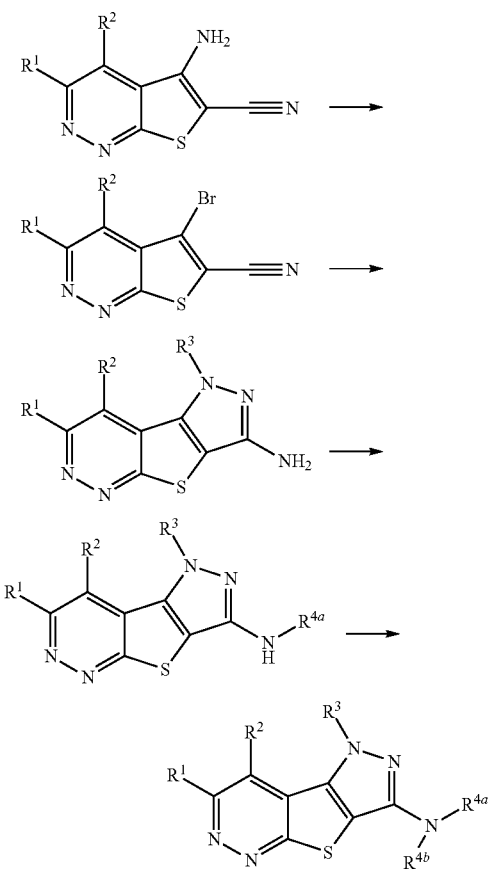

X is halogen

Compounds are represented in generic form, with substituents as noted in compound descriptions elsewhere herein. A more specific example is set forth below.

SCHEME 1B

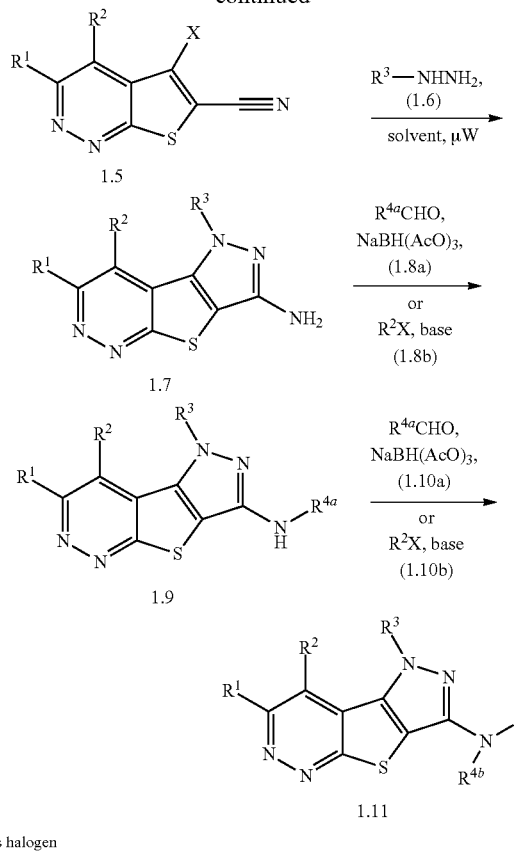

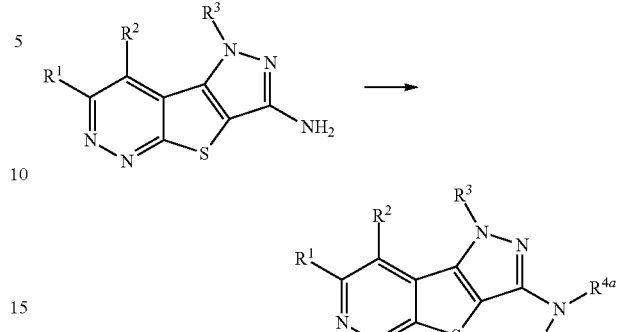

SCHEME 2A

Compounds are represented in generic form, with substituents as noted in compound descriptions elsewhere herein. A more specific example is set forth below.

SCHEME 2B

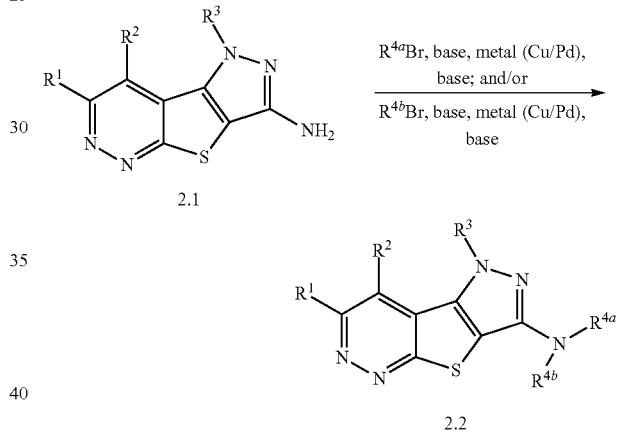

$X^1$ is halogen

X is halogen

In one aspect, Route I begins with converting a 3-halopyrridazine-4-carbonitrile (1.1) to the corresponding 3-thioxo-2,3,dihydropyridazine-4-carbonitrile (1.2) by reaction with sodium sulfide. Suitable 3-halo-pyridazine-4-carbonitriles are commercially available or can be prepared by methods known to one skilled in the art. A 5-amino-thieno[2,3-c]pyridazine-6-carbonitrile (1.4) is formed by reacting a 3-thioxo-2,3,dihydropyridazine-4-carbonitrile (1.2) with a haloacetonitrile. The resultant amine (1.4) can be halogenated (e.g., brominated) to yield the corresponding 5-halothieno[2,3-c]pyridazine-6-carbonitrile (1.5), which compound can be treated with hydrazine (or $R^3$-substituted analog thereof (1.6)) to provide the 1H-pyrazolo[3',4':4,5]thieno[2,3-c]pyridazin-3-amine (1.7).

Compound (1.7) can be modified at the amine moiety, e.g. monoalkylated or dialkylated. Alkylation can be performed in a single step of in two steps. It is appreciated that alkylation can be accomplished by, e.g., nucleophilic substitution (reaction with RX) or by reductive amination. If desired, when $R^3$ is hydrogen, the ring nitrogen can be protected before alkylation and deprotected after alkylation. In a further aspect, when $R^3$ is hydrogen, the ring nitrogen can be subsequently substituted (e.g., alkylated), if desired. In a further aspect, the order of steps can be appropriately modified by one skilled in the art.

3. Route II

In one aspect, substituted pyrazolo[3',4':4,5]thieno[2,3-c] pyridazine-3-amine analogs of the present invention can be prepared generically by the synthetic scheme as shown below.

In one aspect, Route II involves arylation or heteroarylation of compound (2.1) to yield compound (2.2) (i.e. wherein R4a and/or R4b are $Ar^1$ comprising a halo moiety available for the coupling reaction). More specifically, compound (2.1) can, if desired, be monoarylated or diarylated. Further, compound (2.1) can, if desired, be monoheteroarylated or diheteroarylated. In a further aspect, (2.1) can, if desired, be monoarylated and monoheteroarylated.

The (hetero)arylation(s) can be performed in a single step of in two steps. It is appreciated that these transformations can be accomplished by, e.g., metal-mediated coupling reaction with an appropriate aryl halide or heteroaryl halide. If desired, when $R^3$ is hydrogen, the ring nitrogen can be protected before coupling and deprotected after coupling. In a further aspect, when $R^3$ is hydrogen, the ring nitrogen can be subsequently substituted (e.g., alkylated), if desired. In a further aspect, the order of steps can be appropriately modified by one skilled in the art.

4. Route III

In one aspect, substituted pyrazolo[3',4':4,5]thieno[2,3-c] pyridazine-3-amine analogs of the present invention can be prepared generically by the synthetic scheme as shown below.

SCHEME 3A
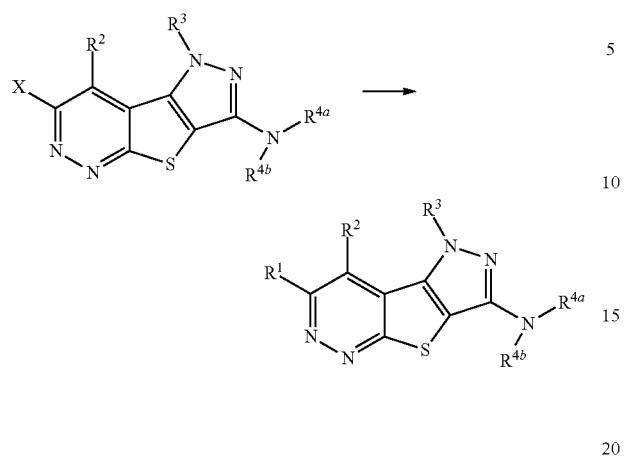
SCHEME 3b
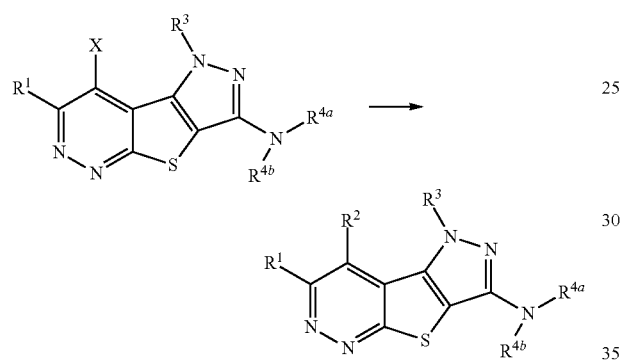
SCHEME 3c
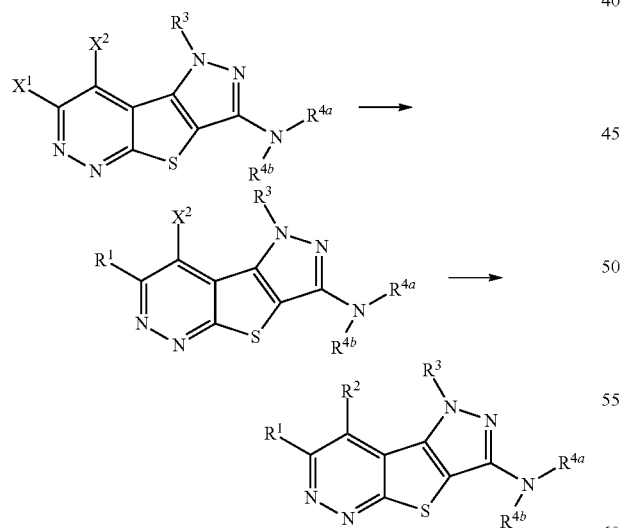
SCHEME 3d
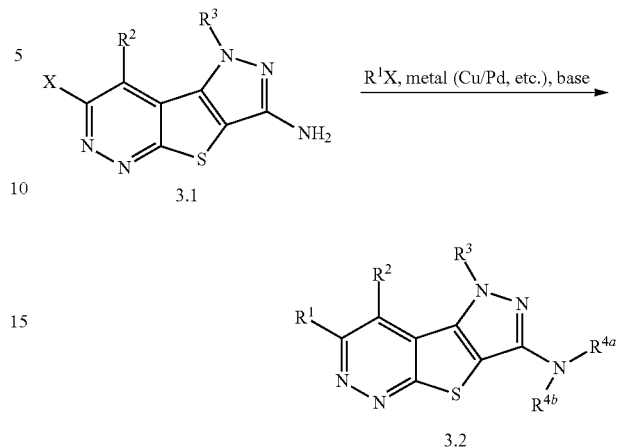
SCHEME 3e
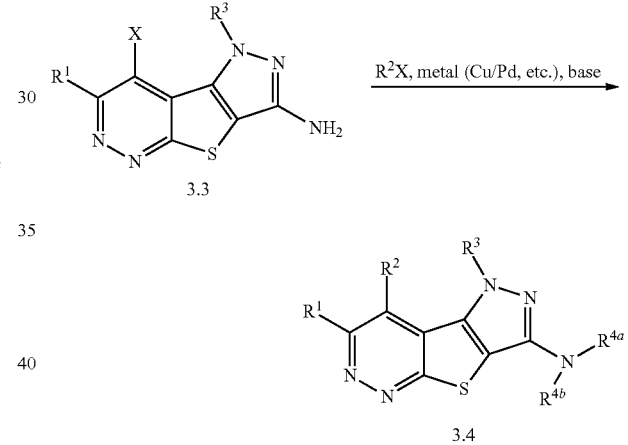
SCHEME 3f
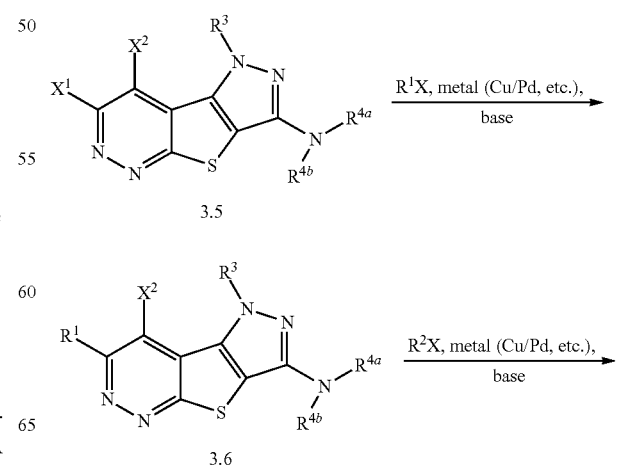
Compounds are represented in generic form, with substituents as noted in compound descriptions elsewhere herein. A more specific example is set forth below.

-continued

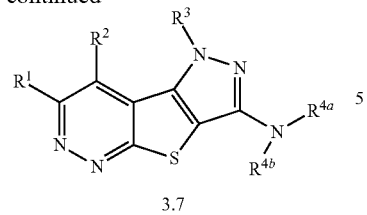

3.7

Compounds are represented in generic form, with substituents as noted in compound descriptions elsewhere herein. In one aspect, Route III involves alkylation of compound (3.1) or (3.3) to yield compounds (3.2) and (3.4), respectively. More specifically, compound (3.1) can, if desired, be substituted upon the pyridazine ring at positions with halogens (shown here as X, $X^1$, and $X^2$), which can be accomplished by, e.g., metal-mediated coupling reaction with an appropriate alkyl halide. If desired, when $R^3$ is hydrogen, the ring nitrogen can be protected before coupling and deprotected after coupling. In a further aspect, when $R^3$ is hydrogen, the ring nitrogen can be subsequently substituted (e.g., alkylated), if desired.

It is contemplated that positional isomerism of the substituents can be selected by appropriate choice of ring halogen. For example, it is appreciated that iodo can be coupled preferentially to bromo, which can be coupled preferentially to chloro. Thus, the order of coupling reaction can achieve selection of substituents $R^1$ and $R^2$, e.g. as shown in the selective alkylation of (3.5) to yield (3.6), followed by alkylation of (3.6) to yield the desired product (3.7). In a further aspect, the order of steps can be appropriately modified by one skilled in the art.

5. Route IV

In one aspect, substituted pyrazolo[3',4':4,5]thieno[2,3-c]pyridazine-3-amine analogs of the present invention can be prepared generically by the synthetic scheme as shown below.

SCHEME 4A

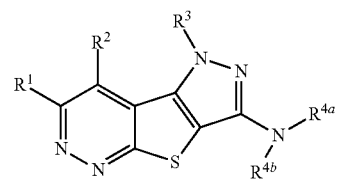

SCHEME 4b

-continued

SCHEME 4c

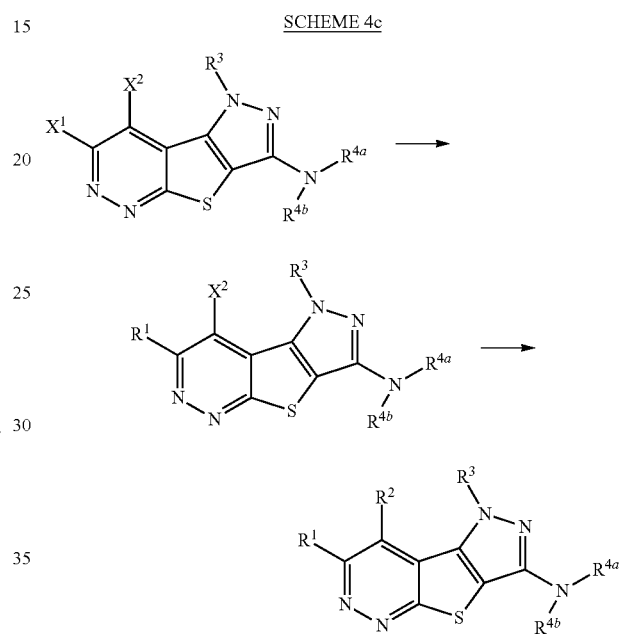

Compounds are represented in generic form, with substituents as noted in compound descriptions elsewhere herein. A more specific example is set forth below.

SCHEME 4d

SCHEME 4e

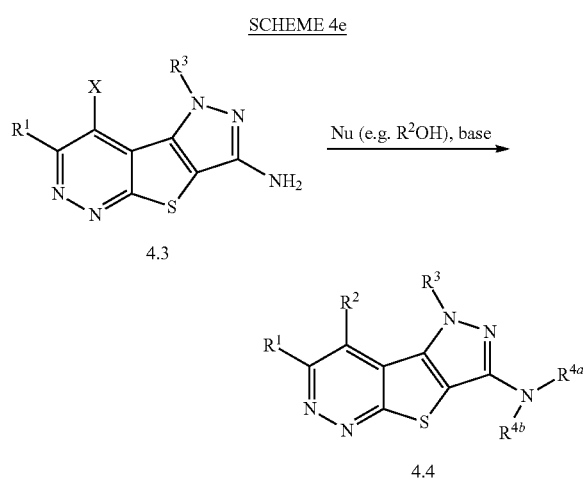

SCHEME 4f

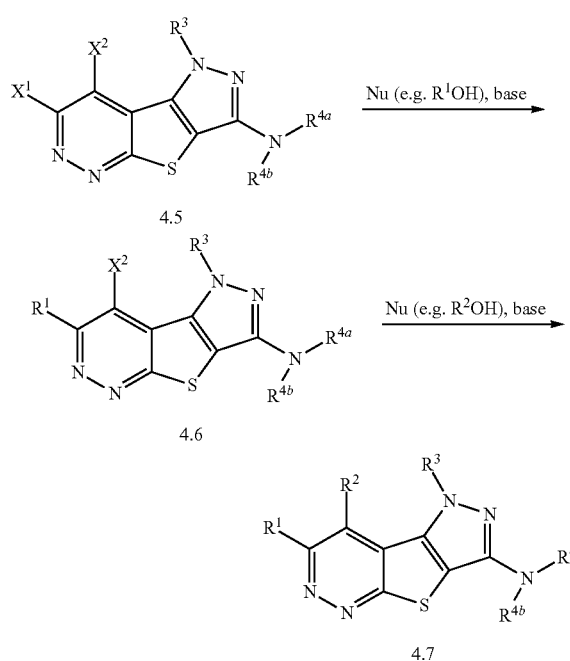

In one aspect, Route IV involves selection of $R^1$ and $R^2$ by employing displacement chemistry. In various aspects, such chemistry can be used to place nucleophilic groups upon the pyridazine ring. For example, nucleophilic displacement reactions with compound (4.1) or (4.3) to yield compounds (4.2) and (4.4), respectively. In the preceding reaction schemes, a halogen is shown here as X, $X^1$, and $X^2$. If desired, when $R^3$ is hydrogen, the ring nitrogen can be protected before coupling and deprotected after coupling. In a further aspect, when $R^3$ is hydrogen, the ring nitrogen can be subsequently substituted (e.g., alkylated), if desired.

It is contemplated that positional isomerism of the substituents can be selected by appropriate choice of ring halogen. For example, it is appreciated that iodo can be coupled preferentially to bromo, which can be coupled preferentially to chloro. Thus, the order of coupling reaction can achieve selection of substituents $R^1$ and $R^2$, e.g. as shown in the selective alkylation of (4.5) to yield (4.6), followed by nucleophilic displacement on (4.6) to yield the desired product (4.7). In a further aspect, the order of steps can be appropriately modified by one skilled in the art.

6. Chiral Resolution

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In one aspect, the disclosed methods of making can provide racemic or scalemic mixtures that can be resolved to pure or substantially pure enantiomers using chiral phase chromatography or other suitable methods known to one skilled in the art. As known to one skilled in the art, a variety specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed.

D. PHARMACEUTICAL COMPOSITIONS

In one aspect, the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and an effective amount of at least one disclosed compound; or a pharmaceutically acceptable salt, hydrate, solvate, or polymorph thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition comprises a disclosed compound. In a yet further aspect, the pharmaceutical composition comprises a product of a disclosed method of making.

In a further aspect, the pharmaceutical composition exhibits positive allosteric modulation of mAChR $M_4$ with an $EC_{50}$ of less than about 10,000 nM. In a still further aspect, the pharmaceutical composition exhibits positive allosteric modulation of mAChR $M_4$ with an $EC_{50}$ of less than about 5,000 nM. In an even further aspect the pharmaceutical composition exhibits positive allosteric modulation of mAChR $M_4$ with an $EC_{50}$ of less than about 1,000 nM. In a further aspect, the pharmaceutical composition exhibits positive allosteric modulation of mAChR $M_4$ with an $EC_{50}$ of less than about 500 nM. In a yet further aspect, the pharmaceutical composition exhibits positive allosteric modulation of mAChR $M_4$ with an $EC_{50}$ of less than about 100 nM. In a further aspect, the pharmaceutical composition exhibits positive allosteric modulation of mAChR $M_4$ with an $EC_{50}$ of between from about 10,000 nM to about 1 nM. In a yet further aspect, the pharmaceutical composition exhibits positive allosteric modulation of mAChR $M_4$ with an $EC_{50}$ of between from about 1,000 nM to about 1 nM. In a still further aspect, the pharmaceutical composition exhibits positive allosteric modulation of mAChR $M_4$ with an $EC_{50}$ of between from about 100 nM to about 1 nM. In an even further aspect, the pharmaceutical composition exhibits positive allosteric modulation of mAChR $M_4$ with an $EC_{50}$ of between from about 10 nM to about 1 nM.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder. In a further aspect, the pharmaceutical composition is used to treat a neurological and/or psychiatric disorder. In a yet further aspect, the disorder is associated with mAChR $M_4$ dysfunction.

In a further aspect, the pharmaceutical composition is used to treat a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the pharmaceutical composition is used to treat a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, the pharmaceutical composition is used to treat a disorder selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carriers) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require positive allosteric modulation of mAChR $M_4$ receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating mAChR $M_4$ receptor activity (e.g., treatment of one or more neurological and/or psychiatric disorder associated with mAChR $M_4$ receptor dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. METHODS OF USING THE COMPOUNDS AND COMPOSITIONS

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with anti-Alzheimer's agents, beta-secretase inhibitors, gamma-secretase inhibitors, orthosteric muscarinic agonists, muscarinic potentiators, cholinesterase inhibitors, HMG-CoA reductase inhibitors, NSAIDs and anti-amyloid antibodies. In a further aspect, the compounds can be administered in combination with sedatives, hypnotics, anxiolytics, antipsychotics (typical and atypical), selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders associated with selective mAChR $M_4$ receptor activation. For example, a treatment can include selective mAChR $M_4$ receptor activation to an extent effective to affect cholinergic activity. Thus, a disorder can be associated with cholinergic activity, for example cholinergic hypofunction. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders associated with mAChR $M_4$ receptor activity in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of a disorder in a mammal comprising the step of administering to the mammal at least one disclosed compound, composition, or medicament.

In one aspect, the disclosed compounds have utility in treating a variety of neurological and psychiatric disorders associated with the mAChR $M_4$ receptor, including one or more of the following conditions or diseases: schizophrenia (paranoid, disorganized, catatonic or undifferentiated), psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, Alzheimer's disease, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, Tourette's syndrome, and anti-NMDA receptor encephalitis. In an even further aspect, the psychotic disorder is due to a general medical condition and substance-induced or drug-induced (phencyclidine, ketamine and other dissociative anesthetics, amphetamine and other psychostimulants and cocaine), In one aspect, the present invention provides a method for treating cognitive disorders, comprising: administering to a patient in need thereof an effective amount of a compound of the present invention. In a further aspect, cognitive disorders include dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In a further specific aspect, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-W-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In a still further aspect, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

In various aspects, the present invention provides a method for treating Huntington's disease comprising administering to a patient in need thereof an effective amount of a compound of the present invention. Huntington's disease (HD) is a neurodegenerative disorder associated with a wide range of progressively worsening symptoms including chorea, motor dysfunction, seizures, impaired cognitive function, memory deficits, dementia, depression, anxiety and a range of other psychiatric disorders. Without wishing to be bound by a particular theory, it is believed that these conditions result from a genetic condition wherein the CAG-repeat region of the huntingtin gene (HTT) contains an abnormally large number of CAG repeats, which then gives rise to a mutated form of the huntingtin protein (mHtt). The mutated huntingtin protein can be toxic to a variety of cells, including, but not limited to, neuronal cells in the brain. It has been reported that the mAChR $M_4$ receptor is selectively co-localized with dopamine receptors on medial striatal spiny projection neurons and in the dorsal and ventral striatum (Jeon, J., et al., J. Neurosci., 2010, 30(6), 2396-2405). Without wishing to be bound by a particular theory, based on the role of dopamine and its function in various regions of the brain related to movement and psychiatric conditions, the disclosed compounds of the present invention can be beneficial in patients with Huntington's disease.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the subject compound can be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound can be administered in conjunction with the use of physical methods such as with light therapy or electrical stimulation.

In a further aspect, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, Ata adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In a further aspect, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In one aspect, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HTJA agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In the treatment of conditions which require activation of mAChR $M_4$ an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to a method for activating mAChR $M_4$ receptor activity in at least one cell comprising the step of contacting the at least one cell with at least one disclosed compound or at least one product of a disclosed method in an amount effective to activate mAChR $M_4$ in the at least one cell. In a further aspect, the cell is mammalian, for example, human. In a further aspect, the cell has been isolated from a subject prior to the contacting step. In a further aspect, contacting is via administration to a subject.

In a further aspect, the invention relates to a method for activating mAChR $M_4$ activity in a subject comprising the step of administering to the subject at least one disclosed compound or at least one product of a disclosed method in a dosage and amount effective to activating mAChR $M_4$ activity in the subject. In a further aspect, the subject is mammalian, for example, human. In a further aspect, the mammal has been diagnosed with a need for mAChR $M_4$ agonism prior to the administering step. In a further aspect, the mammal has been diagnosed with a need for mAChR $M_4$ activation prior to the administering step. In a further aspect, the method further comprises the step of identifying a subject in need of mAChR $M_4$ agonism.

In a further aspect, the invention relates to a method for the treatment of a disorder associated with selective mAChR $M_4$ activation, for example, a disorder associated with cholinergic activity, in a mammal comprising the step of administering to the mammal at least one disclosed compound or at least one product of a disclosed method in a dosage and amount effective to treat the disorder in the mammal. In a further aspect, the mammal is a human. In a further aspect, the mammal has been diagnosed with a need for treatment for the disorder prior to the administering step. In a further aspect, the method further comprises the step of identifying a subject in need of treatment for the disorder.

In one aspect, the disorder can be selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a further aspect, the disorder is Alzheimer's disease. In a further aspect, the disorder is a neurological and/or psychiatric disorder associated with $M_4$ receptor activity dysfunction.

a. Treating a Disorder Associated with Muscarinic Acetylcholine Receptor Activity In one aspect, the invention relates to a method for the treatment of a neurological and/or psychiatric disorder associated with muscarinic acetylcholine receptor dysfunction in a mammal comprising the step of administering to the mammal an effective amount of at least one disclosed compound; or a pharmaceutically acceptable salt, hydrate, solvate, or polymorph thereof.

In a further aspect, the compound administered is a product of a disclosed method of making. In a still further aspect, an effective amount is a therapeutically effective amount. In a yet further aspect, an effective amount is a prophylactically effective amount.

In a further aspect, the compound administered exhibits potentiation of mAChR $M_4$ with an $EC_{50}$ of less than about 10,000 nM. In a still further aspect, the compound administered exhibits potentiation of mAChR $M_4$ with an $EC_{50}$ of less than about 5,000 nM. In an even further aspect, the compound administered exhibits potentiation of mAChR $M_4$ with an $EC_{50}$ of less than about 1,000 nM. In a further aspect, the compound administered exhibits potentiation of mAChR $M_4$ with an $EC_{50}$ of less than about 500 nM. In a yet further aspect, the compound administered exhibits potentiation of mAChR $M_4$ with an $EC_{50}$ of less than about 100 nM.

In a further aspect, the compound administered exhibits potentiation of mAChR $M_4$ with an $EC_{50}$ of between from about 10,000 nM to about 1 nM. In a yet further aspect, the compound administered exhibits potentiation of mAChR $M_4$ with an $EC_{50}$ of between from about 1,000 nM to about 1 nM. In a still further aspect, the compound administered exhibits potentiation of mAChR $M_4$ with an $EC_{50}$ of between from about 100 nM to about 1 nM. In an even further aspect, the compound administered exhibits potentiation of mAChR $M_4$ with an $EC_{50}$ of between from about 10 nM to about 1 nM.

In one aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is a neurological and/or psychiatric disorder associated with a muscarinic receptor dysfunction. In a still further aspect, the muscarinic receptor is mAChR $M_4$. In a yet further aspect, the disorder is a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder.

In a further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the disorder is a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, the disorder is selected from Alzheimer's disease, Parkinson's disease, Huntington's disease, a neurological disorder, a pain disorder and a psychotic disorder. In a still further aspect, the disorder is selected from Alzheimer's disease, Parkinson's disease, Huntington's disease, a pain disorder and a psychotic disorder. In a yet further aspect, the disorder is Alzheimer's disease. In an even further aspect, the disorder is Parkinson's disease. In a still further aspect, the disorder is Huntington's disease. In a yet further aspect, the disorder is a pain disorder. In an even further aspect, the disorder is a neurological disorder.

In a further aspect, the disorder is selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

b. Potentiation of Muscarinic Acetylcholine Receptor Activity

In one aspect, the invention relates to a method for potentiation of muscarinic acetylcholine receptor activity in a mammal comprising the step of administering to the mammal an effective amount of at least one disclosed compound; or a pharmaceutically acceptable salt, hydrate, solvate, or polymorph thereof.

In a further aspect, the compound administered is a product of a disclosed method of making a compound.

In a further aspect, potentiation of muscarinic acetylcholine receptor activity increases muscarinic acetylcholine receptor activity. In a still further aspect, potentiation of muscarinic acetylcholine receptor activity is partial agonism of the muscarinic acetylcholine receptor. In a yet further aspect, potentiation of muscarinic acetylcholine receptor activity is positive allosteric modulation of the muscarinic acetylcholine receptor.

In a further aspect, the compound administered exhibits potentiation of mAChR $M_4$ with an $EC_{50}$ of less than about 10,000 nM. In a still further aspect, the compound administered exhibits potentiation of mAChR $M_4$ with an $EC_{50}$ of less than about 5,000 nM. In an even further aspect, the compound administered exhibits potentiation of mAChR $M_4$ with an $EC_{50}$ of less than about 1,000 nM. In a further aspect, the compound administered exhibits potentiation of mAChR $M_4$ with an $EC_{50}$ of less than about 500 nM. In a yet further aspect, the compound administered exhibits potentiation of mAChR $M_4$ with an $EC_{50}$ of less than about 100 nM.

In a further aspect, the compound administered exhibits potentiation of mAChR $M_4$ with an $EC_{50}$ of between from about 10,000 nM to about 1 nM. In a yet further aspect, the compound administered exhibits potentiation of mAChR $M_4$ with an $EC_{50}$ of between from about 1,000 nM to about 1 nM. In a still further aspect, the compound administered exhibits potentiation of mAChR $M_4$ with an $EC_{50}$ of between from about 100 nM to about 1 nM. In an even further aspect, the compound administered exhibits potentiation of mAChR $M_4$ with an $EC_{50}$ of between from about 10 nM to about 1 nM.

In one aspect, the mammal is a human. In a further aspect, the mammal has been diagnosed with a need for potentiation of muscarinic acetylcholine receptor activity prior to the administering step. In a yet further aspect, the method further comprises the step of identifying a mammal in need of potentiating muscarinic acetylcholine receptor activity. In a still further aspect, the potentiation of muscarinic acetylcholine receptor activity treats a disorder associated with muscarinic acetylcholine receptor activity in the mammal. In an even further aspect, the muscarinic acetylcholine receptor is mAChR $M_4$.

In a further aspect, potentiation of muscarinic acetylcholine receptor activity in a mammal is associated with the treatment of a neurological and/or psychiatric disorder associated with a muscarinic receptor dysfunction. In a yet further aspect, the muscarinic receptor is mAChR $M_4$. In a still further aspect, the disorder is a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, Tourette's syndrome, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the disorder is selected from Alzheimer's disease, Parkinson's disease, Huntington's disease, a neurological disorder, a pain disorder and a psychotic disorder. In a still further aspect, the disorder is selected from Alzheimer's disease, Parkinson's disease, Huntington's disease, Tourette's syndrome, a pain disorder and a psychotic disorder. In a yet further aspect, the disorder is Alzheimer's disease. In an even further aspect, the disorder is Parkinson's disease. In a still further aspect, the disorder is Huntington's disease. In a yet further aspect, the disorder is a pain disorder. In an even further aspect, the disorder is a neurological disorder. In a still further aspect, the disorder is Tourette's syndrome.

In a further aspect, the disorder is a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, disorder is selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

c. Enhancing Cognition

In one aspect, the invention relates to a method for enhancing cognition in a mammal comprising the step of administering to the mammal an effective amount of least one disclosed compound; or a pharmaceutically acceptable salt, hydrate, solvate, or polymorph thereof.

In a further aspect, the compound administered is a product of a disclosed method of making a compound. In a still further aspect, an effective amount is a therapeutically effective amount. In a yet further aspect, an effective amount is a prophylactically effective amount.

In a further aspect, the compound administered exhibits potentiation of mAChR $M_4$ with an $EC_{50}$ of less than about 10,000 nM. In a still further aspect, the compound administered exhibits potentiation of mAChR $M_4$ with an $EC_{50}$ of less than about 5,000 nM. In an even further aspect, the compound administered exhibits potentiation of mAChR $M_4$ with an $EC_{50}$ of less than about 1,000 nM. In a further aspect, the compound administered exhibits potentiation of mAChR $M_4$ with an $EC_{50}$ of less than about 500 nM. In a yet further aspect, the compound administered exhibits potentiation of mAChR $M_4$ with an $EC_{50}$ of less than about 100 nM.

In a further aspect, the compound administered exhibits potentiation of mAChR $M_4$ with an $EC_{50}$ of between from about 10,000 nM to about 1 nM. In a yet further aspect, the compound administered exhibits potentiation of mAChR $M_4$ with an $EC_{50}$ of between from about 1,000 nM to about 1 nM. In a still further aspect, the compound administered exhibits potentiation of mAChR $M_4$ with an $EC_{50}$ of between from about 100 nM to about 1 nM. In an even further aspect, the compound administered exhibits potentiation of mAChR $M_4$ with an $EC_{50}$ of between from about 10 nM to about 1 nM.

In one aspect, the mammal is a human. In a further aspect, the mammal has been diagnosed with a need for cognition enhancement prior to the administering step. In a further aspect, the method further comprises the step of identifying a mammal in need of cognition enhancement. In a further aspect, the need for cognition enhancement is associated with a muscarinic receptor dysfunction. In an even further aspect, the muscarinic receptor is mAChR $M_4$.

In a further aspect, the cognition enhancement is a statistically significant increase in Novel Object Recognition. In a further aspect, the cognition enhancement is a statistically significant increase in performance of the Wisconsin Card Sorting Test.

d. Potentiating Muscarinic Acetylcholine Receptor Activity in Cells

In one aspect, the invention relates to a method for potentiation of muscarinic acetylcholine receptor activity in a mammal comprising the step of administering to the mammal an effective amount of at least one disclosed compound; or a pharmaceutically acceptable salt, hydrate, solvate, or polymorph thereof.

In a further aspect, the compound administered is a product of a disclosed method of making a compound. In a still further aspect, an effective amount is a therapeutically effective amount. In a yet further aspect, an effective amount is a prophylactically effective amount.

In a further aspect, potentiation of muscarinic acetylcholine receptor activity increases muscarinic acetylcholine receptor activity. In a still further aspect, potentiation of muscarinic acetylcholine receptor activity is partial agonism of the muscarinic acetylcholine receptor. In a yet further aspect, potentiation of muscarinic acetylcholine receptor activity is positive allosteric modulation of the muscarinic acetylcholine receptor.

In a further aspect, the compound exhibits potentiation of mAChR $M_4$ with an $EC_{50}$ of less than about 10,000 nM. In a still further aspect, the compound exhibits potentiation of mAChR $M_4$ with an $EC_{50}$ of less than about 5,000 nM. In an even further aspect, the compound exhibits potentiation of mAChR $M_4$ with an $EC_{50}$ of less than about 1,000 nM. In a further aspect, the compound exhibits potentiation of mAChR $M_4$ with an $EC_{50}$ of less than about 500 nM. In a yet further aspect, the compound potentiation of mAChR $M_4$ with an $EC_{50}$ of less than about 100 nM.

In a further aspect, the compound exhibits potentiation of mAChR $M_4$ with an $EC_{50}$ of between from about 10,000 nM to about 1 nM. In a yet further aspect, the compound exhibits potentiation of mAChR $M_4$ with an $EC_{50}$ of between from about 1,000 nM to about 1 nM. In a still further aspect, the compound exhibits potentiation of mAChR $M_4$ with an $EC_{50}$ of between from about 100 nM to about 1 nM. In an even further aspect, the compound exhibits potentiation of mAChR $M_4$ with an $EC_{50}$ of between from about 10 nM to about 1 nM.

In one aspect, the cell is mammalian. In a further aspect, the cell is human. In a still further aspect, the cell has been isolated from a mammal prior to the contacting step. In a yet further aspect, contacting is via administration to a mammal.

In a further aspect, the mammal has been diagnosed with a need for potentiation of muscarinic acetylcholine receptor activity prior to the administering step. In a further aspect, the method further comprises the step of identifying a mammal in need of potentiation of muscarinic acetylcholine receptor activity. In a further aspect, the potentiation of muscarinic acetylcholine receptor activity treats a disorder associated with muscarinic receptor activity in the mammal. In a still further aspect, the muscarinic acetylcholine receptor is mAChR $M_4$.

In a further aspect, potentiation of muscarinic acetylcholine receptor activity in at least one cell is associated with the treatment of a neurological and/or psychiatric disorder associated with mAChR $M_4$ dysfunction. In a still further aspect, the disorder is a psychotic disorder. In a still further aspect, the psychotic disorder is selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the psychotic disorder is selected from schizophrenia, brief psychotic disorder, schizophreniform disorder, schizoaffective disorder, delusional disorder, and shared psychotic disorder. In a still further aspect, the schizophrenia is selected from catastrophic schizophrenia, catatonic schizophrenia, paranoid schizophrenia, residual schizophrenia, disorganized schizophrenia, and undifferentiated schizophrenia. In a yet further aspect, the disorder is selected from schizoid personality disorder, schizotypal personality disorder, and paranoid personality disorder.

In a further aspect, the disorder is selected from Alzheimer's disease, Parkinson's disease, Huntington's disease, a neurological disorder, a pain disorder and a psychotic disorder. In a still further aspect, the disorder is selected from Alzheimer's disease, Parkinson's disease, Huntington's disease, a pain disorder and a psychotic disorder. In a yet further aspect, the disorder is Alzheimer's disease. In an even further aspect, the disorder is Parkinson's disease. In a still further aspect, the disorder is Huntington's disease. In a yet further aspect, the disorder is a pain disorder. In an even further aspect, the disorder is a neurological disorder.

In a further aspect, the disorder is a cognitive disorder. In a still further aspect, the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, disorder is selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

2. Cotherapeutic Methods

The present invention is further directed to administration of a selective mAChR $M_4$ activator for improving treatment outcomes in the context of cognitive or behavioral therapy. That is, in one aspect, the invention relates to a cotherapeutic method comprising the step of administering to a mammal an effective amount and dosage of at least one disclosed compound, or a pharmaceutically acceptable salt, hydrate, solvate, or polymorph thereof.

In a further aspect, the compound administered for the cotherapeutic method is a product of a disclosed method of making. In a still further aspect, an effective amount is a therapeutically effective amount. In a yet further aspect, an effective amount is a prophylactically effective amount.

In a further aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

It is understood that the disclosed cotherapeutic methods can be used in connection with the disclosed compounds, compositions, kits, and uses.

3. Manufacture of a Medicament

In one aspect, the invention relates to a medicament comprising one or more disclosed compounds; or a pharmaceutically acceptable salt, hydrate, solvate, or polymorph thereof. In a further aspect, the one or more compounds are product of a disclosed method of making.

In various aspect, the invention relates methods for the manufacture of a medicament for modulating the activity mAChR $M_4$ (e.g., treatment of one or more neurological and/or psychiatric disorder associated with mAChR $M_4$ dysfunction) in mammals (e.g., humans) comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

4. Use of Compounds

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the compound used exhibits potentiation of mAChR $M_4$ activity with an $EC_{50}$ of less than about 10,000 nM. In a still further aspect, the compound used exhibits potentiation of mAChR $M_4$ activity with an $EC_{50}$ of less than about 5,000 nM. In an even further aspect, the compound used exhibits potentiation of mAChR $M_4$ with an $EC_{50}$ of less than about 1,000 nM. In a further aspect, the compound used exhibits potentiation of mAChR $M_4$ activity with an $EC_{50}$ of less than about 500 nM. In a yet further aspect, the compound used potentiation of mAChR $M_4$ activity with an $EC_{50}$ of less than about 100 nM.

In a further aspect, the compound used exhibits potentiation of mAChR $M_4$ activity with an $EC_{50}$ of between from about 10,000 nM to about 1 nM. In a yet further aspect, the compound used exhibits potentiation of mAChR $M_4$ activity with an $EC_{50}$ of between from about 1,000 nM to about 1 nM. In a still further aspect, the compound used exhibits potentiation of mAChR $M_4$ activity with an $EC_{50}$ of between from about 100 nM to about 1 nM. In an even further aspect, the compound used exhibits potentiation of mAChR $M_4$ activity with an $EC_{50}$ of between from about 10 nM to about 1 nM. In a yet further aspect, potentiation of mAChR $M_4$ activity is positive allosteric modulation of mAChR $M_4$ activity.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for mAChR $M_4$ receptor activation. In one aspect, the use is characterized in that the mammal is a human. In one aspect, the use is characterized in that the disorder is a neurological and/or psychiatric disorder associated with a muscarinic acetylcholine receptor dysfunction. In one aspect, the neurological and/or psychiatric disorder associated with muscarinic acetylcholine receptor dysfunction is treated by potentiation of muscarinic acetylcholine receptor activity in a mammal.

In a further aspect, the use relates to the manufacture of a medicament for the treatment of a disorder associated with a muscarinic acetylcholine receptor dysfunction in a mammal. In a further aspect, the medicament is used in the treatment of a neurological and/or psychiatric disorder associated with a muscarinic acetylcholine receptor dysfunction in a mammal.

In a further aspect, the use relates to potentiation of muscarinic acetylcholine receptor activity in a mammal. In a further aspect, the use relates to partial agonism of muscarinic acetylcholine receptor activity in a mammal. In a further aspect, the use relates to modulating mAChR $M_4$ activity in a mammal. In a still further aspect, the use relates to modulating mAChR $M_4$ activity in a cell. In a yet further aspect, the use relates to partial allosteric agonism of mAChR $M_4$ in a cell. In an even further aspect, the mammal is a human.

In one aspect, the use is associated with the treatment of a neurological and/or psychiatric disorder associated with muscarinic acetylcholine receptor dysfunction. In a further aspect, the use is associated with the treatment of a psychotic disorder. In a still further aspect, the use is associated with the treatment of a psychotic disorder selected from schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In a yet further aspect, the psychotic disorder is a psychosis associated with an illness selected from major depressive disorder, affective disorder, bipolar disorder, electrolyte disorder, neurological disorder, hypoglycemia, AIDS, lupus, and post-traumatic stress disorder. In a yet further aspect, the use is associated with the treatment of a neurological disorder selected from brain tumor, dementia with Lewy bodies, multiple sclerosis, sarcoidosis, Lyme disease, syphilis, Alzheimer's disease, Parkinson's disease, and anti-NMDA receptor encephalitis.

In a further aspect, the use is associated with the treatment of a psychotic disorder selected from schizophrenia, brief psychotic disorder, schizophreniform disorder, schizoaffective disorder, delusional disorder, and shared psychotic disorder. In a still further aspect, the use is associated with the treatment of a schizophrenia selected from catastrophic schizophrenia, catatonic schizophrenia, paranoid schizophrenia, residual schizophrenia, disorganized schizophrenia, and undifferentiated schizophrenia. In a yet further aspect, the use is associated with the treatment of a disorder selected from schizoid personality disorder, schizotypal personality disorder, and paranoid personality disorder.

In a further aspect, the use is associated with the treatment of a disorder is selected from a Alzheimer's disease, Parkinson's disease, Huntington's disease, Tourette's syndrome, a neurological disorder, a pain disorder and a psychotic disorder. In a still further aspect, the disorder is selected from Alzheimer's disease, Parkinson's disease, Huntington's disease, a pain disorder and a psychotic disorder. In a yet further aspect, the disorder is Alzheimer's disease. In an even further aspect, the disorder is Parkinson's disease. In a still further aspect, the disorder is Huntington's disease. In a yet further aspect, the disorder is a pain disorder. In an even further aspect, the disorder is a neurological disorder. In a still further aspect, the disorder is Tourette's syndrome.

In a further aspect, the use is associated with the treatment of a cognitive disorder. In a still further aspect, the use is associated with the treatment of a cognitive disorder selected from amnesia, dementia, delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In a further aspect, the use is associated with the treatment of a disorder selected from conduct disorder, disruptive behavior disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associated with mAChR $M_4$ receptor dysfunction in a mammal. In a further aspect, the disorder is a neurological and/or psychiatric disorder.

5. Kits

In one aspect, the invention relates to kits comprising at least one disclosed compound; or a pharmaceutically acceptable salt, hydrate, solvate, or polymorph thereof, and one or more of:
   (a) at least one agent known to increase mAChR $M_4$ activity;
   (b) at least one agent known to decrease mAChR $M_4$ activity;
   (c) at least one agent known to treat a disorder associated with cholinergic activity;
   (d) instructions for treating a disorder associated with cholinergic activity;
   (e) instructions for treating a disorder associated with $M_4$ receptor activity; or
   (f) instructions for administering the compound in connection with cognitive or behavioral therapy.

In various further aspects, the invention relates to kits comprising at least one disclosed compound and at least one agent known to have $M_4$ receptor agonist activity.

In various further aspects, the invention relates to kits comprising at least one product of a disclosed method of making and at least one agent known to have $M_4$ receptor agonist activity.

In a further aspect, the kit comprises a disclosed compound or a product of a disclosed method of making.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

6. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by activation or modulation of the muscarinic receptor and/or a need for activation or modulation of muscarinic receptor activity prior to the administering step. In some aspects of the disclosed method, the subject has been diagnosed with anxiety or a related disorder prior to the administering step. In some aspects of the disclosed methods, the subject has been identified with a need for treatment prior to the administering step. In some aspects of the disclosed method, the subject has been identified with a disorder treatable by activation of the muscarinic receptor and/or or a need for activation/modulation of muscarinic activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

F. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods $^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard. Coupling constants (J-values) are expressed in Hz units.

Microwave assisted reactions were performed in a single-mode reactor: Emrys™ Optimizer microwave reactor (Personal Chemistry A.B., currently Biotage).

Flash column chromatography was performed using ready-to-connect cartridges from: (a) ISCO, on irregular silica gel, particle size 15-40 μm (normal layer disposable flash columns) on a Companion system from ISCO, Inc.; or, (b) Merck, on irregular silica gel, particle size 15-40 μm (normal layer disposable flash columns) on an SPOT or LAFLASH system from Armen Instrument.

Analytical HPLC was performed on an HP 1100 with UV detection at 214 and 254 nm along with ELSD detection and low resolution mass spectra using an Agilent 1200 series 6130 mass spectrometer.

2. LC-MS Methods

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software. [M+H], means the protonated mass of the free base of the compound and where indicated RT means retention time (in minutes).

In the LC-MS analysis, reversed phase HPLC was carried out on an Agilent 1200 with a Kinetex C18 column (2.6 mm, 2.1×30 mm) from Phenomenex, with a flow rate of 1.5 mL/min, at 45° C. The gradient conditions used are: 93% A (0.1% TFA in water), 7% B (acetonitrile), to 5% A, 95% B in 1.1 minutes. Injection volume was 3.0 μl. Low-resolution ES positive mass spectra (single quadrupole, Agilent 6130) were acquired by scanning from 100 to 700 in 0.25 seconds. The capillary needle voltage was 3 kV.

3. Preparation of Intermediates a. Preparation of 5,6-Dimethyl-3-Thioxo-2,3-Dihydropyridazine-4-Carbonitrile

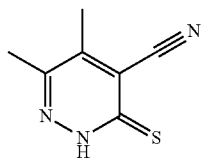

A solution of 3-chloro-5,6-dimethylpyridazine-4-carbonitrile (100 mg, 0.60 mmol) and sodium sulfide was stirred in tert-butanol (2.0 mL) in a microwave reaction vial. The vial was sealed and irradiated at 100° C. for 10 minutes. LC/MS indicated product and no remaining starting material. The reaction solution was diluted with IPA (~10 mL) and stirred at ambient temperature for about 15 minutes, then filtered. The solids on the filter were washed with IPA. The solute was concentrated in vacuo, and the resulting solid was dried overnight at 60° C. in a vacuum oven to give the product. LC/MS: $R_T$=0.24 min., m/z=166 [M+H]$^+$.

b. Preparation of 5-Amino-3,4-Dimethylthieno[2,3-c]Pyridazine-6-Carbonitrile

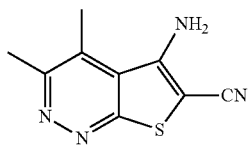

The 5,6,-dimethyl-3-thioxo-2,3-dihydropyridazine-4-carbonitrile (99 mg, 0.60 mmol) was stirred in ethanol (6.0 mL). Sodium acetate (50 mg, 0.60 mmol) and chloroacetonitrile (0.040 mL, 0.60 mmol) were added and the mixture was stirred at ambient temperature for 90 minutes. The mixture was then diluted with IPA, stirred for 15 minutes, and filtered. The solute was concentrated in vacuo, and the resulting solid was dried overnight at 60° C. in a vacuum oven to give the product. LC/MS: $R_T$=0.38 min., m/z=205 [M+H]$^+$.

c. Preparation of 5-Bromo-3,4-Dimethylthieno[2,3-c]Pyridazine-6-Carbonitrile

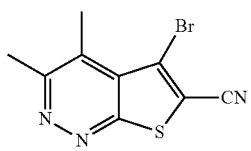

Copper(II) bromide (147 mg, 0.66 mmol) was stirred in acetonitrile (6.0 mL) under argon at ambient temperature. Tert-butyl nitrile (0.10 mL, 0.84 mmol) was added and the mixture was stirred for 10 minutes, then warmed to 60° C. The 5-amino-3,4-dimethylthieno[2,3-c]pyridazine-6-carbonitrile (120 mg, 0.60 mmol) was added and the reaction stirred at 60° C. for about 1.5 hours. The reaction slurry was concentrated in vacuo. The residue was diluted with EtOAc and 10% aqueous NH$_4$OH. The aqueous layer was separated and extracted with EtOAc twice. The combined EtOAc layers were washed with brine, dried over sodium sulfate and con-centrated in vacuo to give the desired product. LC/MS: $R_T$=0.61 min., m/z=268 [M+H]$^+$.

d. Preparation of 1,7,8-Trimethyl-1H-Pyrazole[3',4':4,5]Thieno[2,3-c]Pyridazin-3-Amine

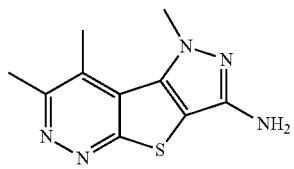 [SMILES: Cc1nnc2sc3c(N)nn(C)c3c2c1C]

The 5-bromo-3,4-dimethylthieno[2,3-c]pyridazine-6-carbonitrile (31 mg, 0.12 mmol) was added to a microwave reaction vial. N-methylpyrrolidone (1.0 mL) was added, followed by methylhydrazine (0.24 mL, 0.46 mmol). The vial was sealed and irradiated in a microwave at 125° C. for 20 min. The reaction was cooled to ambient temperature and then purified, without work up, by reverse-phase HPLC (acetonitrile:water gradient with 0.1% TFA) to give the desired product. LC/MS: $R_T$=0.18 min., m/z=234 [M+H]$^+$.

4. Preparation of N-(4-Methoxybenzyl)-1,7,8-Trimethyl-1H-Pyrazole[3',4':4,5]Thieno[2,3-c]Pyridazin-3-Amine

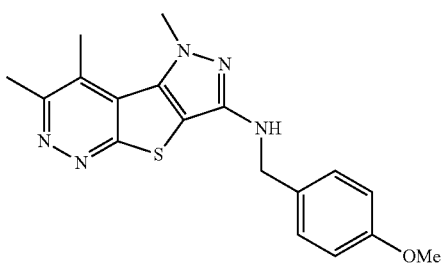 [SMILES: COc1ccc(CNc2nn(C)c3c2sc2nnc(C)c(C)c23)cc1]

The overall synthetic scheme for the preparation of the title compound, including the steps comprising the preparation of the intermediates as described herein above is shown below.

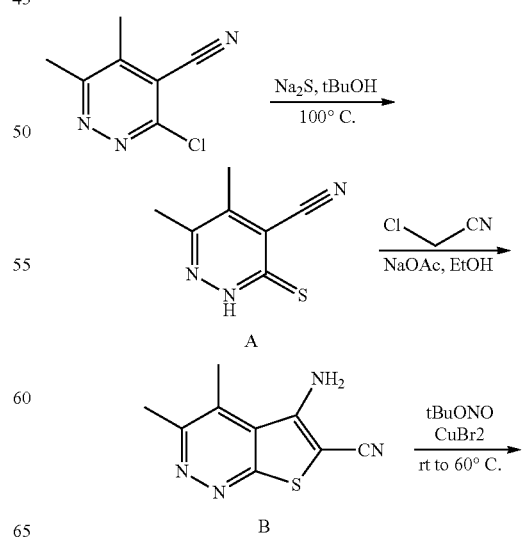

-continued

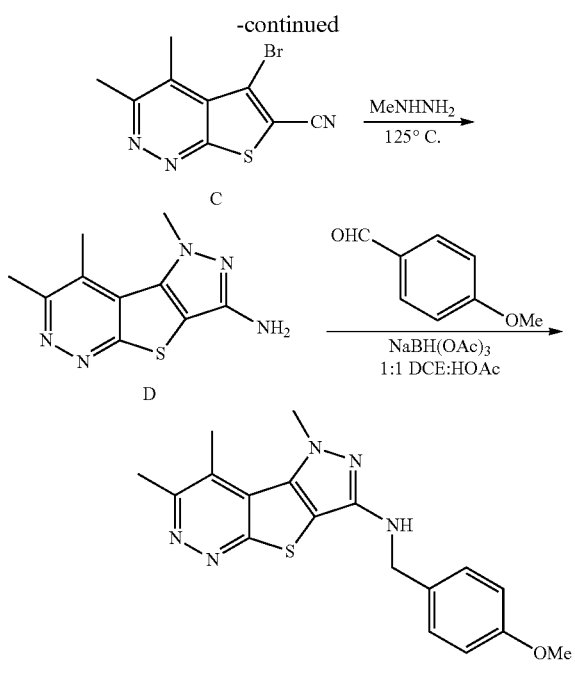

The 1,7,8-trimethyl-1H-pyrazole[3',4':4,5]thieno[2,3-c]pyridazin-3-amine (9 mg, 0.04 mmol) was stirred in 1:1 DCE/acetic acid (1.0 mL). To this solution was added 4-methoxybenzaldehyde (0.006 mL, 0.05 mmol). The reaction was stirred for 10 min, then NaBH(OAc)$_3$ (10 mg, 0.05 mmol) was added. The reaction was stirred an additional 45 min, then diluted with 1:1 DCM/MeOH and concentrated in in vacuo. The residue was purified by reverse-phase HPLC (acetonitrile: water gradient with 0.1% TFA) to give the product. $^1$H NMR (400 MHz, DMSO-d$_6$): δ ppm 7.30 (d, J=8.5 Hz, 2H), 6.86 (d, J=8.5 Hz, 2H), 6.48 (t, J=6.1 Hz, 1H), 4.30 (d, J=6.1 Hz, 2H), 4.14 (s, 3H), 3.70 (s, 3H), 2.76 (s, 3H), 2.73 (s, 3H). LC/MS: R$_T$=0.62 min., m/z=354 [M+H]$^+$. Calculated for C$_{18}$H$_{20}$N$_5$OS: 354.1389. found: 354.1390.

5. Characterization of Exemplary Compounds

The compounds in Table I were synthesized with methods identical or analogous to those described herein. The requisite starting materials were commercially available, described in the literature, or readily synthesized by one skilled in the art of organic synthesis. The mass spectrometry data were obtained using the general LC-MS methods as described above.

TABLE I

| No. | Compound | Name | M + H |
| --- | --- | --- | --- |
| 1 | | N-(4-methoxybenzyl)-1,7,8-trimethyl-1H-pyrazolo[3',4':4,5]thieno[2,3-c]pyridazin-3-amine | 354 |
| 2 | | 1,7,8-trimethyl-N-(4-(methylsulfonyl)benzyl)-1H-pyrazolo[3',4':4,5]thieno[2,3-c]pyridazin-3-amine | 402 |
| 3 | | N-(cyclopropylmethyl)-1,7,8-trimethyl-1H-pyrazolo[3',4':4,5]thieno[2,3-c]pyridazin-3-amine | 288 |
| 4 | | N-(furan-2-ylmethyl)-1,7,8-trimethyl-1H-pyrazolo[3',4':4,5]thieno[2,3-c]pyridazin-3-amine | 314 |

TABLE I-continued

| No. | Compound | Name | M + H |
|---|---|---|---|
| 5 | 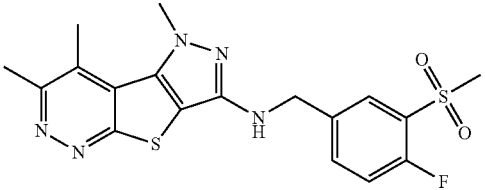 | N-(4-fluoro-3-(methylsulfonyl)benzyl)-1,7,8-trimethyl-1H-pyrazolo[3',4':4,5]thieno[2,3-c]pyridazin-3-amine | 420 |
| 6 | 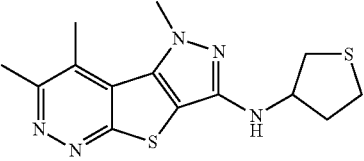 [SMILES: Cc1nnc2sc3c(NC4CCSC4)nn(C)c3c2c1C] | 1,7,8-trimethyl-N-(tetrahydrothiophen-3-yl)-1H-pyrazolo[3',4':4,5]thieno[2,3-c]pyridazin-3-amine | 320 |
| 7 | 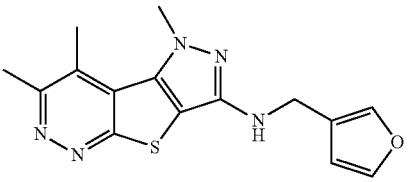 [SMILES: Cc1nnc2sc3c(NCc4ccoc4)nn(C)c3c2c1C] | N-(furan-3-ylmethyl)-1,7,8-trimethyl-1H-pyrazolo[3',4':4,5]thieno[2,3-c]pyridazin-3-amine | 314 |
| 8 | 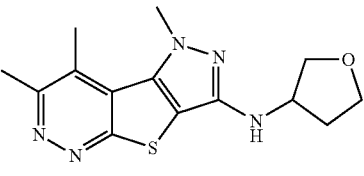 [SMILES: Cc1nnc2sc3c(NC4CCOC4)nn(C)c3c2c1C] | 1,7,8-trimethyl-N-(tetrahydrofuran-3-yl)-1H-pyrazolo[3',4':4,5]thieno[2,3-c]pyridazin-3-amine | 304 |
| 9 | 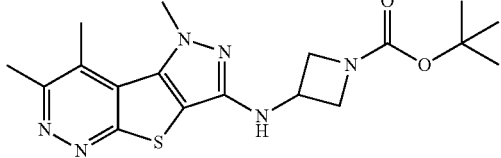 | tert-butyl 3-((1,7,8-trimethyl-1H-pyrazolo[3',4':4,5]thieno[2,3-c]pyridazin-3-yl)amino)azetidine-1-carboxylate | 389 |
| 10 | 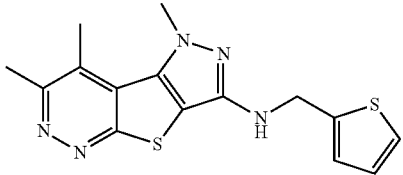 [SMILES: Cc1nnc2sc3c(NCc4cccs4)nn(C)c3c2c1C] | 1,7,8-trimethyl-N-(thiophen-2-ylmethyl)-1H-pyrazolo[3',4':4,5]thieno[2,3-c]pyridazin-3-amine | 330 |
| 11 | 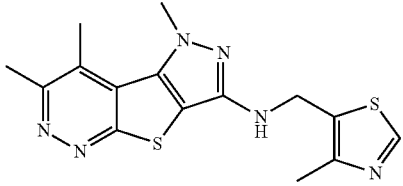 [SMILES: Cc1ncsc1CNc1nn(C)c2c1sc1nnc(C)c(C)c12] | 1,7,8-trimethyl-N-((4-methylthiazol-5-yl)methyl)-1H-pyrazolo[3',4':4,5]thieno[2,3-c]pyridazin-3-amine | 345 |
| 12 | 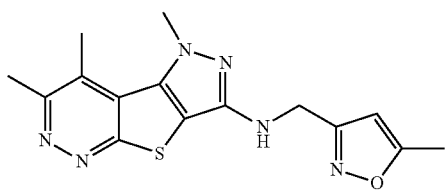 | 1,7,8-trimethyl-N-((5-methylisoxazol-3-yl)methyl)-1H-pyrazolo[3',4':4,5]thieno[2,3-c]pyridazin-3-amine | 329 |

TABLE I-continued

| No. | Compound | Name | M + H |
|---|---|---|---|
| 13 | 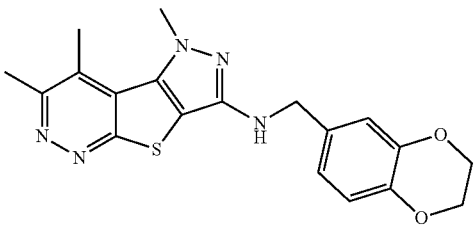 [SMILES: Cc1nnc2sc3c(NCc4ccc5c(c4)OCCO5)nn(C)c3c2c1C] | N-((2,3-dihydrobenzo[b][1,4]dioxin-6-yl)methyl)-1,7,8-trimethyl-1H-pyrazolo[3',4':4,5]thieno[2,3-c]pyridazin-3-amine | 382 |
| 14 | 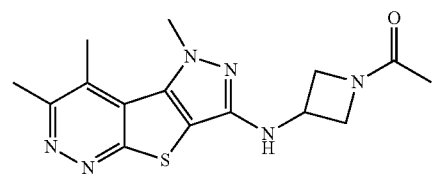 [SMILES: CC(=O)N1CC(Nc2nn(C)c3c2sc2nnc(C)c(C)c23)C1] | 1-(3-((1,7,8-trimethyl-1H-pyrazolo[3',4':4,5]thieno[2,3-c]pyridazin-3-yl)amino)azetidin-1-yl)ethanone | 331 |
| 15 | 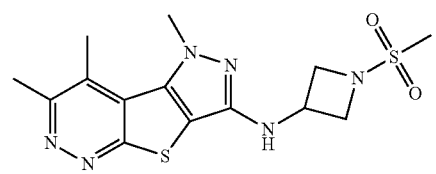 | 1,7,8-trimethyl-N-(1-(methylsulfonyl)azetidin-3-yl)-1H-pyrazolo[3',4':4,5]thieno[2,3-c]pyridazin-3-amine | 367 |
| 16 | 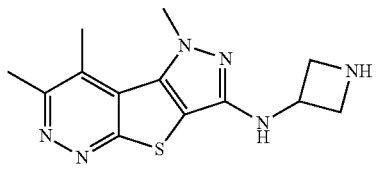 [SMILES: Cc1nnc2sc3c(NC4CNC4)nn(C)c3c2c1C] | N-(azetidin-3-yl)-1,7,8-trimethyl-1H-pyrazolo[3',4':4,5]thieno[2,3-c]pyridazin-3-amine | 289 |
| 17 | 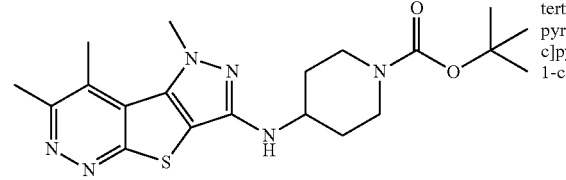 | tert-butyl 4-((1,7,8-trimethyl-1H-pyrazolo[3',4':4,5]thieno[2,3-c]pyridazin-3-yl)amino)piperidine-1-carboxylate | 417 |
| 18 | 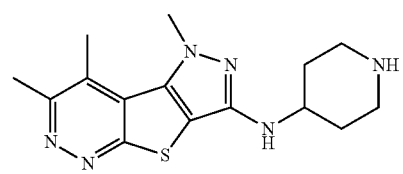 [SMILES: Cc1nnc2sc3c(NC4CCNCC4)nn(C)c3c2c1C] | 1,7,8-trimethyl-N-(piperidin-4-yl)-1H-pyrazolo[3',4':4,5]thieno[2,3-c]pyridazin-3-amine | 317 |
| 19 | 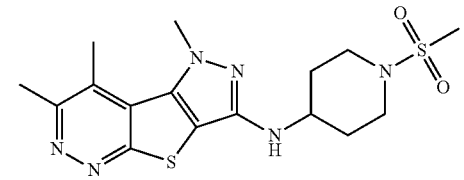 | 1,7,8-trimethyl-N-(1-(methylsulfonyl)piperidin-4-yl)-1H-pyrazolo[3',4':4,5]thieno[2,3-c]pyridazin-3-amine | 395 |
| 20 | 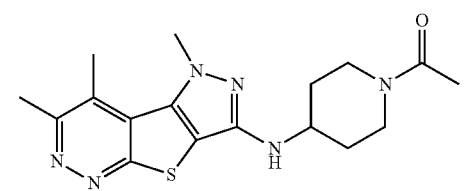 [SMILES: CC(=O)N1CCC(Nc2nn(C)c3c2sc2nnc(C)c(C)c23)CC1] | 1-(4-((1,7,8-trimethyl-1H-pyrazolo[3',4':4,5]thieno[2,3-c]pyridazin-3-yl)amino)piperidin-1-yl)ethanone | 359 |

TABLE I-continued

| No. | Compound | Name | M + H |
|---|---|---|---|
| 21 | | tert-butyl 4-(((1,7,8-trimethyl-1H-pyrazolo[3',4':4,5]thieno[2,3-c]pyridazin-3-yl)amino)methyl)piperidine-1-carboxylate | 431 |
| 22 | | 1,7,8-trimethyl-N-(piperidin-4-ylmethyl)-1H-pyrazolo[3',4':4,5]thieno[2,3-c]pyridazin-3-amine | 331 |
| 23 | | 1-(4-(((1,7,8-trimethyl-1H-pyrazolo[3',4':4,5]thieno[2,3-c]pyridazin-3-yl)amino)methyl)piperidin-1-yl)ethanone | 373 |
| 24 | | 1,7,8-trimethyl-N-((1-(methylsulfonyl)piperidin-4-yl)methyl)-1H-pyrazolo[3',4':4,5]thieno[2,3-c]pyridazin-3-amine | 409 |

6. Cell Lines Expressing Muscarinic Acetylcholine Receptors

Chinese hamster ovary (CHO-K1) cells stably expressing rat (r)$M_1$ were purchased from the American Type Culture Collection and cultured according to their indicated protocol. CHO cells stably expressing human (h)$M_2$, h$M_3$, and h$M_5$ were described previously (Levey A I, et al., (1991) J Neurosci 11:3218-3226.); h$M_1$ and h$M_4$ cDNAs were purchased from Missouri S&T cDNA Resource; r$M_4$ cDNA was provided by T. I. Bonner (National Institutes of Health, Bethesda, Md.). r$M_2$ and r$M_3$ were cloned from a rat brain cDNA library and sequence verified. h$M_1$, r$M_2$, r$M_3$, h$M_4$, and r$M_4$ cDNAs were used to stably transfect CHO-K1 cells purchased from the American Type Culture Collection using Lipofectamine® 2000. To make stable r$M_2$, h$M_2$, rM3, h$M_4$, and r$M_4$ cell lines for use in calcium mobilization assays, these cells also were stably transfected with a chimeric G-protein ($G_{qi5}$) (provided by B. R. Conklin, University of California, San Francisco) using Lipofectamine® 2000. r$M_1$, h$M_1$, r$M_3$, h$M_3$, r$M_5$, and h$M_5$ cells were grown in Ham's F-12 medium containing 10% heat-inactivated fetal bovine serum (FBS), 20 mM HEPES, and 50 µg/mL G418 sulfate. r$M2$-$G_{qi5}$, h$M_2$-$G_{qi5}$, and h$M_4$-$G_{qi5}$ cells were grown in the same medium also containing 500 µg/mL hygromycin B. Stable r$M_4$-$G_{qi5}$ cells were grown in DMEM containing 10% heat-inactivated FBS, 20 mM HEPES, 400 µg/mL G418 sulfate, and 500 µg/mL Hygromycin B.

7. Cell-Based Functional Assay of Muscarinic Acetylcholine Receptor Activity For high throughput measurement of agonist-evoked increases in intracellular calcium, CHO-K1 cells stably expressing the target muscarinic receptor were plated in growth medium lacking G418 and hygromycin at 15,000 cells/20 µL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with four washes (80 µL) of assay buffer then aspirated to 20 µL. Next, 20 µL of 16 µM Fluo-4/acetoxymethyl ester (Invitrogen, Carlsbad, Calif.) prepared as a 2.3 mM stock in DMSO and mixed in a 1:1 ratio with 10% (w/v) Pluronic F-127 and diluted in assay buffer was added to the wells and the cell plates were incubated for 50 mM at 37° C. and 5% $CO_2$. Dye was removed by washing with the ELX 405 (four 80 µL washes of assay buffer) then aspirated to 20 µL. Compound master plates were formatted in an 11 point CRC format (1:3 dilutions) in 100% DMSO with a starting concentration of 10 mM using the BRAVO liquid handler (Agilent). Test compound CRCs were then transferred to daughter plates (240 nL) using the Echo acoustic plate reformatter (Labcyte, Sunnyvale, Calif.) and then diluted into assay buffer (40 µL) to a 2× stock using a Thermo Fisher Combi (Thermo Fisher Scientific, Waltham, Mass.).

Calcium flux was measured using the Functional Drug Screening System (FDSS) 6000 (Hamamatsu Corporation, Tokyo, Japan) as an increase in the fluorescent static ratio. Compounds were applied to cells (20 µL, 2×) using the automated system of the FDSS 6000 at 4 s into the 300 s protocol and the data were collected at 1 Hz. At 144 s into the 300 s protocol, 10 µL of an $EC_{20}$ concentration of the muscarinic receptor agonist acetylcholine was added (5×), followed by the addition of 12 µL an $EC_{80}$ concentration of acetylcholine at the 230 s time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response. Concentration-response curves were generated using a four-parameter logistical equation in XLfit™ curve fitting software (IDBS, Bridgewater, N.J.) for Excel (Microsoft, Redmond, Wash.) or Prism (GraphPad Software, Inc., San Diego, Calif.).

The above described assay was also operated in a second mode where an appropriate fixed concentration of the present compounds were added to the cells after establishment of a fluorescence baseline for about 3 seconds, and the response in cells was measured. 140 s later the appropriate concentration of agonist was added and readings taken for an additional 106 s. Data were reduced as described above and the $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

8. Characterization of Substituted Pyrazolo[3',4':4, 5-]Thieno[2,3-C]Pyridazin-3-Amine Analogs Substituted pyrazolo[3',4':4,5]thieno[2,3-c]pyridazin-3-amine analogs were synthesized as described above. Activity ($EC_{50}$ and $E_{max}$) was determined in the mAChR $rM_4$ cell-based functional assay as described above, and the data are shown in Table II. The compound number corresponds to the compound numbers used in Table I.

TABLE II

| No. | $EC_{50}$ (nM) | $pEC_{50}$ | $E_{max}$ (%)* |
|---|---|---|---|
| 1 | 48 | 7.32 | 55 |
| 2 | 130 | 6.89 | 57 |
| 3 | 340 | 6.47 | 46 |
| 4 | 180 | 6.74 | 50 |
| 5 | 14 | 7.85 | 54 |
| 6 | 97 | 7.01 | 56 |
| 7 | 39 | 7.41 | 60 |
| 8 | 400 | 6.40 | 55 |
| 9 | 25 | 7.60 | 58 |
| 10 | 31 | 7.51 | 53 |
| 11 | 55 | 7.26 | 56 |
| 12 | 500 | 6.30 | 55 |
| 13 | 13 | 7.89 | 55 |
| 14 | 170 | 6.77 | 69 |
| 15 | 63 | 7.20 | 64 |
| 16 | 1400 | 5.85 | 51 |
| 17 | 210 | 6.68 | 47 |
| 18 | 5200 | 5.28 | 31 |
| 19 | 1100 | 5.96 | 58 |
| 20 | 1800 | 5.74 | 51 |
| 21 | 710 | 6.15 | 42 |
| 22 | >10,000 | <5.00 | n.d.** |
| 23 | 1800 | 5.74 | 44 |
| 24 | 2500 | 5.60 | 61 |

*%ACh maximum at 30 µM.
**"n.d." indicates that the experimental parameter was not determined For compounds showing low potency (as indicated by a lack of a plateau in the concentration response curve) but greater than a 20% increase in ACh response, a potency of >10 µM ($pEC_{50}$ <5) is estimated.

The selectivity of the disclosed compounds for mAChR $M_4$ compared to mAChR $M_1$, $M_2$, $M_3$, and $M_5$ was determined using the cell-based functional assay described below using the appropriate cell-lines (prepared as described below). The $EC_{50}$ for each of mAChR $M_1$, $M_2$, $M_3$, and $M_5$ was greater than at least 30 µM for representative compounds (i.e., there was no receptor response up to a concentration of about 30 µM, the upper limit of compound used in the assay).

9. Prophetic Pharmaceutical Composition Examples

"Active ingredient" as used throughout these examples relates to one or more disclosed compounds or products of disclosed methods of making as described hereinbefore, or a pharmaceutically acceptable salt, hydrate, solvate, or polymorph thereof. The following examples of the formulation of the compounds of the present invention in tablets, suspension, injectables and ointments are prophetic. Typical examples of recipes for the formulation of the invention are as given below.

Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

a. Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25; e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g. tablet format: diameter 8 mm, curvature radius 12 mm). The molding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
| --- | --- |
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

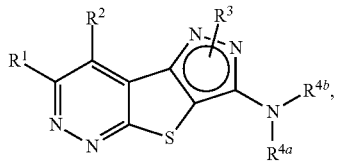

wherein $R^1$ is selected from hydrogen, halogen, —OH, C1-C6 alkyl, C1-C6 monohaloalkyl, C1-C6 polyhaloalkyl, C1-C6 alkoxy, C1-C6 monoalkylamino, and C1-C6 dialkylamino;

wherein $R^2$ is selected from hydrogen, halogen, C1-C6 alkyl, C1-C6 monohaloalkyl, C1-C6 polyhaloalkyl, C1-C6 alkoxy, C1-C6 monoalkylamino, and C1-C6 dialkylamino;

or wherein $R^1$ and $R^2$ are optionally covalently bonded and, together with the intermediate atoms, comprise a 3- to 7-membered cycle and substituted with 0, 1 or 2 groups independently selected from halogen, —NH$_2$, —OH, —CN, C1-C6 alkyl, C1-C6 monohaloalkyl, C1-C6 polyhaloalkyl, C1-C6 alkoxy, C1-C6 monoalkylamino, and C1-C6 dialkylamino;

wherein $R^3$ is selected from hydrogen, C1-C6 alkyl, C1-C6 monohaloalkyl, C1-C6 polyhaloalkyl, C3-C8 cycloalkyl, C2-C7 heterocycloalkyl, (C3-C8 cycloalkyl)-(C1-C8 alkyl)-, and (C2-C7 heterocycloalkyl)-(C1-C8 alkyl)-;

wherein each of $R^{4a}$ and $R^{4b}$ is independently selected from hydrogen, C1-C8 alkyl, C1-C8 monohaloalkyl, C1-C8 polyhaloalkyl, C3-C8 hydroxyalkyl, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{40}$R$^{41}$, —(C1-C6 alkyl)-NR$^{40}$(C=O)R$^{41}$, —(C1-C6 alkyl)-NR$^{40}$(C=O)OR$^{41}$, —(C1-C6 alkyl)-NR$^{40}$(C=O)R$^{41}$, —(C1-C6 monohaloalkyl)-NR$^{40}$(C=O)OR$^{41}$, —(C1-C6 polyhaloalkyl)-NR$^{40}$(C=O)OR$^{41}$, —(C1-C8 alkyl)-Cy$^1$, Cy$^1$, —(C1-C8 alkyl)-Ar$^1$, —(C2-C8 alkynyl)-Ar$^1$, and Ar$^1$;

wherein each $R^{40}$, when present, is independently selected from hydrogen and C1-C8 alkyl;

wherein each $R^{41}$, when present, is independently selected from hydrogen, C1-C8 alkyl, C1-C8 monohaloalkyl, C1-C8 polyhaloalkyl, —(C1-C8 alkyl)-Cy$^1$, Cy$^1$, —(C1-C8 alkyl)-Ar$^1$, and Ar$^1$;

wherein each Ar$^1$, when present, is independently selected from phenyl, naphthyl, and heteroaryl, and wherein each Ar$^1$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C8 alkyl)-Ar$^{20}$, Ar$^{20}$, —(C1-C8 alkyl)-Cy$^{20}$, Cy$^{20}$, and R$^{57}$;

wherein each m is an integer independently selected from 0, 1 and 2;

wherein each Ar$^{20}$, when present, is independently selected from phenyl, naphthyl, and heteroaryl, and wherein each Ar$^{20}$ is independently substituted with 0, 1, 2, or 3 groups independently selected from halogen, —NH$_2$, —OH, —CN, —S(O)$_m$R$^{50}$, C1-C8 alkyl, C1-C8 monohaloalkyl, C1-C8 polyhaloalkyl, C1-C8 alkoxy, C1-C8 alkylamino, and C1-C8 dialkylamino;

wherein each Cy$^{20}$, when present, is independently selected from C3-C9 cycloalkyl and C2-C7 heterocycloalkyl, and wherein each Cy$^{20}$ is independently substituted with 0, 1, 2, or 3 groups independently selected from halogen, —NH$_2$, —OH, —CN, —S(O)$_m$R$^{56}$, C1-C8 alkyl, C1-C8 monohaloalkyl, C1-C8 polyhaloalkyl, C1-C8 alkoxy, C1-C8 alkylamino, and C1-C8 dialkylamino;

wherein each $R^{50}$, when present, is independently selected from hydrogen and C1-C8 alkyl;

wherein each $R^{51}$, when present, is independently selected from hydrogen and C1-C8 alkyl;

wherein each $R^{52}$, when present, is independently selected from hydrogen and C1-C8 alkyl;

wherein each $R^{53}$, when present, is independently selected from hydrogen and C1-C8 alkyl;

wherein each $R^{54}$, when present, is independently selected from hydrogen, C1-C8 alkyl, C3-C9 cycloalkyl, C2-C7 heterocycloalkyl, C1-C8 monohaloalkyl, C1-C8 polyhaloalkyl, —(C1-C6)-Ar$^{21}$, and Ar$^{21}$;

wherein each Ar$^{21}$, when present, is independently selected from phenyl, naphthyl, and heteroaryl, and wherein each Ar$^{21}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino;

wherein each $R^{55}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{22}$, and Ar$^{22}$;

wherein each Ar$^{22}$, when present, is independently selected from phenyl, naphthyl, and heteroaryl, and wherein each Ar$^{22}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino;

wherein each $R^{56}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, —(C1-C6)-Ar$^{23}$, and Ar$^{23}$;

wherein each Ar$^{23}$, when present, is independently selected from phenyl, naphthyl, and heteroaryl, and wherein each Ar$^{23}$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, and C1-C8 dialkylamino;

wherein each $R^{57}$, when present, is independently selected from C1-C4 alkyl, C1-C4 alkoxy, C1-C4 monoalkylamino, or C1-C4 dialkylamino substituted with 1 or 2 groups selected from —F, —CH$_3$, —CF$_3$, —OH, —NH$_2$, and —CN;

wherein each Cy$^1$, when present, is independently selected from C3-C9 cycloalkyl and C2-C7 heterocycloalkyl, and wherein each Cy$^1$ is independently substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C8 alkyl)-Ar$^{20}$, Ar$^{20}$, —(C1-C8 alkyl)-Cy$^{20}$, Cy$^{20}$, and R$^{57}$;

wherein R$^{4a}$ and R$^{4b}$ are optionally covalently bonded and, together with the intermediate nitrogen, comprise a 3- to 10-membered heterocycloalkyl substituted with 0, 1, 2, or 3 groups independently selected from halogen, —NH$_2$, —OH, —CN, —N$_3$, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-O—(C1-C6 alkyl), —(C1-C6 alkyl)-O—(C1-C6 alkyl), —(C1-C6 alkyl)-NR$^{51}$R$^{52}$, —(C1-C6 alkyl)-NR$^{50}$(C=O)R$^{55}$, —(C1-C6 alkyl)-NR$^{50}$(C=O)OR$^{55}$, —(C1-C6 alkyl)-NR$^{50}$(C=O)R$^{55}$, —(C1-C6 alkyl)-NR$^{50}$S(O)$_m$R$^{55}$, —NR$^{50}$(C1-C6 alkyl)-(C=O)R$^{55}$, —NR$^{50}$(C1-C6 alkyl)-(C=O)OR$^{55}$, —NR$^{50}$(C1-C6 alkyl)-(C=O)R$^{55}$, —NR$^{50}$(C1-C6 alkyl)-S(O)$_m$R$^{55}$, —NR$^{50}$(C1-C6 alkyl)-S(O)$_m$NR$^{53}$R$^{54}$, —NR$^{50}$(C=O)R$^{55}$, —NR$^{50}$(C=O)OR$^{55}$, —NR$^{50}$(C=O)R$^{55}$, —NR$^{50}$S(O)$_m$R$^{55}$, —(C1-C6 alkyl)-(C=O)R$^{55}$, —(C1-C6 alkyl)-(C=O)OR$^{55}$, —(C1-C6 alkyl)-(C=O)R$^{55}$, —(C1-C6 alkyl)-S(O)$_m$R$^{55}$, —(C1-C6 alkyl)-S(O)$_m$NR$^{53}$R$^{54}$, —(C=O)R$^{55}$, —(C=O)OR$^{55}$, —S(O)$_m$R$^{55}$, —S(O)$_m$NR$^{53}$R$^{54}$, —(C1-C8 alkyl)-Ar$^{30}$, Ar$^{30}$, —(C1-C8 alkyl)-Cy$^{30}$, Cy$^{30}$, and R$^{57}$;

wherein each Ar$^{30}$, when present, is independently selected from phenyl, naphthyl, and heteroaryl, and wherein each Ar$^{30}$ is independently substituted with 0, 1, 2, or 3 groups independently selected from halogen, —NH$_2$, —OH, —CN, —S(O)$_m$R$^{65}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$;

wherein each R$^{65}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl;

wherein each Ar$^{40}$, when present, is independently selected from phenyl, naphthyl, and heteroaryl, and wherein each Ar$^{40}$ is independently substituted with 0, 1, 2, or 3 groups independently selected from halogen, —NH$_2$, —OH, —CN, —S(O)$_m$R$^{66}$, C1-C8 alkyl, C1-C8 monohaloalkyl, C1-C8 polyhaloalkyl, C1-C8 alkoxy, C1-C8 alkylamino, and C1-C8 dialkylamino;

wherein each R$^{66}$, when present, is independently selected from hydrogen, C1-C8 alkyl, C1-C8 hydroxyalkyl, C1-C8 monohaloalkyl, C1-C8 polyhaloalkyl, C3-C9 cycloalkyl, C2-C7 heterocycloalkyl, phenyl, and monocyclic heteroaryl;

wherein each Cy$^{40}$, when present, is independently selected from C3-C9 cycloalkyl and C2-C7 heterocycloalkyl, and wherein each Cy$^{40}$ is independently substituted with 0, 1, 2, or 3 groups independently selected from halogen, —NH$_2$, —OH, —CN, —S(O)$_m$R$^{66}$, C1-C8 alkyl, C1-C8 monohaloalkyl, C1-C8 polyhaloalkyl, C1-C8 alkoxy, C1-C8 alkylamino, and C1-C8 dialkylamino;

wherein each Cy$^{30}$, when present, is independently selected from C3-C9 cycloalkyl and C2-C7 heterocycloalkyl, and wherein each Cy$^{30}$ is independently substituted with 0, 1, 2, or 3 groups independently selected from halogen, —NH$_2$, —OH, —CN, —S(O)$_m$R$^{65}$, C1-C8 alkyl, C1-C8 monohaloalkyl, C1-C8 polyhaloalkyl, C1-C8 alkoxy, C1-C8 alkylamino, C1-C8 dialkylamino, —(C1-C8 alkyl)-Ar$^{40}$, Ar$^{40}$, —(C1-C8 alkyl)-Cy$^{40}$, and Cy$^{40}$;

or a pharmaceutically acceptable salt thereof.

2. The compound of claim 1, wherein each of R$^{4a}$ and R$^{4b}$ is independently selected from hydrogen, C1-C8 alkyl, C1-C8 monohaloalkyl, C1-C8 polyhaloalkyl, Cy$^1$, Cy$^1$-(C1-C6 alkyl)-, Ar$^1$, and Ar$^1$—(C1-C6 alkyl)-;

wherein each Ar$^1$, when present, is independently selected from phenyl and heteroaryl, and wherein each Ar$^1$ is independently substituted with 0, 1, 2, or 3 groups independently selected from halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein two of the groups are optionally covalently bonded, and together with the intermediate atoms, comprise an optionally substituted 3- to 6-membered fused ring group; and wherein each m is an integer independently selected from 0, 1 and 2;

wherein each Ar$^2$, when present, is independently selected from phenyl and heteroaryl, and wherein each Ar$^2$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, and —S(O)$_m$R$^5$;

wherein each R$^5$, when present, is independently selected from hydrogen, C1-C8 alkyl, C3-C8 cycloalkyl, C1-C8 monohaloalkyl, C1-C8 polyhaloalkyl, —(C1-C3)-Ar$^2$, and Ar$^2$; and wherein each R$^6$, when present, is selected from C1-C4 alkyl, C1-C4 alkoxy, C1-C4 monoalkylamino, or C1-C4 dialkylamino substituted with 1 or 2 groups selected from fluoro, trifluoromethyl, methyl, —OH, —NH$_2$, and —CN;

wherein each Cy$^1$, when present, is independently selected from C3-C8 cycloalkyl and C2-C7 heterocycloalkyl, and wherein each Cy$^1$ is independently substituted with 0, 1, 2, or 3 groups independently selected from halogen, —NH$_2$, —OH, —CN, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$; and wherein two of the groups are optionally covalently bonded, and together with the intermediate atoms, comprise an optionally substituted 3- to 6-membered fused ring group;

or wherein R$^{4a}$ and R$^{4b}$ are optionally covalently bonded and, together with the intermediate nitrogen, comprise a substituted 3- to 7-membered heterocycloalkyl substituted with 0, 1 or 2 groups independently selected from halogen, —NH$_2$, —OH, —CN, C1-C8 alkyl, C1-C8 haloalkyl, C1-C8 polyhaloalkyl, C1-C8 alkoxy, C1-C8 alkylamino, C1-C8 dialkylamino, C3-C8 cycloalkyl, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, and Ar$^2$; and wherein two of the groups are optionally covalently bonded, and together with the intermediate atoms, comprise an optionally substituted 3- to 6-membered fused ring group.

3. The compound of claim 1, wherein each of R$^1$ and R$^2$ is independently selected from hydrogen, methyl, and ethyl.

4. The compound of claim 1, wherein each of R$^1$, R$^2$, and R$^3$ is independently selected from hydrogen, methyl, and ethyl.

5. The compound of claim 1, wherein each of R$^1$, R$^2$, and R$^3$ is methyl.

6. The compound of claim 1, having a structure represented by a formula:

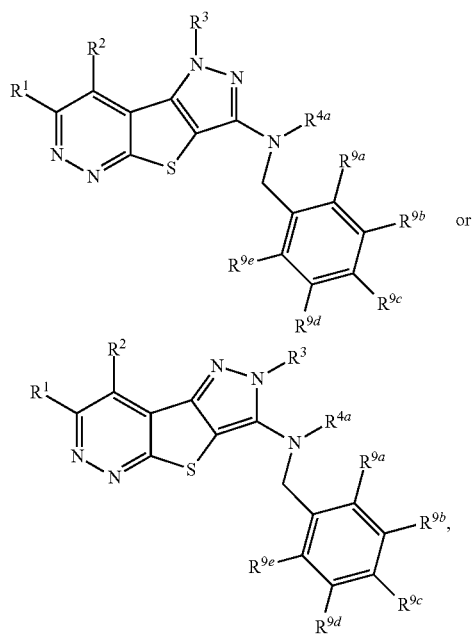

wherein each of R$^{9a}$, R$^{9b}$, R$^{9c}$, R$^{9d}$, and R$^{9e}$ is independently selected from hydrogen, halogen, —NH$_2$, —OH, —CN, —SF$_5$, C1-C8 alkyl, C1-C8 monohaloalkyl, C1-C8 polyhaloalkyl, C1-C8 alkoxy, C1-C8 alkylamino, C1-C8 dialkylamino, —(C1-C6 alkyl)-(C=O)R$^5$, —(C1-C6 alkyl)-(C=O)OR$^5$, —(C1-C6 alkyl)-S(O)$_m$R$^5$, —(C=O)R$^5$, —(C=O)OR$^5$, —S(O)$_m$R$^5$, R$^6$, and Ar$^2$, provided that at least two of R$^{9a}$, R$^{9b}$, R$^{9c}$, R$^{9d}$, and R$^{9e}$ are hydrogen.

7. The compound of claim 6, having a structure represented by a formula:

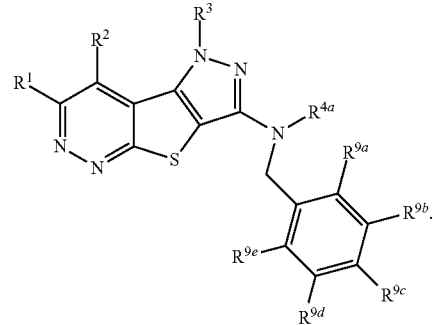

8. The compound of claim 1, having a structure represented by a formula:

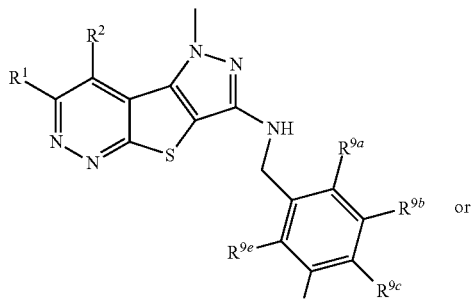

or

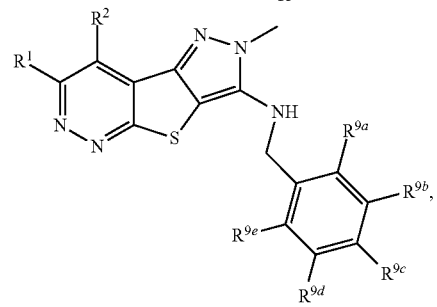

wherein R$^1$ is selected from hydrogen, —F, —Cl, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$;
wherein R$^2$ is selected from —F, —Cl, —Br, methyl, —CH$_2$F, —CH$_2$Cl, —CHF$_2$, —CF$_3$, —CHCl$_2$, —CCl$_3$, —OCH$_3$, —OCH$_2$CH$_3$, —NHCH$_3$, and —N(CH$_3$)$_2$;
wherein each of R$^{9a}$, R$^{9b}$, R$^{9c}$, R$^{9d}$, and R$^{9e}$ is independently selected from hydrogen, —F, —Cl, —Br, —NH$_2$, —OH, —CN, —SF$_5$, methyl, CH$_2$F, —CH$_2$Cl, —CHF$_2$, —CF$_3$, —CHCl$_2$, —CCl$_3$, —OCH$_3$, —OCH$_2$CH$_3$, —NHCH$_3$, —N(CH$_3$)$_2$, —(CH$_2$)—SCH$_3$, —(CH$_2$)—SOCH$_3$, —(CH$_2$)—SO$_2$CH$_3$, —SCH$_3$, —SOCH$_3$, —SO$_2$CH$_3$, —(CH$_2$)—SCF$_3$, —(CH$_2$)—SOCF$_3$, —(CH$_2$)—SO$_2$CF$_3$, —SCF$_3$, —SOCF$_3$, —SO$_2$CF$_3$, —(CH$_2$)—(C=O)CH$_3$, —(C=O)CH$_3$, —(CH$_2$)—(C=O)OCH$_3$, —(C=O)OCH$_3$, —CF(CF$_3$)CH$_3$, —C(OH)(CF$_3$)CH$_3$, —C(CF$_3$)(NH$_2$)CH$_3$, —C(CF$_3$)(CN)CH$_3$, —C(CF$_3$)$_2$CH$_3$, —CF(OH)CH$_3$, —CF(NH$_2$)CH$_3$, —CF(CN)CH$_3$, —C(OH)(NH$_2$)CH$_3$, —C(OH)(CN)CH$_3$, —C(CN)(NH$_2$)CH$_3$, and Ar$^2$; wherein each Ar$^2$, when present, is phenyl independently substituted with 0, 1, or 2 groups independently selected from —F, —NH$_2$, —OH, —CN, methyl, —CH$_2$F, —CHF$_2$, —CF$_3$, —OCH$_3$, —NHCH$_3$, —N(CH$_3$)$_2$, —SCH$_3$, —SCH$_2$F, —SCHF$_2$, —SCF$_3$, —(S=O)CH$_3$, —(S=O)CH$_2$F, —(S=O)CHF$_2$, —(S=O)CF$_3$, —SO$_2$CH$_3$, —SO$_2$CH$_2$F, —SO$_2$CHF$_2$, —SO$_2$CF$_3$, —SO$_2$-cyclopropyl, and —SO$_2$-phenyl; and wherein at least two of R$^{9a}$, R$^{9b}$, R$^{9c}$, R$^{9d}$, and R$^{9e}$ are hydrogen.

9. The compound of claim 8, having a structure represented by a formula:

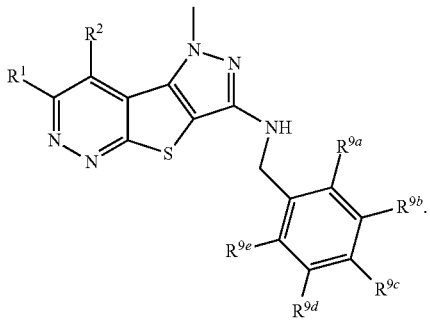

10. A pharmaceutical composition comprising a therapeutically effective amount of a compound of claim 1, or pharmaceutically acceptable salt thereof, and a pharmaceutically acceptable carrier.

11. A method for the treatment of Alzheimer's Disease in a mammal comprising the step of administering to the mammal an effective amount of at least one compound of claim 1.

12. The method of claim 11, wherein the effective amount is a therapeutically effective amount.

13. The method of claim 11, wherein treatment is symptom amelioration or prevention, and wherein the effective amount is a prophylactically effective amount.

14. The method of claim 11, wherein the mammal has been diagnosed with a need for treatment of Alzheimer's Disease prior to the administering step.

* * * * *